US008022178B2

(12) United States Patent
Horii et al.

(10) Patent No.: US 8,022,178 B2
(45) Date of Patent: Sep. 20, 2011

(54) MODIFIED SELF-ASSEMBLING PEPTIDES

(75) Inventors: Akihiro Horii, Hachiouji (JP);
Shuguang Zhang, Lexington, MA (US);
Xiumei Wang, Beijing (CN); Fabrizio Gelain, Milan (IT)

(73) Assignee: Massachusetts Institute of Technology, Cambridge, MA (US)

( * ) Notice: Subject to any disclaimer, the term of this patent is extended or adjusted under 35 U.S.C. 154(b) by 736 days.

(21) Appl. No.: 11/904,278

(22) Filed: Sep. 26, 2007

(65) Prior Publication Data
US 2009/0162437 A1 Jun. 25, 2009

Related U.S. Application Data

(60) Provisional application No. 60/847,303, filed on Sep. 26, 2006.

(51) Int. Cl.
*C07K 14/00* (2006.01)
(52) U.S. Cl. .................. 530/324; 514/1.1; 514/21.3
(58) Field of Classification Search .................. 530/324; 514/1.1, 21.3
See application file for complete search history.

(56) References Cited

U.S. PATENT DOCUMENTS

| | | | | |
|---|---|---|---|---|
| 4,315,074 | A | * | 2/1982 | Royer .......................... 435/68.1 |
| 4,737,487 | A | * | 4/1988 | Watts et al. .................. 514/21.5 |
| 5,109,113 | A | * | 4/1992 | Caras et al. .................. 530/350 |
| 5,670,483 | A | | 9/1997 | Holmes et al. |
| 5,763,212 | A | * | 6/1998 | Varshavsky et al. ......... 435/69.1 |
| 5,766,927 | A | * | 6/1998 | Baker et al. ................ 435/255.1 |
| 5,955,343 | A | | 9/1999 | Holmes et al. |
| 6,489,116 | B2 | | 12/2002 | Wagner et al. |
| 7,429,567 | B2 | | 9/2008 | Lee et al. |
| 2002/0160471 | A1 | | 10/2002 | Kisiday et al. |
| 2005/0181973 | A1 | | 8/2005 | Genove et al. |

FOREIGN PATENT DOCUMENTS

| | | |
|---|---|---|
| EP | 0278781 | 8/1988 |
| WO | WO9509659 | 4/1995 |
| WO | WO0185180 | 11/2001 |
| WO | WO2006076042 | 7/2006 |
| WO | WO2006116524 | 11/2006 |

OTHER PUBLICATIONS

Beck, et al., "Structure and Function of Laminin: Anatomy of a Multidomain Glycoprotein", FASEB J. 4, 148-160, 1990.
Bell, et al., "Differential Gene Expression During Capillary Morphogenesis in 3D Collagen Matrices: Regulated Expression of Genes Involved in Basement Membrane Matrix Assembly, Cell Cycle Progression, Cellular Differentiation and G-Protein Signaling", J. Cell Science, 114: 2755-2773, 2001.
Binning, et al., "Atomic Force Microscope" Phys. Rev. Lett., 12, 930-933, 1986.
Brown, S. "Metal Recognition by Repeating Polypeptides", Nat. Biotechnol., 15:269-92, 1997.
Busse, et al., "Regulation of Endothelium-Derived Vasoactive Autacoid Production by Hemodynamic Forces", Trends in Pharmacological Sciences, 24: 24-29, 2003.
Caplan, et al., "Self-Assembly of a Beta-Sheet Oligopeptide is Governed by Electrostatic Repulsion", Biomacromolecules, 1, 627-631, 2000.
Caplan, et al., "Control of Self-Assembling Oligopeptide Matrix Formation through Systematic Variation of Amino Acid Sequence," Biomaterials, 23, 219-227, 2002.
Caplan, et al., "Effects of Systematic Variation of Aminoacid Sequence on the Mechanical Properties of a Self-Assembling, Oligopeptide Biomaterial", J. Biomater. Sci. Polymer Edition, 13, 225-236, 2002.
Carmeliet, P., "Mechanisms of Angiogenesis and Arteriogenesis", Nat.Med., 6: 389-395, 2000.
Cassell, et al., "Vascularization of Tissue-Engineered Grafts: The Regulation of Angiogenesis in Reconstructive Surgery and in Disease States", Br. J. Plast. Surg., 55: 603-610, 2002.
Charonis, et al., "Binding of Laminin to Type IV Collagen: a Morphological Study" J. Cell Biol. 100, 1848-1853, 1985.
Cines, et al., "Endothelial Cells in Physiology and Pathophysiology of Vascular Disorders", Blood, 91, 3527-3561, 1998.
Colton, C., "Implantable Biohybrid Artificial Organs", Cell Transplantation, 4: 415-436, 1995.
Davis, et al., "Capillary Morphogenesis During Human Endothelial Cell Invasion of Three-Dimensional Collagen Matrices", In Vitro Cell. Dev. Biol. Animal, 36: 513-519, 2000.
Davis, et al., "Molecular Basis of Endothelial Cell Morphogenesis in Three-Dimensional Extracellular Matrices", Anat. Rec., 268: 252-275, 2002.
Dorsett, et al., "siRNAs: Applications in Functional Genomics and Potential as Therapeutics", Nat. Rev. Drug Discovery, 3: 318-329, 2004.
Dziadek, et al., "Expression of Nidogen and Laminin in Basement Membranes During Mouse Embryogenesis and in Teratocarcinoma Cells" Dev. Biol. 111, 372-382, 1985.
Engel, J., et al., "Shapes, Domain Organizations and Flexibility of Laminin and Fibronectin, Two Multifunctional Proteins of the Extracellular Matrix", J. Mol. Biol. 150, 97-120, 1981.
Engel, J. "Laminins and Other Strange Proteins," Biochemistry, 31, 10643-10651, 1992.

(Continued)

Primary Examiner — David Lukton
(74) Attorney, Agent, or Firm — Choate Hall & Stewart LLP

(57) ABSTRACT

The present invention provides a self-assembling peptide comprising: (a) a first amino acid domain that mediates self-assembly, wherein the domain comprises alternating hydrophobic and hydrophilic amino acids that are complementary and structurally compatible and self-assemble into a macroscopic structure when present in unmodified form; and (b) a second amino acid domain that does not mediate self-assembly in isolated form, wherein the second amino acid domain comprises at least one minimal biologically active sequence. Such self-assembling peptides are described herein as "modified self-assemblingpeptides." The present invention also provides pharmaceutical compositions, kits and matrices comprising a modified self-assembling peptide, and methods of using and making such compositions, kits and matrices.

95 Claims, 33 Drawing Sheets
(25 of 33 Drawing Sheet(s) Filed in Color)

OTHER PUBLICATIONS

Fujiwara, et al., "Structure and Interaction of Heparan Sulfate Proteoglycans from a Mouse Tumor Basement Membrane", Eur. J. Biochem. 143, 145-157, 1984.

Gloe, et al., "The 67-kDa Laminin-Binding Protein is Involved in Shear Stress-Dependent Endothelial Nitric-Oxide Synthase Expression", J. Biol. Chem., 274: 15996-16002, 1999.

Graf, J., et al., "Identification of an Amino Acid Sequence in Laminin Mediating Cell Attachment, Chemotaxis and Receptor Binding", Cell 48, 989-996, 1987.

Grant, et al., "Interaction of Endothelial Cells with a Laminin A Chain Peptide (SIKVAV) in Itro and Induction of Angiogenic Behavior in Vivo", J. Cell. Physiol., 153, 614-25, 1992.

Grant, et al., "Two Different Laminin Domains Mediate the Differentiation of Human Endothelial Cells into Capillary-Like Structures in Vitro", Cell, 58, 933-43, 1989.

Han, et al., "Angiogenesis State of the Art" Int J Hematol; 70(2):68-82, 1999.

Hartgerink, et al., "Self-Assembly and Mineralization of Peptide-Amphiphile Nanofibers" Science; 294: 1684-1688, 2001.

Holmes, et al., "Extensive Neurite Outgrowth and Active Synapse Formation on Self-Assembling Peptide Scaffolds", PNAS, 97, 6728-6733, 2000.

Hsieh, et al., "Local controlled intramyocardial delivery of platelet-derived growth factor improves postinfarction ventricular function without pulmonary toxicity" Circulation, vol. 114, No. 7 Aug. 15, 2006.

Iwamoto, et al., "A Synthetic Laminin Pentapeptide, Inhibits Experimental Metastasis Formation", Science 238, 1132-1134, 1987.

Kanemoto, et al., "Identification of an Aminoacid Sequence from the Laminin A Chain that Stimulates Metastasis and Collagenase IV Production", Proc. Natl. Acad. Sci.,USA, 87, 2279-83, 1990.

Kavanagh, et al., "Rheological Characterization of Polymer Gels", Prog. Polym. Sci., 23, 533-562, 1998.

Kisiday, et al., "Self-Assembling Peptide Hydrogel Fosters Chondrocyte Extracellular Matrix Production and Cell Division: Implications for Cartilage Tissue Repair", Proc. Natl. Acad. Sci. USA, 99: 9996-10001, 2002.

Kisiday, et al., "Effects of Dynamic Compressive Loading on Chondrocyte Biosynthesis in Self-Assembling Peptide Scaffolds", J. Biomech, 37(5): 595-604, 2004.

Klein, et al., "Differential Expression of Laminin A and B Chains During Development of Embryonic Mouse Organs", Development 110, 823-837, 1990.

Kleinman, et al., "Identification of a Second Active Site in Laminin for Promotion of Cell Adhesion and Migration and Inhibition of Melanoma Lung Colonization", Arch. Biochem. Biophys. 272, 39-45, 1989.

Koliakos, et al., "The Binding of Heparin to Type IV Collagen: Domain Specificity with Identification of Peptide Sequences from the Alpha 1(IV) and Alpha 2(IV) Which Preferentially Bind Heparin" J. Biol. Chem. 264, 2313-2323, 1989.

Kubota, et al., "Role of Laminin and Basement Membrane in the Morphological Differentiation of Human Endothelial Cells into Capillary-like Structures", J. Cell. Biol., 107, 1589-1598, 1988.

Lendahl, et al., "CNS Stem Cells Express a New Class of Intermediate Filament Protein", Cell, 60:585-595, 1990.

Leon, et al., "Mechanical Properties of a Self-Assembling Oligopeptide Matrix", J. Biomater. Sci. Polymer Edition, 9, 297-312, 1998.

Lin, et al., "Synthesis, Surface, and Cell-Adhesion Properties of Polyurethanes Containing Covalently Grafted RGD-Peptides", J. Biomed. Mater. Res. 3: 329-342, 1994.

Malinda, et al., "Identification of Laminin [alpha]1 and [beta]1 Chain Peptides Active for Endothelial Cell Adhesion, Tube Formation and Aortic Sprouting", FASEB, 13, 53-62, 1999.

Mann, et al., "Cell Adhesion Peptides Alter Smooth Muscle Cell Adhesion, Proliferation, Migration, and Matrix Protein Synthesis on Modified Surfaces and in Polymer Scaffolds",. Biomed. Mater. Res. 60(1):86-93, 2002.

Martin, et al., "Laminin and Other Basement Membrane Components", Annu. Rev. Cell. Biol. 3, 57-85, 1987.

Massia, et al., "Human Endothelial Cell Interactions with Surface-Coupled Adhesion Peptides on Non-Adhesive Glass and Two Polymeric Biomaterials", J. Biomed. Mater. Res. 2: 223-242, 1991.

Nomizu, et al., "Identification of Homologous Biologically Active Sites on the N-Terminal Domain of Laminin Alpha Chains", Biochemistry, 40, 15310-17, 2001.

Nomizu, et al., "The All-D-Configuration Segment Containing the IKVAV Sequence of Laminin A Chain has Similar Activities to the All-L-Peptide in Vitro and in Vivo", J. Biol. Chem. 267, 14118-14121, 1992.

Nomizu, et al., "Identification of Cell Binding Sequences in Mouse Laminin a1 Chain by Systematic Peptide Screening", J. Biol. Chem. 272, 32198-32205, 1997.

Nomizu et al. "Cell adhesive sequences in mouse laminin beta1 chain" Archive of Biochemistry and Biophysics vol. 378, pp. 311-320, 2000.

Paulsson, et al., "Laminin-Nidogen Complex. Extraction with Chelating Agents and Structural Characterization", Eur. J. Biochem. 166, 11-19, 1987.

Ponce, et al., "Identification of Endothelial Cell Binding Sites on the Laminin [gamma]1 Chain", Circ. Res., 84, 688-694, 1999.

Poschl, et al., "Site-Directed Mutagenesis and Structural Interpretation of the Nidogen Binding Site of the Laminin Gamma 1 Chain", EMBO J. 15, 5154-5159, 1996.

Sagnella, et al., "Human Microvascular Endothelial Cell Growth and Migration on Biomimetic Surfactant Polymers", Biomaterials, 25: 1249-1259, 2004.

Sakamoto, et al.. "Inhibition of Angiogenesis and Tumor Growth by a Synthetic Laminin Peptide, CDPGYIGSR-NH2", Cancer Res, 51, 903-6, 1991.

Sarikaya, et al., Materials Assembly and Formation Using Engineered Polypeptides, Annu. Rev. Mater. Res. 34:373-408. Published online Apr. 2, 2004.

Sarnat, ., et al., "Neuronal Nuclear Antigen (NeuN): a Marker of Neuronal Maturation in Early Human Fetal Nervous System", Brain Research, 20:88-94, 1998.

Schmedlen, et al.. "Photocrosslinkable Polyvinyl Alcohol Hydrogels that Can be Modified with Cell Adhesion Peptides for Use in Tissue Engineering", Biomaterials; 23: 4325-4332, 2002.

Semino, et al., "Functional Differentiation of Hepatocyte-Like Spheroid Structures from Putative Liver Progenitor Cells in Three-Dimensional Peptide Scaffolds", Differentiation, 71: 262-270, 2003.

Semino, et al., "Entrapment of Migrating Hippocampal Neural Cells in 3-D Peptide Nanfiber Scaffold", Tissue Engineering, 10(3-4): 643-655, 2004.

Skubitz, et al., "Definition of a Sequence, RYVVLPR, within Laminin Peptide F-9 that Mediates Metastatic Fibrosarcoma Cell Adhesion and Spreading", Cancer Res., 50, 7612-22, 1990.

Stack, et al.., "Modulation of Plasminogen Activation and Type IV Collagenase Activity by a Synthetic Peptide Derived from the Laminin A chain", Biochemistry, 30, 2073-2077, 1990.

Tashiro, et al., "A Synthetic Peptide Containing the IKVAV Sequence from the A Chain of Laminin Mediates Cell Attachment, Migration, and Neurite Outgrowth",. J. Biol. Chem., 264, 16174-16182, 1989.

Timpl, R. "Structure and Biological Activity of Basement Membrane Proteins", Eur. J. Biochem. 180, 487-502., 1989.

Timpl, R. "Macromolecular Organization of Basement Membranes" Curr. Opin. Cell Biol. 8, 618-624, 1996.

Tsilibary, et al., "Identification of a Multifunctional, Cell-Binding Peptide Sequence from the a1(NC1) of Type IV Collagen", J. Cell Biol. 111, 1583-1591, 1990.

Tsilibary, et al.,. "Heparin Type IV Collagen Interactions: Equilibrium Binding and Inhibition of Type IV Collagen Self-Assembly", J. Biol. Chem. 263, 19112-19118, 1988.

Whaley, et al.,. "Selection of Peptides with Semiconductor Binding Specificity for Directed Nanocrystal Assembly", Nature, 405(6787):665-8, 2000.

Whitesides, et al., "Molecular Self-Assembly and Nanochemistry: a Chemical Strategy for the Synthesis of Nanostructures" Science, 254, 1312, 1991.

Yamada, K.M. "Adhesive Recognition Sequences", J. Biol. Chem. 266, 12809-12812, 1991.

Yamada, et al., "Functional Domains of Cell Adhesion Molecules", Curr. Opin. Cell. Biol. 4, 819-823, 1992.

Yurchenco, et al., "Self-Assembly and Calcium-Binding Sites in Laminin. A three-arm interaction model", J. Biol. Chem. 268, 17286-17299, 1993.

Zhang, et al., "Zuotin, a Putative Z-DNA Binding Protein in *Saccharomyces cervsiae*", EMBO, J., 11: 3787-3796, 1992.

Zhang, et al., "Peptide Self-Assembly in Functional Polymer Science and Engineering", Reactive & Functional Polymers, 41: 91-102, 1999.

Zhang, et al., "Spontaneous Assembly of a Self-Complementary Oligopeptide to Form a Stable Macroscopic Membrane", Proc. Natl. Acad. Sci. USA, 90: 3334-3338, 1993.

Zhang, et al., "Self-Complementary Oligopeptide Matrices Support Mammalian Cells Attachment", Biomaterials, 16: 1385-1393, 1995.

Zhang et al., "Emerging biological material through molecular self-assembly" Biotechnology Advances v. 20, pp. 321-339, 2002.

Zhang, et al., "Designer self-assembling peptide nanfiber scaffolds for 3D tissue cell cultures" Seminars in Cancer Biology, Saunders Scientific Publicatiosn, vol. 15, No. 5, Oct. 2005, pp. 413-420.

Bellamkonda, et al. "Laminin oligopeptide derivatized agarose gels allow three dimensional neurite extension in vitro" J. of Neuroscience Research, vol. 41, No. 4, Jul. 1995.

Ciu, et al. "Cerebrum repair with PHPMA hydrogel immobilized with neurite-promoting peptides in traumatic brain injury of adult rat model" J. of Bioactive and Compatible Polymers, vol. 18, No. 6 Nov. 2003.

Davis, et al. "Local mycardial insulin-like growth factor 1 (IGF-1) delivery with biotinylated peptide nanofibers improves cell therapy for myocardial infarction" PNAS, vol. 103, No. 21May 2006.

Gelain, et al. "Designer self-assembling peptide nanofiber scaffolds for adult mouse neural stem cell 3-dimensional cultures" PLOS ONE 2006, vol. 1, 2006 p. e119.

Genove, et al., "The effect of functionalized self-assembling peptide scaffolds on human aortic endothelial cell function" Biomaterials, vol. 26, No. 16 Jun. 2005.

Horii, et al. "Biological designer self-assembling peptide nanofiber saffolds significantly enhance osteoblast proliferation, differentional and 3-D migration." PLOS ONE 2007, vol. 2, No. 2, p. e190 2007.

Hucknall, et al., A Self-Assembling Peptide Scaffold Functionalized for Use with Neural Stem Cells MIT, Jul. 2005 http://dspace.mit.edu/handle/1721.1/33.

Eiselt, et al., "Development of Technologies Aiding Large-Tissue Engineering" Biotechnology Progress vol. 14 pp. 134-140, 1999.

\* cited by examiner (A) RAD  (B) RAD2  (C) PFSmx
(D) FLGmx  (E) ALKmx  (F) PRGmx
(G) DGRmx  (H) PRFmx  (I) COLmx Scale=200mm

TOP VIEW (A) RAD16-1

(B) FHR

SIDE VIEW (C) RAD16-1

(D) FHR

← 1400um →

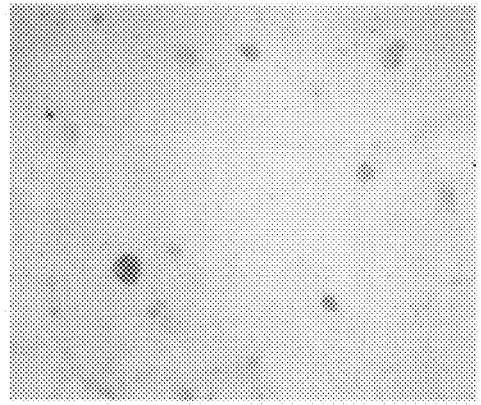 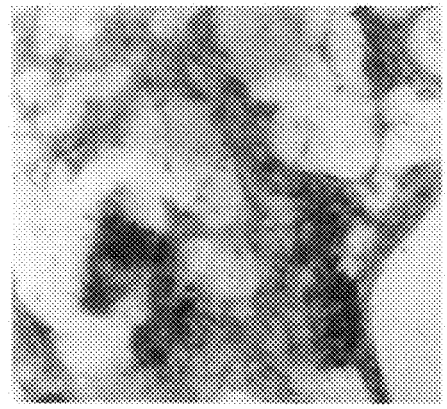
(A) RAD  (B) FHR
FIGURES 16A-16B
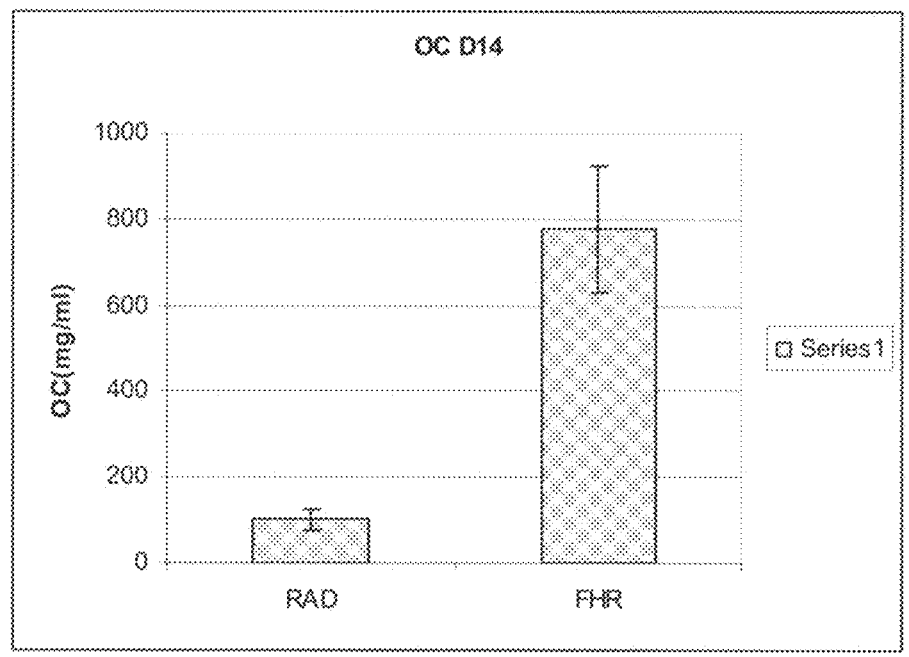
FIGURE 17

(A) Day 1

Scale = 100μm (B) Collagen, Day 2

(C) MatriGel, Day 2

(D) RAD, Day 2

(E) PRGmx, Day 2

(F) KLTmx, Day 2

(A) RAD  (B) PRGmx  (C) KLTmx

Scale=100μm (A)  (B)

Scale=50μm

RAD (A)

(B)

PRGmx (E)

COLLAGEN (F)

(A) EIK (B) EPRG (C) EPRGmx (D) EPFS (E) EPFSmx (H) FKF (F) ESKP (G) ESKPmx (I) KFHRmx (J) KPRG (K) KPRGmx scale=200μm

VERTICAL VIEW (A) RAD  (B) PRGmx  (C) FHRmx

HORIZONAL VIEW (D) RAD  (E) PRGmx  (F) FHRmx

Scale=100μm

VERTICAL VIEW (G) PFSmx (H) SKPmx

HORIZONAL VIEW (I) PFSmx (J) SKPmx

Scale=100μm (A)

(B)

A

B

MODIFIED SELF-ASSEMBLING PEPTIDES

PRIORITY INFORMATION

This application claims priority under 35 U.S.C. §119(e) to United States provisional patent application, U.S. Ser. No. 60/847,303, filed Sep. 26, 2006, which is incorporated herein by reference.

BACKGROUND OF THE INVENTION

The extracellular matrix (ECM) is composed of a diverse set of macromolecules, including both proteins and polysaccharides, which form the three-dimensional environment within which cells exist in the body and constitute the space-filling material between cells. The ECM can also be organized into a sheet-like layer known as the basal lamina or basement membrane. In many regions of the body, the basement membrane lies beneath layers or tubes of epithelial cells (e.g., endothelial cells lining blood vessels) or surrounds individual cells of various types such as muscle cells, often serving to separate cell layers from one another or from adjacent connective tissue.

The ECM consists primarily of molecules that are secreted locally and assemble into a matrix that stabilizes and supports the physical structure of cell layers and tissues. However, rather than being merely an inert substrate for cell attachment, the ECM constitutes an environment that is rich in biological information. It is recognized that the ECM, and various biomolecules associated with it (e.g., biomolecules secreted locally or transported to a particular site from elsewhere), exert a significant influence on many aspects of cell behavior and phenotype, regulating processes such as migration and proliferation, influencing cell development and differentiation, and affecting cell shape and function. The structure of the ECM is, in turn, influenced by the cells within it. Not only do these cells secrete many ECM constituents, but they also help to pattern the matrix. Thus it is evident that cell-ECM interactions are of vital importance.

While a vast amount of useful biological information has been gathered from experiments performed on cells grown on traditional tissue culture substrates, such as glass or plastic, there has been increasing interest in developing culture systems and materials that would more accurately reflect the native cellular environment. Such materials would have use not only for cell culture but also for tissue repair and tissue engineering, such as for growing cells, tissues, and/or artificial organs or for use in cell-based bioreactors for production of biomolecules.

Many previous efforts to develop such systems have involved the use of materials such as proteins and peptides obtained from animal sources. However, these materials have a number of disadvantages as compared with synthetic materials. For example, they present an increased risk for the transmission of disease. Even when harvested under supposedly sterile conditions, there is a significant risk of contamination. If animal sources are used, there is concern about immunogenicity if the materials are subsequently introduced into the human body, such as for tissue repair or as components in artificial organs. Additionally, it can be difficult to ensure that different preparations of material have a consistent, reproducible composition.

Even when it is possible to achieve consistency with respect to the known components of a material isolated from a natural source, it is hard or impossible to ensure that unknown and/or unidentified components that may affect cell properties are excluded. Furthermore, in the course of harvesting, processing, and/or reconstituting, the material may become damaged and/or degraded, thus potentially reducing the fidelity with which they replicate in the native cellular environment.

Another approach to the development of materials that would mimic the EMC environment provided is to produce various ECM constituents by recombinant DNA techniques. For example, expression constructs encoding ECM proteins can be introduced into prokaryotic or eukaryotic cells, and the protein of interest can be purified from the cells or from the medium in the case of secreted proteins. Proteins can be combined in vitro in desired ratios. While likely reducing the likelihood of disease transmission, this approach also suffers from several disadvantages. For example, whenever proteins are manufactured through a biological rather than purely synthetic process, there remains the possibility that undefined components from the culture system will be present even in highly purified preparations. In addition, purification can be time-consuming and costly and can result in protein degradation or denaturation.

Although native ECM consists largely of proteins and proteoglycans, significant efforts have been directed to development of cell culture and tissue engineering materials based on a variety of synthetic, non-amino acid based polymers. For example, aliphatic hydroesters have been widely used for various tissue engineering applications. Among the commonly used fully synthetic materials are polyglycolic acid (PGA), poly(lactic-co-glycolic acid) (PLGA), poly(ethylene glycol) (PEG), poly(propylene glycol), and various copolymers of these and other compounds. However, these materials also suffer from a number of disadvantages. For example, they form fibers with diameters on the order of tens of microns, and the methods required to introduce cells into matrices formed from such materials are not readily compatible with the physiological requirements for cell viability.

Thus there remains a need for synthetic compositions and materials for cell culture and tissue engineering purposes that would allow the creation of an environment that mimics the native cellular environment, but without the disadvantages associated with materials derived from natural sources. For example, it would be desirable to develop a material that could provide biologically relevant stimuli to cells akin to those provided by native ECM components. For applications involving implantation into the body, there remains a particular need for such compositions and materials that elicit no or minimal immune or inflammatory response and for compositions and materials that are degradable within the body. In addition, there remains a need in the art for compositions and materials that would influence cell properties and functions in desirable ways.

SUMMARY OF THE INVENTION

The present invention addresses these needs, among others. The invention encompasses the discovery that it is possible to modify self-assembling peptides by incorporating an additional domain that does not self-assemble, while still permitting assembly of the self-assembling portion. The additional domain can confer a variety of properties on the resulting peptide. In certain embodiments, the resulting peptide self-assembles to form nanofibers, beta-sheets and/or a macroscopic structure. Materials formed by self-assembly of the peptides have a wide variety of uses, particularly in the areas of cell culture, tissue engineering, and tissue repair.

In a first aspect, the present invention includes a self-assembling peptide comprising: (a) a first amino acid domain that mediates self-assembly, wherein the domain comprises alternating hydrophobic and hydrophilic amino acids that are complementary and structurally compatible and self-assemble into a macroscopic structure when present in unmodified form; and (b) a second amino acid domain that does not mediate self-assembly in isolated form, wherein the second amino acid domain comprises at least one minimal biologically active sequence. Such self-assembling peptides are described herein as "modified self-assembling peptides."

In certain embodiments, the second amino acid domain comprises at least two minimal biologically active sequences. In certain embodiments of the invention, the modified self-assembling peptide comprises a minimal biologically active sequence which has an affinity to, or complexes with, a biological molecule.

In a second aspect, the present invention provides a solution comprising a modified self-assembling peptide.

In a third aspect, the present invention provides a pharmaceutical composition comprising a modified self-assembling peptide.

In a fourth aspect, the present invention provides a matrix comprising a modified self-assembling peptide. In certain embodiments, the matrix is a gel or hydrogel. The present invention also provides methods of making the matrix, and of using the matrix as a defect filler for bone and/or tissue (e.g., for use in tissue engineering and tissue repair). For example, this invention describes matrices comprising a modified self-assembling peptide which enhance orthopedic tissue regeneration by increasing progenitor cell activity in proliferation and differentiation. These matrices can be used in vivo as defect fillers for bone and/or tissue to promote bone and/or tissue regeneration.

In a fifth aspect, the present invention provides methods of enhancing cell differentiation or functional activity comprising administering a modified self-assembling peptide, a solution thereof, a pharmaceutical composition thereof, or a matrix made therefrom, to a subject in need thereof.

In a sixth aspect, the present invention provides a method of treating a subject comprising introducing a modified self-assembling peptide, a solution thereof, a pharmaceutical composition thereof, or a matrix made therefrom, to a site on or within the subject's body. In certain embodiments, the site is of an orthopedic field; a bone defect; a bone adjent; an ectopic bone formation; an ischemic region; a myocardial infarction region; peripheral vascular region; cerebral infarction region; or a skin defect.

In a seventh and final aspect, the present invention also provides kits comprising a modified self-assembling peptide, a solution thereof, a pharmaceutical composition thereof, or a matrix made therefrom, and methods of using such kits.

The details of one or more embodiments of the invention are set forth in the accompanying Figures and the Detailed Description of Certain Embodiments, as described below. Other features, objects, and advantages of the invention will be apparent from the description, the figures, and from the claims.

INCORPORATION BY REFERENCE

This application refers to various issued patents, published patent applications, journal articles, and other publications, all of which are incorporated herein by reference. In addition, the following publications are incorporated herein by reference:

Clark A H, Ross-Murphy, S B, *Structural and mechanical properties of biopolymer gels*, Springer-Verlag, Berlin, 1987; Vol. 83, pp. 58-192 (85-86);

*Current Protocols in Molecular Biology, Current Protocols in Immunology, Current Protocols in Protein Science*, and *Current Protocols in Cell Biology*, all John Wiley & Sons, N.Y., Edition July 2002; Sambrook, Russell, and Sambrook;

Freshney, R. I., *Culture of Animal Cells: A Manual of Basic Technique*, 4$^{th}$ ed., John Wiley & Sons, New York, 2000;

Goodman and Gilman's *The Pharmacological Basis of Therapeutics*, 10$^{th}$ Ed. McGraw Hill, 2001;

*Guidebook to the Extracellular Matrix, Anchor, and Adhesion Proteins* (The Guidebook Series), by Thomas Kreis, Ronald Vale Sambrook and Tooze Publication at Oxford Univ; 2$^{nd}$ edition, 1999;

Havel, Editor. (1996) *Spectroscopic methods for determining protein structure in solution*. VCH Publishers, Inc., New York;

Harlow, E., Lane, E., and Harlow, E., (Eds.) *Using Antibodies: A Laboratory Manual*, Cold Spring Harbor Laboratory Press, Cold Spring Harbor, 1998;

Katzung, B. (Ed.) *Basic and Clinical Pharmacology*, McGraw-Hill/Appleton & Lange; 8$^{th}$ edition (Sep. 21, 2000);

Kandel, E., Schwartz, J. H., Jessell, T. M., (eds.), *Principles of Neural Science*, 4$^{th}$ edition, McGraw Hill, 2000;

Kreis T, Vale R (ed.). *Guidebook of the extracellular, anchor and adhesion proteins*, 2$^{nd}$ Edition. A Sambrook & Tooze publication at Oxford University Press, UK 1999;

Schramm G. (1994) *A practical approach to rheology and rheometry*, Gebrueder HAAKE GmbH, Karlsruhe, Germany;

Zhang, S. (2001) *Molecular self-assembly*. Encyclopedia of Materials: Science & Technology, Elsevier Science, Oxford, UK, pp. 5822-5829.

*Molecular Cloning: A Laboratory Manual*, 3$^{rd}$ Ed., Cold Spring Harbor Laboratory Press, Cold Spring Harbor, 2001;

*The Cytokine Handbook*, 4$^{th}$ Ed., A. Thomson, Michael T. Lotze, Angus W. Thomson, Lotze M. Academic Press, 2003;

*The Extracellular Matrix Factsbook*, by Shirley Ayad, Ray Boot-Handford Academic Press; 2nd edition, 1998;

Beck, K., Hunter, I., & Engel, J. (1990). "Structure and function of laminin: anatomy of a multidomain glycoprotein," *FASEB J* 4:148-160;

Bell, S. E., Mavila, A., Salazar. R., Bayless K. J., Kanagala, S., Maxwell S. A., Davis, G. E., (2001) "Differential gene expression during capillary morphogenesis in 3D collagen matrices: regulated expression of genes involved in basement membrane matrix assembly, cell cycle progression, cellular differentiation and G-protein signaling," *J. Cell Science*, 1:2755-2773;

Binning, G. B., Quate, C. F., Gerber, Ch. (1986) "Atomic Force Microscope," *Phys. Rev. Lett.*, 12:930;

Boeynaems, J. M., Pirroton, S. (1994) "Regulation of the vascular endothelium: signals and transduction mechanisms," R.G. Landes Company, Austin, USA;

Brown, S. (1997) "Metal recognition by repeating polypeptides" *Nat. Biotechnol.*, 15:269-292;

Busse, R., Fleming, I. (2003) "Regulation of endothelium-derived vasoactive autacoid production by hemodynamic forces," *Trends in Pharmacological Sciences*, 24:24-29;

Caplan, M. R., Moore, P., Zhang, S., Kamm, R. D., Lauffenburger, D. A. (2000) "Self-assembly of a beta-sheet oligopeptide is governed by electrostatic repulsion," *Biomacromolecules*, 1:627-631;

Caplan, M. R., Schwartzfarb, E. M, Zhang, S., Kamm, R. D., Lauffenburger, D. A. (2002a) "Control of self-assembling oligopeptide matrix formation through systematic variation of amino acid sequence," *Biomaterials*, 23:219-227;

Caplan, M. R., Schwartzfarb, E. M., Zhang, S., Kamm, R. D., Lauffenburger, D. A. (2002b) "Effects of systematic variation of amino acid sequence on the mechanical properties of a self-assembling, oligopeptide biomaterial," *J. Biomater. Sci. Polymer* 13: 225-236;

Carmeliet P. (2000) "Mechanisms of angiogenesis and arteriogenesis" *Nat Med* 6:389-395;

Cassell, O. C., Hofer, S. O., Morrison, W. A., Knight, K. R. (2002) "Vascularization of tissue-engineered grafts: the regulation of angiogenesis in reconstructive surgery and in disease states," *Br. J. Plast. Surg.*, 55:603-610;

Charonis, A. S., Tsilibary, E. C., Yurchenco, P. D., & Furthmayr, (1985). "Binding of laminin to type IV collagen: a morphological study," *J. Cell Biol.* 100:1848-1853;

Cines, E D. B., Pollak, E. S., Buck, C. A., Loscalzo, J., Zimmerman, G. A., McEver, R. P., Pober, J. S., Wick, T. M., Konkle, B. S., Schwartz, B. S., Barnathan, E. S., McRae, K. R., Hug, B. A., Schmidt, A. M., Stern, D. M. (1998) "Endothelial cells in physiology and pathophysiology of vascular disorders," *Blood* 91:3527-3561;

Colton, C. (1995) "Implantable biohybrid artificial organs," *Cell transplantation,* 4:415-436;

Davis, G. E., Black, S. M., Bayless, K. J. (2000) "Capillary morphogenesis during human endothelial cell invasion of three-dimensional collagen matrices," *In Vitro Cell. Dev. Biol. Animal,* 36:513-19;

Davis, G. E., Bayless K. J., Mavila A. (2002) "Molecular basis of endothelial cell morphogenesis in three-dimensional extracellular matrices," *Anat. Rec.,* 268:252-75;

Dorsett, Y. and Tuschl, T., (2004) *Nat Rev Drug Discovery,* 3:318-329;

Dziadek, M. & Timpl, R. (1985). "Expression of nidogen and laminin in basement membranes during mouse embryogenesis and in teratocarcinoma cells," *Dev. Biol.* 111:372-382;

Eiselt, P., Kim, B-S., Chacko, B., Isenberg, B., Peters, M. C., Greene, K. G., Roland, W. D., Loebsack, A. B., Burg, K. J. L., Culberson, C. R., Halberstadt, C. R., Holder, W. D., Mooney, D. J. (1998) "Development of technologies aiding large tissue engineering," *Biotechnol. Prog,* 14:134-40;

Engel, J., Odermatt, E., Engel, A., Madri, J. A., Furthmayr, H., Rhode, H., n Timpl, R. (1981) "Shapes, domain organizations and flexibility of laminin and fibronectin, two multifunctional proteins of the extracellular matrix" *J. Mol. Biol.* 150:97-120;

Engel, J. (1992). "Laminins and other strange proteins," *Biochemistry,* 31: 10643-10651;

Fujiwara, S., Wiedeman, H., Timpl, R., Lustig, A., & Engel, J. (1984). "Structure and interaction of heparan sulfate proteoglycans from a mouse tumor basement membrane," *Eur. J. Biochem.* 143:145-157;

Gloe, T., Riedmayr, S., Sohn, H-Y., Pohl, U. (1999) "The 67-kDa Laminin-binding protein is involved in shear stress-dependent endothelial nitric-oxide synthase expression," *J. Biol. Chem.,* 274:15996-16002;

Graft, J., Iwamoto, Y., Sasaki, M., Martin, G. R., Kleinman, H. K., Robey, F. A., & Yamada, Y. (1987). "Identification of an amino acid sequence in laminin mediating cell attachment, chemotaxis and receptor binding," *Cell* 48:989-996;

Grant, D. S., Kinsella, J. L., Frideman, R., Auerbach, R., Piasecki, B. A., Yamada, Y., Zain, M., Kleinman, H. Y. (1992) "Interaction of endothelial cells with a laminin A chain peptide (SIKVAV) in vitro and induction of angiogenic behavior in vivo," *J. Cell. Physiol.,* 153:614-25;

Grant, D. S., Tashirom, K. I., Segui-Real, B., Yamada, Y., Martin, G. R., Kleinman, H. K. (1989) "Two different laminin domains mediate the differentiation of human endothelial cells into capillary-like structures in vitro," *Cell* 58:933-43;

Han Z C, Liu Y. (1999) "Angiogenesis: state of the art," *Int J. Hematol* 70:68-82;

Hartgerink J D, Beniash E, Stupp S I. (2001) "Self-assembly and mineralization of peptide-amphiphile nanofibers," *Science* 294: 1684-1688;

Holmes T. C., De Lacalle, S., Su, X., Liu, G., Rich, A., Zhang, S. (2000) "Extensive neurite outgrowth and active synapse formation on self-assembling peptide matrices," *PNAS,* 97:6728-6733;

Iwamoto, Y., Robey, F. A., Graf, J., Sasaki, M., Kleinman, H. K., Robey, F. A., & Yamada, Y. (1987). "YIGSR, a synthetic laminin pentapeptide, inhibits experimental metastasis formation," *Science* 238:1132-1134;

Kanemoto, T., Reich, R., Royce, L., Greatorex, D., Adler, S. H., Shiraishi, N., Martin, G. R., Yamada, Y., Kleinman, H. K. (1990) "Identification of an amino acid sequence from the laminin A chain that stimulates metastasis and collagenase IV production," *Proc. Natl. Acad. Sci., USA,* 87:2279-83;

Kavanagh, G. M., Ross-Murphy, S. B. (1998) "Rheological characterization of polymer gels," *Prog. Polym. Sci.,* 23:533-562;

Kisiday, J., Jin, M., Kurz, B., Hung, H., Semino, C., Zhang, S., Grodzinsky, A. J. (2002) "Self-assembling peptide hydrogel fosters chondrocyte extracellular matrix production and cell division: implications for cartilage tissue repair," *Proc. Natl. Acad. Sci. USA,* 99:9996-10001;

Kisiday J D, Jin M, DiMicco M A, Kurz B, Grodzinsky A J., J. (2004) "Effects of dynamic compressive loading on chondrocyte biosynthesis in self-assembling peptide matrices," *J. Biomech.* 37:595-604;

Klein, G., Ekblom, M., Fleker, L., Timpl, R. & Ekblom, P. (1990). "Differential expression of laminin A and B chains during development of embryonic mouse organs," *Development* 110:823-837;

Kleinman, H. K., Graf, J., Iwamoto, Y., Sasaki, M., Schasteen, C. S., Yamada, Y., Martin, G. R., & Robey, F. A. (1989). "Identification of a second active site in laminin for promotion of cell adhesion and migration and inhibition of melanoma lung colonization," *Arch. Biochem. Biophys.* 272:39-45;

Koliakos, G. G., Koliakos, K. K., Furcht, L. T., Reger, L. A., & Tsilibary, E. C. (1989). "The binding of heparin to type IV collagen: domain specificity with identification of peptide sequences from the alpha 1 (IV) and alpha 2(IV) which preferentially bind heparin," *J. Biol. Chem.* 264:2313-2323;

Kubota, Y., Kleinman, H. K., Martin, G. R., Lawley T. J. (1988) "Role of laminin and basement membrane in the morphological differentiation of human endothelial cells into capillary-like structures," J. Cell. Biol., 107:1589-98;

Lendahl, U., et al., (1990) "CNS stem cells express a new class of intermediate filament protein," *Cell,* 60:585-595;

Leon, E. J., Verma, N., Zhang, S., Lauffenburger, D. A., Kamm, R. D. (1998) "Mechanical properties of a self-assembling oligopeptide matrix," *J. Biomater. Sci. Polymer Edition,* 9:297-312;

Lin H B et al. (1994) "Synthesis, surface, and cell-adhesion properties of polyurethanes containing covalently grafted RGD-peptides," *J. Biomed. Mater. Res.* 3: 329-342;

Malinda, K. M., Nomizu, M., Chung, M., Delgado, M., Kuratomi, Y., Yamada, Y., Kleinman H. K. (1999) "Identification of laminin .alpha.1 and .beta.1 chain peptides active for endothelial cell adhesion, tube formation and aortic sprouting," *FASEB,* 13:53-62;

Mann B K, West J L (2002) "Cell adhesion peptides alter smooth muscle cell adhesion, proliferation, migration, and matrix protein synthesis on modified surfaces and in polymer scaffolds," *J. Biomed. Mater. Res.* 60 (1):86-93;

Martin, G. R., & Timpl, R. (1987). "Laminin and other basement membrane components," *Annu. Rev. Cell. Biol.* 3:57-85;

Massia S P, Hubbell J A. (1991) "Human endothelial cell interactions with surface-coupled adhesion peptides on non-adhesive glass and two polymeric biomaterials," *J. Biomed. Mater. Res.* 2: 223-242;

Nomizu, M., Yokohama, F., Suzuki, N., Okazaki, I., Nishi, N., Ponce, M. L., Kleinman, H. K., Yamamoto, Y., Nakagawa, S., Mayumi, T. (2001) "Identification of homologous biologically active sites on the N-terminal domain of laminin alpha chains," *Biochemistry*, 40:15310-17;

Nomizu, M., Utani, A., Shiraishi, N., Kibbey, M. C., Yamada, Y., & Roller, P. P. (1992). "The all-D-configuration segment containing the IKVAV sequence of laminin A chain has similar activities to the all-L-peptide in vitro and in vivo," *J. Biol. Chem.* 267:14118-14121;

Nomizu, M., Kuratomi, Y, Song, S-Y., Ponce, M. L., Hoffman, M. P., Powell, S. K., Miyoshi, K., Otaka, A., Kleinman, H. K., & Yamada, Y. (1997). "Identification of cell binding sequences in mouse lamininal chain by systematic peptide screening," *J. Biol. Chem.* 272:32198-32205;

Paulsson, M., Aumailley, M., Deutzman, R., Timpl, R., Beck, K., & Engel, J. (1987). "Laminin-nidogen complex. Extraction with chelating agents and structural characterization," *Eur. J. Biochem.* 166:11-19;

Ponce, M. L., Nomizu, M., Delgado, M. C., Kuratomi, Y., Hoffman, M. P., Powell, S., Yamada, Y., Kleinman, H. K., Malinda, K. M. (1999) "Identification of endothelial cell binding sites on the laminin gamma 1 chain," *Circ. Res.*, 84:688-694;

Poschl, E., Mayer, U., Stetefeld, J., Baumgartner, R., Holak, T. A., Huber, R., & Timpl, R. (1996). "Site-directed mutagenesis and structural interpretation of the nidogen binding site of the laminin gamma 1 chain," *EMBO J.* 15:5154-5159;

Russell, P., Batchelor, D., Thornton, J. (2001) "SEM and AFM: complementary techniques for high resolution surface investigations," www.veeco.com;

Sarikaya, M., Tamerler, C., Schwartz, D T, and Baneyx, F., (2004) "Materials Assembly and Formation Using Engineered Polypeptides," *Annu. Rev. Mater. Res.* 34:373-408;

Sagnella S M, Kligman F, Anderson E H, King J E, Murugesan G, Marchant R E, Kottke-Marchant K. (2004) "Human microvascular endothelial cell growth and migration on biomimetic surfactant polymers," *Biomaterials* 25: 1249-1259;

Sakamoto, N., Iwahana, M., Tanaka, N. G., Osada, Y. (1991) "Inhibition of angiogenesis and tumor growth by a synthetic laminin peptide, CDPGYIGSR-NH$_2$," *Cancer Res*, 51:903-906;

Sarnat, H., et al., (1998) "Neuronal nuclear antigen (NeuN): a marker of neuronal maturation in early human fetal nervous system," *Brain Research*, 20:88-94;

Schmedlen R H, Masters K S, West J L. (2002) "Photocrosslinkable polyvinyl alcohol hydrogels that can be modified with cell adhesion peptides for use in tissue engineering," *Biomaterials* 23: 4325-4332;

Semino, C. E, Merok, J. R, Crane, G., Panagiotakos, G., Zhang, S. (2003) "Functional differentiation of hepatocyte-like spheroid structures from putative liver progenitor cells in three-dimensional peptide matrices," *Differentiation* 71:262-270.

Semino, C. E., Kasahara, J., Hayashi Y. & Zhang, S. (2004) "Entrapment of migrating hippocampal neural cells in 3-D peptide nanofiber matrix," *Tissue Engineering* 10: 643-655;

Silva G A, Czeisler C, Niece K L, Harrington D, Kessler J, Stupp S I. (2004) "Selective differentiation of neuronal progenitor cells by high-epitope density nanofibers," *Sciencexpress*.

Skubitz, A. P., McCarthy J. B., Zhao, Q., Yi, X. Y., Furcht, L. T. (1990) "Definition of a sequence, RYVVLPR, within laminin peptide F-9 that mediates metastatic fibrosarcoma cell adhesion and spreading," *Cancer Res.*, 50:7612-22;

Stack, S., Gray, R. D., Pizzo, S. V. (1990). "Modulation of plasminogen activation and type IV collagenase activity by a synthetic peptide derived from the laminin A chain," *Biochemistry*, 30:2073-2077;

Tashiro, K., Sephel, G. C., Weeks, B., Sasaki, M., Martin, G. R., Kleinman, H. K., Yamada, Y. (1989) "A synthetic peptide containing the IKVAV sequence from the A chain of laminin mediates cell attachment, migration, and neurite outgrowth," *J. Biol. Chem.*, 264:16174-82;

Tsilibary, E. C., Regel, L. A., Vogel, A. M., Koliakos, G. G., Anderson, S. S., Charonis, A. S., Alegre, J. N., & Furcht, L. T. (1990). "Identification of a multifunctional, cell-binding peptide sequence from the a1(NC1) of type IV collagen," *J. Cell Biol.* 111:1583-1591;

Tsilibary, E. C., Koliakos, G. G., Charonis, A. S., Vogel, A. M., Regel, L. A., & Furcht, L. T. (1988). "Heparin type IV collagen interactions: equilibrium binding and inhibition of type IV collagen self-assembly," *J. Biol. Chem.* 263:19112-19118;

Timpl, R. (1989). "Structure and biological activity of basement membrane proteins," *Eur. J. Biochem.* 180:487-502;

Timpl, R. (1996). "Macromolecular organization of basement membranes," *Curr. Opin. Cell Biol.* 8:618-624;

Whaley S R, English D S, Hu E L, Barbara P F, Belcher A M. (2000) "Selection of peptides with semiconductor binding specificity for directed nanocrystal assembly," *Nature* 405: 665-8;

Whitesides, G. M., Mathias, J. P., Seto, C. T. (1991) "Molecular self-assembly and nanochemistry: a chemical strategy for the synthesis of nanostructures," *Science* 254: 1312;

Yamada, K. M. (1991). "Adhesive recognition sequences," *J. Biol. Chem.* 266:12809-12812;

Yamada, Y., Kleinman, H. K. (1992). "Functional domains of cell adhesion molecules," *Curr. Opin. Cell. Biol.* 4:819-823;

Yasumitsu, T., Nomizu, M., Gullber, D., MacKrell, A. J., Keene, D. R., Yamada, Y., & Fessler, J. H. (1996). "Conserved neuron promoting activity in *Drosophila* and vertebrate laminin alpha 1," *J. Biol. Chem.* 271:18074-18081;

Yurchenco, P. D., Cheng, Y. S. (1993). "Self-assembly and calcium-binding sites in laminin. A three-arm interaction model," *J. Biol. Chem.* 268:17286-17299;

Yurchenco, P. D., O'Rear, J. J. (1994). "Basement membrane assembly," *Methods Enzymol.* 145:489-518.

Zhang, S., Lockshin, C., Herbert, A., Winter, E., Rich, A. (1992) "Zuotin, a putative Z-DNA binding protein in *Saccharomyces cervsiae*," *EMBO J.*, 11:3787-3796;

Zhang, S., Altman, M. (1999) "Peptide self-assembly in functional polymer science and engineering," *Reactive & Functional Polymers*, 41:91-102.

Zhang, S. Holmes, T., Lockshin, C., Rich, A. (1993) "Spontaneous assembly of a self-complementary oligopeptide to form a stable macroscopic membrane," *Proc. Natl. Acad. Sci. USA*, 90:3334-3338;

Zhang, S., Holmes, T., DiPersio, M., Hynes, R. O., Su, X., Rich, A. (1995) "Self-complementary oligopeptide matrices support mammalian cell attachment," *Biomaterials*, 16:1385-1393;

Further information useful for various embodiments of the present invention is also described in U.S. Patent Application Publication No. 20050181973, incorporated herein by reference. If there is a conflict between any of the incorporated references and the instant specification, the specification shall control.

DEFINITIONS

The following definitions are of use in understanding the invention.

Amino acid domain: By "amino acid domain" is meant a contiguous polymer of at least 2 amino acids joined by peptide bond(s). The domain may be joined to another amino acid or amino acid domain by one or more peptide bonds. An amino acid domain can constitute at least two amino acids at the N-terminus or C-terminus of a peptide or can constitute at least two amino acids in the middle of a peptide.

Antibody: In general, the term "antibody" refers to an immunoglobulin, which may be natural or wholly or partially synthetically produced in various embodiments of the invention. An antibody may be derived from natural sources (e.g., purified from a rodent, rabbit, chicken (or egg) from an animal that has been immunized with an antigen or a construct that encodes the antigen) partly or wholly synthetically produced. An antibody may be a member of any immunoglobulin class, including any of the human classes: IgG, IgM, IgA, IgD, and IgE. The antibody may be a fragment of an antibody such as an Fab', F(ab')$_2$, scFv (single-chain variable) or other fragment that retains an antigen binding site, or a recombinantly produced scFv fragment, including recombinantly produced fragments. See, e.g., Allen, T., (2002) *Nature Reviews Cancer*, 2:750-765, and references therein. In certain embodiments, antibodies, antibody fragments, and/or protein domains comprising an antigen binding site may be generated and/or selected in vitro, e.g., using techniques such as phage display (Winter, G. et al. 1994. Annu. Rev. Immunol. 12:433-455, 1994) and/or ribosome display (Hanes, J., and Pluckthun, A. Proc. Natl. Acad. Sci. USA. 94:4937-4942, 1997), etc. In various embodiments of the invention the antibody is a "humanized" antibody in which for example, a variable domain of rodent origin is fused to a constant domain of human origin, thus retaining the specificity of the rodent antibody. It is noted that the domain of human origin need not originate directly from a human in the sense that it is first synthesized in a human being. Instead, "human" domains may be generated in rodents whose genome incorporates human immunoglobulin genes. See, e.g., Vaughan, et al., Nature Biotechnology, 16: 535-539, 1998. An antibody may be polyclonal or monoclonal.

Approximately or About: As used herein, the term "approximately" or "about" means that the measurement or number may deviate by up to 10% of the numeral given, in either direction.

Biologically-active peptide motif: A "biologically active peptide motif" is a peptide that induces a phenotypic response or change in an appropriate cell type when the cell is contacted with the peptide. The peptide may be present either in isolated form or as part of a larger polypeptide or other molecule. The ability of the peptide to elicit the response may be determined, for example, by comparing the relevant parameter in the absence of the peptide (e.g., by mutating or removing the peptide when normally present within a larger polypeptide). Phenotypic responses or changes include, but are not limited to, enhancement of cell spreading, attachment, adhesion, proliferation, secretion of an ECM molecule, or expression of a phenotype characteristic of a particular differentiated cell type.

Biomolecule: As used herein, a "biomolecule" refers to a molecule such as a protein, peptide, proteoglycan, lipid, carbohydrate, or nucleic acid having characteristics typical of molecules found in living organisms. A biomolecule may be naturally occurring or may be artificial (i.e., not found in nature and not identical to a molecule found in nature). For example, a protein having a sequence or modification resulting from the mental process of man, and not occurring in nature, is considered an artificial biomolecule.

Chemotatic substance: A "chemotactic substance," as used herein, refers to a substance having the ability to recruit cells to a site at which the substance is present. Such cells may, for example, have the potential to contribute to the formation or repair of a tissue (e.g., by providing growth factors) or to contribute to an immune response. Certain chemotactic substances may also function as proliferation agents.

Complementary: By "complementary," as used herein, is meant having the capability of forming ionic or hydrogen bonding interactions between hydrophilic residues from adjacent peptides in a fiber of macroscopic matrix. Each hydrophilic residue in a peptide either hydrogen bonds or ionically pairs with a hydrophilic residue on an adjacent peptide, or is exposed to solvent. Pairing may also involve van der Waals forces Endothelial cell: The term "endothelial cell," as used herein, is to be given its meaning as generally accepted in the art, i.e., the innermost layer of cells that line the cavities of the heart, blood vessels (including capillaries), and lymph vessels. The terms "endothelium" and "vascular endothelium" are used interchangeably herein.

Gellation agent: By "gellation agent," as used herein, is meant an agent which transforms a solution of a modified self-assembling peptide into a matrix (e.g., a gel or a hydrogel) upon mixing or contacting the gellation agent with the solution. In certain embodiments, the peptide solution before gellation can be a non-viscous fluid, viscous fluid or Sol form. Exemplary gellation agents include, but are not limited to, electrolytes (e.g., NaOH, KCl, NaCl, saline (NaCl-aqueous), phosphate buffered saline (PBS-aqueous)), cell culture mediums (e.g., a mammalian cell culture medium such as MEM), basic solutions (e.g., NaOH solution) or biological fluids (e.g., blood, lymph, etc.)

Isolated: As used herein, "isolated" means 1) separated from at least some of the components with which it is usually associated in nature; 2) prepared or purified by a process that involves the hand of man; and/or 3) not occurring in nature.

Iso-osmotic solute: By "iso-osmotic solute" is meant a non-ionizing compound dissolved in an aqueous solution such that the resulting solution (i.e., an "iso-osmotic solution") has an osmotic pressure or osmolality compatible with cell viability a period of time greater than about 1 minute, about 5 minutes, about 10 minutes, about 20 minutes, about 30 minutes, about 40 minutes, about 50 minutes, or about 1 hour. In certain embodiments, an iso-osmotic solution has an osmotic pressure that approximates the osmotic pressure of the extracellular or intracellular environment of cells (for example, an in vitro environment such as a tissue culture medium, or an in vivo environment such as that within a subject). For example, an iso-osmotic solution may have an osmotic pressure that is within 290±10 mosm/kg $H_2O$. Exemplary iso-osmotic solutes include, but are not limited to, carbohydrates, salts (e.g., NaCl, KCl), and glycerol. In certain embodiments, an iso-osmotic solute is a carbohydrate. In some embodiments, an iso-osmotic solute is a monosaccharide or a disaccharide. In other embodiments, an iso-osmotic solute is selected from the group consisting of sucrose, glucose, galactose, fructose, ribose, mannose, arabinose and xylose. In yet other embodiments, an iso-osmotic solute is a salt. In still yet other embodiments, an iso-osmotic solute is glycerol. In still yet other embodiments, an iso-osmotic solute is glycerol, and the iso-osmotic solution resulting therefrom is between 5 to 20% (v/v) glycerol.

Macroscopic: By "macroscopic" is meant having dimensions large enough to be visible under magnification of 10-fold or less. In certain embodiments, a macroscopic structure is visible to the naked eye. In some embodiments, a macroscopic structure may be transparent. In other embodiments, a macroscopic structure is two-dimensional. In yet other embodiments, a macroscopic structure is three-dimensional. If two-dimensional, in certain embodiments, the macroscopic structure comprises more than a single layer of molecules, e.g., at least two or more layers of molecules. Typically each dimension is at least 10 µm in size. In certain embodiments at least two dimensions are at least 100 µm, or at least 1000 µm in size. Frequently at least two dimensions are at least 1-10 mm in size, 10-100 mm in size, or more. Dimensions may be measured by, for example, length, width, depth, breadth, height, radius, diameter, circumference, or an approximation of any of the foregoing in the case of structures that do not have a regular two or three-dimensional shape such as a sphere, cylinder, cube, and the like. Other relevant dimensions may also be used.

Marker: A "marker" may be any gene or gene product (e.g., a protein, peptide, mRNA, and the like) that indicates or identifies a particular cell type, tissue type, embryological origin, differentiation state, or physiological or metabolic state, and/or that indicates or identifies a particular diseased or physiological state (e.g., carcinoma, normal, dysplasia, and the like). The expression level, or lack of expression, of a marker gene may indicate that the cell or tissue under examination is of a particular cell type or tissue type, or has a particular embryological origin, differentiation state, physiological state, or metabolic state. The expression level, or lack of expression, of a marker gene may indicate a particular physiological or diseased state of a patient, organ, tissue, or cell. In certain embodiments, the expression or lack of expression may be determined using standard techniques such as, for example, Northern blotting, in situ hybridization, RT-PCR, sequencing, immunochemistry, immunoblotting, oligonucleotide or cDNA microarray, oligonucleotide or cDNA membrane array, protein microarray analysis, mass spectrometry, and the like. In some embodiments, the level of expression of a marker gene is quantifiable. The expression of various markers can also be determined by functional assays. For example, expression a cytochrome P450 genes (e.g., in hepatocytes) can be assessed by measuring the ability of a cell or cell lysate to perform a reaction characteristic of the presence of the P450 protein (e.g., to metabolize a particular substrate). Other markers that indicate or identify a particular cell type can also be used. For example, production of or uptake of a particular compound may be used as a marker. For example, uptake of LDL or production of nitric oxide are useful markers for endothelial cells. Markers are further discussed herein.

Microfiber: As used herein, the term "microfiber" refers to a fiber having a diameter of microscale dimensions. In certain embodiments, a microscale fiber has a diameter of between about 5 um to about 1000 um, of between about 5 um to about 900 um, of between about 5 um to about 800 um, of between about 5 um to about 700 um, of between about 5 um to about 600 um, of between about 5 um to 500 um, of between about 5 um to about 400 um, of between about 5 um to about 300 um, of between about 5 um to about 200 um, of between about 5 um to about 100 um, of between about 5 um to about 90 um, of between about 5 um to about 80 um, of between about 5 um to about 70 um, of between about 5 um to about 60 um, of between about 5 um to about 50 um, of between about 5 um to about 40 um, of between about 5 um to about 30 um, of between about 5 um to about 20 um, of between about 5 um to about 10 um, or of between about 10 um to about 20 um.

Microscale: As used herein, "microscale" generally refers to structures having dimensions that may most conveniently be expressed in terms of micrometers. For example, the term "microscale structure" may refer to a structure having dimensions of approximately 500 µm or less, approximately 100 µm or less, approximately 50 µm or less, approximately 20-50 µm, approximately 10-20 µm, approximately 5-10 µm, or 1-5 µm. One of ordinary skill in the art will recognize that the length of such structures may run into the millimeters, but that most dimensions are in the micrometer range.

Nanoscale: As used herein, the term "nanoscale" generally refers to materials of structures having dimensions that may most conveniently be expressed in terms of nanometers. For example, the term "nanoscale structure" or "nanoscale matrix" may refer to a structure having dimensions of less than 1 µm, e.g., approximately 500 nm or less, approximately 100 nm or less, approximately 50 nm or less, approximately 20-50 nm (inclusive), approximately 10-20 nm, approximately 5-10 nm, approximately 1-5 nm, approximately 1 nm, or between 0.1 and 1 nm. The ranges listed are assumed to include both endpoints. The relevant dimensions may be, e.g., length, width, depth, breadth, height, radius, diameter, circumference, or an approximation of any of the foregoing in the case of structures that do not have a regular two or three-dimensional shape such as a sphere, cylinder, cube, etc. Any other relevant dimensions may also be used to determine whether a structure is a nanoscale structure, depending on the shape of the structure. One of ordinary skill in the art will recognize that one or more dimensions of a nanoscale structure need not be in the nanometer range. For example, the length of such structures may run into the micron range or longer. However, generally, at least one or more of the dimensions are in the nanometer range.

Minimal Biologically Active Sequence: As used herein, a "minimal biologically active sequence" refers to the minimum length of a sequence of a peptide which has a specific biological function. In a first example, -SEIKLLIS- (SEQ ID NO. 70) is the biologically active cell attachment sequence from Laminin, wherein -IKLLI- (SEQ ID NO. 64) has the sole function of cell attachment. Thus, in this case, -IKLLI- (SEQ ID NO. 64) is a "minimal biologically active sequence." In a second example, the sequence -DGRGDSVAYG- (SEQ ID NO. 55) contains the sequence -RGD-; -RGD-has a cell attachment function. However, -DGRGDSVAYG-(SEQ ID NO. 55) also has the function of osteoblastic differentiation. Thus, in this case, both -DGRGDSVAYG-(SEQ ID NO. 55) and -RGD- are considered a "minimal biologically active sequence." As is understood from the present invention, the second amino acid domain of the modified peptide contains at least one minimal biologically active sequence. This minimal biologically active sequence is any length of sequence from an original protein sequence. Moreover, with the exception of the amino acids of the minimal biologically active sequence, the amino acids of the second amino acid domain can be exchanged, added or removed according to the design of the molecule to adjust its overall hydrophilicity and/or net charge. In certain embodiments, the minimal biologically active sequence refers to any one of the sequences provided in Table 2a.

Nanofiber: As used herein, the term "nanofiber" refers to a fiber having a diameter of nanoscale dimensions. Typically a nanoscale fiber has a diameter of 500 nm or less. According to certain embodiments of the invention a nanofiber has a diameter of 100 nm or less. According to certain other embodiments of the invention a nanofiber has a diameter of 50 nm or less. According to certain other embodiments of the invention a nanofiber has a diameter of 20 nm or less. According to certain other embodiments of the invention a nanofiber has a diameter of between 10 and 20 nm. According to certain other embodiments of the invention a nanofiber has a diameter of between 5 and 10 nm. According to certain other embodiments of the invention a nanofiber has a diameter of less than 5 nm. The ranges listed are assumed to include both endpoints.

Nanoscale environment matrix: The term "nanoscale environment matrix," as used herein, refers invention at least 50% of the fibers comprising the matrix are nanofibers. According to certain embodiments of the invention at least 75% of the fibers comprising the matrix are nanofibers. According to certain embodiments of the invention at least 90% of the fibers comprising the matrix are nanofibers. According to certain embodiments of the invention at least 95% of the fibers comprising the matrix are nanofibers. According to certain embodiments of the invention at least 99% of the fibers comprising the matrix are nanofibers. Of course the matrix may also comprise non-fiber constituents, e.g., water, ions, growth and/or differentiation-inducing agents such as growth factors, therapeutic agents, or other compounds, which may be in solution in the matrix and/or bound to the matrix.

Naturally occurring: As used herein, "naturally occurring" means found in nature. A naturally occurring biomolecule is, in general, synthesized by an organism that is found in nature and is unmodified by the hand of man, or is a degradation product of such a molecule. A molecule that is synthesized by a process that involves the hand of man (e.g., through chemical synthesis not involving a living organism or through a process that involves a living organism that has been manipulated by the hand of man or is descended from such an organism) but that is identical to a molecule that is synthesized by an organism that is found in nature and is unmodified by the hand of man is also considered a naturally occurring molecule.

Peptide, polypeptide, or protein: As used herein, a "peptide", "polypeptide", or "protein" comprises a string of at least two amino acids linked together by peptide bonds. A peptide generally represents a string of between approximately 2 and 200 amino acids, more typically between approximately 6 and 64 amino acids. Typically, the self-assembling portion of a self-assembling peptide is about 8-24, frequently about 12-20, or 16-20 amino acids. Peptide may refer to an individual peptide or a collection of peptides. Inventive peptides typically contain only natural amino acids, although non-natural amino acids (i.e., compounds that do not occur in nature but that can be incorporated into a polypeptide chain; see, for example, the Web site having URL www.cco.caltech.edu/~dadgrp/Unnatstruct.gif, which displays structures of non-natural amino acids that have been successfully incorporated into functional ion channels) and/or amino acid analogs as are known in the art may alternatively be employed. In particular, D-amino acids may be used. Also, in various embodiments of the invention one or more of the amino acids in an inventive peptide may be altered or derivatized, for example, by the addition of a chemical entity such as an acyl group, a carbohydrate group, a carbohydrate chain, a phosphate group, a farnesyl group, an isofarnesyl group, a fatty acid group, a linker for conjugation or functionalization, etc. In certain embodiments of the invention a peptide is branched, in which case it contains at least two amino acid polymers, each of which consists of at least 3 amino acids joined by peptide bonds, but the two amino acid polymers themselves are not linked by a peptide bond. Proliferation agent and mitogenic agent are used herein interchangeably to refer to the ability of a substance to enhance the proliferation of cells. Proteases, as used herein, are protein-cleaving enzymes that cleave peptide bonds fragments. A large collection of proteases and protease families has been identified, and specific sites at which these proteases cleave target proteins are known in the art. Some exemplary proteases include serine proteases, aspartyl proteases, acid proteases, alkaline proteases, metalloproteases (e.g. matrix metalloproteases), carboxypeptidase, aminopeptidase, cysteine protease, etc.

Regeneration: Regeneration of tissue, as used herein, includes any aspect of anatomical or functional restoration of the condition of the tissue prior to an injury or a degenerative or degradative process, which involves production of new tissue (by which is meant either cells or portions of cells). In certain embodiments of the invention production of new tissue includes growth of existing cells. For example, in the case of endothelial cells, regeneration may comprise formation of new blood vessels or extension or growth of existing vessels. In the case of neurons regeneration may thus include growth of axons or other neuron processes. Such processes may arise directly from the cell body or may be extensions of processes that were severed or damaged due to injury. The new tissue may replace tissue that was previously present. In certain embodiments of the invention production of new tissue includes division of existing cells.

Repair: Repair of tissue, as used herein, may include any aspect of anatomical or functional restoration of the condition of the tissue prior to damage or degeneration. For example, it may include restoration of physical continuity between portions of tissue that were separated by an injury. Preferably such restoration of physical continuity includes reapposition or reconnection of the portions of tissue without appreciable separation by tissue of a type that was not present prior to the injury, such as scar tissue. Repair may thus include filling of a tissue defect, e.g., by reapposition of portions of tissue separated by the defect and/or by growth of new tissue of the type that was subject to damage or degradation, rather than by development of scar tissue. Repair may, but need not, include growth or development of new tissue. Thus regeneration may be considered one aspect of repair, but repair can occur without evidence of new tissue growth.

Solution that is substantially free of ions: By "solution that is substantially free of ions" is meant a solution to which no ions (or salts thereof) have been added or in which the concentration of ions (or salts thereof) is less than 0.01 or 0.001 mM. Small molecule:

Small molecule: As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

Specific binding or Affinity to or Complexes with: As used herein, the terms "specific binding" or "affinity to" or complexes with" refers to a physical association between two molecules, which may be referred to as a target molecule (e.g., a target peptide, a biomolecule) and modified and/or unmodified self-assembling peptide. The interaction is typically dependent upon the presence of a particular structural feature of the target molecule such as a target domain that is recognized by the self-assembling peptide. For example, if a self-assembling peptide is specific for a target molecule that contains target domain A, the presence of a polypeptide comprising target domain A, or the presence of free unlabeled target domain A in a reaction containing both free labeled A and the self-assembling peptide specific thereto, it will reduce the amount of labeled A that binds to the self-assembling peptide. It is to be understood that specificity need not be absolute but generally refers to the context in which the binding is performed. Target domains and self-assembling peptides having a sufficient degree of specificity to perform appropriately in any given application can be selected by one of ordinary skill in the art. It is also to be understood that specificity may be evaluated in the context of additional factors such as the affinity of the self-assembling peptide for the target molecule versus the affinity of the self-assembling peptide for other targets, e.g., competitors. Once the specificity of the self-assembling peptide is established in one or more contexts, it may be employed in other, preferably similar, contexts without necessarily re-evaluating its specificity. Preferred target molecules in the context of the present invention include proteins that are present on the cell surface, proteins that are present within the body in the extracellular environment (e.g., extracellular matrix proteins, secreted or cell surface proteins including proteases, growth factors, and proteins that circulate in the blood). In certain embodiments of the invention the target molecule is an antibody. In the context of an interaction between a self-assembling peptide and a target molecule, according to certain embodiments of the invention, a target molecule exhibits specific binding if it binds to the self-assembling peptide at least 2 times as strongly as to other peptides or polypeptides present in the body within the extracellular environment. According to certain embodiments of the invention, a target molecule exhibits specific binding if it binds to self-assembling peptide at least 5 times as strongly as to other peptides or polypeptides present in the body within the extracellular environment. According to certain embodiments of the invention, a target molecule exhibits specific binding if it binds to the self-assembling peptide at least 10 times as strongly as to other peptides or polypeptides present in the body within the extracellular environment. According to certain embodiments of the invention, a target molecule exhibits specific binding if it binds to the self-assembling peptide at least 50 times as strongly as to other peptides or polypeptides present in the body within the extracellular environment. According to certain embodiments of the invention, a target molecule exhibits specific binding if it binds to the self-assembling peptide at least 100 times as strongly as to other peptides or polypeptides present in the body within the extracellular environment.

Structurally compatible: By "structurally compatible" is meant capable of maintaining a sufficiently constant intrapeptide distance to allow structure formation. In certain embodiments of the invention the variation in the intra-peptide distance is less than 4, 3, 2, or 1 angstroms. It is also contemplated that larger variations in the intra-peptide distance may not prevent structure formation if sufficient stabilizing forces are present. This distance may be calculated based on molecular modeling or based on a simplified procedure that has been previously calculated by taking the sum of the number of unbranched atoms on the sidechains of each amino acid in a pair. For example, the intrapeptide distance for a lysine-glutamic acid ionic pair is 5+4=9 atoms, and the distance for a glutamineglutamine hydrogen bonding pair is 4+4=8 atoms. Using a conversion factor of 3 angstroms per atom, the variation in, the intrapeptide distance of peptides having lysine-glutamic acid pairs and glutamine-glutamine pairs (e.g., 9 versus 8 atoms) is 3 angstroms.

Subject: The term subject, as used herein, refers to an individual to whom an agent is to be delivered, e.g., for experimental, diagnostic, and/or therapeutic purposes. Preferred subjects are mammals, such as veterinary/domestic animals (e.g., horses, pigs, primates, dogs, cats, etc.) and humans (e.g., male or female infant, child, adolescent, adult or elderly adult).

Substantially uniformly distributed: In general, in the case of an inventive matrix encapsulating cells, the phrase "substantially uniformly distributed" is intended to convey that the majority of cells are approximately equidistant from one another. For example, cells are considered substantially uniformly distributed if, at any particular time (e.g., immediately after matrix formation) the center of mass of at least 50, 60, 70, 80, 90, or 100% of the cells encapsulated by the matrix is separated from the center of mass of the closest cell (i.e., the cell with the closest center of mass) by a distance that varies by less than 500, 100, 50, 20, 10, or 1 µM. Alternatively, cells are considered substantially uniformly distributed if, at any particular time, when the matrix is divided into contiguous portions (e.g., cubes) having equivalent volumes, the number of cells whose center of mass is contained within a given volume of matrix differs from the average number of cells whose center of mass is contained within such a volume by less than 50%, less than 40%, less than 30%, less than 20%, or less than 10% of the average number of cells, for at least 50%, at least 60%, at least 70%, at least 80%, or at least 90% of the portions. Matrices in which cells are substantially uniformly distributed may retain this property over time, or cells may eventually become substantially uniformly distributed in a matrix in which cells are not initially substantially uniformly distributed.

Therapeutic molecule, compound, or agent or Biologically active agent: A "therapeutic molecule, compound, or agent" or "biologically active agent" is a molecule or combination of molecules of any type that, when administered to a subject in need thereof, alleviates one or more symptoms of a disease or undesired clinical condition, reduces the severity of a disease or clinical condition, prevents or lessens the likelihood of development of a disease or undesired clinical condition, or facilitates repair or regeneration of tissue in a manner other than simply providing general nutritional support to the subject. It is to be understood that a therapeutic molecule is generally to be administered in an effective amount, i.e., an amount sufficient to achieve a clinically significant result. A therapeutic molecule can be a small molecule, a biomolecule, etc. See Goodman and Gilman's The Pharmacological Basis of Therapeutics, $10^{th}$ Ed., and Katzung, Basic and Clinical Pharmacology, for examples.

Three-dimensional arrangement: By "three-dimensional arrangement" is meant existing in three dimensions. Cells having a three-dimensional arrangement are not all part of the same monolayer. As used herein, a monolayer is a cross section of the matrix encapsulating the cells and that includes at least one encapsulated cell. The average diameter of a cell may be determined by measuring the average diameter of the cell body. An encapsulated cell is considered part of the monolayer if at least 51% of the volume of the cell is contained in the monolayer. In certain embodiments, immediately after matrix formation, at least one monolayer contains less than 75, 50, 25, 20, 15, 10, 5, or 1% of the encapsulated cells. More preferably, immediately after matrix formation, less than 75, 50, 25, 20, 15, 10, 5, or 1% of the encapsulated cells are part of the same monolayer.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 7 shows that distance between functional motif (RGD) and self-assembling sequence (RADA) should be at least more than 2 mer (6.9A) of peptide bonds.

FIG. 9A shows when DSG ratio is 10%; FIG. 9B shows when DSG ratio is 70%. In FIG. 9A, cells stayed on the surface of the peptide matrix, while in FIG. 9B, cells migrated into the matrix (up to 300 um). This data shows that cell behavior can be controlled by changing the ratio of the functionalized peptide.

FIGS. 16A-16B. ALP Staining images of RAD (FIG. 16A) and FHR (FIG. 16B).

FIG. 17. Osteocalcin secreted in culture medium

FIG. 29A: shows the capillary cavity (arrows). FIG. 29B: shows the cross-section at the dotted line in FIG. 29A. The capillary cavity are also shown in the cross section image (dotted circle).

FIG. 36A depicts a needle with two compartments. The peptide solution and gelation agent are pre-mixed in the needle immediately prior to injection. FIG. 36B depicts a needle with two compartments. The peptide solution and a cell-suspension are pre-mixed in the needle immediately prior to injection.

Figure 1A:
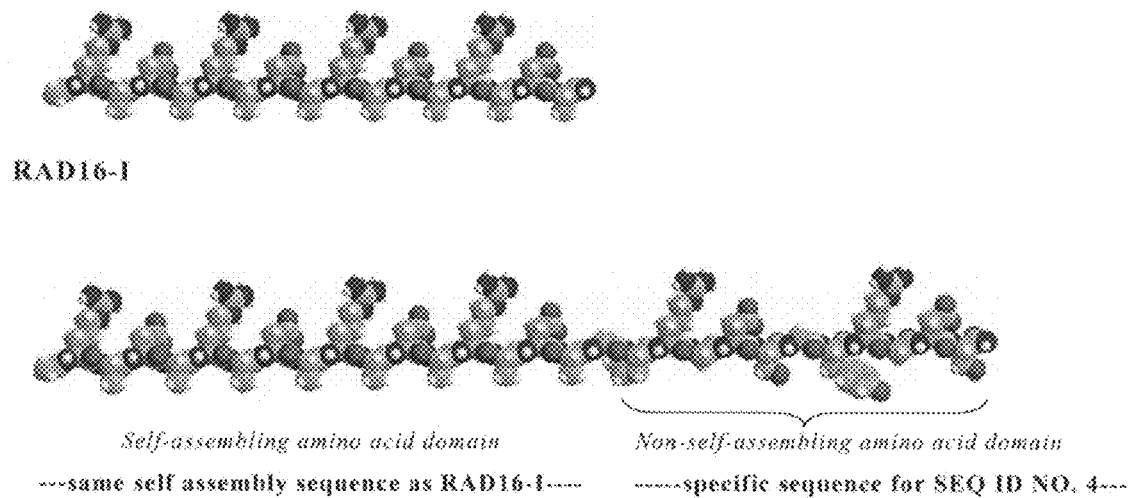
FIG. 1A. Molecular models representing a representative self-assembling peptide RAD16-I (top) and peptide RAD16-I modified to include a non self-assembling amino acid domain (PRGDSGYRGDS: SEQ ID NO. 71) at its C terminus (bottom).
Figure 1B:
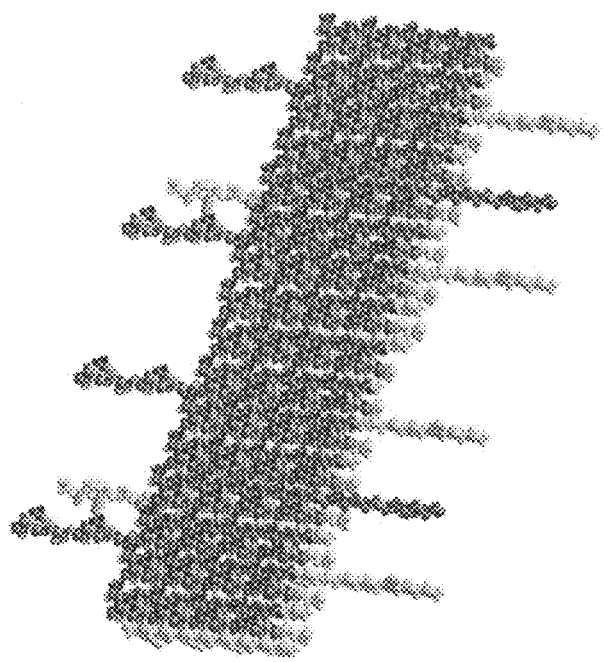
FIG. 1B. A schematic model representing a double Q-sheet tape of a self-assembled peptide nanofiber formed by self-assembly of a mix composed of peptide RAD16-I and a modified RAD16-I peptide extended at its N terminus with the amino acid domain (PRGDSGYRGDS: SEQ ID NO. 71) in a 9:1 blend (based on volume ratio of peptides dissolved at equal concentrations on a w/w basis). The sequences (PRGDSGYRGDS: SEQ ID NO. 71) extending out from the nanofiber tape. In general, the modifying amino acid domain may ex tend from a lateral edge of an assembly of peptides (e.g., a nanofiber or macroscopic structure) or from a surface. Other arrangements are also possible.
Figure 1C:
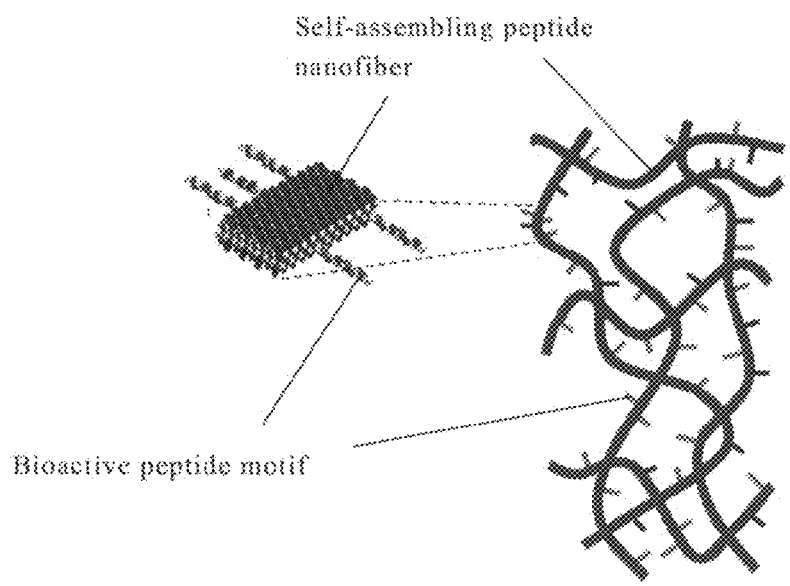
FIG. 1C. A schematic representation of a generic peptide hydrogel network (Solid thick lines) in which some of the peptides are modified to include bioactive peptide motifs (Short thin lines) extending from the amino termini of the base peptide. Close up: stacked self-assembling peptide nanofiber (Solid thick lines) and the extended sequence of the bioactive peptide motif at the amino termini of one of the sequences (Short thin lines).

DETAILED DESCRIPTION OF CERTAIN
EMBODIMENTS OF THE INVENTION

I. Overview

The development of new biological materials, particularly biologically compatible materials that serve as permissive substrates for cell growth, differentiation, and biological function has broad implications for advancing medical technology and for understanding basic biological characteristics of cells. The present invention encompasses the recognition that it is possible to produce compositions that possess the advantages typically associated with a fully synthetic material and yet possess certain desirable features of materials derived from natural sources. The compositions can be used either in vitro or in vivo for purposes including, but not limited to, cell culture or tissue engineering, tissue regeneration and/or repair, and/or as delivery agents for biologically active molecules such as therapeutic agents.

A class of biologically inspired materials that are made through self-assembly of ionic or polar self-complementary peptides has previously been described (see, for example, Zhang (1993); Zhang (1995); and U.S. Pat. Nos. 5,955,343 and 5,670,483). The peptides are complementary and structurally compatible. They are composed of repeating units of alternating hydrophilic and hydrophobic amino acids, in which the charged residues can include alternating positive and negative charges. In general, these peptides self-assemble into various macroscopic structures upon exposure to a sufficient concentration of ions (e.g., monovalent cations) to form a stable macroscopic porous matrix. The matrix can assume various physical forms such as ribbons, tape-like structures, two or three dimensional matrices, etc. Preferred matrices are composed of orderly interwoven filaments typically approximately 10-20 nm or 10-30 nm in diameter, with a pore size on the order of 50-100 nm in diameter (or other relevant dimension). In certain embodiments, the materials are hydrogels which contain approximately at least 50%, 55%, 60%, 65%, 70%, 75%, 80%, 85%, 90%, 95%, or 99% or greater water content. Certain of the peptides undergo self-assembly to form nanofibers that are very highly hydrated (e.g., up to 99.5-99.9% (1-5 mg/ml) water). Because the hydrogel has such an extremely high water content, cells can freely migrate and form intercellular contacts when cultured on or within the matrix. Such an environment also permits diffusion of small molecules including proteins and signaling molecules. In addition, certain of the hydrogels have a low elastic modulus. While not wishing to be bound by any theory, it has been suggested that the low elastic modulus may facilitate cell-cell communication. The properties of the hydrogels contrast with those of many synthetic materials that are being explored for cell culture and/or tissue engineering or repair. For example, many of these materials comprise microfibers and have much larger pore sizes, presenting an environment that is likely not on the appropriate scale by comparison with cells and their natural environment. In addition, the hydrogels can be formed so as to encapsulate cells during the gel formation process, rather than preformed structures in which cells and seeded and/or embedded.

An important characteristic of these materials is that their properties and mechanical strength can be controlled through manipulation of various peptide parameters (see, for example, Caplan et al., *Biomacromolecules* (2000) 1:627-631; Caplan et al., *Biomaterials* (2000) 23: 219-227; and Caplan (2002)). For example, it has been shown that the stiffness of the gel increases strongly with peptide concentration. The sequences, characteristics, and properties of the peptides and the structures formed by them upon self-assembly are further discussed in the next section.

The inventors and others have shown that structures made by self-assembly of these peptides are able to support cell attachment, viability, and growth when cells are cultured on the surface of the structure. In addition, a peptide structure formed by self-assembly of RAD16-I (AcN-RADARA-DARADARADA-CONH$_2$) (SEQ ID NO: 21) was able to serve as a substrate for neurite outgrowth and formation of functionally active synapses when neurons were grown on their surface (Holmes (2000)). It has also been demonstrated that the peptide gels support endothelial cell attachment, migration, proliferation and capillary-like structure formation and survival for a period of at least 3 weeks (see, for example, PCT application Publication WO2003/096972). In contrast to other three-dimensional substrates that have been used for studies of angiogenesis in vitro, including collagen or fibrin gels or Matrigel, this angiogenic response was observed in the absence of externally supplied angiogenic factors, and with no significant signs of apoptosis or proteolytic gel degradation.

In addition, it has been shown that cells can be encapsulated within the peptide hydrogels, thus placing the cells in a three-dimensional arrangement within a peptide matrix, and that the cells maintain viability and function when so encapsulated (see, for example, U.S. Patent Application Publication No. US 2002-0160471 and U.S. Pat. No. 6,800,116). Furthermore, chondrocytes encapsulated within a hydrogel structure formed by self-assembly of KLD12 (AcNKLD-LKLDLKLDL-CONH$_2$) (SEQ ID NO:53) retained their morphology and developed a cartilage-like, mechanically functional ECM rich in proteoglycans and type-II collagen, indicative of a stable chondrocyte phenotype (see, for example, Kisiday (2002)). Liver progenitor cells encapsulated within a peptide matrix made by self-assembly of RAD16-I expressed markers indicative of hepatocyte phenotype (Semino (2003)). Results such as these indicate that the nanoscale environment provided by the self-assembling peptide gels can enhance functional activity of a diverse set of cell types and is permissive for cellular instruction and expression of differentiated cell phenotypes.

Unlike many natural or artificial materials that have been used heretofore in an effort to provide a suitable environment for cell culture, tissue engineering, etc., the materials of the present invention interact with cells on a nanoscale rather than a microscale. The materials are made of nanofibers rather than the microfibers believed that the small size of the fibers and/or the open weave structure of the materials promote extension of cell processes and allow diffusion of nutrients, waste products, etc., in a manner that provides unique advantages for cell growth. The nanofibers that comprise the material may be ordered during self assembly in a complementary fashion due to weak interactive molecular forces. However, they may also be randomly ordered, which may be preferred for certain applications. In other words, while the fibers may have an orderly internal structure, they may lack directionality or alignment with respect to one another. For example, the fibers may not be substantially parallel to one another.

As described further below, the inventors have now unexpectedly discovered that it is possible to extensively modify the previously described self-assembling peptides by incorporating additional amino acid domains (which may also referred to herein as peptide domains if at least 3 amino acids in length) that does not necessarily conform to the structural requirements for self-assembly, without eliminating the ability of the modified peptides to self-assemble to form a macroscopic structure. For example, the self-assembling peptides can be modified to incorporate a non self-assembling amino acid domain which can comprise, for example, a minimal biologically active sequence for interaction with a biomolecule. The resulting peptides thus comprise a first self-assembling peptide domain and a second non-self-assembling amino acid domain. By non-self-assembling amino acid domain is meant an amino acid domain that does not self-assemble when present as an isolated peptide (i.e., when not joined to an unmodified self-assembling peptide) under conditions (e.g., ionic concentration, peptide concentration, pH, temperature) that would result in self-assembly of an unmodified self-assembling peptide, and as designed in accordance with the principles described herein. By "does not self-assemble" is meant that the amino acid domain or peptide does not form nanofilaments, nanofibers, β-sheets, nanofibers, and the like, or does not form a macroscopic structure.

The following section describes the self-assembling peptides that can be modified in accordance with the present invention and methods by which the process of self-assembly and/or the features of the assembled structure may be controlled. Subsequent sections describe the methods and compositions of the invention, methods for characterizing structures formed from the inventive modified self-assembling peptides, methods for evaluating cell phenotype and for selecting amino acid domains that are used for modification, etc., in further detail.

II. Self-Assembling Peptides, Structures Made Therefrom and Methods of Use (A) Peptide Sequences and Macroscopic Structures The previously described unmodified self-assembling peptides comprise a family of complementary and structurally compatible molecules. The peptides and their properties are described in U.S. Patent Application Publication Nos. 2002/0160471, 2005/0181973, and in U.S. Pat. Nos. 5,955,343 and 5,670,483. These materials are composed of repeating units of hydrophilic and hydrophobic amino acids, in various alternating patterns.

The first molecule of this class, EAK16-II (AEAEAKAKAEAEAKAK, A, alanine, E, glutamine, and K, lysine; SEQ ID NO:38), a 16 amino acid peptide, was identified as a segment in a yeast protein, zuotin which was originally characterized by binding to left-handed Z-DNA (Zhang (1992)). Based on this peptide, a large number of self-assembling ionic self-complementary peptides have been systematically designed by changing the amino acid sequence and following a periodic pattern. Preferred peptides assume regular secondary structures, such as β-sheet structures, in solution (e.g., aqueous solution). This is thought to occur because the peptides contain two distinct surfaces, one hydrophilic and the other hydrophobic, and form complementary ionic bonds with regular repeats on the hydrophilic surface (Zhang (1999)). The side-chains of the peptides partition into two faces, a polar face with charged ionic side chains and a non-polar face, e.g., with alanines or other hydrophobic groups. These ionic side chains are self-complementary to one another in that the positively charged and negatively charged amino acid residues can form complementary ionic pairs. These peptides are therefore called "ionic self-complementary peptides."

The complementary ionic sides have been classified into several moduli, i.e., modulus I, II, III, IV, etc., and mixed moduli (Zhang (1999)). If the ionic residues alternate with one positively and one negatively charged residue (−+−+−+−+), the peptides are described as "modulus I;" if the ionic residues alternate with two positively and two negatively charged residues (−−++−−++), the peptides are described as "modulus II"; if the ionic residues alternate with four positively and two negatively charged residues (−−−−++++), the peptides are described as "modulus IV." Peptides meeting the afore-mentioned criteria may be referred to herein as "unmodified self-assembling peptides" to distinguish them from the modified self-assembling peptides of the present invention, which includes a peptide domain that does not meet the foregoing criteria and does not self-assemble.

Many modulus I and II self-complementary peptides such as EAKA16-I (SEQ ID NO:26), RADA16-I (SEQ ID NO:21), RAEA16-I (SEQ ID NO:28), and KADA16-I (SEQ ID NO:30) have been analyzed previously (Table 1). These peptides are also referred to as RAD16-I, RAE16-I, KAD16-I, etc. (i.e., the last amino acid in the four amino acid module may be omitted in the abbreviation). Modulus IV ionic self-complementary peptides containing 16 amino acids; such as EAK16-IV, KAE16-IV, DAR16-IV and RAD16-IV; have also been studied. If the charged residues in these self-assembling peptides are appropriately substituted without changing the overall pattern described above (e.g., the positive charged lysines are replaced by positively charged arginines and the negatively charged glutamates are replaced by negatively charged aspartates), there are essentially no significant effects on the self-assembly process. However, if the positively charged residues, lysine and arginine are replaced by negatively charged residues, such as aspartate and glutamate, the peptides can no longer undergo self-assembly to form macroscopic structures; however, they can still form a sheet structure in the presence of salt.

Other hydrophilic residues, such as asparagine and glutamine, that form hydrogen bonds may be incorporated into the peptides instead of or in addition to charged residues. If the alanines in the peptides are changed to more hydrophobic residues, such as leucine, isoleucine, phenylalanine or tyrosine, these peptides have a greater tendency to self-assemble and form peptide matrices with enhanced strength. Some peptides that have similar compositions and lengths as these aforementioned peptides form α-helices and random-coils rather than β-sheets. Such peptides typically do not form macroscopic structures although structure formation is not absolutely precluded. Thus, in addition to self-complementarity, other factors are likely to be important for the formation of macroscopic structures, such as the peptide length, the degree of intermolecular interaction, and the ability to form staggered arrays.

It is noted that in certain embodiments of the invention a group or radical such as an acyl group (RCO—, where R is an organic group), e.g., an acetyl group ($CH_3CO$—; Ac—) is present at the N terminus of the peptides in order to neutralize an extra charge positive that may otherwise be present (e.g., a charge not resulting from the side chain of the N-terminal amino acid). Similarly, a group such as an amine group ($-NH_2$) may be used to neutralize an extra negative charge that may otherwise be present at the C terminus (e.g., a charge not resulting from the side chain of C-terminal amino acid), thus converting the C terminus into an amide ($-CONH_2$). While not wishing to be bound by any theory, the neutralization of charges on the terminal N and C molecules may facilitate self-assembly. One of ordinary skill in the art will be able to select other suitable groups.

The peptides self-assemble to form macroscopic structures under a variety of conditions, e.g., upon the addition of monovalent cations to an aqueous peptide solution or upon the introduction of a peptide solution to a solution containing monovalent cations. Prior to self-assembly the peptides may be dissolved in a solution that is substantially free of monovalent ions (e.g., cations) or contains only a low concentration of such ions, e.g., less than 10 mM, 5 mM, 1 mM, 0.5 mM or 0.1 mM. Self-assembly may be initiated or substantially accelerated by the addition of an ionic solute to a peptide solution or by a change in pH. For example, NaCl at a concentration of between 5 mM and 5 M induces the assembly of the peptides to form macroscopic structures within a few minutes. Lower concentrations of NaCl may also induce assembly but at a slower rate. Certain of the peptides can also self-assemble in the absence of significant concentrations of ions, in a process that may be dependent on pH. For example, certain of the peptides may remain in solution at a pH of approximately 3.0 but may self-assemble when the pH is raised.

Alternately, self-assembly may be initiated by introducing the peptides into a solution comprising ions, e.g., standard phosphate buffered saline (PBS), tissue culture medium, or a physiological fluid such as blood, cerebrospinal fluid (CSF), and the like. The peptides can thus self-assemble at a location in vivo. Exemplary ions include, but are not limited to, $Li^+$, $Na^+$, $K^+$ and $Cs^+$. In certain embodiments, the concentration of the ion is at least 5 mM, 10 mM, 20 mM or 50 mM in order to induce or substantially accelerate self-assembly. One of ordinary skill in the art will be able to select preferred concentrations of ions based on the particular peptide sequence and/or concentration and desired speed of assembly. In general, the strength of the resulting structure is increased in the presence of ions relative to the strength in the absence of ions, or at a lower ionic concentration, although it is noted that a plateau may be reached at which an increase in ion concentration does not result in increased strength.

As mentioned above, preferred peptides self-assemble to form a network of nanofibers, resulting in hydrogels of water content higher than 99%, when dissolved water in a range of 1-10 mg/ml (see, for example, Zhang (1993); Zhang (1995); Leon (1998); Holmes (2000); Kisiday (2002); Caplan (2000); Caplan (2000b); and Caplan (2002)). FIG. 1A shows the structure of a representative peptide, RAD16-II (RARADA-DARARADADA, R, arginine, A, alanine, D, aspartic acid) (SEQ ID NO. 24). The material self-assembles into interwoven fibers of Å 10-20 nm diameter forming enclosures of Å 50-100 nm diameter. The nanofiber network can give rise to hydrogel formation, creating a macroscopic structure preferably of a size that can be observed with the naked eye and can be three-dimensional.

Modified or unmodified self-assembling peptides forming the macroscopic structure may contain between 8 and 200 amino acids, between 8 to 64 amino acids, between 8 to 46 amino acids, between 8 to 36 amino acids, or between 8 to 16 amino acids, inclusive. In certain embodiments, modified or unmodified self-assembling peptides contain between 8-46 amino acids, between 8-36 amino acids, between 8-26 amino acids, between 8-16 amino acids, between 10-16 amino acids, or between 12-16 amino acids, inclusive. The concentration of the self-assembling peptide solution prior to matrix formation can range, for example, between 0.01% (0.1 mg/ml) and 99.99% (999.9 mg/ml), inclusive. In certain embodiments, the concentration of the self-assembling peptide solution prior to matrix formation is between 0.1% (1 mg/ml) and 10% (100 mg/ml), inclusive, particularly for cell culture and/or therapeutic applications. In some embodiments, the concentration of the self-assembling peptide solution prior to matrix formation is between 0.1% (1 mg/ml) and 5% (50 mg/ml), inclusive, or between 0.5% (5 mg/ml) and 5% (50 mg/ml), inclusive. In yet other embodiments, the concentration of the self-assembling peptide solution prior to matrix formation is approximately 5 mg/ml, approximately 10 mg/ml, approximately 15 mg/ml, or approximately 20 mg/ml.

If desired, matrices may be "three dimensional," i.e., can be formed with a predetermined shape or volume. To form a matrix with a desired geometry or dimension, an aqueous peptide solution may be placed in a pre-shaped casting mold, and the peptides induced to self-assemble into a matrix by the addition of an ion, as described herein. Matrices having a three-dimensional is meant that the matrix is not just a thin flat coating substance on the other material, but has a thickness which at least plurality of cells can embedded into the thickness.

Alternately, the ion may be added to the modified or unmodified self-assembling peptide solution shortly before placing the solution into the mold, provided that care is taken to place the solution into the mold before substantial assembly occurs. The resulting material characteristics, time required for assembly, and geometry and dimensions of the macroscopic peptide matrix are governed by parameters including the concentration and amount of peptide solution that is applied, the concentration of ion used to induce assembly of the matrix, the pH, the particular modified self-assembling peptide sequence, and the dimensions of the casting apparatus. Where the peptide structure or matrix is to be implanted into the body, the shape may be selected based upon the intended implantation site. According to various embodiments of the invention, the matrix can exist as a thin layer, such as a coating at the bottom of a conventional tissue culture or floating in a solution. The layer can be several microns thick, e.g., 10 microns, 10-50 microns, 50-100 microns, 100-200 microns, etc. The layer may comprise multiple β-sheet layers.

Modified or unmodified self-assembling peptide nanoscale matrices can be formed with varying degrees of stiffness or elasticity. The peptide matrices typically have a low elastic modulus, e.g., in the range of 1-10 kPa as measured in a standard cone-plate rheometer. Such low values permit matrix deformation as a result of cell contraction, and this deformation may provide a means for cell-cell communication. Matrix stiffness can be controlled by a variety of techniques including changes in peptide sequence, changes in peptide concentration, and changes in peptide length. Other methods for increasing stiffness can also be used, such as by attaching a biotin molecule to the amino- or carboxy-terminus of the peptides or between the amino and carboxy-termini, which may then be cross-linked.

TABLE 1

Representative "Unmodified" Self-Assembling Peptides

| No. | Name | Sequence | Modulus |
|---|---|---|---|
| SEQ ID NO: 21 | RADA16-I | n-RADARADARADARADA-c | I |
| SEQ ID NO: 22 | RGDA16-I | n-RADARGDARADARGDA-c | I |
| SEQ ID NO: 23 | RADA8-I | n-RADARADA-c | I |
| SEQ ID NO: 24 | RAD16-II | n-RARADADARARADADA-c | II |
| SEQ ID NO: 25 | RAD8-II | n-RARADADA-c | II |
| SEQ ID NO: 26 | EAKA16-I | n-AEAKAEAKAEAKAEAK-c | I |
| SEQ ID NO: 27 | EAKA8-I | n-AEAKAEAK-c | I |
| SEQ ID NO: 28 | RAEA16-I | n-RAEARAEARAEARAEA-c | I |
| SEQ ID NO: 29 | RAEA8-I | n-RAEARAEA-c | I |
| SEQ ID NO: 30 | KADA16-I | n-KADAKADAKADAKADA-c | I |
| SEQ ID NO: 31 | KADA8-I | n-KADAKADA-c | I |
| SEQ ID NO: 32 | EAH16-II | n-AEAEAHAHAEAEAHAH-c | II |
| SEQ ID NO: 33 | EAH8-II | n-AEAEAHAH-c | II |
| SEQ ID NO: 34 | EFK16-II | n-FEFEFKFKFEFEFKFK-c | II |
| SEQ ID NO: 35 | EFK8-II | n-FEFKFEFK-c | I |
| SEQ ID NO: 36 | ELK16-II | n-LELELKLKLELELKLK-c | II |
| SEQ ID NO: 37 | ELK8-II | n-LELELKLK-c | II |
| SEQ ID NO: 38 | EAK16-II | n-AEAEAKAKAEAEAKAK-c | II |
| SEQ ID NO: 39 | EAK12 | n-AEAEAEAEAKAK-c | IV/II |
| SEQ ID NO: 40 | EAK8-II | n-AEAEAKAK-c | II |
| SEQ ID NO: 41 | KAE16-IV | n-KAKAKAKAEAEAEAEA-c | IV |
| SEQ ID NO: 42 | EAK16-IV | n-AEAEAEAEAKAKAKAK-c | IV |
| SEQ ID NO: 43 | RAD16-IV | n-RARARARADADADADA-c | IV |
| SEQ ID NO: 44 | DAR16-IV | n-ADADADADARARARAR-c | IV |
| SEQ ID NO: 45 | DAR16-IV* | n-DADADADARARARARA-c | IV |
| SEQ ID NO: 46 | DAR32-IV | n-(ADADADADARARARAR)-c | IV |
| SEQ ID NO: 47 | EHK16 | n-HEHEHKHKHEHEHKHK-c | N/A |
| SEQ ID NO: 48 | EHK8-I | n-HEHEHKHK-c | N/A |
| SEQ ID NO: 49 | VE20* | n-VEVEVEVEVEVEVEVEVEVE-c | N/A |
| SEQ ID NO: 50 | RF20* | n-RFRFRFRFRFRFRFRFRFRF-c | N/A |
| SEQ ID NO: 51 | KFQ12 | n-FKFQFKFQFKFQ-c | I |
| SEQ ID NO: 52 | EIK8 | n-IEIKIEIK-c | I |
| SEQ ID NO: 53 | KLD12 | n-KLDLKLDLKLDL-c | I |

N/A: denotes not applicable
*These peptides form a Q-sheet when incubated in a solution containing NaCl, however they have not been observed to selfassemble to form macroscopic structures.

The modified and/or unmodified self-assembling peptides may include L-amino acids, D-amino acids, natural amino acids, nonnatural amino acids, or a combination thereof. If L-amino acids are present in the matrix, degradation produces amino acids that may be reused, e.g., by cells in culture or by cells in a host tissue. The fact that the basic monomeric subunit of the peptides in certain embodiments of the invention are L-amino acids, which occur naturally within the body, distinguishes this class of compounds from numerous other biocompatible substances and may offer unique advantages. The peptides may be chemically synthesized or purified from natural or recombinant sources, and the amino- and carboxy-termini of the peptides may be protected or not protected. The peptide matrix may be formed from one or more distinct molecular species of peptides which are complementary and structurally compatible with each other. Peptides containing mismatched pairs, such as the repulsive pairing of two similarly charged residues from adjacent peptides, may also form structures if the disruptive force is dominated by stabilizing interactions between the peptides. Peptide matrices may also be referred to herein as peptide hydrogels or peptide hydrogel matrices.

Peptides, including peptides capable of being cross-linked, and modified or unmodified self-assembling peptides, may be synthesized using standard F-moc chemistry, which includes both solution and solid phase synthesis, and purified using high pressure liquid chromatography. The formation of a peptide matrix may be initiated by the addition of ions or salts thereof as described herein. Hydrophobic residues with aromatic side chains may be cross-linked by exposure to UV irradiation. The extent of the cross-linking may be precisely controlled by the predetermined length of exposure to UV light and the predetermined peptide concentration. The extent of cross-linking may be determined by light scattering, gel filtration, or scanning electron microscopy using standard methods. Furthermore, the extent of cross-linking may also be examined by HPLC or mass spectrometry analysis of the structure after digestion with a protease. Material strength may be determined before and after cross-linking.

B. Cell Culture and Encapsulation

Peptide matrices (e.g., gels, hydrogels) formed either from unmodified self-assembling peptides or the modified self-assembling peptides of the present invention may be used in a variety of ways for culturing cells and tissues. Cells and tissues can be cultured on the surface of a matrices structure. While not wishing to be bound by any theory, inventors suggest that such an environment more closely mimics the natural cellular environment than culture on a rigid substrate such as a conventional plastic tissue culture dish. If the matrix forms a three-dimensional structure, cells can extend processes into the structure or migrate into it.

Cells can also be encapsulated within the matrix. To encapsulate cells within a peptide structure, peptides and living cells may be incubated in an aqueous solution having an iso-osmotic solute at an appropriate concentration to support cell viability, under conditions that in which the peptides are not substantially self-assembled. In certain embodiments of the invention the solution contains a monovalent cation concentration of less than 10 mM, 5 mM, 1 mM or 0.1 mM, or is substantially free of monovalent cations. The solution may also contain less than less than 10 mM, 5 mM, 1 mM or 0.1 mM or be substantially free of other ionic species, e.g., other cations or anions. Sufficient ion (e.g., monovalent cation) is added to the solution to initiate self-assembly of the peptides into a macroscopic structure, such as a Q-sheet macroscopic structure, whereby the cells are encapsulated by the formation of the macroscopic structure. In certain embodiments, the encapsulated cells are present in the macroscopic structure in a three-dimensional arrangement. The solution may be contained in a pre-shaped mold dimensioned to establish a desired volume or shape of the macroscopic structure.

In certain embodiments of the invention the concentration of the added ion is at least 5 mM, 10 mM, 20 mM or 50 mM. Suitable ions include, but are not limited to, $Li^+$, $Na^+$, $K^+$ and $Cs^+$. In some embodiments, the concentration of the iso-osmotic solute is at least 50 mM, 150 mM or 300 mM. In other embodiments, the concentration of the iso-osmotic solute is contained in one of the following ranges 200 to 250 mM, 250 to 270 mM, 270 to 300 mM, 300 to 400 mM, 400 to 500 mM, 500 to 600 mM, 600 to 700 mM, 700 to 800 mM, or 800 to 900 mM, inclusive. Suitable iso-osmotic solutes include, but are not limited to, carbohydrates, such as sucrose, mannitol, and the like. Other iso-osmotic solutes, preferably non-toxic to cells at the concentration used, may be employed. Self-assembly can also be effected by a change in pH (e.g., a rise from a low pH to a higher pH).

Cells and agents such as biological molecules (e.g., differentiation-inducing agents, proliferation agents, growth factors, and the like) and therapeutic compounds may be introduced into the peptide solution prior to self-assembly. The self-assembly process then forms a structure that encapsulates the cells or molecules. To achieve even distribution of the cells or molecules within the structure it may be desirable to thoroughly mix the solution prior to initiation of self-assembly. It may be desirable to maintain the cells or agents in a solution that contains substantially no ions or only low concentration of ions in order to avoid initiation or acceleration of self-assembly immediately upon combining the cells or agents with the peptide solution. In certain embodiments, the cells are maintained in an iso-osmotic solution (e.g., a sucrose solution) prior to combination with the peptide solution. The peptides themselves may be dissolved in an iso-osmotic solution to which cells (e.g., a cell pellet, cell suspension) or agents are added. The resulting composition may be mixed to achieve a more uniform distribution of cells and/or agents, following which the composition is exposed to ions (e.g., ions are added to the composition, or the composition is mixed with a solution containing ions).

Cells may be cultured on the surface of a peptide matrix structure in a similar manner to that in which they are cultured on a conventional substrate such as a tissue culture dish or slide, or a tissue culture dish or slide that is coated with a biologically derived material such as collagen, Matrigel, and the like. In general, cells can be cultured at any desired degree of confluence. In certain embodiments, encapsulated cells are present in the macroscopic structure in a three-dimensional arrangement. The density of the cells may be, for example, between $5 \times 10^3$/ml to $5 \times 10^4$/ml, between $5 \times 10^4$/ml to $5 \times 10^5$/ml, between $5 \times 10^5$/ml to $5 \times 10^6$/ml, or between $5 \times 10^6$/ml to $5 \times 10^7$/ml, with endpoints included. Other ranges may also be used.

The conditions for culturing should be close to physiological conditions. For example, in certain embodiments, the pH of the culture medium is close to physiological pH. In some embodiments, the pH is between about 6-8. In other embodiments, the pH is between about 7 to 7.8. In yet other embodiments, the pH is about 7.4. In certain embodiments, the temperatures of the culture medium is close to physiological temperature. Physiological temperatures range between about 30° C. to 40° C. for mammalian cells. In certain embodiments, cells are cultured at temperatures between about 32° C. to about 38° C., or between about 35° C. to about 37° C.

Cells may be cultured on or within the peptide structure for any appropriate time, depending upon the cell number and density desired, the proliferation rate of the cells, and the time required for the desired cellular reprogramming to occur. These parameters will vary depending upon the particular cells and purposes for which the invention is to be used. One of ordinary skill in the art will be able to vary these parameters and to observe the effects of doing so, in order to determine the optimal time for maintaining cells in culture on or within the structure. In certain embodiments of the invention the cell are cultured for approximately 3 days, 7 days, 14 days, 21 days, 28 days, 56 days, or 90 days. In certain embodiments of the invention the cells are cultured for between 1 and 3 days inclusive, between 4 and 7 days inclusive, between 8 and 14 days inclusive, between 15 and 21 days inclusive, between 22 and 28 days inclusive, between 29 and 56 days inclusive, or between 57 and 90 days inclusive. Longer or shorter culture periods may also be used.

In certain embodiments, at least 40%, 50%, 60%, 70%, 80%, 90% or 95% of the cells (either cultured on a surface or encapsulated) are viable 1, 2, 3, 4, 5, 6 or more weeks after formation of the macroscopic matrix. In other embodiments, at least 50%, at least 60%, at least 70%, at least 80% or at least 90% of the cells are viable one day or one week after formation of the macroscopic matrix.

In general, any cell type can be cultured and/or encapsulated in accordance with the present invention including, but not limited to, vascular endothelial cells and precursors thereof, bone marrow cells, periosteal cells, perichondrial cells, fibroblasts, skeletal myoblasts or myocytes, neuronal cells, hippocampal cells, epidermal cells, non-vascular endothelial cells or smooth muscle cells, keratinocytes, basal cells, spinous cells, granular cells, stem cells (e.g., embryonic, fetal, cord blood, adult), lung cells, immune system cells, ovarian cells, pancreatic cells, cervical cells, liver cells, or foreskin cells. The cells may comprise embryonic stem cells, fetal stem cells, cord blood stem cells, or adult stem cells, e.g., stem cells that are able to or can be induced to differentiate into any of the preceding cell types.

Sources of the cells may also include fetal or adult organisms, particularly mammals or established cell lines. Numerous established cell lines are known in the art, many of which are available through the American Type Culture Collection (see web site having URL www.atcc.org, which also provides references describing these cell lines). In discussing cells and cell lines, the phrase "derived from" indicates that a cell is obtained from a particular source, or that the cell is a descendant of a cell obtained from that source. For example, a liver-derived cell is a cell that is obtained from the liver or the progeny or descendant of such a cell. When the term "progeny" is used herein, it refers not only to the immediate products of cell division but also to the products of subsequent cell divisions, i.e., to cells that are descendants of a particular cell. A cell that is derived from a cell line is a member of that cell line or is the progeny or descendant of a cell that is a member of that cell line. A cell derived from an organ, tissue, individual, cell line, etc., may be modified in vitro after it is obtained. Such a cell is still considered to be derived from the original source.

Methods for isolating cells are known in the art. Cells harvested from an individual may be used either with or without a period of expansion in culture. Alternately, cells that have been propagated in culture as a stable cell line may be used. In certain embodiments of the invention, e.g., in certain therapeutic applications as provided herein, the cells are autologous while in other embodiments of the invention the cells are allogeneic or xenogeneic. When non-autologous cells are used, the cells may be treated in various ways prior to introduction into the body in order to reduce the likelihood or reduce the extent of an immune system response by the subject. Such treatments can include modifying, masking, or eliminating an antigen on the surface of a cell as described, for example, in PCT Application Publication No. WO/2001/007568.

In certain embodiments, cells are harvested from a subject (such as, for example, a human patient), and a clonal cell line is derived from one or more of these cells. Clonal lines may be obtained by limiting dilution plating or single cell sorting. Methods for deriving clonal cell lines are well known in the art and are described in, for example, Puck and Marcus, *Experimental Medicine* (1956) 103:653; C. V. Ramakrishnan, Ed., *Cell Culture*, "Clone size distribution in the study of inhomogeneity of growth rates in tissue culture," Dr. W. Junk Publishers, Netherlands:1965; and Leong et al., *Mutat. Res.* (1985) 150:403-410. Cells from the cell line are used in the practice of the invention. When intended for treatment of a particular patient, cells from a matched donor may be advantageously used. Cells isolated from an individual or maintained as a cell line may be cultured according to any appropriate technique including standard cell culture techniques prior to their use in the practice of the present invention.

It may also be desirable to genetically alter the cells prior to their use in the invention. Numerous methods for introducing exogenous genetic material into cells are well known in the art (see, for example, PCT Application Publication No. WO/2001/007568). Such methods typically include introducing genetic material such as a nucleic acid molecule (e.g., DNA) into the cell, wherein the nucleic acid molecule encodes a product to be expressed by the cell. The product can be, for example, a reprogramming agent such as a growth factor, a transcription factor which will in turn induce expression of other gene products, and the like. In certain embodiments of the invention, a selectable marker is introduced into the cells. In other embodiments of the invention, a gene that encodes a selectable marker is introduced into the cells, such as, for example, a gene encoding a protein that confers drug resistance or a detectable marker (e.g., GFP) under the control of a tissue-specific promoter. In certain embodiments, the expression of the detectable marker is used as a means to determine whether the cell or its progeny has differentiated, dedifferentiated, or transdifferentiated along a particular cell lineage pathway characteristic of that tissue. In other embodiments, the detectable marker is used for isolating cells that have differentiated, dedifferentiated, or transdifferentiated along a particular pathway, e.g., by using immunological methods, FACS, or other methods well known in the art. Numerous selectable and detectable markers are known in the art. In addition, tissue-specific, organ-specific, and lineage-specific promoters are well known. Genes may be introduced under the control of either a constitutive or an inducible promoter of which many are known in the art.

Matrices on which cells are cultured or in which cells are encapsulated may be subjected to various environmental conditions that may affect cell phenotype. For example, matrices may be subjected to various defined or predetermined mechanical stresses, e.g., shear stress, compression schemes, and the like, that may result in altered synthesis of ECM components. It is well known, for example, that flow, e.g., pulsatile flow, can alter the secretion of proteins by cells cultured in vitro. Cells in native articular cartilage and in tissue-engineered constructs respond to mechanical stimuli through multiple regulatory pathways. Such stimuli result in altered intra- and intercellular signalling, alterations in transcription level, protein translation, post-translational modifications, and synthesis of intracellular and extracellular macromolecules (Kisiday (2002)).

C. Modification of Self-Assembling Peptides by Addition of an Amino Acid Domain

The inventors have discovered an unanticipated flexibility in that the self-assembling peptides (as provided in Table 1) can be modified by the addition of additional amino acid domains that would not self-assemble if present in isolated form under conditions (e.g., ionic strength, peptide concentration, pH, temperature) to form modified self-assembling peptides. Furthermore, in certain embodiments, the addition of one or more non self-assembling amino acid domains does not prevent the modified peptide from self-assembling, e.g., to form nanofibers and/or a macroscopic structure. In certain embodiments, the modified peptide self-assembles to form a macroscopic structure comprising nanofibers. Although the resulting structure may be less strong and/or stable than a structure resulting from self-assembly of the unmodified peptide, visual observation and/or rheological studies, as described in the examples, confirm that hydrogel formation occurs.

The modified peptides may thus be used for the various purposes described above and herein. For purposes of the present invention, a self-assembling peptide that possesses the structural features described in the previous section and does not include a portion lacking those characteristics will be referred to as an "unmodified self-assembling peptide." It is to be understood that an unmodified self-assembling peptide may be altered in any of a number of ways described above that do not include addition of amino acids to the peptide. Such altered self-assembling peptides are not referred to as "modified" within the meaning of the term as used herein but rather as "altered" or "derivatized". The modified self-assembling peptides of the invention are distinct from naturally occurring molecules, i.e., they are not found in naturally occurring molecules, although one or more of the amino acid domains in an inventive peptide may occur in a naturally occurring molecule. They can therefore be considered "isolated" or "synthetic", meaning that the total sequence of the peptide does not occur in nature without the intervention of man.

A peptide that includes an amino acid domain comprising an unmodified self-assembling peptide and a second amino acid domain that lacks one or more of the structural features of an unmodified self-assembling peptide, and thus does not self-assemble to form nanofibers or to form a macroscopic structure under conditions that would result in self-assembly of an unmodified self-assembling peptide, is referred to as a "modified self-assembling peptide" if it is capable of self-assembly (e.g., to form nanofibers and/or a macroscopic structure) under conditions that would result in self-assembly of an unmodified self-assembling peptide. It will be appreciated that, in general, a modified self-assembling peptide will correspond to a particular unmodified self-assembling peptide that does not include the second amino acid domain but that has the same self-assembling portion. In certain embodiments of the invention the conditions under which self-assembly of the modified self-assembling peptide occurs are the same as the conditions under which the corresponding unmodified self-assembling peptide assembles. In other embodiments of the invention, the conditions under which self-assembly of the modified self-assembling peptide occurs are different from the conditions under which the corresponding unmodified self-assembling peptide assembles. In this case, the conditions for self-assembly of the modified self-assembling peptide are the same as the conditions under which a different (non-corresponding) unmodified self-assembling peptide self-assembles.

The inventive modified self-assembling peptides thus comprise (a) a first amino acid domain that mediates self-assembly, wherein the domain comprises alternating hydrophobic and hydrophilic amino acids that are complementary and structurally compatible and self-assemble into a macroscopic structure; and (b) a second amino acid domain that does not self-assemble in isolated form (i.e., when present as the only peptide in a solution under conditions that would result in assembly of an unmodified self-assembling peptide as described above).

In certain embodiments, the second amino acid domain permits assembly of the first amino acid domain so that the peptide assembles to form nanofibers, and/or a macroscopic structure. In other embodiments of the invention the peptide forms β-sheets.

In certain embodiments of the invention an amino acid domain is at least 3 amino acids; at least 4 amino acids, at least 5 amino acids, at least 6 amino acids, at least 7 amino acids, at least 8 amino acids, at least 9 amino acids, at least 10 amino acids, or more, e.g., 15, 16, 17, 18, 19, 20 etc. amino acids. In certain embodiments of the invention, the first amino acid domain (self-assembling portion) is at least 3 amino acids; at least 4 amino acids, at least 5 amino acids, at least 6 amino acids, at least 7 amino acids, at least 8 amino acids, at least 9 amino acids, at least 10 amino acids, or more, e.g., at least 15, 16, 17, 18, 19 or 20 amino acids. In certain embodiments, the first amino acid domain is at least 12 to 16 amino acids in length. In certain embodiments of the invention, the second amino acid domain (non-assembling portion) is at least 3 amino acids; at least 4 amino acids, at least 5 amino acids, at least 6 amino acids, at least 7 amino acids, at least 8 amino acids, at least 9 amino acids, at least 10 amino acids, or more, e.g., at least 15, 16, 17, 18, 19 or 20 amino acids. However, in some embodiments, the second amino acid domain is limited to 20 amino acids or less, 18 amino acids or less, 16 amino acids or less, 14 amino acids or less, 12 amino acids or less, 10 amino acids or less, 9 amino acids or less, 8 amino acids or less, 6 amino acids or less, or 4 amino acids or less.

It may be desirable to maintain a certain ratio of amino acids in the self-assembling and non self-assembling portions of the peptide. For example, in certain embodiments of the invention, the second amino acid domain is 50% or less of the total number of amino acids in the peptide. In certain embodiments, the non-self assembling amino acid domain is present between two self assembling domains. In some embodiments, each of the self-assembling domains flanking the non self-assembling domain is greater than 8, 12, 14, 16, 18 or 20 amino acids in length.

FIG. 1A shows molecular models representing a representative self-assembling peptide RAD16-I (top) and peptide RAD16-I modified to include a non self-assembling amino acid domain at its C terminus (bottom).

Figure 1D:
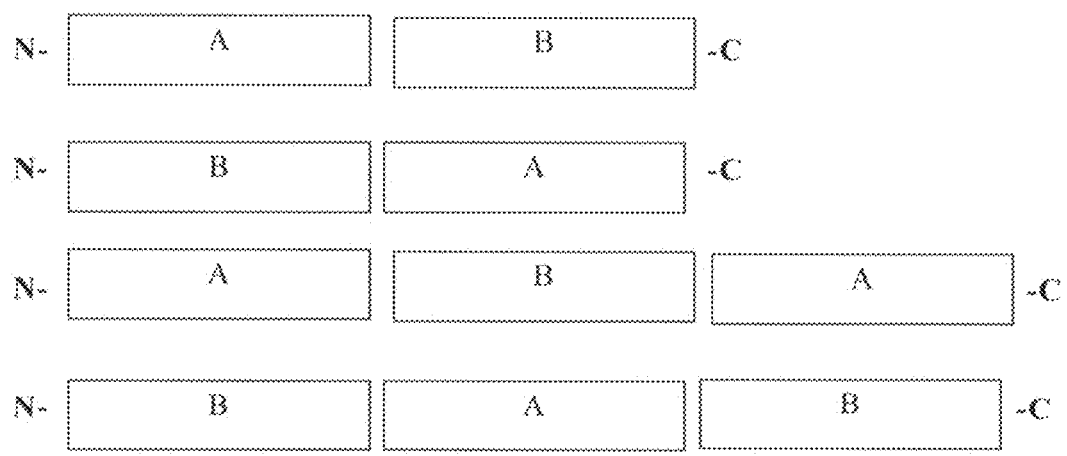
FIG. 1D. Depiction of a variety of possible configurations for modified self-assembling peptides in accordance with the invention. Domain A represents a self-assembling amino acid domain. Domain B represents a non self-assembling amino acid domain (modifying domain). As indicated in the figure, a modifying domain may be present at the N and/or C terminus of the self-assembling domain, or may be present between two self-assembling domains.
Figure 2:
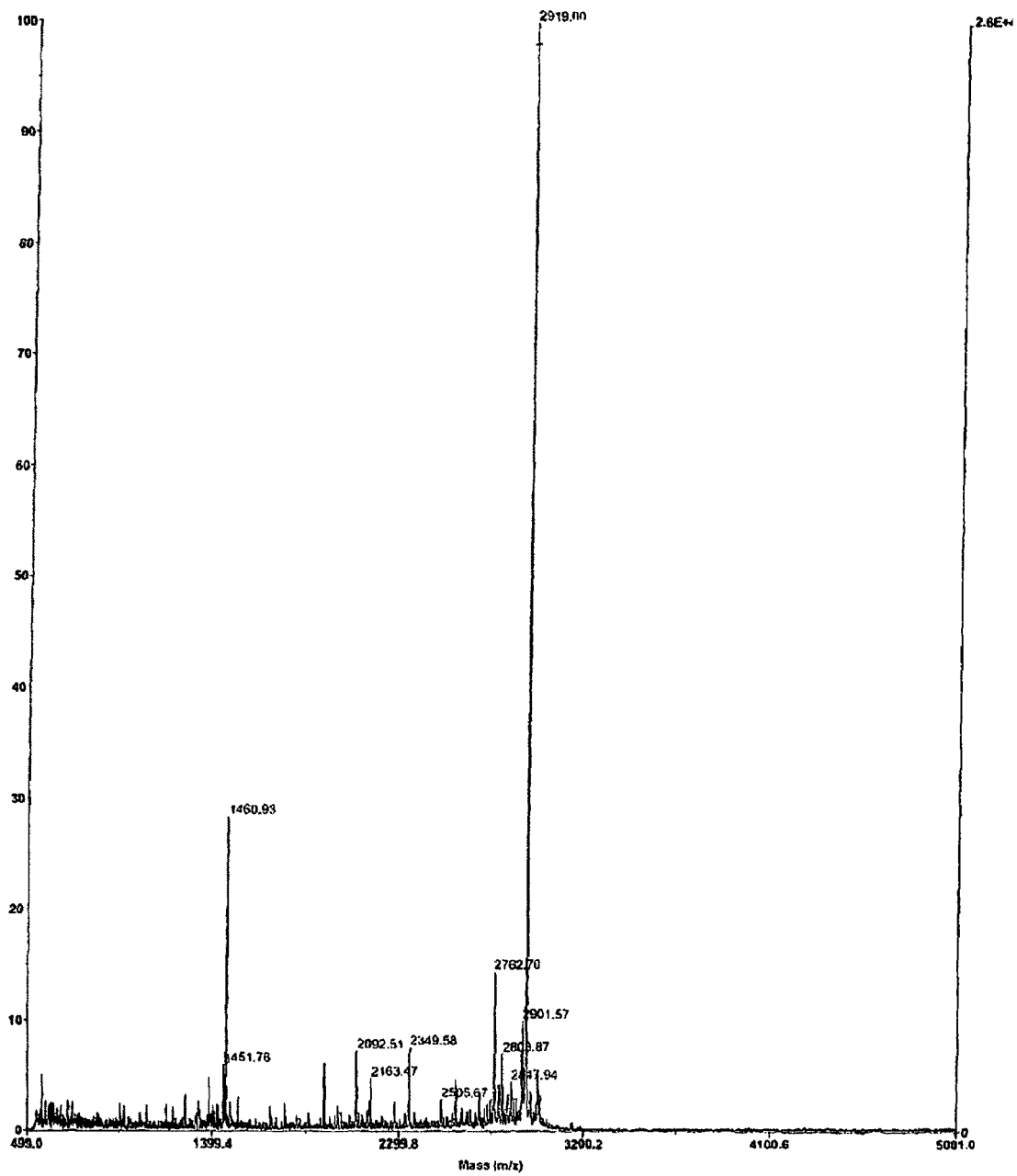
FIG. 2. Mass spectroscopy data of SEQ4 peptide.

FIG. 1D shows a variety of possible configurations for modified self-assembling peptides in accordance with the invention. Domain A represents a self-assembling amino acid domain. Domain B represents a non self-assembling amino acid domain (modifying domain). As indicated in the figure, a modifying domain may be present at the N and/or C terminus of the self-assembling domain, or may be present between two self-assembling domains.

The amino acid domains may be joined via a linker group comprising one or more amino acids or a different molecular entity. An amino acid linker group consisting of one or more glycine or alanine residues, e.g., 1, 2, 3, 4, 5, etc. glycines, may be used. In certain embodiments, the amino acid linker group consists of one or more glycine residues. As glycine and alanine are small and nonpolar, incorporation of such a linker group minimizes the likelihood of interference with self-assembly.

While the modified peptides described in the examples were made by solid phase synthesis of the extended peptide, resulting in a linear chain, variations in which the modifying motif is conjugated or cross-linked to a side chain are also encompassed within the present invention. Methods for achieving such conjugation or cross-linking are well known in the art. For example, a peptide containing a cysteine residue (or any amino acid modified to include a sulfur atom) can be coupled to a second peptide containing a sulfur atom by formation of disulfide bonds. Thus, in general, the modified self-assembling peptide may be a single linear polymer of amino acids joined by peptide bonds, or may have a branched structure in which two polymers of amino acids (e.g., each being a polymer of amino acids joined by peptide bonds) are attached to one another either covalently (e.g., via di-sulfide bonds, carbon-carbon bonds, and the like) or non-covalently (e.g., via a biotin-avidin interaction).

Examples of cross-linking methods include, but are not limited to, the glutaraldehyde method which couples primarily through the V-amino group and W-amino group, maleimide-sulfhydryl coupling chemistries (e.g., the maleimidobenzoyl-N-hydroxysuccinimide ester (MBS) method) and periodate oxidation methods. In addition, numerous cross-linking agents are known. Exemplary cross-linking agents include, but are not limited to, carboiimides, N-hydroxysuccinimidyl-4-azidosalicylic acid (NHS-ASA), dimethyl pimelimidate dihydrochloride (DMP), dimethylsuberimidate (DMS), and 3,3'-dithiobispropionimidate (DTBP). For additional information on conjugation methods and crosslinkers, see the *Journal Bioconjugate Chemistry*, published by the American Chemical Society, Columbus Ohio, PO Box 3337, Columbus, Ohio, 43210. See also "Cross-Linking," Pierce Chemical Technical Library, available at the Web site having URL www.piercenet.com, and originally published in the 1994-1995 Pierce Catalog, and references cited therein and Wong, *Chemistry of Protein Conjugation and Crosslinking*, CRC Press Publishers, Boca Raton, 1991.

Bifunctional crosslinking reagents contain two reactive groups, thereby providing a means of covalently linking two target groups. The reactive groups in a chemical crosslinking reagent typically belong to the classes of functional groups including succinimidyl esters, maleimides, and iodoacetamides. A number of common schemes for forming a heteroconjugate involve the indirect coupling of an amine group on one biomolecule to a thiol group on a second biomolecule, usually by a two or three step reaction sequence. The high reactivity of thiols and their relative rarity in most biomolecules make thiol groups good targets for controlled chemical crosslinking. If neither molecule contains a thiol group, then one or more can be introduced using one of several thiolation methods. The thiol-containing biomolecule may then be reacted with an amine-containing biomolecule using a heterobifunctional crosslinking reagent, e.g., a reagent containing both a succinimidyl ester and either a maleimide or an iodoacetamide. Amine-carboxylic acid and thiol-carboxylic acid crosslinking may also be used. For example, 1-ethyl-3-(3-dimethylaminopropyl) carbodiimide (EDAC) can react with biomolecules to form "zero-length" crosslinks, usually within a molecule or between subunits of a protein complex. In this chemistry, the crosslinking reagent is not incorporated into the final product.

Several methods are available for introducing thiols into biomolecules, including the reduction of intrinsic disulfides, as well as the conversion of amine, aldehyde or carboxylic acid groups to thiol groups. Disulfide crosslinks of cystines in proteins can be reduced to cysteine residues by dithiothreitol (DTT), tris-(2-carboxyethyl)phosphine (TCEP), or tris-(2-cyanoethyl)phosphine. Amines can be indirectly thiolated by reaction with succinimidyl 3-(2-pyridyldithio)propionate (SPDP) followed by reduction of the 3-(2-pyridyldithio)propionyl conjugate with DTT or TCEP. Amines can be indirectly thiolated by reaction with succinimidyl acetylthioacetate followed by removal of the acetyl group with 50 mM hydroxylamine or hydrazine at near-neutral pH. Tryptophan residues in thiol-free proteins can be oxidized to mercaptotryptophan residues, which can then be modified by iodoacetamides or maleimides.

D. Peptide Mixtures

The invention encompasses the recognition that it is possible to mix one or more unmodified self-assembling peptides together with one or more modified self-assembling peptides of the present invention in various ratios, and that macroscopic structures comprising both unmodified and modified self-assembling peptides can be formed from such mixtures. The resulting structures can have certain advantageous features relative to structures formed by self-assembly of a homogeneous self-assembling peptide (i.e., 100% of a single peptide). For example, as described above and herein, the modified self-assembling peptides may result in macroscopic structures that are weaker than structures formed from the corresponding unmodified peptide, e.g., they may have less gel-like character.

However, the modified peptides may induce certain physiological effects. For example, in certain embodiments, the modified peptides induce desirable cell phenotypes. In other embodiments, the modified peptides alter cell behavior. In yet other embodiments, the modified peptides alter the binding of ECM molecules. A macroscopic structure formed from a composite (also referred to as a blend) of unmodified and modified self-assembling peptide(s) may have mechanical properties resembling those of macroscopic structures formed by self-assembly of the unmodified peptide while possessing the ability to influence cell behavior, phenotype, etc., in desirable ways.

In general, a wide variety of ratios of unmodified to modified peptide can be used, depending on the desired properties of the macroscopic matrix to be formed. For example, the ratio of unmodified to modified peptide can be, for example, 100:1, 99:1, 50:1, 25:1, 10:1, 9:1, 5:1, 2:1, 1:1, 1:2, 1:5, 1:10, 1:25, 1:50, 1:100, 1:99, 1:50, 1:25, 1:10, 1:9, 1:5, 1:4, 1:2, 1:1, and the like. These ratios are listed for exemplary purposes and are not intended to be limiting. The peptides can be mixed on a molar basis or based on weight, volume of peptide solution, etc. The peptides can be mixed in dry form, following which a mixed peptide solution is formed.

Alternately, each peptide may be dissolved, and the resulting solutions mixed together. The invention also encompasses mixing multiple modified self-assembling peptides with or without the addition of an unmodified self-assembling peptide so as to generate a macroscopic structure that combines desired features of the different modified self-assembling peptides. The various modified self-assembling peptides may contain different amino acid domains, either from the same naturally occurring protein or from different proteins, or entirely artificial amino acid domains, etc.

In certain embodiments of the invention a modified self-assembling peptide does not self-assemble when present as the sole peptide in a solution under conditions that would result in assembly of the corresponding unmodified peptide, but does self-assemble together with unmodified self-assembling peptides when present in combination with such peptides. In certain embodiments, self-assembly results in a composition comprising nanofibers optionally forming a macroscopic structure that contain a mixture of both unmodified peptides and modified peptides, e.g., primarily unmodified peptides. Alternatively, self-assembly results in a composition comprising some nanofibers that do not contain any modified peptides while other nanofibers which do contain such peptides.

E. Functionalized Peptide Motifs

In general, any of a wide variety of different amino acid domains may be added to the unmodified self-assembling peptides, provided that the presence of the additional domain does not prevent self-assembly (e.g., to form nanofibers, beta-sheets and/or a macroscopic structure). The additional domains may confer any of a number of desirable properties on the resulting peptides. For example, the additional domain may mediate a biological activity, e.g., may affect the behavior of cells contacted with a matrix made by self-assembly of the peptides. The additional domain may bind to either a naturally occurring or artificial biomolecule, such as an ECM protein, cell-surface molecule, growth factor, protein, peptide, antibody, etc. The additional domain may bind to an inorganic substance such as a metal, ion, etc. The presence of the additional domain may alter the material properties (e.g., strength, elasticity, etc.) of a macroscopic structure created by self-assembly of the peptide, relative to the properties of a macroscopic structure created by self-assembly of the unmodified peptide. Thus by modifying a self-assembling peptide to include a non self-assembling domain, the material properties of a macroscopic structure can be tuned according to the needs of the user. For example, for implantation into the body it may be desirable to employ materials with different material properties, depending on the site of implantation and/or the tissue that the implant is to replace (e.g., bone, connective tissue, soft tissue such as muscle, ocular tissue, solid organ tissue, etc.). The following sections provide a non-limiting description of exemplary amino acid domains that can be added to an unmodified self-assembling peptide and methods for their selection.

Table 2a presents a non-limiting list of various minimal biologically active sequences that have been shown to have biological activities in various systems. Any of these sequences can be incorporated into or used as the second amino acid domain for modification of an "unmodified" self-assembling peptide to form a "modified" one. In certain embodiments, the second amino acid domain comprises at least one minimal biologically active sequence. In certain embodiments, the second amino acid domain comprises at least two minimal biologically active sequences. It is to be understood that any of these sequences, or others, can be tested by actually synthesizing the modified peptide and testing its ability to self-assemble, e.g., to form beta-sheets, nanofibers, and/or a macroscopic structure, under conditions that would result in self-assembly of an unmodified peptide. Methods for performing such tests are described below, and the tests themselves require no more than routine experimentation. Testing can be carried out under conditions suitable for self-assembly of unmodified self-assembling peptides. In certain embodiments, modified peptides that self-assemble into beta-sheets, nanofibers, and/or macroscopic structures are selected.

Any of a wide variety of additional minimal biologically active sequences in addition to those listed in Table 2a can be used as biologically active peptide sequences to modify the unmodified self-assembling peptides. These sequences may be derived from any of a diverse range of naturally occurring proteins and peptides including ECM components, cell adhesion molecules, cell surface receptors, growth factors, cytokines, chemokines, etc. For example, the -RGD- sequence is a prototypic cell recognition sequence found in fibronectin and well known to be recognized by integrins and to mediate cell attachment.

TABLE 2a

Exemplary minimal biologically active sequences provided in functionalized motifs

| PRGDSGYRGD | DGRGDSVAYG | ALKRQGRTLYGF |
|---|---|---|
| (SEQ ID NO. 54) | (SEQ ID NO. 55) | (SEQ ID NO. 56) |
| PFSSTKT | FLGFPT | KLTWQELYQLKYKGI |
| (SEQ ID NO. 57) | (SEQ ID NO. 58) | (SEQ ID NO. 59) |
| SKPPGTSS | STFTKSP | IKVAV |
| (SEQ ID NO. 60) | (SEQ ID NO. 61) | (SEQ ID NO. 62) |
| FHRRIKA | IKLLI | RGD |
| (SEQ ID NO. 63) | (SEQ ID NO. 64) | |
| REDV | LKKTETQ | |
| (SEQ ID NO. 65) | (SEQ ID NO. 66) | |

As described herein, the inventors created a variety of modified peptides (Table 2b) incorporating the above minimal biologically active sequences and tested their ability to assemble into macroscopic structures that could be used for purposes such as cell culture, tissue engineering, or therapeutic applications either with or without cells. Surprisingly, it was found that extensive modifications may be made without preventing matrix formation. The inventors tested the ability of these new materials to support monolayer formation, growth, and function of mouse pre-osteoblast cells, human umbilical vein endothelial cells (HUVEC), human adipose derived stem cells (ADSC) and human mesenchymal stem cell (MSC). The addition of a number of the above minimal biologically active sequences conferred new biological activities on the peptides as evidenced by alteration in cell behavior when cultured in the presence of matrices made from the modified peptides.

TABLE 2b

Exemplary modified self-assembing peptides

| No. | Sequence | Description |
|---|---|---|
| SEQ ID NO.1 | Ac-(RADA)$_4$GGPFSSTKT-CONH$_2$ | Bone marrow homing |
| SEQ ID NO.2 | Ac-(RADA)$_4$GGFLGFPT-CONH$_2$ | MP-1 (bone marrow purification) |
| SEQ ID NO.3 | Ac-(RADA)$_4$GGALKRQGRTLYGF-CONH$_2$ | Osteogenic growth Peptide |

TABLE 2b-continued

Exemplary modified self-assembing peptides

| No. | Sequence | Description |
|---|---|---|
| SEQ ID NO.4 | Ac(RADA)$_4$GPRGDSGYRGDS-CONH$_2$ | Repetitive RGD binding sequence |
| SEQ ID NO.5 | Ac(RADA)$_4$GGDGRGDSVAYG-CONH$_2$ | Cell adhes dom. (Osteopontin) |
| SEQ ID NO.6 | Ac(RADA)$_4$GGFHRRIKA-CONH$_2$ | Heparin binding domain |
| SEQ ID NO.7 | Ac(RADA)$_4$GPRGDSGYRGDSG-CONH$_2$ | Repetitive RGD binding sequence |
| SEQ ID NO.8 | Ac(RADA)$_4$GGRGDSCONH$_2$ | RGD binding sequence with 2 linker Glycine |
| SEQ ID NO.9 | Ac(RADA)$_4$GGGGRGDSCONH$_2$ | RGD binding sequence with 4 linker Glycine |
| SEQ ID NO.10 | Ac(RADA)$_4$GGGGREDV-CONH$_2$ | Fibronectin/Endothelial cells adhesion |
| SEQ ID NO.11 | Ac(RADA)$_4$GGGGKLTWQELYQLKYKGI-CONH$_2$ | VEGF mimicking peptide/Bind to VEGF receptors |
| SEQ ID NO.12 | Ac(RADA)$_4$GGSKPPGTSS-CONH$_2$ | Bone marrow homing |
| SEQ ID NO.13 | AcIEIKIEIKIGGPRGSYRGDS-CONH$_2$ | Repetitive RGD binding sequence |
| SEQ ID NO.14 | AcIEIKIEIKIGGPFSSTKT-CONH$_2$ | Bone marrow homing |
| SEQ ID NO.15 | AcIEIKIEIKIGGSKPPGTS-CONH$_2$ | Bone marrow homing |
| SEQ ID NO.16 | AcFKFQFKFQFKFQGPRGDSGYRGDS-CONH$_2$ | Repetitive RGD binding sequence |
| SEQ ID NO.17 | AcFKFQFKFQFKFQGGFHRRIKA-CONH$_2$ | Heparin binding domain |
| SEQ ID NO.18 | Ac(RADA)$_4$GGSTFTKSP-CONH$_2$ | Bone marrow homing |
| SEQ ID NO.19 | Ac(RADA)$_4$GGSIKVAVS-CONH$_2$ | Laminin (110 kDa laminin receptor protein) |
| SEQ ID NO.20 | Ac(RADA)$_4$GGSEIKLLIS-CONH$_2$ | Laminin (a3b1 and cell surface heparin) |

Repetitive RGD binding sequence (-PRGDSGYRGD-, SEQ ID NO. 54: PRGmx, SEQ ID NO. 7: DSG): RGD is a key binding sequence for cell attachment specifically working with integrins. -PRGDS- (SEQ ID NO. 72)and -YRGDS- (SEQ ID NO. 73) are the most commonly appeared RGD motifs in natural proteins. -RGD- binding can affect structural conformations of the protein (Kantlehner et al., *Chembiochem* (2000) 1:107-114). Repetitions of the RGD binding sequence increases the possibility of the cell attachment and increases the possibility of effective conformation Osteopontin motif for osteoclast and osteoblasts (-DGRGDSVAYG-, SEQ ID NO. 55: DGRmx): Osteopontin, which has 264-301 amino acids depending on species, is synthesized and phosphorylated by both osteoblasts and osteoclasts in bone, and is also synthesized by odontoblasts during semetogenesis. It is also referred to as uropontin or bone sialoprotein1 (BSP1), 2aR, 2B7, eta-1, 44Kd bone phosphoprotein and secrete phosphoprotein (Kreis and Vale, (1999) Guide book to the extracellular matrix, anchor, and adhesion proteins, 2$^{nd}$ Edition, Oxford University Press. Oxford, UK). Osteopontin regulates cell adhesion, migration, and survival, NF-kB activity, NO synthesis, and calcium crystal formation. Several motifs have been found to be important for this protein.

Osteogenic growth peptide (-ALKRQGRTLYGF-, SEQ ID NO. 56: ALKmx): The osteogenic growth peptide (OGP) (ALKRQGRTLYGFGG)(SEQ ID NO. 74) is a key factor in the mechanism of the systemic osteogenic response to local bone marrow injury. When administered in vivo, OGP stimulates osteogenesis and hematopoiesis. The C-terminal pentapeptide OGP (10-14) is the minimal amino acid sequence that retains the full OGP-like activity. It is apparently also the physiologic active form of OGP. Residues Tyr(10), Phe(12), Gly (13), and Gly (14) of OGP are essential for the OGP (10-14) activity. (Greenberg et al., *J Cell Biochem.* (1997) 65: 359-67; Chen et al., *J Med Chem.* (2002) 45:1624-1632). Thus both the full length and the active form of the OGP were used as the functional motifs for tailor-made matrix for bone cells.

Phage display selected bone marrow peptide (-PFSSTKT-, SEQ ID NO. 57: PFSmx, -SKPPGTSS-; SEQ ID NO. 60: SKP, -STFTKSP-, SEQ ID NO. 61: STF): Becker and colleagues used phage display 7-peptide residue library to select bone marrow homing assay. They found a family of peptides rich in K, P, F, S, S, T, and T. These peptides bind to stem cells and 85% home in vivo into bone marrow (Nowakowski et al., "Bone marrow homing heptapeptides bears homology to CD84," Preventive Oncology & Intervention Strategies (Conference); Paris, Feb. 9th to 12th, 2002). One of these peptides which homes into bone marrow and also binds to primitive stem cells, is homologous to N-terminal CD84, a cell surface protein expressed by lymphocytes (Palou et al., *Tissue Antigens* (2000) 55:118-127).

Myelopeptides (MPs)(-FLGFPT-, SEQ ID NO. 58: FLGmx): Bone marrow cells of humans and various animals also produce a group of bioregulatory mediators, peptides called myelopeptides (MPs). One of these, MP-1 (Phe-Leu-Gly-Phe-Pro-Thr) has been synthesized and their biological activities comprehensively studied. The hexapeptide displayed pronounced immunoregulatory activity (Petrov et al., *Biopolymers* (1997) 43: 139-146). The peptide has been used in clinical trials in Russia to treat a number of diseases (Petrov et al., *Ann N.Y. Acad Sci.* (1993) 685:351-361). MPs influence the differentiation of bone marrow and peripheral blood cells derived from healthy and leukemic donors. They induce terminal differentiation in the leukemic human HL-60 cell line. MPs seem to provide not only immunoregulation but also participate in complex interactions between different systems in the organism (Petrov et al., *Biosci Rep.* (1995) 15, 1-14). MP-1 enhances a decreased level of antibody production in cyclophosphamide (Cy)-treated mice, but does not influence the antibody formation in normal animals. (Mikhailova et al., *Regul Pept.* (2003) 114:183-187).

Heparin-binding motif sequence (-FHRRIKA-, SEQ ID NO. 63: FHR). There are heparin binding motif sequences in cell attachment proteins such as fibronectin, vitronectin, laminin, collagen, VEGF, FGFs, PDGF, HGF, TGF-β and BMP. Many of these sequences maintain heparin-binding motif consensus sequences -XBBXBX- and -XBBBXXBX-, wherein X represents non-charged or hydrophobic amino acid (e.g., F, I, L, P, M, W, Y, V, A, C and Q), and B represents positive charged peptides (e.g., R, H and K). Heparin binding motif also synergistically work with -RGD- motif to promote mineralization of osteoblast (Rezania A et.al, Biotechnol. Prog. 1999,15, 19-32). By using the heparin binding motifs as functional motifs of modified peptide in self-assembly peptide matrices, heparin or heparan sulfate can be incorporated into the matrices. Self-assembly peptide matrices incorporated heparin or heparan sulfate binds can be used for controlled release of heparin-binding growth factors.

Laminin cell adhesion domain (-IKVAV-, SEQ ID NO 62: SIK; -IKLLS-, SEQ ID NO 75: SEI). Laminin is the main component in basement membrane and considered to be important for stem cell maintenance. -IKVAV- (included in SEQ. 62) and IKLLS (included in SEQ 75) are known as the cell adhesion sequences in laminin. They are useful to preserve viability, reduce apoptosis and reduce secretion of insulin in encapsulated beta-cells (Laney et al., *Biomaterials* (2007) 28:3004-3011).

III-CS domain of human plasma fibronectin (-REDV-, SEQ ID NO. 65: REDmx). III-CS domain of human plasma fibronectin (REDV)(SEQ ID NO. 65) supports the attachment of vascular endothelial cells and the spreading of endothelial cells (Shin et al., *Biomaterials* (2003) 24:4353-4364; Welsh et al., *Biomaterials* (2000) 1:23-30).

Actin binding site on thymosin β4 (-LKKTETQ-, SEQ ID NO. 66: LKKmx). The actin binding site on thymosin β4 (-LKKTETQ-)(SEQ ID NO. 66) can promote endothelial cell migration and adhesion, tubule formation, aortic ring sprouting, and angiogenesis (Huff et al., FASEB Journal (2003) 17:2103-2105)

Fibronectin cell adhesive domains (-RGD-, SEQ ID NO.: 4: PRGmx; SEQ ID NO:5: DGRmx; SEQ ID NO. 7:DSG; SEQ ID NO. 8:2 G; SEQ ID NO. 9: 4G). An Arg-Gly Asp (RGD) sequence located in the 10th type III repeating unit in fibronectin. RGD is present not only in fibronectin but also many other extracellular matrix proteins such as laminin, bone sianoprotein, osteopontin and vitronectin. RGD sequence is important for cell adhesion. Immobilization of RGD motif to polymers and alginate gel improves bone formation in vitro and in vivo (Alsberg E et. al, J Dent Res 80:2025-2029.DJ (2001))

F. Biologically Active Molecules which Interact with Minimal Biologically Active Sequences Efforts to modify the previously identified self-assembling peptides were inspired in part by a desire to create a fully synthetic material that would recreate important features of the microenvironment provided by the cellular basement membrane. The cellular basement membrane is a three-dimensional network mainly composed primarily of laminins, collagens and proteoglycans. Basement membranes underlie sheets and tubes of epithelial cells and also surround individual cells of various types such as muscle cells, fat cells, and Schwann cells. In certain locations (e.g., lung, kidney glomerulus) the basement membrane separates sheets of cells and serves as a filter. Under electron microscopic visualization, basement membranes can be seen to include two distinct layers: an electron-lucent layer adjacent to the basal plasma membrane of cells resting on the basement membrane and an electron-dense layer below. Basement membranes may also include a third layer that connects the lower layer to underlying connective tissue.

In addition to its importance as a structural component, supporting cell attachment and acting as a barrier that separates various cells, tissues, and organs, it also provides cells with an instructive microenvironment that interacts with them and modulates their function. Cell polarity, metabolism, differentiation, and migration are among the aspects of cell function modulated by the basement membrane. In addition, molecules in the basement membrane can contribute to the structural organization of plasma membrane and intracellular molecules. Basement membrane molecules also interact with one another.

The role of the ECM in modulating cell function is of particular interest in the context of the vascular system, in which vessels and heart chambers contain an inner endothelial cell monolayer resting atop a basement membrane that separates the endothelial cells from muscular layers below. The basement membrane is believed to play an important role in processes such as vascularization, and its integrity is important in maintaining proper vascular function. Damage or alterations in the endothelial cell layer and/or underlying basement membrane are likely to play a key role in various disease processes such as atherosclerosis.

Short peptide sequences present in proteins of the basement membrane have been identified as participating in a variety of important biological functions including cell attachment, proliferation, differentiation and migration (see, for example, Iwamoto (1987) Kleinman. (1989); Koliakos (1989); Skubitz (1990); Tsilibary (1998); and Sakamoto (1991)). Peptide sequences that mediate binding between different ECM molecules or binding between ECM molecules and non-ECM molecules in the body have also been identified. The following sections describe features of various basement membrane molecules that can interact with minimal biologically active sequences, as described above and herein, and provide further details regarding relevant aspects of the vascular system, endothelial cells, and the endothelial basement membrane.

(i) Laminin-1

Laminins represent a protein family of heterotrimers containing alpha, beta and gamma chains. Laminins are primarily located in basement membranes but also in mesenchymal compartments. Laminins create physical boundaries between stromal matrix and epithelial, endothelial, muscle, and nerve cells. So far at least 11 laminin isoforms containing various combinations of alpha, beta and gamma chains have been identified. Common to all of them is a coiled-coil domain which plays a key role in heterotrimer assembly. Laminin-1 is the earliest laminin produced during mouse development prior to the blastocyst stage, contributing to epithelial tissues during organogenesis (see, for example, Dziadek and Timpl (1985)). Laminin-1 ($M_r$=900,000) is formed from $alpha_1$, $beta_1$ and $gamma_1$ subunits, which assemble into a cross-like structure (see Engel (1981)). It forms a complex with nidogen, resulting in networks with a quasi-hexagonal pattern and three-dimensional structures. Formation of the complex occurs in a calcium, temperature, and concentration manner (see Yurchenco and Cheng (1993)).

Laminin-1 is involved in a number of important interactions including both homotypic interactions or between different isoforms. It also interacts with other proteins of the extracellular matrix forming bridges between the protein complex and cell membranes through cell-membrane receptors, or directly interacting with cells through several integrin and non-integrin receptors (see Kreis and Vale (1999)). Major biological functions attributed to laminin-1 include promoting cell adhesion, cell migration, cell differentiation and proliferation, enhancing neurite outgrowth, regulation of cell shape, and establishment of cell polarity of a variety of cell types (see, for example, Martin & Timpl (1987), Timpl, (1980), Beck (1990); and Engel (1992)).

(ii) Collagen IV

Collagenous proteins constitute a superfamily of extracellular matrix proteins with a structural role as their primary function. All collagens have domains with a triple helical conformation. Such domains are formed by three subunits (alpha chains), each containing a $(Gly-X-Y)_n$ repetitive sequence motif.

Collagen IV is the major collagenous component of the basement membrane, forming a network structure that involve the interaction with other basement membrane components including laminin, nidogen, and heparan sulfate proteoglycan (Kreis and Vale, (1999)). Collagen molecules are composed of two $alpha_1$(IV) chains and one $alpha_2$ (IV) chain. Collagen IV is believed to interact with cells indirectly through laminin via direct low affinity interactions (Yurchenco and O'Rear (1994); Charonis (1985)) or by strong binding mediated by nidogen, a glycoprotein of about 150 KDa, which binds tightly to laminin (Paulsson (1987); Poschl (1996)) and has binding sites also for collagen IV (Timpl (1996)). Type IV collagen also binds to heparin and heparan sulfate proteoglycan (see, for example, Yurchenco and O'Rear (1994); Tsilibary (1988); Koliakos (1989); and Fujiwata (1984)).

(iii) Nidogen

Nidogen (previously referred to in the literature as entactin) consists of a single polypeptide chain that binds to the laminin-1 .gamma. chain by a single module (LE) of 56 residues (Poschl (1996)). Nidogen also interacts with collagen type IV via a separate epitope and it is considered to act as a linker molecule between laminin-1 and collagen IV in basement membranes. In addition, nidogen contains RGD sequences which may serve as cell attachment sites via integrin molecules (Timpl (1989)).

(iv) Proteoglycans

Proteoglycans are a set of proteins found in a variety of locations including cell surfaces, within intracellular vesicles, and incorporated into extracellular matrices. They are defined and classified by the presence of a common post-translational modification, a special type of polysaccharides, the family of glycosaminoglycans. Proteoglycans are a diverse set of macromolecules composed of a core protein which can consist of a small or large polypeptide chain (10-400 kDa) carrying from one to hundreds of glycosaminoglycan chains. There are many known activities of proteoglycans. Among those, they are known to regulate cell-cell and cell-matrix interactions by binding with other extracellular matrix proteins. They regulate extracellular matrix assembly and structure and they immobilize diffusible molecules within the extracellular matrix as storing and releasing compartments (Kreis and Vale (1999)).

Additional basement membrane components. In addition to the proteins described above, a number of other proteins are present in the basement membrane and play significant roles. Among them are perlecan, agrin, BM-40/SPARC, fibulin-1, fibulin-2 (Timpl (1996) and references therein). A number of proteins related to these have also been discovered.

Vascular system and the ECM. Vascular endothelial cells provide an interface between the systemic circulation and soft tissues and participate in critical processes including inflammation, coagulation and hemostasis. Vascular endothelium also plays a role in a diverse set of pathological conditions ranging from atherosclerosis to diabetic nephropathy. Extension of pre-existing blood vessels and/or generation of new blood vessels from existing vasculature (angiogenesis) plays an essential role in tissue repair and regeneration as well as in embryonic development. In general, these processes involve the formation of a three-dimensional vascular network that provides nutrients and oxygen and removes waste products from the cells. Angiogenesis has been the subject of intensive research efforts during the past two decades (Carmeliet (2000), and Han and Liu, (1999)).

The generation of vascularised three-dimensional structures is today one of the major challenges in tissue engineering (Eiselt (1998)). Cells can stay alive by diffusion of nutrients only when they are located within .about.100-200 .mu.m of a blood supply (Colton (1995)). It would be desirable to develop methods of creating artificial vascular networks for use in tissue engineering applications that go beyond thin structures such as skin in which nutrients and oxygen can be delivered by diffusion (Cassell (2002)), or avascular tissues such as cartilage.

The general structure of a blood vessel comprises an inner lining of flattened endothelial cells with a cobblestone morphology forming a cell monolayer that is separated from the underlying smooth muscle cells by a thin extracellular matrix, the basement membrane. Endothelial cells possess a negative outer charge that repels platelet adherence, produce glycosaminoglycans that bind antithrombin III, as well as tissue plasminogen activator, which facilitate the anticoagulant and fibrinolytic activities of endothelial cells. In common with most other basement membranes, the basement membrane of blood vessels is mainly composed of laminin-1, collagen IV, nidogen, and proteoglycans. It is well established that the behavior of endothelial cells is influenced by interaction with the basement membrane (Tsilibary (1988); Tashiro (1989); Grant (1989); Skubitz (1990); Sakamoto (1991); Kanemoto (1990); Grant (1990); Nomizu (1997); Ponce (1999); and Malinda (1999)).

(v) Heparin

Heparin and heparan sulfate (HS) are members of the glycosaminoglycan group of complex polysaccharides that includes other carbohydrates such as condroitin sulfate, dermatan sulfate, and keratan sulfate etc. HS is ubiquitously distributed on the cell surface and in the extracellular matrix. Heparin and HS are known to interact with a variety of proteins such as heparin-binding growth factors, extracellular matrix components, selecting, protease inhibitors and lipoprotein lipase and are thereby, implicated not only in various dynamic cellular behaviors including cell proliferation, differentiation, adhesion, migration, and morphological regulation during development. Utilizing the strong affinity between Heparin and heparin-binding growth factors (VEGF, FGFs, PDGF, HGF, TGF-β and BMPs), controlled release of growth factors by biomaterials incorporate Heparin and HS has been investigated (Ishihara et. al, J Biomed Mater Res 64A: 551-559, 2003).

(vi) Growth Factors

Growth factors are naturally occurring proteins capable of promoting cellular proliferation, differentiation and maturation. There are many growth factors well known: Basic fibroblast growth factor (acidic FGF(FGF1) and basic FGF (FGF2)), Vascular endothelial growth factors (VEGF), BMP (bone morphogenic protein), Transforming growth factor beta (TGF-β), Nerve growth factor (NGF), Platelet-derived growth factor (PDGF), Epidermal growth factor (EGF), Hepatocyte growth factor (HGF). The growth factors are not only used for in vitro cell culturing, but also therapeutic purpose. EGF and FGF is used for accelerating wound healing. VEGF and HGF are used for promoting angiogenesis in ischemic disease. BMP is used for accelerating bone regeneration. Although many studies to use growth factors have been performed in the field of tissue regeneration, they have not always been achieved successfully in vivo. One of the reasons for this difficulty is the high diffusibility and the very short half-life time of growth factors in vivo to keep their biological activity. Thus various kinds of controlled release and retention methodology for growth factors has been investigated. (Ishihara et. al, J Biomed Mater Res 64A: 551-559, 2003).

Figure 20:
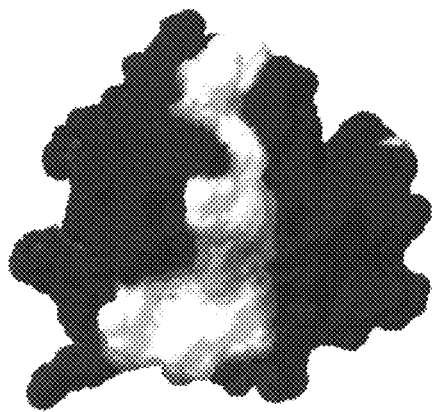
FIG. 20. Molecular charge distribution of bFGF. Dark sections represents positive charge and white sections represents negative charge.

Growth factors are proteins which have total charge and local charge distribution as shown in FIG. 20, for example. The growth factors have local hydrophobic interaction field as well. Thus each of growth factors has different affinity to the different amino acid sequence which has different total charge, local charge distribution and local hydrophobic interaction field. The difference in amino acid sequence used in self-assembling sequence or functional sequence leads to different affinity to certain growth factor, thus the modified self-assembling peptide matrices can be used for controlled release and retention of growth factors.

(vii) Endothelial Cell Function

The endothelial monolayer has multiple functions including facilitating blood flow by providing a nonthrombogenic surface, being a permeable barrier and transport interface for metabolites, modulating the inflammatory response, modulating the contractility of the vascular smooth muscle and the myocardium, and regulating vascular tone and homeostasis, among others (Boeynaems and Pirroton (1994); and Cines (1998)).

Endothelial cells continuously produce, secrete, and remodel their own basement membrane and also synthesize vasoactive autacoids (from Greek autos-self and akos-remedy), that contribute to regulate vascular tone and homeostasis (Busse and Fleming (2003)). Nitric oxide (NO) is one of the best known vasodilators. In biological systems, NO is synthesized from L-arginine by the action of nitric oxide synthase being the other reaction product L-citrulline. Another potent vasodilator and inhibitor of platelet aggregation is prostacyclin (or also called prostaglandin $I_2$, $PGI^2$). $PGI_2$ belongs to the family of eicosanoids, and it is formed from arachidonic acid via prostaglandin $H_2$ ($PGH_2$) by prostacyclin synthetase. A 21 amino acid peptide, endothelin-1 (ET-1) has been shown to promote vasoconstriction. These three substances (and likely others as well) act together as regulators of vessel tone.

It is known that the lack of a healthy endothelium can contribute to major vascular pathologies such as thrombosis. For example, disruption of the smooth endothelial monolayer may occur due to the deposition of lipids and other materials found in atherosclerotic plaques and/or may contribute to the development of atherosclerotic lesions (Cines (1998)). The presence of a confluent monolayer of endothelial cells could improve thromboresistance. It may also prevent or ameliorate other diseases such as pseudointimal hyperplasia, e.g., by preventing the adhesion of platelets, which release bioactive factors that can contribute to smooth muscle recruitment and/or proliferation. In addition, the ability to generate a smooth endothelial monolayer would be useful to restore the integrity of the endothelium following invasive procedures such as angioplasty, catheterization, etc. Therefore, considerable efforts are currently directed to the study of endothelization, both in vitro and in vivo.

A number of researchers have studied the role of extracellular matrix in vascularization. Many such studies involved observation of EC behavior on extracellular matrix derived materials such as Matrigel, a basement membrane derived material obtained from the Engelbreth-Holm-Swarm mouse tumor, or collagen (Grant (1989); Davis (2000); Bell (2001); Davis (2002)). Angiogenic processes such as tube formation have been studied in both 2D and 3D systems (Davis (2000); Bell (2001); Davis (2002)). The interaction of EC with several synthetic peptides (Grant (1989); Grant (1992); Ponce (1999); Nomizu (2001)) has been explored.

G. Tests for Biological Activity

This section describes a variety of tests that can be used to determine whether a peptide is biologically active. The tests described below are provided for exemplary purposes only, and one of ordinary skill in the art will be able to select and employ a variety of additional tests and variations of the tests described herein, depending on the cell type and cell behavior of interest. In any of these tests, soluble peptide can be used as a control. A range of peptide concentrations (both substrate-bound, present as part of a modified self-assembling peptide, or in soluble form) may be used.

Also, it may be desirable to assess and/or monitor any of a variety of indicators of cell phenotype, cell viability or proliferation, cell phenotype, and/or the functional state of the cells or various cellular behaviors. As is well known in the art, there are a number of methods for assessing cell viability, proliferation, and for assessing various aspects of cell behavior and phenotype. In general, any appropriate method may be employed to investigate and assess the effects of culturing cells under the conditions described herein. In addition, the effects of the cells on the overall composition and properties of a cell/hydrogel assembly may be monitored. Such features as protein content, strength, etc., can be examined.

(i) Cell Viability and Proliferation

Cell viability may be assessed by examining vital dye exclusion (e.g., trypan blue exclusion). Cell division may be observed by light microscopy and is indicated by the presence of mitotic figures. An increase in cell number accompanying division may also be observed, e.g., by counting with a hemacytometer. Morphological changes such as cell rounding may also accompany division. DNA synthesis may be monitored by detecting and/or measuring incorporation of various substances such as radiolabeled nucleotides (e.g., $^3$[H] thymidine), bromodeoxyuridine (BrdU), etc., into DNA. Numerous other assays are also available. For example, according to the MTS assay, when the MTS reagent (a tetrazolium salt) is applied to living cells, it is converted to a color compound (formazan) with the emission of light at 490 nm. Kits such as the LIVE/DEAD™ Viability/Cytotoxicity Assay Kit (Molecular Probes, catalog #L-3224) are widely available. Immunostaining using antibodies that bind to proteins indicative of cell proliferation such as proliferating cell nuclear antigen (PCNA) can also be used. Methods for assessing apoptosis are well known in the art and include visual examination, TUNEL, and determination of the level of mRNA or proteins associated with apoptosis, e.g., caspases.

(ii) Cell Attachment

A convenient method to measure cell attachment promoting activity of a peptide is to conjugate the peptide to beads (e.g., sepharose beads) and incubate cells in the presence of the functionalized beads with or without added soluble peptide. Nonfunctionalized beads can be used as a control. Following incubation, cells can be detached using various methods such as treatment with an EDTA-containing solution, stained, and analyzed by microscopy, FACS, etc. (See Nomizu (2001) for further details). Similar methods can be used to test cell attachment to matrices comprising modified and/or unmodified self-assembling peptides.

(iii) Cell Morphology and Spreading

Cell spreading involves a number of morphological features that may differ depending on the cell type. For example, human foreskin fibroblasts typically assume an elongated polygonal cell shape (Hem and Hubbell (1998)) when spread and display an organized F-actin stress fiber network. Cell morphology can be assessed by light microscopy, and the number of cells assuming a morphology characteristic of cell spreading on the modified versus unmodified matrices and/or in the presence or absence of competitor soluble peptide can be assessed.

(iv) Cytoskeletal Organization

Certain peptides affect the organization of the cytoskeleton, which influences cell shape and migration. The organization of F-actin stress fibers within cells can be examined by staining with rhodamine-conjugated phalloidin (Hern and Hubbel, (1998)). For example, cells cultured on a peptide matrix can be fixed in 4% formaldehyde solution, permeabilized (e.g., with 0.1% Triton X-100 in PBS), incubated with rhodamine-conjugated phalloidin, and fixed again. They can then be visualized microscopically, e.g., using epifluorescence microscopy.

(v) Cell Migration

A number of assays are available to quantify cell migration on or through various substrates including matrices comprising the modified self-assembling peptides of the invention. For example, migration can be assessed using a fence-style assay in which cells are cultured on a substrate, e.g., a matrix comprising modified self-assembling peptides, in the presence of a barrier. The location of the barrier is recorded. The barrier is then removed, and the cells are maintained for a period of time. The number of cells that cross the barrier in a given period of time is a measure of cell migration. Values can be corrected to account for cell proliferation, which may differ depending on the substrate. In a variation of the above approach, substrates comprising two or more different surfaces can be created by separating regions of a container by a barrier which is then removed. Differential migration onto various surfaces can be assessed. Migration can also be quantified using a radial Teflon fence migration assay as described for smooth muscle cells (Mann (2002)) and human microvascular endothelial cells (HMVEC) (Sagnella (2004)).

(vi) Cell Differentiation, Dedifferentiation, and Transdifferentiation

These features can be assessed based on a number of parameters, including morphology. Cell differentiation, dedifferentiation, and transdifferentiation may also be assessed by detecting and/or measuring the presence of certain polypeptides or polynucleotides known as markers. The latter approach is widely used, and cellular markers characteristic of numerous different cell types have been identified. mRNA and/or protein expression may be detected by techniques well known in the art. For example, mRNA may be detected and quantified using Northern blots, cDNA or oligonucleotide microarray analysis, RT-PCR, etc. Protein expression may be detected and quantified using immunoblotting analysis, immunofluorescence, FACS analysis, ELISA assays, etc. Such immunological techniques may employ monoclonal or polyclonal antibodies that bind to the protein.

The variety of markers is immense, and new markers are routinely being identified. For example, nestin is an intermediate filament protein expressed in neuroepithelial neuronal precursor stem cells, and its expression decreases with neuronal maturation (Lendahl (1990)). Nestin is considered a marker for immature neurons, and nestin-positive cells can differentiate into either neurons or glia. NeuN is a neuron-specific marker expressed in postmitotic cells (Sarnat (1998)). Glial fibrillarary acidic protein (GFAP) is a classic glial astrocyte marker. Beta III tubulin is another neuron-specific protein. Expression of CYP450 proteins is characteristic of hepatocytes.

Of particular significance in the context of the present invention are markers that may be used to identify vascular endothelial cells and to evaluate functional activity of vascular endothelial cells. Von Willebrand factor is a widely recognized marker for vascular endothelial cells. Other markers for vascular endothelial cells include CD31, DC102, CD106, and isolectin B4 (Williams K S, 1995; "Microvascular endothelium from adipose tissue" Endothelial Cell Culture. Roy Bicknell (ed). Cambridge University Press, 1996). In certain embodiments of the invention the peptide matrix promotes angiogenesis. Markers of angiogenesis include angiogenesis-related growth factors VEGF, Angiopoietins 1 and 2, and their receptors Flt-1, Flk-1, Tie2 (Ferrara (2001); Gale and Yancopoulos (1999)). Monoclonal antibodies directly conjugated with fluorescent dyes that bind to various of these markers are commercially available, e.g., from Dako, Chemicon, etc.

Functional assays can also be used to assess cell phenotype or state. For example, the ability of a cell to take up, produce, or secrete a certain molecule characteristic of a particular cell type, or to perform an enzymatic reaction characteristic of a particular cell type, can be assessed. Uptake of low density lipoprotein (LDL) and release of NO are characteristic of endothelial cells.

(vii) ECM Component Production

It may be of particular interest to assess the effect of various candidate biologically active peptide motifs, active biomolecules, environmental parameters such as application of mechanical forces, etc., on production of ECM components and/or to monitor production of such components over time. A variety of methods for doing so are available. Western blots (or other immunological methods) can be used to quantify production of ECM proteins. For histological analysis, toluidine blue staining of glycosaminoclycan (GAG), a proteoglycan component, can be performed according to standard protocols. Collagen deposition can be measured using known techniques (Toannidis et al., *Cell Tissue Res*. (1999) 297:141-147; Domm et al., *Orthopde* (2000) 29:91-99). Extracellular protein production can be measured by addition of [$^3$H]-proline to the media. The radiolabeled proline is taken up by the cells and incorporated into newly synthesized proteins. Following a time period (e.g., 16-24 hours) in the radiolabeled media, free [$^3$H]-proline is removed by rinsing. The extracellular protein may be digested, e.g., by incubation in a proteinase K solution overnight at approximately 60° C., and the radioactivity present in the digested protein quantitated by scintillation counting. Proteoglycan production can be measured similarly, except that [$^{35}$S]-sulfate is added to the media instead of [$^3$H]-proline. The total accumulation of GAG can be measured based on fluorometric analysis of the amount of DMMB dye bound (Chandrasekhar et al., *Analytical Biochemistry* (1987) 161:103-108).

(viii) Nervous System Assays

There is considerable interest in developing materials that would be useful for in vitro culture of nervous system tissue (e.g., nerves, glial cells), repair and regeneration of nervous system tissue. Various parameters indicative of nervous tissue function can be measured. For example, neurite outgrowth can be assessed by microscopic examination (and, optionally digital image processing) of isolated cells cultured on top of peptide matrices, e.g., PC12 cells (Holmes (2000)). Such cells can also be encapsulated. Another approach is to encapsulate dorsal root ganglia dissected from animals such as chicken and measure average neurite length extending from the ganglia at different time points (Schense and Hubbell (1999); Schense et al., *Nature Biotechnology* (2000) 18: 415-419). Synapse formation can be assessed as described, for example, in Holmes (2000). Production of neurotransmitters and enzymes known to be involved in neurotransmitter synthesis provide additional means of assessing nervous tissue functional activity.

(ix) Endothelial Sprouting

An aortic ring assay, in which aortic rings are isolated from animals such as rats, cultured on top of peptide matrices for a period of time to allow sprouting, followed by fixing and microscopic examination can be used to quantify the ability of a candidate biologically active peptide to induce endothelial sprouting, an important aspect of angiogenesis (Malinda (1999)).

(x) Endothelial Tubeformation

Cell organization and formation of capillary-like structures following culture of ECs on the surface of or encapsulated within peptide matrices can be quantitated at various time points, e.g., 2 hr, 8 hr, 12 hr, 24 hr, 3 days, 1 week and 2 weeks after seeding by determining the correlation length as described in PCT Application Publication No. WO/2003/096972. Staining with hematoxylin and eosin, Massone's trichrome, as well as immunostaining for actin enables visual assessment of endothelial cell cluster formation, sprouting, capillary-like structure formation. The presence of a lumen in the capillary-like structures can be assessed visually and by using automated imaging systems including three-dimensional imaging systems. Methods for assessing tube formation are well known in the art (e.g., Davis (2000); Bell (2001); Davis (2002)).

H. Identification of Additional Amino Acid Domains of Interest

One approach to identifying additional amino acid domains that may be used as the non self-assembling portion of an inventive peptide is to systematically screen peptides derived from the sequence of a naturally occurring protein that is believed to interact with cells, bind to a particular molecule, etc. This approach has been used to identify numerous biologically active peptides as described above. In general, a set of peptides, optionally overlapping, that together encompass all or a significant portion of the sequence is synthesized in vitro. Cells, or a potential binding molecule, are then contacted with individual peptides, and the cellular response, degree of binding, etc., is assessed. The peptides can be labelled to facilitate detection.

In general, peptides obtained from the sequence of any naturally occurring protein can be screened including, but not limited to, the proteins specifically discussed above. One of ordinary skill in the art will readily be able to locate the complete sequence for these proteins, related proteins, other proteins of interest (e.g., other ECM proteins), genes encoding the proteins, etc., in publicly available databases such as those available through the National Center for Biotechnology Information (see web site having URL www.ncbi.nlm.nih.gov) using, for example, the Entrez search engine. Databases can be searched by gene or protein name, by nucleotide sequence (e.g. by searching GenBank) or protein sequence, etc. For example, genes encoding collagen IV proteins can be identified by searching the Gene database using the term "collagen." The results contain links to the protein sequence, from which candidate amino acid domains of interest can be selected (links have been removed). Proteins containing a particular sequence domain or a domain related in sequence to a particular domain can be identified by searching with the sequence of interest. Proteins containing similar but not identical sequences could readily be identified.

As mentioned above, other proteins of interest include additional ECM proteins, e.g., additional basement membrane proteins. Peptide matrices particularly suitable for different cell types may be created by screening proteins known to be present in the ECM on or in which that cell type is typically found. For example, the basement membrane in which different cell types are commonly found may contain different isoforms of laminin, collagen, etc. Amino acid domains can be selected from proteins present in the extracellular environment of any cell type of interest. While not wishing to be bound by any theory, it is possible that such proteins will be favorable for culture of that cell type and/or for introduction into the body at a site known to contain cells of that type or at which it is desired to implant or attract cells of that type.

Thus the invention provides a method for designing a self-assembling peptide for formation of a peptide matrix for a cell type of interest comprising identifying an amino acid domain present in a naturally occurring protein present in the extracellular environment of that cell type (e.g., in the ECM or basement membrane on or in which the cell type is naturally found), screening the peptide to determine whether it produces a biological effect on the cell (either when present in a peptide matrix or otherwise present in the environment of a cell, as described above), utilizing the amino acid domain as the second amino acid domain of a modified self-assembling peptide, and testing a matrix comprising the modified self-assembling peptide to determine whether it is favorable for cell growth, results in altered cell phenotype, etc. The screening step can be omitted, i.e., the candidate peptide can be directly incorporated as part of a modified self-assembling peptide without first testing it for biological effect, if desired.

Another approach is to employ display techniques involving peptide libraries such as phage display, cell surface display, or ribosome display (see Sarikaya (2004) and references therein). Phage display and cell surface display employ chimeric proteins that are naturally present on the surface of a phage or cell. The chimeric protein generally contains all or part of a naturally occurring phage or cell surface protein, and a second domain that contains a random peptide sequence encoded by a nucleic acid expressed by the phage or cell. A portion of the nucleic acid has typically been randomized by any of various molecular biological techniques prior to its introduction into the phage or cell (or a precursor thereof), or can be altered thereafter by mutation. A library of phage or cells, each expressing a different version of the chimeric protein on its surface, is contacted with a target (e.g., a ligand which can be immobilized or a population of cells). Following the contacting step, weakly binding cells or phage expressing chimeric proteins are washed away while strong binders remain. The process is repeated to enrich for tight binders (biopanning). Various methods of performing directed evolution can also be used.

Another approach to identifying useful amino acid domains is to make a limited number of mutations to known biologically active peptide motifs, binding peptides, etc., e.g., by substitution of one or more amino acids. This may identify peptides with improved properties relative to the starting sequence. The invention encompasses the use of amino acid domains whose sequence differs from that of sequences listed herein by 1, 2, or 3 amino acid residues.

I. Characterization of Self-Assembling Peptides

Structures (e.g., nanofibers, macroscopic structures, hydrogels) formed by any of the unmodified self-assembling peptides or the modified self-assembling peptides of the present invention, or composites thereof, may be characterized using various biophysical and optical techniques. Suitable techniques include visual inspection, circular dichroism (CD), dynamic light scattering, Fourier transform infrared spectroscopy (FTIR), rheological assays such as oscillatory rheometry, atomic force microscopy (ATM), scanning electron microscopy (SEM), and transmission electron microscopy (TEM). For example, biophysical methods may be used to determine the degree of beta-sheet secondary structure in the peptide matrix. Additionally, filament and pore size, fiber diameter, length, elasticity, and volume fraction may be determined using quantitative image analysis of scanning and transmission electron microscopy.

Peptide matrices may also be examined using several standard mechanical testing techniques to measure the extent of swelling, the effect of pH and ion concentration on matrix formation, the level of hydration under various conditions, and the tensile strength. Parameters such as the elastic modulus can be measured. These methods allow one of ordinary skill in the art to determine which of the various modifications and additions to the peptides described below are suitable for use in the methods of the invention. Non-limiting descriptions of certain techniques that may be used are described in the following sections.

In addition to, or instead of, assessing gel formation in a quantitative manner, e.g., using the rheological tests described herein, more qualitative assessments, including simple visual examination, can be used. A reproducible assessment of gel formation involves probing a composition using a paperclip by stirring and sweeping the material up the sides of a vessel containing the composition, such as a microfuge tube (Sperinde, J C and Griffith L G, *Macromolecules* (2000), 33:5476-5480). A composition can be considered to undergo gelation when it seizes to the paper clip. Further gelation or reversibility of the gel state can be assessed with additional probing. Further gelation would result in a stronger, less viscous material.

(i) Rheometry

Rheological assays can be performed to test the vicoelastic properties of the peptide matrices. For example, oscillatory rheometry, which subjects samples to oscillating stresses or oscillating strains, can be performed, e.g., using a controlled strain rheometer, which shears the sample at a controlled strain within a range of frequencies. Various rheometers that can be used are commercially available. Principles of rheometry and its applications to gels, are described, for example, in Clark A H, Ross-Murphy, S B, Structural and Mechanical Properties of Biopolymer Gels, Springer-Verlag, Berlin, 1987; Vol. 83, pp. 58-192 (85-86); and Kavanagh, G. M., Ross-Murphy, S B, "Rheological characterization of polymer gels," *Prog. Polym. Sci.* (1998) 23:533-562.

In general, the output from such a test is G*, the complex modulus. This complex modulus can be defined as:

$$G^* = G' + iG'' \qquad [\text{eq. 1}]$$

In this equation:

G' is the storage modulus which represents the elastic/solid character of the material.

G" is the loss modulus which represents the viscous/fluid character of the material.

In oscillatory rheometry, for a viscous solution, the viscous component of the complex modulus, the loss modulus (G") typically decreases with decreasing oscillatory frequencies, and the storage modulus G' is low. For gels, G' and G" are relatively constant with oscillatory frequency. For example, in preferred embodiments of the invention, the magnitudes of dG'/dw and dG"/dw are less than 2 or, more preferably, less than 1, over a frequency range within the linear region, when measured with a dynamic frequency sweep test, where G' and G" are measured in Pascals (Pa) and w represents frequency in rad/s. The frequency range can be, for example, between 0.1 and 1 rad/s, between 1 and 10 rad/sec, etc. In other preferred embodiments of the invention, the magnitudes of dG'/dw and dG"/dw are less than 0.5, less than 0.2, or less than 0.1 over a frequency range within the linear region, when measured with a dynamic frequency sweep test, where G' and G" are measured in Pa and w represents frequency in rad/s.

For gels, G' is typically greater than zero. In preferred embodiments of the invention G' of a composition formed by self-assembly of an inventive modified self-assembling peptide is greater than or equal to 0.5 Pa. In other preferred embodiments of the invention, G' of a composition formed by self-assembly of an inventive modified self-assembling peptide is greater than or equal to 1.0 Pa, greater than or equal to 5 Pa, greater than or equal to 10 Pa, between 10 and 100 Pa, or greater than 100 Pa when measured in a linear region using a dynamic frequency sweep test. The linear region may be, for example, between 0.1 and 1 rad/s, between 1 and 10 rad/sec, or between 10 and 100 rad/sec. When performing such measurements, a dynamic strain sweep may first performed on the material to set the linear viscoelastic region of the test and to select a fixed strain for dynamic frequency sweep tests. This linear viscoelastic range is generally defined by constant moduli, G' and G". It is important to select a strain within this range to obtain reliable results (see, for example, Schramm G. (1994) *A Practical Approach to Rheology and Rheometry*, Gebrueder HAAKE GmbH, Karlsruhe, Germany). For example, for the peptide matrices tested in Example 1 the strain selected was 0.01 (dimensionless) and was applied in all assays.

The above description is not intended to limit the invention but simply relates to certain embodiments thereof. Indeed it is noted that a gel has been defined as "any substance that in solution or not creates cross-linking interactions (covalent or non-covalent) to form a network," with the understanding that the substance retains some elastic properties in terms of the deformation of the material under low stress (Scaling Concepts in Polymer Physics by Pierre-Gilles de Gennes, Cornell University Press (1979)). In the case of a hydrogel, the network retains a significant amount of water.

(ii) Atomic Force Microscopy

Atomic force microscopy (AFM) is a technique that allows resolution of surface structures down to the nanometer scale by measuring the interaction of a microscopic sharp tip used to scan the sample surface and the sample. AFM involves scanning a sharp tip on the end of a flexible cantilever across a sample surface while maintaining a small, constant force. The scanning motion is conducted by a piezoelectric tube scanner which scans the tip in a raster pattern with respect to the sample (or scans the sample with respect to the tip). The tip-sample interaction is typically monitored by a reflecting laser off the back of the cantilever into a split photodiode detector. By detecting the difference in the photodetector output voltages, changes in the cantilever deflection or oscillation amplitude can determined.

There are two most commonly used modes of operation: contact mode AFM and TappingMode.TM. AFM which are conducted in air or liquid environments. Contact mode AFM operates by measuring repulsive forces between a tip and the sample (Binning et al, 1986). The instrument lightly touches the tip. In TappingMode.TM. AFM, the images are derived from measurements of attractive forces, the tip does not touch the sample. It oscillates at its resonance frequency lightly "tapping" on the surface during scanning. TappingMode.TM. AFM may be particularly appropriate for assessing nanofiber formation in peptide matrices of the invention because it allows measurements to be made on soft, fragile and adhesive surfaces without damaging them, which can be a drawback for contact mode AFM.

J. Therapeutic Applications

A peptide structure made by self-assembly of the modified self-assembling peptides of the invention or by self-assembly of combinations of modified and unmodified self-assembling peptides described herein, may be used to treat a variety of tissue defects and diseases. Peptide hydrogel structures, either with or without cells growing on the surface or encapsulated within may be implanted into the body, e.g., surgically or using any other type of suitable procedure. Other routes, including oral, percutaneous, intramuscular, intravenous, and subcutaneous may be employed. One of ordinary skill in the art will be able to select an appropriate delivery technique.

In general, the methods and compositions of the invention may be useful in any situation involving injury or damage to tissue. Such injury may occur as a result of surgery, trauma, tumor, degenerative disease, or other diseases or conditions. The injury may, but need not, involve death of cells. The methods and compositions are useful to restore structural and/or functional integrity to the tissue, i.e., to aid in restoring the tissue to the functional or structural condition that existed prior to the injury. Certain injuries may result in physical barriers that can impede regeneration or repair of tissue. Such barriers may include areas of necrosis, cavitation, or scar tissue formation. In certain embodiments of the invention introducing the materials described herein at a site of injury allows cell or tissue growth from a location proximal to the site of injury or barrier to a location distal to the site of injury or barrier.

Certain compositions and methods of the present invention may be used to ameliorate the effects of disease or degeneration of an organ, to repair an injury to an organ or other body structure or to form an organ or other body structure. Such organs or body structures include, but are not necessarily limited to, vascular tissue, brain, nervous tissue, esophagus, fallopian tube, heart, intestines, gallbladder, kidney, liver, lung, ovaries, pancreas, prostate, bladder, bone, spinal cord, spleen, stomach, testes, thymus, thyroid, trachea, ureter, urethra, uterus, and skin.

In general, a variety of devices may be used to introduce the matrix material at the site of injury. Delivery via a syringe is one convenient technique. Peptides can also be introduced by catheter or directly at a site of surgery. In certain embodiments of the invention a peptide solution in which peptides are unassembled or minimally assembled (i.e., a solution that has not formed a gel) is introduced into the body. In other embodiments of the invention matrix formation is allowed to occur in vitro and the assembled matrix is introduced into the body.

Peptide scaffolds encapsulating cells may be used for a variety of therapeutic purposes. Unassembled peptides and cells may be mixed in vitro and the structure may then self-assemble after administration and encapsulate the cells in vivo. As described above, in certain embodiments of the invention the administered solution contains less than 10 mM, 5 mM, 1.0 mM, or 0.1 mM ion (e.g., cation) or is substantially free of ions (e.g., cations), and the concentration of the iso-osmotic solute is at least 50 mM, 150 mM, or 300 mM. In other embodiments, the concentration of iso-osmotic solute is contained in one of the following ranges 200 to 250 mM, 250 to 270 mM, 270 to 300 mM, 300 to 400 mM, 400 to 500 mM, 500 to 600 mM, 600 to 700 mM, 700 to 800 mM, or 800 to 900 mM, inclusive. Suitable iso-osmotic solutes have been described above and herein, and include, but are not limited to, carbohydrates, such as sucrose.

Any of the cell types mentioned above may be used. Thus in addition to or instead of vascular endothelial cells, the compositions of the present invention may include a variety of other cell types and/or precursors of such cell types. The cell(s) may be autologous or non-autologous. They may be allogeneic or non-allogeneic. They may be from the same species as the subject into which they are to be introduced or from a different species. They may be fetal or adult.

In various embodiments of the invention one or more additional substances is added to the peptide matrix either prior to or following self-assembly. The substance may serve any of a number of purposes, including, but not limited to, those described below. If the matrix is implanted into the body, growing cell processes or tissues may contact the substance as they extend or grow into the area occupied by the peptide matrix. In certain embodiments of the invention the substance is released from the matrix, e.g., by diffusion, or by release from the matrix as it degrades over time. The particular peptide sequence, and/or peptide concentration and parameters such as degree of cross-linking may be selected to provide a desired rate of degradation and release of the substance. The substance may contact cells and tissues at or near the site of implantation and/or may enter the bloodstream and travel to more distant locations. Substances that can be added include, but are not limited to, antibiotics or antifungal agents to treat or reduce the risk of infection, chemotherapeutic agents to treat tumors, etc. The peptide solution, of a macroscopic structure formed therefrom may thus comprise a therapeutically active compound or chemoattractant. Examples of such compounds include natural or synthetic small molecules; nucleic acid molecules such as nucleic acid molecules that mediate RNA interference (RNAi) (Dorsett and Tuschl (2004), and references therein), e.g., short inteferering RNAs (siRNAs) or short hairpin RNAs (shRNAs), ribozymes, or plasmids; peptides or proteins such as integrins or cell adhesion molecules; proteins such as antibodies, etc.

In certain embodiments of the invention the peptide solution, or a macroscopic structure formed therefrom, incorporates an agent that enhances or promotes differentiation, dedifferentiation, or transdifferentiation, e.g., a growth factor, such as vascular endothelial growth factor, granulocyte macrophage colony stimulating factor, angiopoietin 1 or 2, epidermal growth factor, nerve growth factor, transforming growth factor-.alpha., transforming growth factor-beta, tumor necrosis factor alpha, platelet-derived growth factor, insulin-like growth factor, acidic fibroblast growth factor, basic fibroblast growth factor, hepatocyte growth factor, brain-derived neurotrophic factor, keratinocyte growth factor, a bone morphogenetic protein, or a cartilage-derived growth factor. Combinations of growth factors and/or therapeutic agents or chemoattractants may be used. Peptide hormones may also be used. Naturally occurring peptides or modified versions including peptides such as atrial natriuretic peptide may be used.

The macroscopic structure may incorporate an agent that induces reentry into the cell cycle. Such agents may be added to the peptide solution or to the electrolyte solution prior to initiation of self-assembly. In this case the concentration of the agent will likely be substantially uniform within the assembled structure. In certain embodiments of the invention the agent is added to media with which the peptide structure is incubated before or after addition of cells. After addition to the media, a portion of the agent enters the peptide structure, e.g., through diffusion. This process may create a gradient. Cells on or in different regions of the structure may exhibit different responses to the agent depending upon the concentration of the agent at the location of the cell. Substances that counteract the effect of a molecule that is inhibitory for tissue regeneration or repair, whether by causing degradation, sequestering, reducing expression, or blocking interaction of the molecule with a cell, may also be incorporated.

Growth factors are typically used at concentrations ranging between about 1 fg/ml to 1 mg/ml. Frequently growth factors are used at concentrations in the low nanomolar range, e.g., 1-10 nM. In certain embodiments of the invention growth factors are used at concentrations that are not typically used in the prior art or that are not typically found in vivo under normal conditions. For example, growth factors may be used at concentrations that are 5 fold greater, 10 fold greater, 20 fold greater, 100 fold greater, etc., than is typically required to produce effects or than typically occurs in vivo. Titration experiments can be performed to determine the optimal concentration of a particular agent, such as a growth factor, depending upon the particular effects desired. Factors may be added in purified form or as components of a complex biological mixture such as serum.

As described above, repair and regeneration of tissue can be enhanced by supplying factors such as growth factors, cell adhesion molecules, integrins, etc. One way to provide such molecules (or others), is to deliver cells at the site of injury. The cells may produce molecules that promote regeneration or otherwise contribute to producing an environment permissive for regeneration. Various progenitor cells may also be useful. Any of these cell types may be incorporated into the matrix. In addition, any of these cell types (or others) can be genetically modified, e.g., to increase the production of a regeneration promoting factor, prior to incorporation into the matrix.

Gene therapy techniques may be used to increase expression of genes that encode desirable products. Gene therapy encompasses delivery of nucleic acids comprising templates for synthesis of a molecule of interest to a cell of interest. The nucleic acid (or a nucleic acid derived from the nucleic acid as, for example, by reverse transcription) may be incorporated into the genome of the cell or remain permanently in the cell as an episome. However, gene therapy also encompasses delivery of nucleic acids that do not integrate or remain permanently in the cell to which they are delivered. Such approaches permit temporary or transient synthesis of a molecule of interest.

Vectors and vehicles that provide nucleic acids comprising templates for synthesis of desirable molecules may be incorporated into peptide matrices, from which they may be taken up by cells at or near a site of injury. Preferably the nucleic acid includes a coding sequence for a gene to be expressed in a cell of interest and also includes appropriate expression signals, e.g., promoters, terminators, etc., to ensure proper expression. In certain embodiments of the invention the expression signal(s) are cell type specific, so that the gene will only be expressed in cells of a particular cell type.

In general, either viral or non-viral vectors may be used. In certain embodiments of the invention the vector is a viral vector that is able to infect neurons. For example, herpes virus, adenovirus, adeno-associated virus, retroviruses, or lentiviruses may be used. It may be preferable to avoid the use of intact viruses in delivering templates to cells. Thus it may be preferable to deliver DNA vectors or linear DNA molecules. These vectors may, but need not, include viral sequences such as long terminal repeats, etc. Any of a wide variety of agents useful for transfection may be used to enhance uptake of nucleic acids by cells. Such agents include a wide variety of cationic polymers and modified cationic polymers, lipids, etc. Cell-type specific targeting ligands, e.g., ligands or antibodies that specifically bind to a molecule expressed on a cell type of interest may be attached to a gene therapy delivery agent to allow introduction of the agent into only certain cell types. In general, the nucleic acid and any appropriate gene therapy delivery agent (e.g., a cationic polymer) may be incorporated into the matrix in any of the ways discussed herein.

In certain embodiments of the invention a therapeutically desirable genetic modification may be made. For example, in a case where an individual harbors a mutation in a particular gene it may be desirable to introduce a wild-type copy of the gene into the progenitor cell for gene therapy purposes. In certain embodiments of the invention it may be desired to introduce a gene encoding a particular receptor, e.g., a growth factor receptor, in order to confer or enhance a particular differentiation, dedifferentiation, or transdifferentiation potential by allowing cells to respond to the growth factor.

The number of cells to be administered for therapeutic purposes, the relative proportion of cells of different phenotypes, and/or the concentration of cells within a peptide structure can be altered as appropriate for the particular condition or injury to be treated.

In certain embodiments of the invention cells, e.g., vascular endothelial cells and/or their progeny that have proliferated and/or differentiated on or within a peptide structure are removed or extracted from the structure. Removal or extraction may be accomplished by any suitable means, including removal with a suction pipette, mechanical disruption of the matrix, enzymatic degradation of the structure in vitro, etc. In certain embodiments of the invention the method selected results in removal or extraction of approximately 10% of cells, between 10% and 25% of the cells inclusive, between 25% and 50% of the cells inclusive, between 50% and 75% of the cells inclusive, or between 75% and 100% of the cells inclusive. Methods that result in any convenient range may be selected. The method selected may depend upon the purposes for which the cells are to be used, the number of cells required, etc. In certain embodiments of the invention the viability of the removed or extracted cells is approximately 10% of cells, between 10% and 25% inclusive, between 25% and 50% of cells inclusive, between 50 and 75% of cells, inclusive, or between 75% and 100% of cells inclusive. Methods that result in any convenient range may be selected. The method selected may depend upon the purposes for which the cells are to be used, the number of cells required, etc.

The extracted cells may be further cultured in vitro, either on or in a peptide hydrogel structure or in any other culture vessel. The extracted cells may be administered to a subject by any appropriate route, including intravenous, subcutaneous, oral, percutaneous, intramuscular, or surgical. The administered cells may be used to supplement a tissue, organ, or body structure, e.g., a tissue, organ, or body structure suffering from a deficiency of vascular tissue. The administered cells may synthesize or otherwise supply a therapeutic agent. For example, the administered cells may supply a protein, e.g., an enzyme that the individual lacks. The administered cells may be genetically modified and thus used as a means to deliver gene therapy.

The self-assembling peptides of the invention may be used to promote formation of a layer of vascular endothelium at a site of injury, e.g., following a procedure such as angioplasty. They can also be used as coating materials, e.g., for devices such as vascular grafts or stents, to promote endothelialization. In an alternate approach, the peptides form a layer on the inner surface of an artificial conduit such as an artificial blood vessel. Endothelial cells are cultured on the layer formed by self-assembly of the peptides for a period of time. The cells secrete ECM components. The cells may then be removed, leaving behind an intact basement membrane layer containing ECM molecules synthesized by the cells. The artificial conduit is then implanted into a host. In another approach, the conduit is implanted into a host without removal of the endothelial cells.

The inventive self-assembling modified peptides and structures containing them can be used as or within nerve guides, e.g., to promote regeneration of axons and nerves in the peripheral nervous system.

The inventive self-assembling modified peptides and structures containing them can be used as or within bone, e.g., to promote the regeneration of bone cells and acceleration of bone regeneration, and/or by the enhancement of osteoblast activity mineralization and pre-osteoblast or stem cell proliferation differentiation.

K. Kits

The invention provides kits that may be used for culturing cells and/or for forming peptide matrices that can be introduced into the body of a subject. The kits comprise one or more self-assembling peptides of the invention, which may be provided in dry or lyophilized form, in solution, or in assembled or partially assembled form. The kits may further comprise one or more of the following items: a population of cells, cell or tissue culture medium, a predetermined amount of a growth factor, a predetermined amount of an ion or salt thereof, instructions for preparing the self-assembling peptide for cell culture, instructions for culturing cells on or within a peptide hydrogel structure (e.g., for encapsulating cells), instructions for introducing the self-assembling peptide into a subject, a vessel in which cell culture may be performed, a liquid in which the peptide can be dissolved, a syringe, an ion or salt thereof for initiating peptide self-assembly, one or more growth or differentiation factors, medium for tissue culture, cells (e.g., vascular endothelial cells), control peptide, etc. Additional items may also be included.

III. Summary of Various Embodiments of the Present Invention (i) Modified Self Assembling Peptide Thus, as is described and discussed generally above, the present invention provides a modified self-assembling peptide comprising:

(a) a first amino acid domain that mediates self-assembly, wherein the domain comprises alternating hydrophobic and hydrophilic amino acids that are complementary and structurally compatible and self-assemble into a macroscopic structure when present in unmodified form; and (b) a second amino acid domain that does not mediate self-assembly in isolated form, wherein the second amino acid domain comprises at least one minimal biologically active sequence.

In certain embodiments, first amino acid domain comprises at least two instances of any one of the following amino acid sequences: -RADA- (SEQ ID NO.67); -IEIK- (SEQ ID NO.68); or -FKFQ-(SEQ ID NO.69). In some embodiments, the first amino acid domain comprises any one of the amino acid sequences provided in Table 1. In other embodiments, the first amino acid domain comprises -RADARADARA-DARADA- (SEQ ID NO: 21); -FKFQFKFQFKFQ- (SEQ ID NO: 51); -IEIKIEIK- (SEQ ID NO: 52) or-KLDLKLD-LKLDL-(SEQ ID NO: 53).

In certain embodiments, the second amino acid domain comprises at least two minimal biologically active sequences. In other embodiments, the second amino acid domain comprises at least three minimal biologically active sequences. In yet other embodiments, the minimal biologically active sequences are selected from the sequences as provided in Table 2a. In certain embodiments, the at least one minimal biologically active sequence includes -RGD-.

In some embodiments, the second amino acid domain is covalently or non-covalently attached to the C-terminus of the first amino acid domain. In other embodiments, the second amino acid domain is covalently attached to the C-terminus of the first amino acid domain by a covalent peptide bond. In still yet other embodiments, the second amino acid domain is covalently attached to the C-terminus of the first amino acid domain by an amino acid linker group, as is described herein.

In certain embodiments, the distance between the last amino acid of the first amino acid domain and the first amino acid of the minimal biological active sequence in the second amino acid domain is at least 2-mer (6.9 Angstrom). In other embodiments, the distance between the last amino acid of the first amino acid domain and the first amino acid of the minimal biological active sequence in the second amino acid domain is about 2-mer (6.9 Angstrom). In yet other embodiments, the distance between the last amino acid of the first amino acid domain and the first amino acid of the minimal biological active sequence in the second amino acid domain is less than about 2-mer (6.9 Angstrom).

In certain embodiments, the distance between the last amino acid of the first amino acid domain and the first amino acid of the minimal biological active sequence in the second amino acid domain is at least 4-mer (13.8 Angstrom). In other embodiments, the distance between the last amino acid of the first amino acid domain and the first amino acid of the minimal biological active sequence in the second amino acid domain is about 4-mer (13.8 Angstrom). In yet other embodiments, the distance between the last amino acid of the first amino acid domain and the first amino acid of the minimal biological active sequence in the second amino acid domain is less than about 4-mer (13.8 Angstrom).

In certain embodiments, the distance between the last amino acid of the first amino acid domain and the first amino acid of the minimal biological active sequence in the second amino acid domain is at least 8-mer (27.5 A Angstrom). In other embodiments, the distance between the last amino acid of the first amino acid domain and the first amino acid of the minimal biological active sequence in the second amino acid domain is about 8-mer (27.5 A Angstrom). In yet other embodiments, the distance between the last amino acid of the first amino acid domain and the first amino acid of the minimal biological active sequence in the second amino acid domain is less than about 8-mer (27.5 A Angstrom).

In certain embodiments, the second amino acid domain is biologically active in isolated form.

In certain embodiments, the second amino acid domain is derived from a heparin binding domain of a cell attachment protein. In some embodiments, the cell attachment protein is selected from the group consisting of fibronectin, vitronectin, laminin, collagen, VEGF, FGFs, PDGF, HGF, TGF-β and BMP. In other embodiments, the heparin binding domain is of the formulae (I) or (II):

-XBBXBX- (I)

or

-XBBBXXBX- (II)

wherein X represents a hydrophobic amino acid selected from the group consisting of F, I, L, P, M, W, Y, V, A, C and Q;

and B represents a positively charged amino acid selected from the group consisting of R, H and K.

In certain embodiments, the modified self-assembling peptide, as defined above and herein, has a net positive or negative charge. In some embodiments, this charge is measured in an aqueous solution of pH of between about 5-9, inclusive. In other embodiments, the self-assembling peptide has a pI of greater than or equal to 8. In still yet other embodiments, the net charge of the self-assembling peptide is greater than or equal to about 2 when the pH of the solution is between about 6-8, inclusive.

In certain embodiments, the first amino acid domain is near-neutral, or has a positive or negative charge. In some embodiments, this charge is measured in an aqueous solution of pH of between about 5-9, inclusive. In other embodiments, the first amino acid domain is has a charge of between −1 to 1 when the pH of the solution is between about 6-8, inclusive. In yet other embodiments, the first amino acid domain has a pI of between 5 to 9, inclusive.

In other embodiments, the second amino acid domain has a positive or negative charge. In some embodiments, this charge is measured in an aqueous solution of pH of between about 5-9, inclusive. In other embodiments, the second amino acid domain has a charge of less than or equal to −2 when the pH of the solution is between about 6-8, inclusive.

In certain embodiments, the second amino acid domain does not self-assemble when present in isolated form but permits assembly of the first amino acid domain such that the peptide assembles to form a macroscopic structure. In certain embodiments, this macroscopic structure comprises nanofibers and/or beta-sheets.

In other embodiments, the peptide self-assembles when present as the sole peptide in a solution. In certain embodiments, the solution is an aqueous solution.

In yet other embodiments, the self-assembling peptide does not self-assemble when present as the only peptide in a solution but does self-assemble when present in a solution with an unmodified self-assembling peptide, as is defined herein.

In still yet other embodiments, the modified self-assembling peptide further comprises a third amino acid domain, wherein the third amino acid domain comprises either:

(a) a first amino acid domain that mediates self-assembly, wherein the domain comprises alternating hydrophobic and hydrophilic amino acids that are complementary and structurally compatible and self-assemble into a macroscopic structure, or (b) a second amino acid domain that does not self-assemble in isolated form but permits assembly of the first amino acid domain such that the peptide assembles to form a macroscopic structure. Such a modified self-assembling peptide (which incorporates this third amino acid domain) may be a linear peptide chain in which an amino acid domain that comprises the minimal biologically active sequence or target site for an interaction with a biomolecule is located between two amino acid domains that mediate self-assembly, wherein the domains that mediate self-assembly comprise alternating hydrophobic and hydrophilic amino acids that are complementary and structurally compatible and self-assemble into a macroscopic structure (e.g., nanofibers and/or beta-sheets).

In certain embodiments, the modified self-assembling peptide is selected from the peptides of Table 2b.

In certain embodiments of the invention, the modified self-assembling peptide comprises a minimal biologically active sequence which has an affinity to, or complexes with, a biological molecule. Such biological molecules are described herein, and include, but are not limited to, proteins or peptides (e.g., heparin, heparan sulfate, growth factors, and the like) and/or cells (e.g., osteoblasts, chondrocytes, bone marrow cells, osteocytes, periosteal cells, perichondrial cells, fibroblasts, mesenchymal cell, mesenchymal stem cell, adipose derived cells, adipose derived stem cells, neuronal cells, hippocampal cells, epidermal cells, endothelial cells, epithelial cells, keratinocytes, basal cells, spinous cells, granular cells, embryonic stem cells, ovarian cells, pancreatic cells, cervical cells, liver cells, foreskin cells, neutrophils, lymphocytes, macrophages, dendritic cells, or precursors of any of the foregoing).

(ii) Pharmaceutical Compositions

The present invention also provides pharmaceutical compositions comprising a modified self-assembling peptide, as described above and herein.

The modified self-assembling peptides, pharmaceutical compositions thereof and/or matrices of the present invention may be injected or surgically implanted into the body. The peptide/composition/matrix may be injected into the body via a variety of routes, such as intravenous, intramuscular, intraarterial, intramedullary, intrathecal, subcutaneous, and/or intraventricular injection. Specifically contemplated routes are regional administration via blood and/or lymph supply, and/or direct surgical administration to the site of the defect. In general the most appropriate route of administration will depend upon a variety of factors including the nature of the peptide/composition/matrix employed (e.g., its stability in the environment delivered), the location of the defect, and the condition of the subject (e.g., whether the subject is able to tolerate such administration), etc.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

The self-assembling peptides, pharmaceutical compositions thereof and/or matrices thereof may be administered (via injection and/or surgical implantation) using any amount/weight/concentration effective for treatment. The compositions may be formulated in dosage unit form for ease of administration. The specific therapeutically effective amount for any particular subject or organism will depend upon a variety of factors, including, but not limited to, the nature and/or activity of the peptide/composition/matrix employed; the age, body weight, general health, sex and diet of the subject; the time and/or route of administration; the biodegradation rate of the peptide/composition/matrix employed; the duration of the treatment; and/or additional biologically active agents used in combination or coincidental with the administration of the peptide/composition/matrix.

A variety of pharmaceutical formulations are contemplated by the present invention. For example, in certain embodiments, the pharmaceutical formulation is a modified self-assembling peptide solution (e.g., for injection). In certain embodiments, the pharmaceutical formulation is a matrix comprising a modified self-assembling peptide (e.g., for injection and/or implantation). In certain embodiments, the matrix is a gel or hydrogel.

Figure 36A:
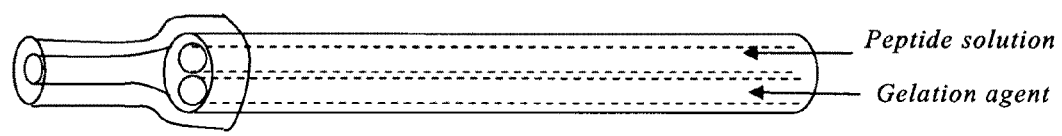
FIGS. 36A-36B. Exemplary administration of modified self-assembling peptides, pharmaceutical compositions thereof, and/or matrices made therefrom.

In certain embodiments, the present invention provides a pharmaceutical composition comprising an injectable modified self-assembling peptide solution. In certain embodiments, the composition is injected to a defect by syringe with a needle or thick tube. In certain embodiments, the composition is injected by syringe to a defect by catheter (e.g., for trans vascular delivery and endoscopic delivery). In certain embodiments, the pharmaceutical composition comprises pre-mixing a gellation agent and an injectable modified self-assembling peptide solution immediately prior to injection (see, for example, FIG. 36A which depicts administration of a peptide solution and a gellation agent via syringe/catheter, wherein the peptide solution and gellation agent pre-mix at the tip of the syringe/catheter immediately prior to injection into a body).

In certain embodiments, the present invention provides a pharmaceutical composition comprising an injectable modified self-assembling peptide matrix. In certain embodiments, the composition is injected to a defect by syringe with a needle or thick tube. In certain embodiments, the composition is injected by syringe to a defect by catheter (e.g., for trans vascular delivery and endoscopic delivery).

In certain embodiments, the pharmaceutical composition further comprises one or more growth factors. In certain embodiments, one or more growth factors are pre-mixed with a modified self-assembling peptide solution prior to injection. In certain embodiments, the pre-mixed composition is stored in a sterilized syringe or container (e.g., a storage bottle, vial, etc). However, in certain embodiments, the a solution of one or more growth factors and the peptide solution are separately stored, and the growth factor solution is pre-mixed with a modified self-assembling peptide solution only immediately prior to injection (such as, for example, the set-up depicted in FIG. 36A).

In certain embodiments, the pharmaceutical composition further comprises a solid material (e.g., a granule). In certain embodiments, a solid material is pre-mixed with a modified self-assembling peptide solution prior to injection. In certain embodiments, the pre-mixed composition is stored in a sterilized syringe or container (e.g., a storage bottle, vial, etc). However, in certain embodiments, a solid material and the peptide solution are separately stored, and the solid material is pre-mixed with a modified self-assembling peptide solution only immediately prior to injection (such as, for example, the set-up depicted in FIG. 36A).

In certain embodiments, the pharmaceutical composition further comprises an biological molecule (e.g., such as a protein or peptide, as described herein). In certain embodiments, the biological molecule is pre-mixed with a modified self-assembling peptide solution prior to injection. In certain embodiments, the biological molecule is stored in a sterilized syringe or container (e.g., a storage bottle, vial, etc). However, in certain embodiments, the biological molecule and the peptide solution are separately stored, and a solution of the biological molecule is pre-mixed with a modified self-assembling peptide solution only immediately prior to injection (such as, for example, the set-up depicted in FIG. 36A).

Figure 36B:
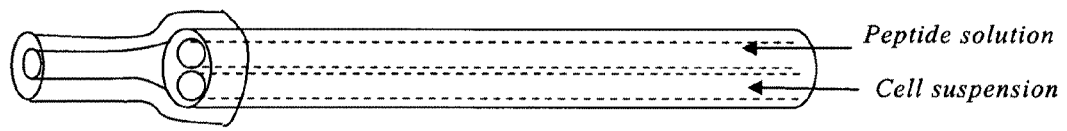

In certain embodiments, the pharmaceutical composition further comprises cells. In certain embodiments, cells are pre-mixed with a modified self-assembling peptide solution prior to injection. In certain embodiments, the pre-mixed composition is stored in a sterilized syringe or container (e.g., a storage bottle, vial, etc). However, in certain embodiments, cells/cell suspension and the peptide solution are separately stored, and the cells/cell suspension is pre-mixed with a modified self-assembling peptide solution only immediately prior to injection (such as, for example, the set-up depicted in FIG. 36B).

In certain embodiments, the pharmaceutical composition further comprises an additional unmodified self-assembling peptide (e.g., such as the peptides depicted in Table 1) comprising alternating hydrophobic and hydrophilic amino acids that are complementary and structurally compatible and self-assemble into a beta-sheet, and wherein the additional self-assembling peptide does not contain an amino acid domain that reduces compatibility of the peptide with cell attachment or cell viability. In certain embodiments, the modified self-assembling peptide and the additional (unmodified) self-assembling peptide are present in a ratio of approximately 1:1, 5:1, 9:1, or 99:1.

In certain embodiments, the stored peptide solution is at an acidic pH. In certain embodiments, the pH of the stored peptide solution is adjusted to near-neutral pH prior to administration. In certain embodiments, the peptide solution is adjusted to near pH prior to administration and stored in a sterilized syringe or container. In certain embodiments, the pH is adjusted to near-neutral pH with an adjusting solution (e.g., a basic solution such as an NaOH solution).

In certain embodiments, the pharmaceutical composition is substantially free of a gellation agent and self-assembles within the body to form a macroscopic structure (e.g., nanofibers and/or beta-sheets). In certain embodiments, such pharmaceutical composition self-assembles within the body upon contact with bodily fluids (e.g., blood, lymph, etc.)

In certain embodiments, the pharmaceutical composition further comprises a pharmaceutically acceptable excipient. Exemplary pharmaceutically acceptable excipients include any and all solvents, dispersion media, diluents, or other liquid vehicles, dispersion or suspension aids, surface active agents, isotonic agents, thickening or emulsifying agents, preservatives, solid binders, lubricants and the like, as suited to the particular form of administration and dosage. Remington's *The Science and Practice of Pharmacy*, 21$^{st}$ Edition, A. R. Gennaro, (Lippincott, Williams & Wilkins, Baltimore, Md., 2006) discloses various carriers used in formulating pharmaceutical compositions and known techniques for the preparation thereof. Except insofar as any conventional carrier medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

(iii) Matrices

As discussed above, the present invention also provides inventive matrices comprising modified self assembling peptides, as is described above and herein. In certain embodiments, the matrix is a gel or a hydrogel. In other embodiments, the matrix is three-dimensional (i.e., has a shape).

In certain embodiments, the matrix further comprises an additional biological molecule. In some embodiments, the additional biological molecule has a net positive or negative charge. In other embodiments, the additional biological molecule is a protein or peptide. In yet other embodiments, the additional biological molecule is a growth factor or a self-assembling peptide.

In some embodiments, the additional biological molecule is a self-assembling peptide. In other embodiments, the additional biological molecule is a modified self-assembling peptide (e.g., as described in Table 2a). In yet other embodiments, the additional biological molecule is an unmodified self-assembling peptide (e.g., as described in Table 1).

In certain embodiments, the additional biological molecule is a growth factor. In certain embodiments, the additional biological molecule is a heparin-binding growth factor. In some embodiments, the heparin-binding growth factor is selected from the group consisting of VEGF, FGFs, PDGF, HGF, TGF-$\beta$ and BMP.

In other embodiments, the additional biological molecule is a glycosaminoglycan. In some embodiments, the glycosaminoglycan is heparin or heparin sulfate.

In certain embodiments, the matrix, as described above and herein, further comprises a plurality of cells attached to the surface of the matrix or encapsulated within the matrix. In some embodiments, the cells are substantially uniformly distributed within the matrix. In certain embodiments, the cells are selected from the group consisting of osteoblasts, chondrocytes, bone marrow cells, osteocytes, periosteal cells, perichondrial cells, fibroblasts, mesenchymal cell, mesenchymal stem cell, adipose derived cells, adipose derived stem cells, neuronal cells, hippocampal cells, epidermal cells, endothelial cells, epithelial cells, keratinocytes, basal cells, spinous cells, granular cells, embryonic stem cells, ovarian cells, pancreatic cells, cervical cells, liver cells, foreskin cells, neutrophils, lymphocytes, macrophages, dendritic cells, or precursors of any of the foregoing.

In certain embodiments, the matrix, as described above and herein, further comprises a solid material. In certain embodiments, the solid material is a salt. In certain embodiments, the solid material is an inorganic salt. In certain embodiments, the inorganic salt comprises calcium and/or phosphate. In other embodiments, the inorganic salt is selected from the group consisting of calcium phosphate, tricalcium phosphate, hydroxyapatite and calcium carbonate.

In certain embodiments, the solid material, as described above, has pore diameter of between about 100-500 microns, inclusive.

In other embodiments, the solid material, as described above, has a block-like, cylindrical, plate-like or granule-like shape.

(iv) Making Matrices of the Invention

As described generally above and herein, the present invention also provides methods of making inventive matrices. For example, in certain embodiments, the present invention provides a method of making a matrix of the present invention comprising the steps of (i) dissolving a modified self-assembling peptide in an aqueous solution and (ii) adjusting the pH. In certain embodiments, the method further comprises the step of (iii) adding a gellation agent.

In other embodiments, the present invention provides a method of making a matrix of the present invention comprising the steps of (i) dissolving the self-assembling peptide in an aqueous solution and (ii) adding a gellation agent. In certain embodiments, the method further comprises (iii) adjusting the pH of the solution.

In certain embodiments, the gellation agent is an electrolyte. In some embodiments, the gellation agent is NaCl, saline, PBS, cell culture medium, or a biological fluid (e.g., blood, lymph, and the like).

In certain embodiments, the pH is adjusted from acidic (e.g., a pH of between about 2-3) to basic. In certain embodiments, the pH is adjusted to about 5-9, inclusive. In some embodiments, the pH is adjusted to about 6-8, inclusive. In other embodiments, the pH is adjusted to about 5-7, inclusive. In other embodiments, the pH is adjusted to about 6-8, inclusive. In other embodiments, the pH is adjusted to about 5.7 to 5.8, inclusive.

(v) Other Methods of the Invention

As described generally above and herein, the present invention provides methods of using the inventive modified self-assembling peptides, self-assembling peptide, a pharmaceutical composition thereof, and/or a matrix made therefrom as a defect filler of bone and/or tissue. "Tissue" includes any external or internal bodily tissue. Exemplary tissues include, but are not limited to, brain, skin, liver, pancreas, stomach, kidney, gastrointestinal tract, esophageal tract, heart, muscle, connective tissue, cartilage, nerve, fat, or bone marrow tissue.

Furthermore, as described generally above and herein, the present invention provides methods of enhancing cell differentiation or functional activity comprising administering a self-assembling peptide, a pharmaceutical composition thereof, or a matrix made therefrom to a subject in need thereof.

Additionally, as described generally above and herein, the present invention provides a method of treating a subject comprising introducing a administering a self-assembling peptide, a pharmaceutical composition thereof, or a matrix made therefrom to a site on or within the subject's body. In certain embodiments, the site is of an orthopedic field; a bone defect; a bone adjent; an ectopic bone formation; an ischemic region; a myocardial infarction region; peripheral vascular region; cerebral infarction region; or a skin defect.

(vi) Kits

As described generally above and herein, the present invention also provides kits comprising the inventive self-assembling peptide, a pharmaceutical composition thereof, or a matrix made therefrom. Kits are typically provided in a suitable container (e.g., for example, a foil, plastic, or cardboard package). In certain embodiments, an inventive kit may include one or more pharmaceutical excipients, pharmaceutical additives, and the like, as is described herein. In certain embodiments, an inventive kit may include means for proper administration or for culturing cells within inventive matrices, such as, for example, graduated cups, syringes, needles, cleaning aids, and the like. In certain embodiments, an inventive kit may include instructions for proper administration or culturing and/or preparation for proper administration or culturing.

For example, in certain embodiments, the present invention provides a culture kit comprising: (a) an inventive self-assembling peptide, a pharmaceutical composition thereof, or a matrix made therefrom; (b) instructions for initiating self-assembly of the peptide into a macroscopic structure; and (c) at least one component selected from the group consisting of: a population of cells, cell or tissue culture medium, a predetermined amount of a growth factor, a predetermined amount of an ion or salt thereof, instructions for preparing the self assembling peptide for cell culture, instructions for culturing cells on or within a peptide hydrogel structure, instructions for introducing the self-assembling peptide into a subject, a vessel in which cell culture may be performed, a liquid in which the peptide can be dissolved, a syringe, an ion or salt thereof for initiating peptide self-assembly, and one or more growth or differentiation factors.

In other embodiments, the present invention provides a method of culturing cells comprising contacting the cells with an inventive self-assembling peptide, a pharmaceutical composition thereof, or a matrix made therefrom and maintaining the matrix for a period of time under conditions suitable for cell culture. In certain embodiments, the cells are cultured on the surface of the matrix and/or are cultured embedded within the matrix.

EXEMPLIFICATION

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance, which can be adapted to the practice of this invention in its various embodiments and the equivalents thereof.

Example 1

Pre-osteoblast Proliferation and Differentiation Effects

Recently, due to the aging society, problems associated with bone degeneration and bone fracture has become a significant problem both for quality of life of the patient and the social medical cost. Bone fracture in an older person is a prevalent problem due to osteoporosis but also due to poor bone regeneration. Thus, the acceleration of bone regeneration by implanting biomaterials and/or a tissue engineering approach are of interest. Also of interest is the enhancement of osteoblast activity mineralization and pre-osteoblast or stem cell proliferation differentiation.

Bone regeneration was tested using functional motifs as provided in Table 2 (Synpep Corporation). Mouse preosteoblast cell line (MC3T3-E1) was used to compare the proliferation and differentiation effects of the motifs with RAD16-1 and Collagen-I hydrogels as controls. The proliferation was measured by DNA contents and the differentiation effects were evaluated using Alkaline phosphatase (ALP) activity and secreted Osteocalcin. Alkaline phosphatase is known to be differentiation marker of osteoblast in earlier stage. Secreted Osteocalcin is known to be differentiation marker of osteoblast in later stage and its activity is correlated with the bone mineralization.

FIG. 1 shows the mass spectroscopy data of SEQ ID NO. 4 peptide, which was synthesized by the Fmoc solid phase synthetic method as described in Grant, G. A. ed.: Synthetic Peptides. A User's Guide, UWBC Biotechnical Resource Series (Burgess, R. R. Series Editor), Oxford University Press (1992) and Atherton, E. and Sheppard, R. C.: Solid phase peptide synthesis. A practical approach, IRL Press, Oxford (1989). The relative intensity of signal is related to the amount of the peptide belong to the peak, although it is not quantitative (see Table 3). The data shows that placing the functionalized motif at C-terminal side successfully preserves the functional motif sequence.

TABLE 3

Mass spectroscopy peaks in SEQ4 peptide manufactured by Fmoc synthesis

| MW | Rel. Intensity | Description |
| --- | --- | --- |
| 2919.00 | 100 | The peptide (SEQ4) Ac-(RADA)$_4$GPRGDSGYRGDS-CONH$_2$ (SEQ ID NO. 4) |
| 2762.76 | 15 | Without "R" of N-terminal Ac-ADA(RADA)$_3$GPRGDSGYRGDS-CONH$_2$ (SEQ ID NO. 77) |
| 2349.58 | 8 | Without "RADAR" of N-terminal Ac-ADA(RADA)$_2$GPRGDSGYRGDS-CONH$_2$ (SEQ ID NO. 78) |
| 2062.51 | 8 | Without "RADARADA" of N-terminal Ac-(RADA)$_2$GPRGDSGYRGDS-CONH$_2$ (SEQ ID NO. 79) |
| 1460.93 | 28 | The peptide (SEQ4) (Double charged signal) Ac-(RADA)$_4$GPRGDSGYRGDS-CONH$_2$ (SEQ ID NO. 4) |

Typically in peptide synthesis, such as Fmoc or tBoc solid phase synthetic methodology, the peptide is synthesized starting from the C-terminus. The most common of synthetic by-products are shorter peptides, and are typically the main source of impurity. When the functionalized motif is placed at C-terminus, the material produced will have shorter self-assembling sequence but they have full sequence in the functionalized motif. The one or a few amino acid missing in self-assembling peptide component does not affect the functionality of whole hydrogel. In contrast, even one or a few amino acid missing in the functionalized motif causes a loss in functionality. Thus, the functionalized motif should be placed at C-terminus side of self-assembling sequence to ensure functionality.

The functional motif can be placed on both sides of the self-assembling sequence; and in doing so can increase the concentration of the functional motif. These functional motifs at the end of the self-assembling sequence can be the same amino acid sequence (functional motif) or a different amino acid sequence (functional motif). The cost of manufacturing a peptide with two different functional motifs on each side of the self-assembling sequence is relatively inexpensive compared to the synthesis of individual peptides.

1% RAD16-I solution [self-assembling peptide solution] was obtained as RAD16-I (Puramatrix™, 3DM Inc./BD Bioscience). The functionalized peptides of Table 2 were dissolved in water at final concentration of 1% (v/w). The functionalized peptide solutions were then mixed with 1% RAD16-I solution at a ratio of 1:1 (Table 4). Each peptide solution was loaded in the Culture plate inserts (10 mm diameter, Millicell-CM, Millipore). The maintenance medium described below was added to induce hydrogel formation. Collagen I gel from rat tail (BD Bioscience) was loaded in the Culture plate inserts as control.

TABLE 4

Hydrogel components

| Code | Hydrogel contents |
|---|---|
| RAD | 1% RAD16-1 peptide solution |
| RAD2 | 0.5% RAD16-1 peptide solution |
| PFSmx | 1% SEQ ID NO. 1 peptide solution and 1% RAD16-I peptide solution mix by 1:1 |
| FLGmx | 1% SEQ ID NO. 2 peptide solution and 1% RAD16-I peptide solution mix by 1:1 |
| ALKmx | 1% SEQ ID NO. 3 peptide solution and 1% RAD16-I peptide solution mix by 1:1 |
| PRGmx | 1% SEQ ID NO. 4 peptide solution and 1% RAD16-I peptide solution mix by 1:1 |
| DGRmx | 1% SEQ ID NO. 5 peptide solution and 1% RAD16-I peptide solution mix by 1:1 |
| PRFmx | 1% SEQ ID NO. 4 peptide solution, 1% SEQ6 peptide solution and 1% RAD16-I peptide solution mix by 1:1:2 |
| COL | Collagen-1 gel |

Cell culture and evaluation. MC3T3-E1 cells were obtained from ATCC. The cells were maintained by the maintenance medium. The maintenance medium is an α-modified minimum essential medium (α-MEM, Gibco) containing 10% fetal calf serum (FCS, Gibco) and antibodies (penicillin and streptomycin). Cells were plated at $2\times10^4$ cells on the hydrogels in the inserts. The cells were cultured in the maintenance medium Day 0 through Day 2 and then converted into the differentiation media containing L-Ascorbic acid (Sigma) 50 ug/ml and β-glycerophosphate (Sigma) 10 mM. The medium was changed every three days. The gel, cell lysis and culture medium were harvested after 14 days of culturing for analysis.

Cell proliferation was evaluated using DNA contents in the hydrogel using PicoGreen dsDNA Kits (Molecular Probes). ALP activity was quantitatively measured from cell lysis using Alkaline Phosphatase Fluorescence Assay Kit (Sigma). Osteocalcin was measured from cell culture medium using Mouse Osteocalcin EIA Kit (Biomedical Technologies Inc.).

Figure 3:
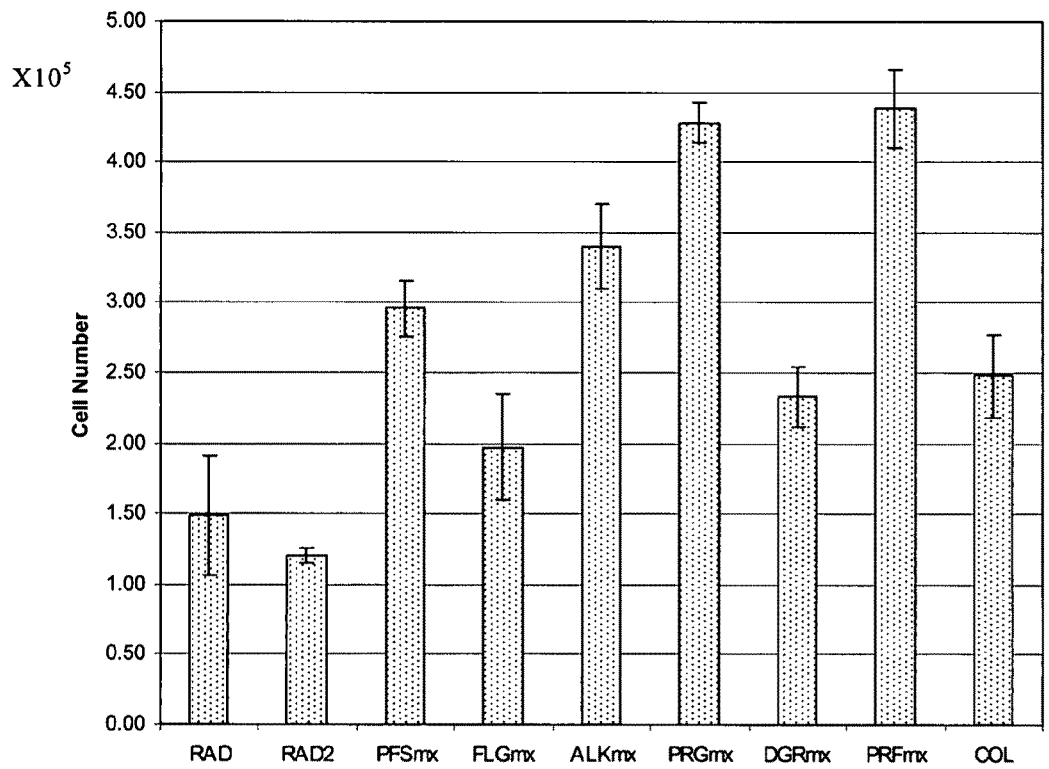
FIG. 3. Cell numbers from DNA content in the hydrogels show that the functional peptides in combination with RAD16-I promote greater cell proliferation compared to RAD16-I alone and Collagen-1 gels.

Cell proliferation results. Cell numbers from DNA content in the hydrogels show that the functional peptides in combination with RAD16-I promote greater cell proliferation compared to RAD16-I alone and Collagen-1 gels (FIG. 3).

Figure 4:
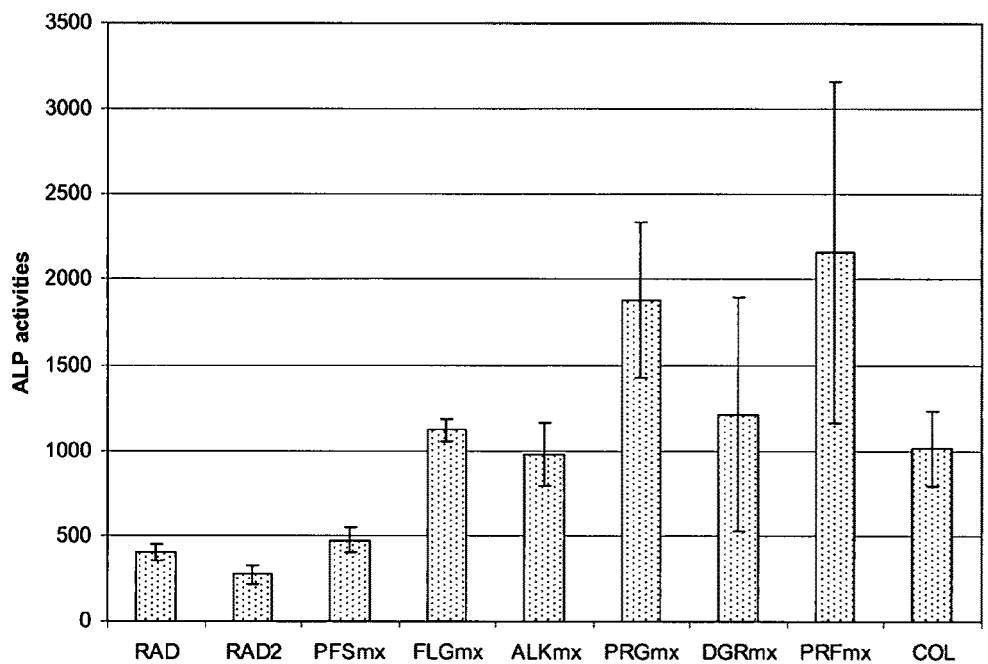
FIG. 4. Alkaline phosphatase (ALP) activity normalized by DNA amount.
Figures 5A, 5B, 5C, 5D, 5E, 5F, 5G, 5H, 5I:
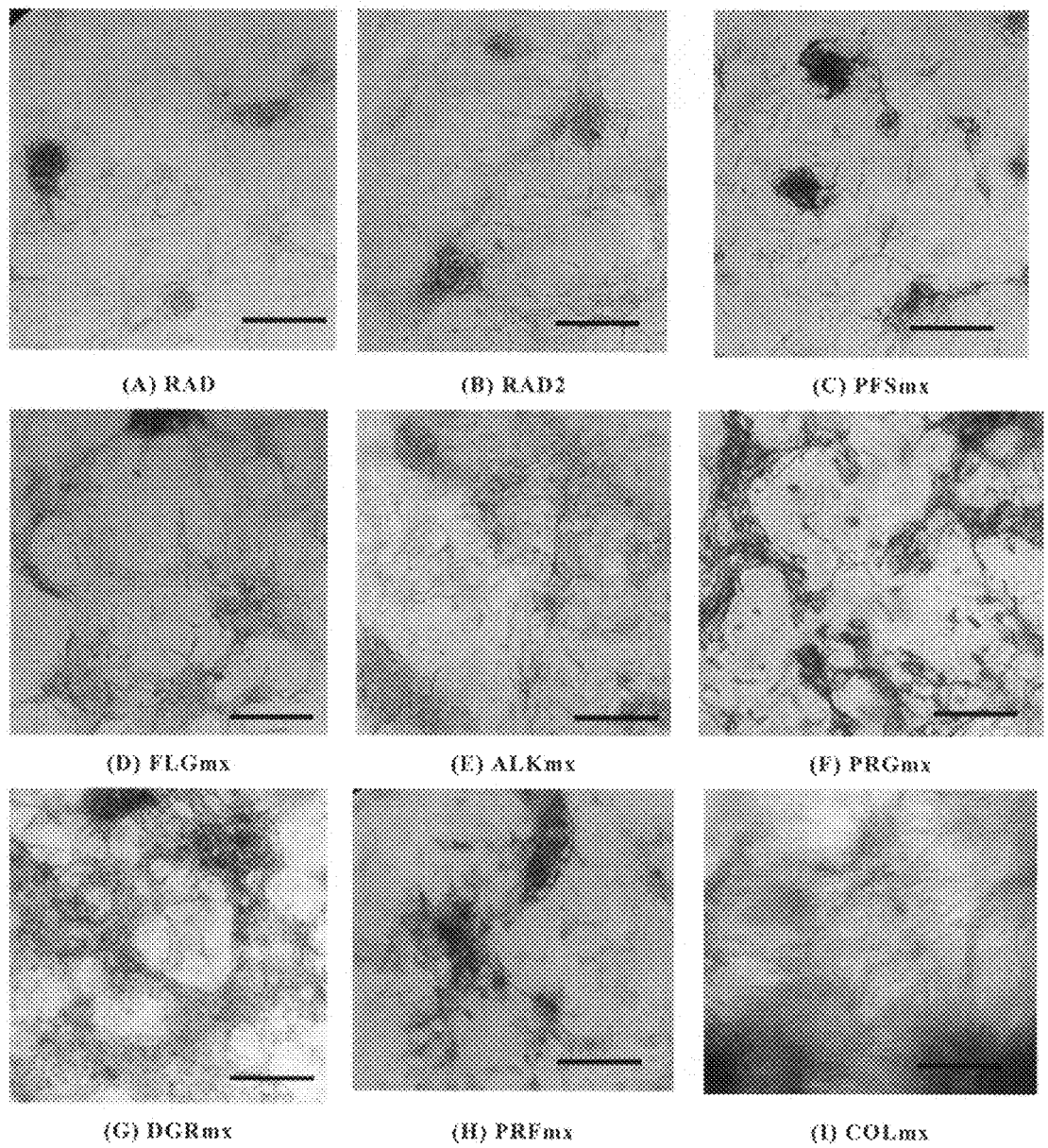
FIGS. 5A-5I. Alkaline phosphatase staining images confirm high ALP activity.

Alkaline phosphatase (ALP) activity. Alkaline phosphatase (ALP) activity of the functional peptides) is larger or similar compared to controls (RAD16-I, Collagen-I) (FIG. 4). These results are confirmed by the alkaline phosphatase staining (FIGS. 5A-5I). The darker (bluish) areas depicted in FIGS. 5A-5I show higher areas of ALP activity.

Figure 6:
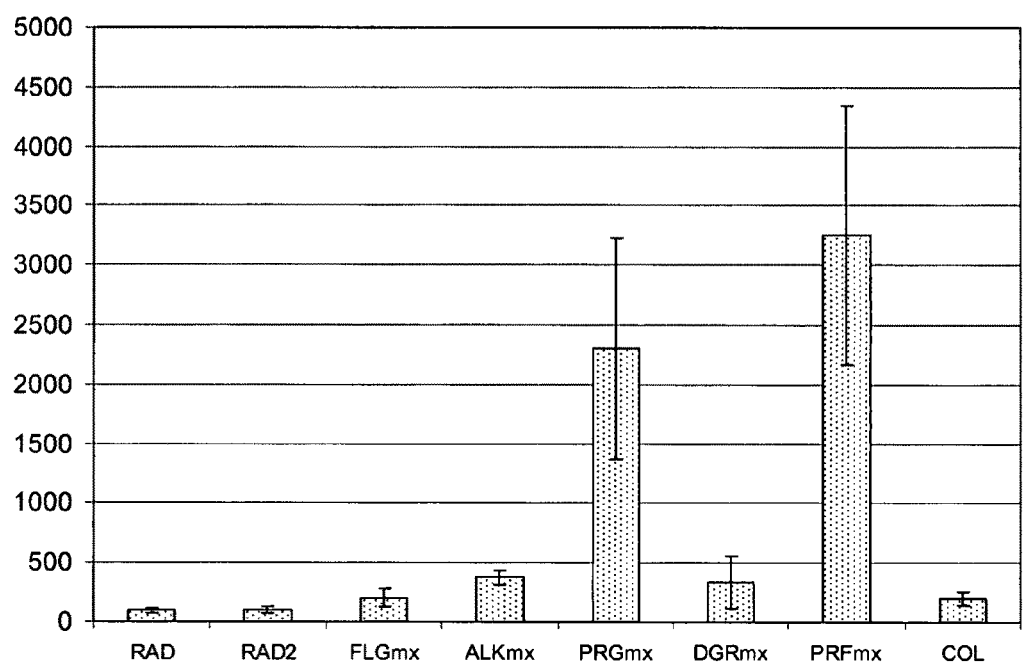
FIG. 6. Osteocalcin secreted in culture medium results show that self-assembling peptides with functional motif have the potential to promote differentiation of pre-osteoblasts.

Osteocalcin secretion in culture medium. For the results of Osteocalcin secretion, the functionalized peptides had higher concentration compared to controls (FIG. 6). The results shows that self-assembling peptides with functional motif have the potential to promote differentiation of pre-osteoblasts. The functionalized self-assembling peptide matrices have potential to enhance osteoblast proliferation and osteoblastic differentiation. They may be useful as matrices for bone tissue regeneration and bone metabolism studies.

The hydrogels PRGmx, DGRmx and PRFmx have -RGD- adhesion motif(s) in common. This shows that having RGD motif promotes both proliferation and differentiation. PRGmx and PRFmx, which have the motif -PRGDSGY RGDS, (SEQ ID NO. 71) have several times higher osteocalcin secretion than other peptides. One reason for this is because RGD is well presented to the cell compared to the motif -DGRGDSVAYG (SEQ ID NO. 55). When the RGD motif is close to the self-assembled fiber, the cell's integrin is not connected to RGD because the fiber interferes with the cell surface.

The effect of the linker length was evaluated by changing the distance between functional motif (RGD) and self-assembling sequence (RADA) (SEQ ID NO. 67) (Tables 5-7). Cells were cultured on hydrogels for 7 days. Cell proliferation was evaluated using DNA contents in the hydrogel as same as previous experiment.

TABLE 5

Functionalized peptides for evaluating linker length effects

| No. | Sequence | Description |
|---|---|---|
| SEQ ID NO. 8 | Ac(RADA)₄GGRGDSCONH₂ | RGD binding sequence with 2 linker Glycine |
| SEQ ID NO. 9 | Ac(RADA)₄GGGGRGDSCONH₂ | RGD binding sequence with 4 linker Glycine |

TABLE 6

The distance between functional motif (RGD) and self-assembling sequence (RADA)

| No. | | Distance |
|---|---|---|
| SEQ ID NO. 8 (2G) | 2 mer (peptide bonds) | 6.9 A (angstrom) |
| SEQ ID NO. 9 (4G) | 4 mer (peptide bonds) | 13.8 A (angstrom) |
| SEQ ID NO. 5 (DGRmx) | 4 mer (peptide bonds) | 13.8 A (angstrom) |
| SEQ ID NO. 4 (PRGmx) | 8 mer (peptide bonds) | 27.5 A (angstrom) |

TABLE 7

Hydrogel components

| Code | Hydrogel contents |
|---|---|
| RAD | 1% RAD16-1 peptide solution |
| RAD2 | 0.5% RAD16-1 peptide solution |
| 2G | 1% SEQ ID NO. 8 peptide solution and 1% RAD16-I peptide solution mix by 1:1 |
| 4G | 1% SEQ ID NO. 9 peptide solution and 1% RAD16-I peptide solution mix by 1:1 |
| PRGmx | 1% SEQ ID NO. 4 peptide solution and 1% RAD16-I peptide solution mix by 1:1 |

Figure 7:
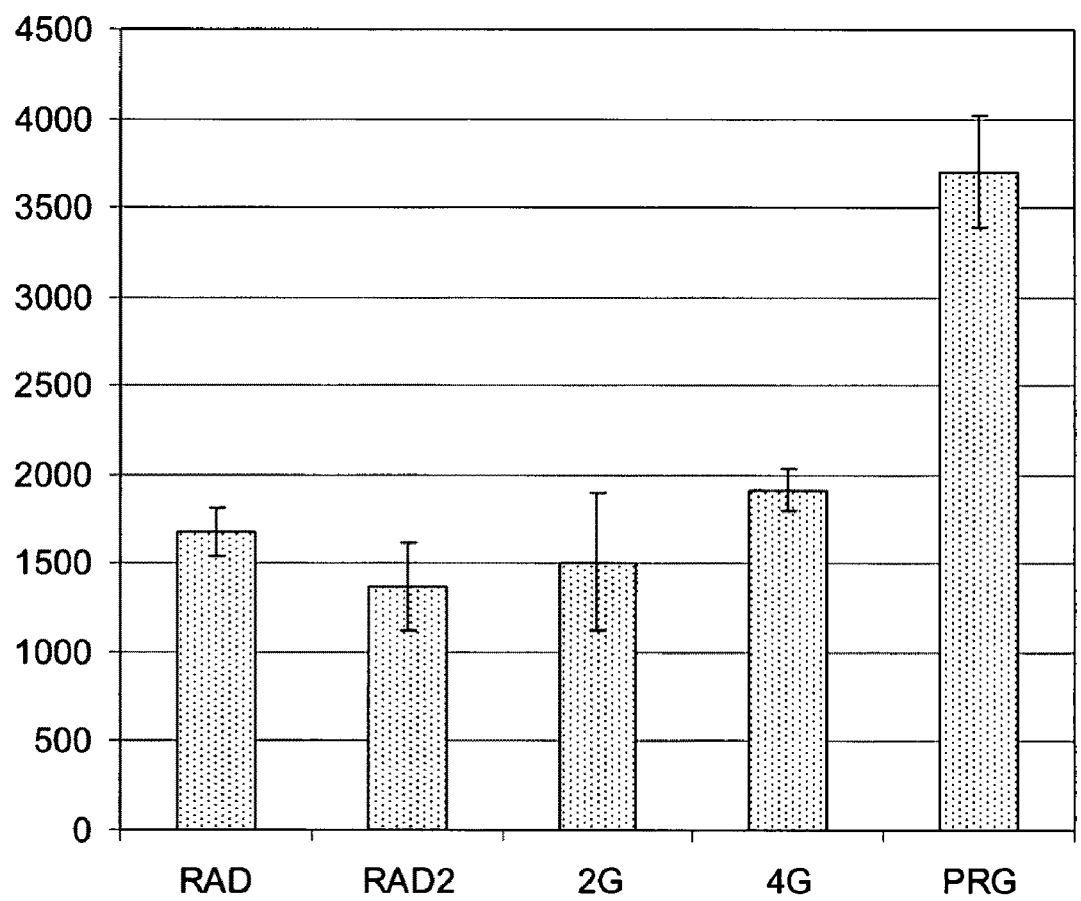
FIG. 7. Distance between functional motif and self-assembling sequence and cell proliferation.

The results are depicted in FIG. 7. The Y axis shows the fluorescence intensity which is linear to the DNA contents. These results show that distance between functional motif (RGD) and self-assembling sequence (RADA) (SEQ ID NO. 67) should be at least more than 2 mer (6.9A) of peptide bonds. The distance more than 4 mer (13.8 A) of peptide bonds is preferable. The other reason is that as -PRGDSGY RGDSG (SEQ ID NO. 82) has multiple RGD motifs, the chance that cell's integrin attaches to a RGD motif in the three-dimensional structure is further increased.

Example 2

Effect of the Mixed Ratio of Functionalized Peptide

Effect of a mixture of self-assembling sequence peptide (e.g., 1% RAD16-1 peptide solution) and a functionalized peptide (SEQ ID NO. 7) with self-assembling sequence (RADA) (SEQ ID NO. 67) and functional motif (RGD), was evaluated (Tables 8-9) SEQ ID NO. 7 has an additional Glycine at the N-terminus (compared to SEQ ID NO. 4), which causes an increase in hydrophobicity of the hydrogel. Biologically SEQ ID NO. 4 and SEQ ID NO. 7 are considered to have similar effects.

TABLE 8

| No. | Sequence | Description |
|---|---|---|
| SEQ ID NO. 7 | Ac(RADA)$_4$ GPRGDSGYRGDSGCONH$_2$ | Repetitive RGD binding sequence |

TABLE 9

| Hydrogel contents | |
|---|---|
| Code | Hydrogel contents |
| RAD | 1% RAD16-1 peptide solution |
| DSG | 1% SEQ ID NO. 7 peptide solution |

Figure 8:
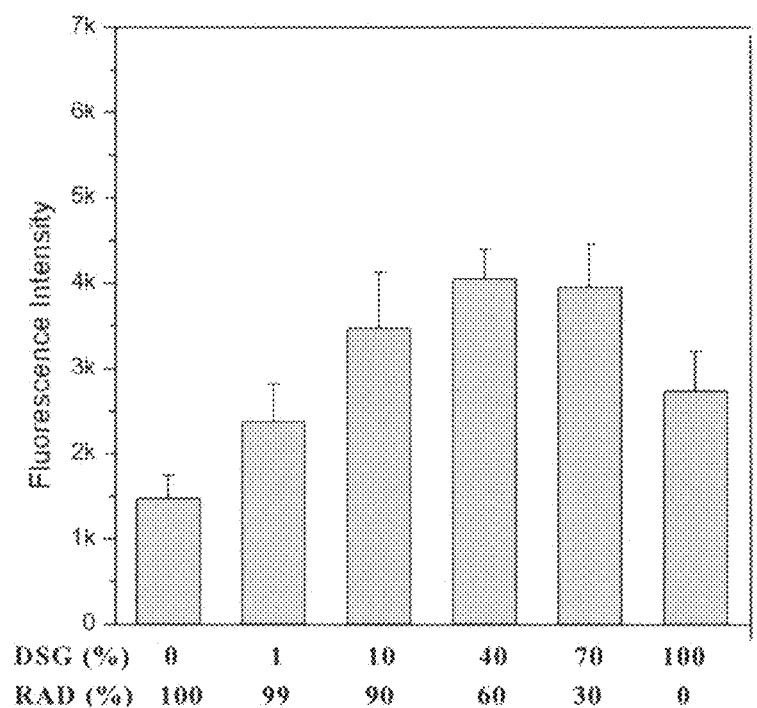
FIG. 8. Effect of the mixture ratio of functionalized peptide. The Y axis shows the fluorescence intensity value which is linear to the DNA contents. Mixtures from at least from RAD:DSG=99:1 to 67:33 increase cell proliferation. The drop in fluorescence with 100% DSG hydrogel may be caused by a difference in the mechanical properties of the hydrogel, as DSG forms a less stiff gel compared to RAD.

Hydrogels were prepared so that the mixture ratio of RAD and DSG was varied from 100:0 to 0:100 (FIG. 8). Cells were prepared and seeded as described in Example 1. Cells were cultured on hydrogels for 7 days. Cell proliferation was evaluated using DNA contents in the hydrogel as same as Example 1.

The results are depicted in FIG. 8. The Y axis shows the fluorescence intensity value which is linear to the DNA contents. This shows that mixture increase cell proliferation in broad range from at least from RAD:DSG=99:1 to 67:33. The drop in DSG 100% hydrogel may caused by the difference of the mechanical properties of the hydrogel, as DSG form lower stiffness gel compared to RAD.

Figures 9A, 9B:
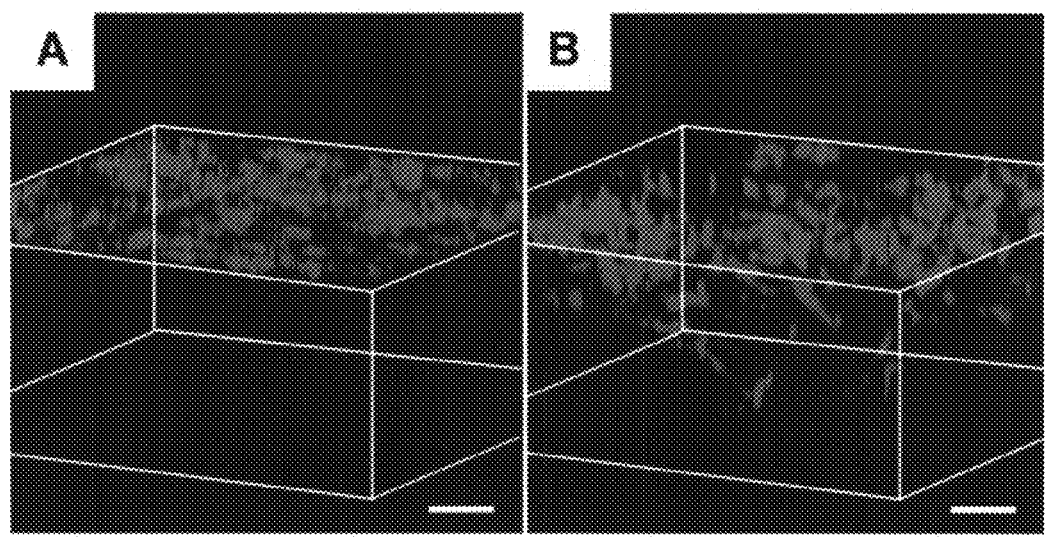
FIGS. 9A-9B. 3D reconstruction of confocal microscopy of the cell cultured on the different functional peptide concentration.

FIG. 9 shows the 3D reconstruction of confocal microscopy of the cell cultured on the different functional peptide concentration. FIG. 9A shows when DSG ratio is 10%; FIG. 9B shows when DSG ratio is 70%. In FIG. 9A, cells stayed on the surface of the peptide matrix, while in FIG. 9B, cells migrated into the matrix up to 300 um. This data shows that cell behavior can be controlled by changing the ratio of the functionalized peptide.

Example 3

Three Dimensional Culturing Using the Charged Functionalized Motif

Self assembling peptides hydrogels described above and herein provides cells with a synthetic extra cellular matrix (ECM) environment for 3-dimensional growth similar to that of collagen. When seeding the cells 3 dimensionally, the self assembling peptide solution should be stored at low pH (usually a pH of between 2-3) to keep viscous solution state. However, mixing living cells into low pH solution for long time significantly impacts cell viability (e.g., it is known that a few minutes in pH 2-3 solution, most human cell viability is significantly lost). Thus, when seeding the cells with a solution of the self assembling peptide at low pH, (1) the cells are added, and (2) the pH is immediately brought to near-neutral (pH between 5-8) or basic.

Figure 10:
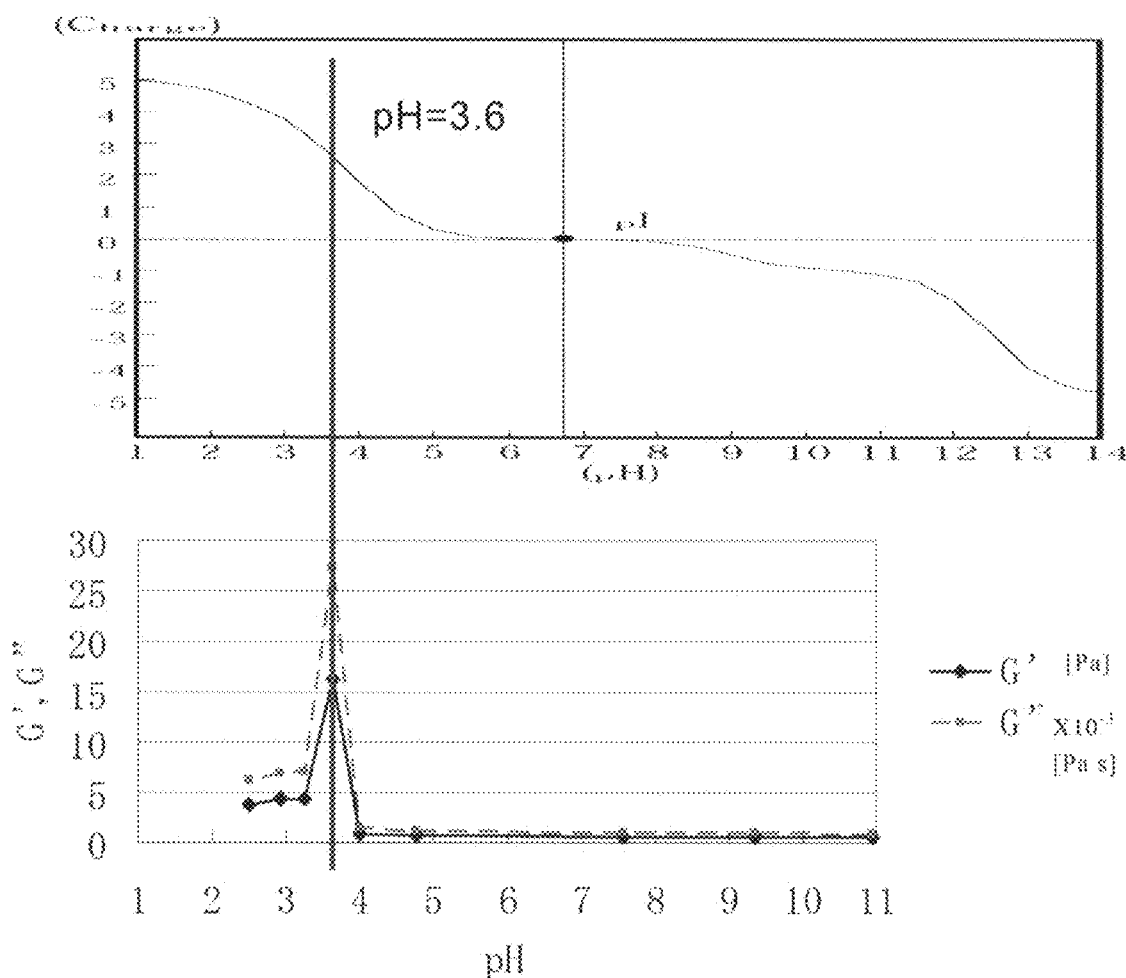
FIG. 10. Isoelectric plot and rheological data of RAD16-1 1% solution when 0.1 N NaOH solution is added.

FIG. 10 shows the isoelectric plot and corresponding rheological rheological data when 0.1 N NaOH solution is added to RAD16-1 1% solution. At the point of pH 3.6, the viscous solution become gel and has a higher G' (stiffness), G" (viscosity) value. When the pH is increased, the gel breaks into small pieces and it becomes a solution with precipitated peptides. At lower pH, the peptide forms fibers and the fibers make the solution viscous. When the pH becomes higher, and approaches the pI value, the peptide fibers lose their charge and aggregate to form gel. The same gel formation happens when the peptide charge is screened by salts in a salt-containing solution (e.g., a solution containing a gellation agent or an iso-osmotic solute). Once the gel is formed, the fiber structure is broken into pieces to form a precipitate particle.

Figure 11:
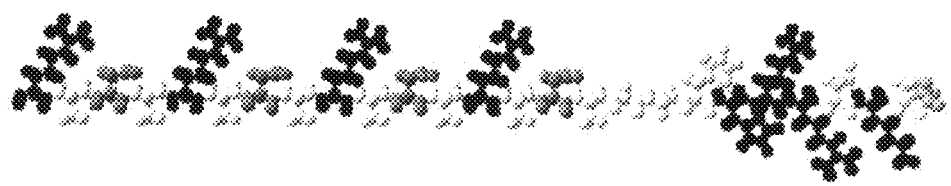
FIG. 11. Structure of Ac(RADA)$_4$GGFHRRIKA-CONH$_2$ (SEQ ID NO. 6). Black represents positively charged amino acids, Gray shows negatively charged amino acids.

Self assembling peptides are known to be supportive for cell growth are composed by the repetitive sequence of [positive charge]-[hydrophobic]-[negative charge]-[hydrophobic]-, such as -RADA- (SEQ ID NO. 67) or -KLDL-, and pI value is close to 7 (neutral). Self assembling peptides behave similarly with respect to changes in pH (i.e., as the pH becomes higher, and approaches the pI value, the peptide fibers lose their charge and aggregate to form gel). For example, the heparin-binding motif consensus sequences are -XBBXBX- and -XBBBXXBX-, which are both highly positively charged. X represents non-charged or hydrophobic amino acid. B represents positive charged peptides. FIG. 11 depicts the structure of self assembling peptide Ac(RADA)$_4$ GGFHRRIKA-CONH$_2$ (SEQ6) (Table 10). Black areas represent positively charged amino acid(s); grey areas represent negatively charged amino acid(s).

TABLE 10

| Code | Hydrogel contents |
|---|---|
| FHR | 1% SEQ ID NO. 6 peptide (Ac(RADA)$_4$GGFHRRIKA CONH$_2$) solution |

Figure 12:
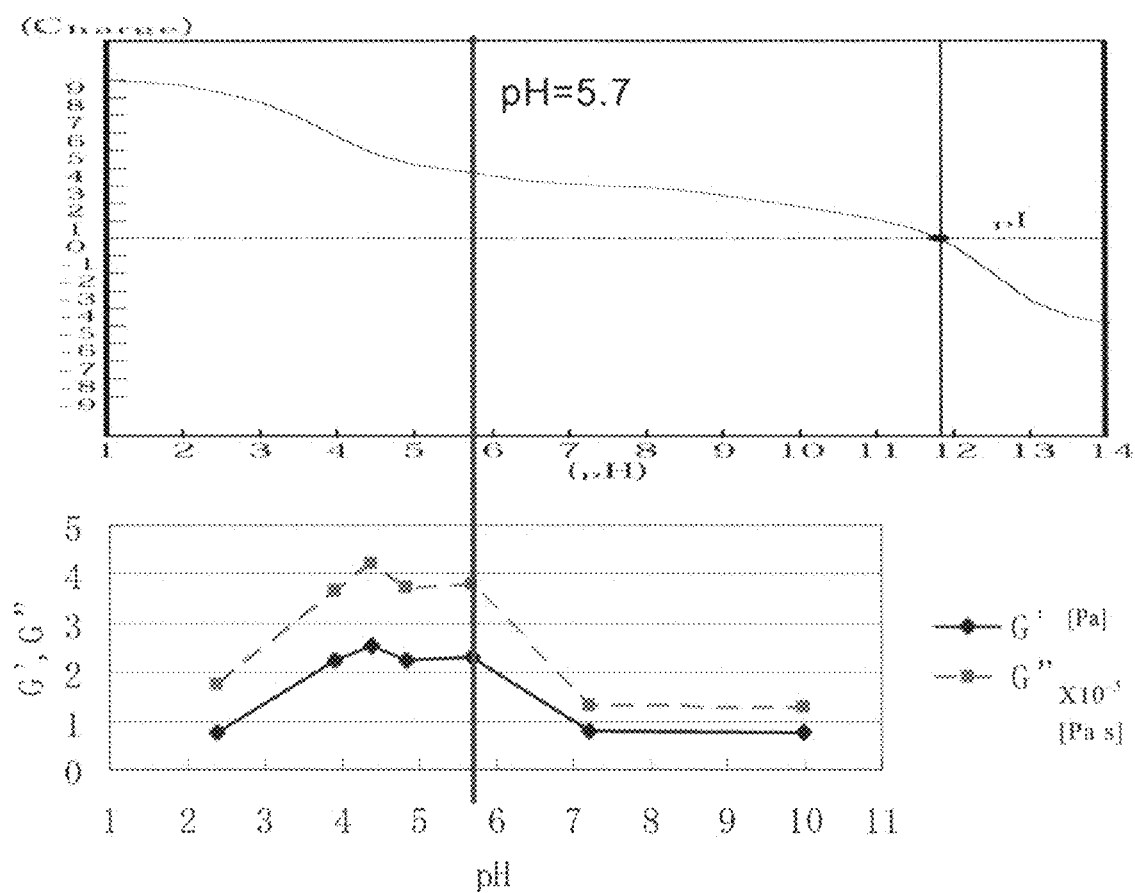
FIG. 12. Isoelectric plot and rheological data of FHR solution when 0.1 N NaOH solution is added.
Figure 13A:
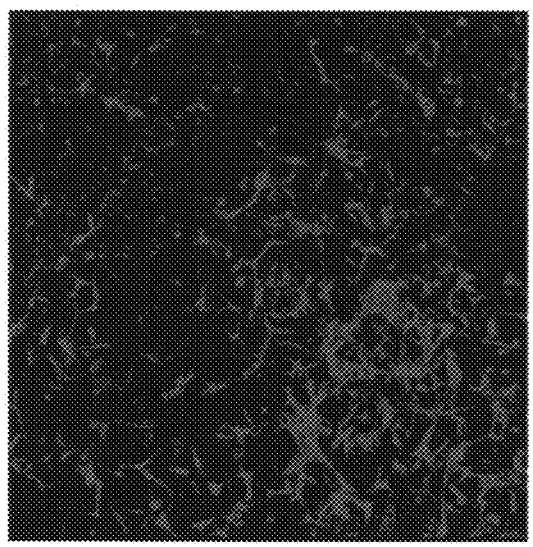
FIGS. 13A-13D. 3 dimensional reconstruction of the confocal microscope observation showing that FHR peptide provides superior 3-Dimensional cell proliferation.
Figure 13B:
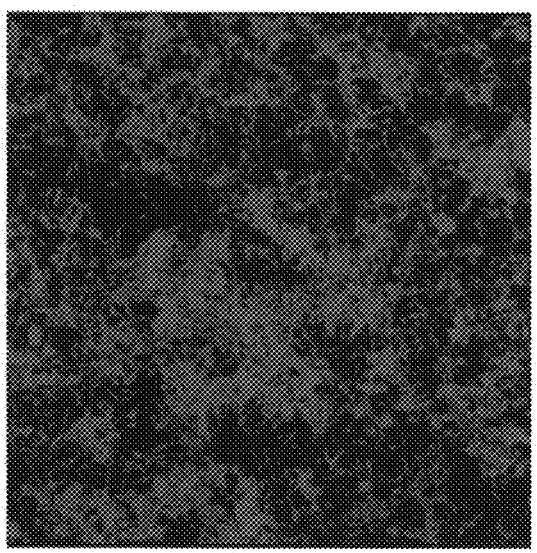
Figure 13C:
Figure 13D:
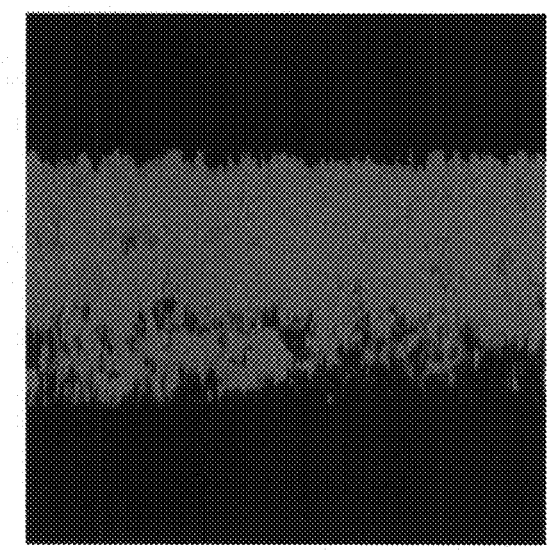
Figure 14:
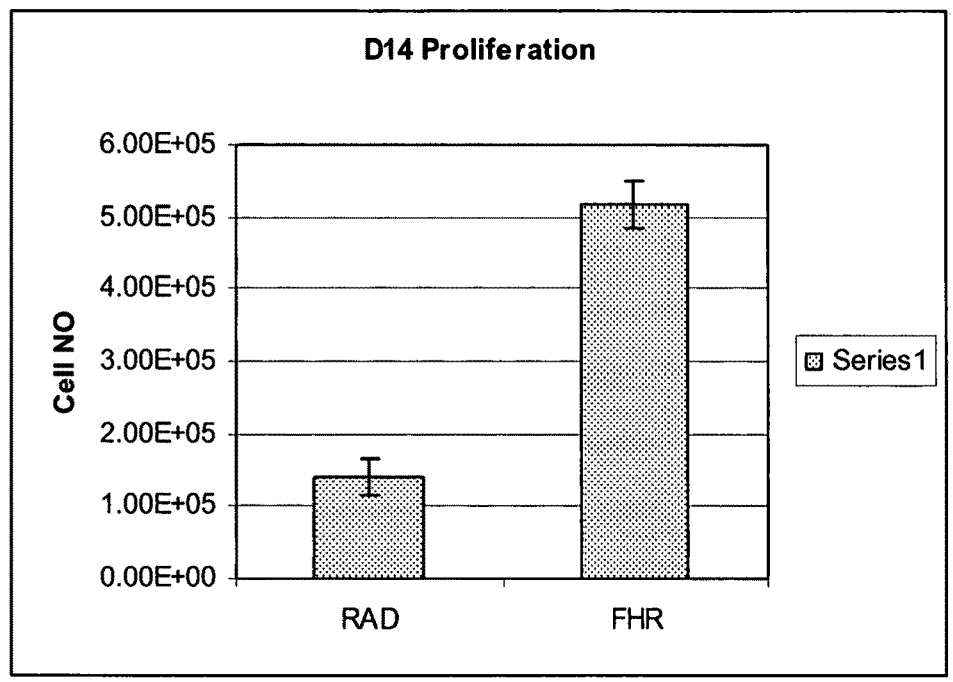
FIG. 14. Cell numbers calculated from DNA content in gel measuring proliferation and differentiation effects by the FHR peptide hydrogel.
Figure 15:
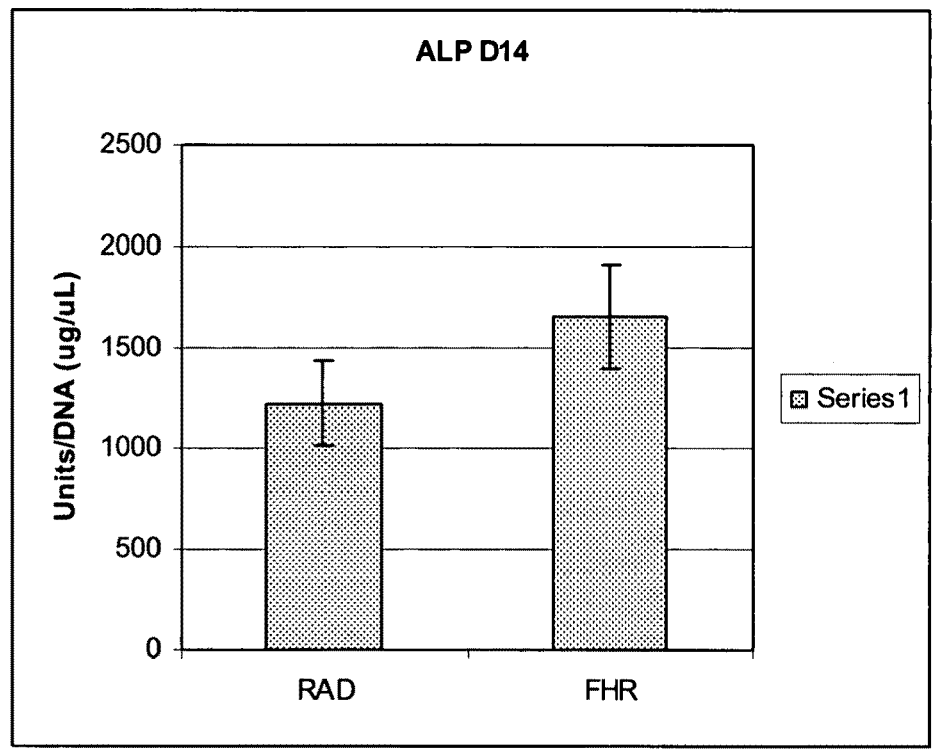
FIG. 15. ALP activity normalized by DNA amount measuring proliferation and differentiation effects by the FHR peptide hydrogel.

A comparison of the pH dependent property of 1% Ac(RADA)$_4$GGFHRRIKA CONH$_2$ (SEQ ID NO. 6) solution (Code: FHR), self assembling peptide sequence was compared with the heparin-binding motif. FIG. 12 depicts the isoelectric plot and corresponding rheological data when 0.1 N NaOH solution is added to FHR solution to adjust pH. The net charge of the peptide molecule is kept $\geq 2$ when pH<10. Until at point of pH 5.7, the solution keeps viscous state. This movement of pH point where the peptide solution become gel is controlled by the charge induced by the additional motif to the self-assembling peptide. The induced charge prevents the peptide to aggregate to form the gel. Thus, the cell and the peptide solution can be mixed near neutral pH. After complete mixing, the gel formation can be made by adding salt containing solution (e.g., a solution containing a gellation agent or an iso-osmotic solute).

Changing the pH value of the gelling point by changing the charge of the near-neutral self assembling peptide is important because this is done without losing the basic self-assembling function and biological properties of original self-assembly sequence.

Positively charged self-assembling peptides can be dissolved in distilled water. Adjusting the pH of the solution (i.e., by using a basic solution such as an NaOH solution) enables the peptides solution to stay in Sol status (i.e., a pH=5.7 for the FHR peptide). In this case, using a high concentration of a buffer salt to stabilize the pH should be avoided, as the salt concentration above the critical concentration drives the peptide solution in formation of a hydrogel (Caplan 2000, Caplan 2002a).

For 3-dimensional cell culturing, cells suspended in osmotic adjusted fluid without salt can be mixed with the pH adjusted peptide solution. Hydrogel containing cells can be formed by adding a salt-containing solution (e.g., containing a gelling agent or an iso-osmotic solute) (Caplan 2000, Caplan 2002a).

For in vivo use, the pH adjusted peptide solution can be mixed with a cell containing solution/suspension (e.g., a stem cell suspension, adipose derived cell containing solution/suspension or a bone marrow cell containing solution/suspension). The peptide solution can form a hydrogel by contacting the cell-containing solution or by contacting bodily fluid such as blood or lymph. The peptide solution can be directly injected with or without cell-containing solution. Upon injection to the body, the cells migrate to and from the hydrogel into adjacent tissue or blood (Caplan 2000, Caplan 2002a).

Three dimensional culturing experiment. MC3T3-E1 cells were obtained and grown to be seeded using the same protocol as described in Example 1. Cells were centrifuged and re-suspended into sucrose solution (10%) at $4\times10^6$ cells/ml. FHR peptide was dissolved into water to provide a 1.0% w/t solution. 1% RAD16-I solution was obtained as RAD16-I (Puramatrix™, 3DM Inc./BD Bioscience). The pH of the FHR peptide solution was adjusted to pH 5.7 by NaOH solution (i.e., so that cells can be mixed near neutral pH). The cell suspension and the peptide solution (FHR/RAD16-I) were mixed in a ratio of 1:5. The mixed solution were placed in the inserts and the cell culture medium was added to the insert to form the hydrogel. The cells were maintained by the maintenance medium (as described herein).

Fluorescence observation of the cells. After 14 days of culture, the inserts were washed by PBS and then stained by Calcein AM solution (4 uM, Invitrogen). This solution stains the live cells by the green fluorescence when excited by 480 nm light.

The RAD16-1 and FHR hydrogels in the insert was observed by confocal microscope. FIGS. 13A-13D shows the reconstruction of the 3-Dimensional reconstruction of the fluorescent images. The bright areas show the cells presence. This data indicates that that the FHR peptide provides superior 3-Dimensional cell proliferation compared to RAD16-1. The quantitative measurement of proliferation and differentiation effects by the FHR peptide hydrogel were also evaluated (FIGS. 14-16A/B). The analysis methods used are same as Example 1, except that 1% FHR peptide aqueous solution was used to form the hydrogel.

The peptide matrix promotes three dimensional and two dimensional cell proliferation because the peptide fiber is positively charged in neutral solution. As the cells are negatively charged, the cell is attracted by the positively charged fibers. Thus, this effect is also possible by attaching the other positively charged sequence such as poly-lysine.

FIGS. 14-16A/B show that FHR has also some function to promote differentiation pre-osteoblast, compared to FIGS. 3-4. However, when comparing FIG. 17 to FIG. 6, FHR's effect to promote differentiation is not so strong when compared to PRGmx or PRFmx which both contain the RGD sequence.

Figure 18:
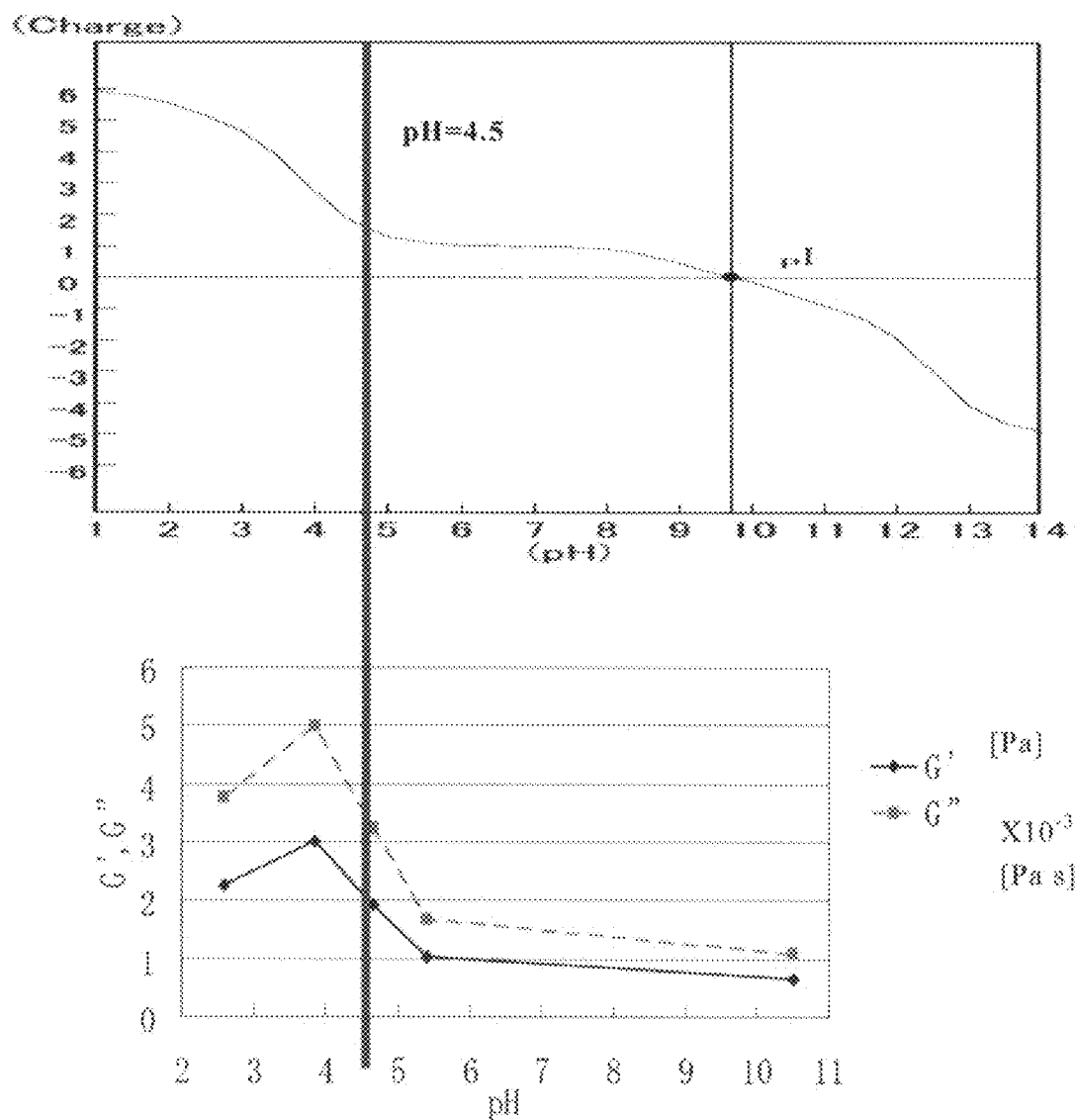
FIG. 18. Isoelectric plot and rheological data of PFS 1% solution when 0.1 N NaOH solution is added.

FIG. 18 depicts the isoelectric plot and Rheological data of PFS 1% solution when 0.1 N NaOH solution is added. 1% Ac(RADA)$_4$GGSKPPGTSS-CONH$_2$ solution (Code: SKP, peptide sequence: SEQ ID NO. 7) is a hydrogel composed of peptides with a self-assembling sequence and positively-charged functional motif. Although the pI value of the peptide is 9.74 and it keeps positive charge at near pH 7 range, the gel is formed at the point of pH 4.5. This is because the charge of the molecule around pH 7 range is +1 and smaller than the charge of Ac(RADA)$_4$GGFHRRIKA CONH$_2$ (FHR) (bigger than 3). The charge of the whole peptide should be larger than 2 when the cell is mixed. This pH should be somewhere in 6-8 in order to minimize the damage to the cells. As this sequence is heparin-binding motif, the fiber can attach to the heparin molecule which is abundant at cell surface. This heparin-binding motif provides a specific anchor to the cell. As described in Example 1, this binding synergistically works with the other binding motif (e.g., RGD) to induce biological stimuli for cell proliferation and differentiation. This effect is not limited to the sequences previously describe, but the other motifs, including -XBBXBX- and -XBBBXXBX- sequences.

Example 4

Protein Retention and Delivery Using the Self-assembling Peptide

The self-assembling peptide with heparin-binding motif described previously is also useful for growth factor and/or the therapeutic protein retention and/or delivery in tissue engineering and other therapeutic purpose. Many growth factors such as VEGF, FGFs, PDGF, HGF, TGF-β and BMPs are known to bind to heparin or heparan sulfate. When the heparin or heparan sulfate is mixed with the heparin-binding peptide solution and other growth factors, the peptide binds heparin or heparan sulfate by the heparin-binding motif and the bound heparin or heparan sulfate binds growth factors. The growth factors are thus held for a longer time in the peptide matrix, continuously stimulating the cells, and are slowly released by the degradation of the peptide matrix. However, heparin and/or growth factors are not necessary to add to the matrix in order to have desired biological properties. For example, the peptide matrix can be implanted in the subject's body, and heparin and/or growth factors present in the subject's body can be supplied (e.g., migrate to) to the implanted matrix.

The addition of positively or negatively charged motif to the self-assembling sequence is also useful for growth factor retention and delivery in tissue engineering and other therapeutic purpose. Many growth factors such as VEGF, FGFs, PDGF, HGF, TGF-β and BMPs are polar charged and they have affinity to positively or negatively charged peptide matrix according to the molecularly charge distribution of both growth factors and peptide matrix. One example of such peptide is Ac(RADA)$_4$-GGDGRGDSVAYG-CONH$_2$ (SEQ ID NO. 9). SEQ ID NO. 9 has itself cell binding function. By adding of positively or negatively charged functional motif to the self-assembling sequence, the protein retention can be achieved by introducing biological function at the same time, maintaining self-assembling function of the original self-assembling sequence.

The other possibility is to use self-assembling sequence which has a charge. Ac(FKFQ)$_3$-CONH$_2$ (SEQ ID NO. 51) is positively charged molecule which have self-assembling property. Although this is the simple approach, the properties of self-assembling peptide matrix cannot help but be affected by changing the self-assembling sequence.

The effect of protein retention and delivery using the self-assembling peptide were studied (Table 11). bFGF was used as a model protein. The retention of bFGF in different peptide matrix in different charge condition was measured by ELISA after washing by PBS. After washing out unbound bFGF, the effect of protein retention to self-assembling peptide matrix were evaluated the using cell culturing of HUVEC (human umbilical vein endothelial cells).

TABLE 11

Self-assembling peptides for protein retention

| No. | Sequence | Description | pI, charge |
|---|---|---|---|
| RAD16-I | Ac(RADA)$_4$-CONH$_2$ | | 6.1, neutral |
| SEQ ID NO. 5 | Ac(RADA)$_4$GGDGRGDSVAYG-CONH$_2$ | Cell adhesion domain (Osteopontin) | 4.78, negatively charged |
| SEQ ID NO. 6 | Ac(RADA)$_4$GGFHRRIKA-CONH$_2$ | Heparin binding domain | 11.32, positively charged |
| SEQ ID NO. 51 | Ac(FKFQ)$_3$-CONH$_2$ | Charged self assembly sequence | 10.30, positively charged |

The self-assembling peptides in different charge condition were selected as shown in Table 12. RAD16-I has neutral self-assembling sequence. SEQ ID NO. 5 has neutral self-assembling sequence but negatively charged cell attachment sequence (-DGRGDSVAYG-) (SEQ ID NO. 55) is attached using linker sequence. SEQ ID NO. 6 has neutral self-assembling sequence and positively charged heparin binding sequence (-FHRRIKA-) (SEQ ID NO. 63) is attached using linker sequence. SEQ ID NO. 51 consists of positively charged self-assembling sequence.

TABLE 12

Hydrogel components

| Code | Hydrogel contents |
|---|---|
| RAD-2P | 2% RAD16-1 peptide solution |
| DGR-2P | 2% SEQ ID NO. 5 peptide solution |
| FHR-2P | 2% SEQ ID NO. 6 solution |
| FKF-2P | 2% SEQ ID NO. 51 peptide solution |

The peptide solutions provided in Table 12 were loaded in the culture inserts (10 mm diameter, Millicell-CM, Millipore) and gels were formed using PBS. After gelation, bFGF solution in PBS was added inside and outside and plated for overnight. bFGF was loaded at 175 ng/insert. After loading bFGF, the PBS inside and outside the inserts were exchanged three times (2 hours, 9 hours and 12 hours) to remove unbound bFGF (Washing). After the washing, the PBS was exchanged to the cell culture medium (EGM-2-MV, Camblex) without attached growth factor (bFGF, VEGF and EGF) and placed more than a day (such that the fluid contained in the gel is exchanged from PBS to cell culture medium), then HUVEC (human umbilical vein endothelial cells) were plated at 7.5×10$^4$ cells on the inserts and cultured for three days.

Cell culturing using cell culture medium (EGM-2-MV) was used without attached growth factor on peptide matrix as negative control. Cell culturing using cell culture medium (EGM-2-MV) was used with attached growth factor on peptide matrix without loading growth factor as positive control. The bFGF concentration in washing buffer (PBS) and cell culture medium (EGM-2-MV) was measured using ELISA. The washing buffer and cell culture medium were exchanged at each measurement period (2 hours, 9 hours and 12 hours for washing, and at the cell seeding (D0), Day 1 (D 1), Day 2 (D2) and Day 3 (D3)). Growth factor retention rate was calculated by accumulating the amount of measured bFGF.

Figure 19:
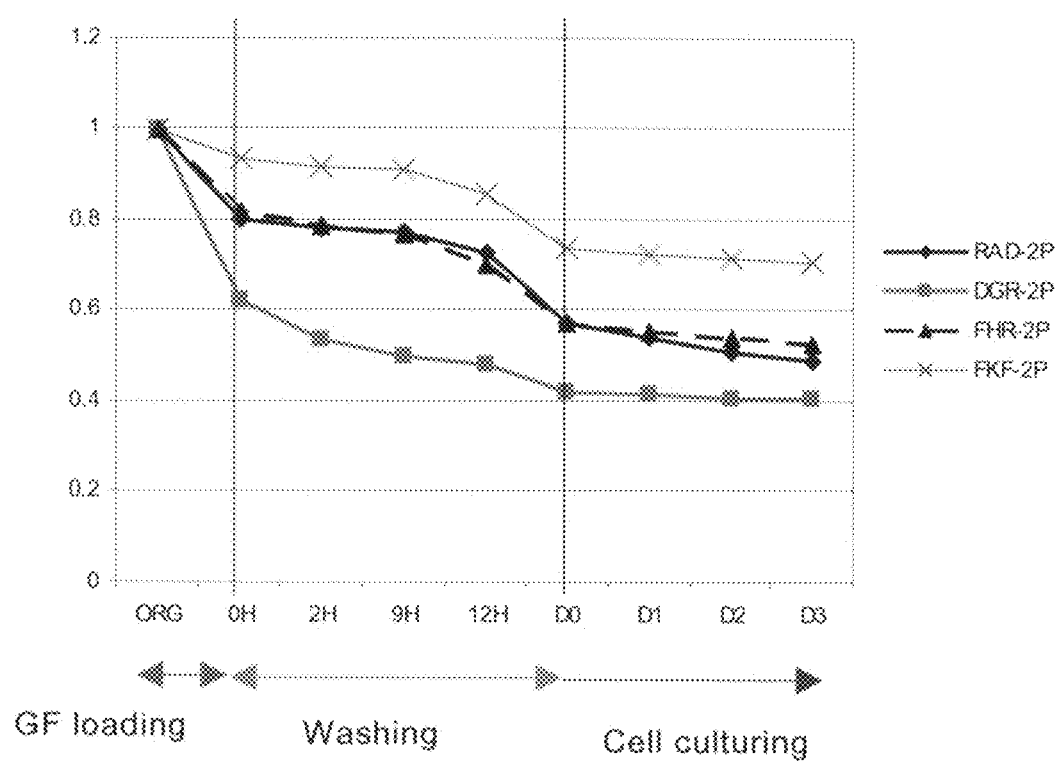
FIG. 19. Growth factor retention during washing and culturing.

The results are shown in FIG. 19. The retention rate is high in the order of KFQ-2P, FHR-2P, RAD-2P then DGR-2P. There is difference in protein retention/release profile according to the charge properties of the hydrogel. KFQ-2P and FHR-2P are positively charged and DGR-2P is negatively charged. Although bFGF is positively charged molecule, the local charge distribution of bFGF has disparity as shown in FIG. 20, thus positively charged matrix can attract positively charged protein. Increasing the protein release rate is just opposite of increasing the retention rate. The protein release rate can be also controlled by molecular charge distribution of the peptide matrix.

FIG. 20 depicts the molecular charge distribution of bFGF. These results show that the protein retention in the peptide matrix and release profile from the peptide matrix can be controlled by changing the charge properties of the peptide matrix. This profile is controlled by the local molecular affinity, such as molecular charge distribution of protein and the peptide matrix fiber.

Figures 21A, 21B, 21C, 21D, 21E, 21F:
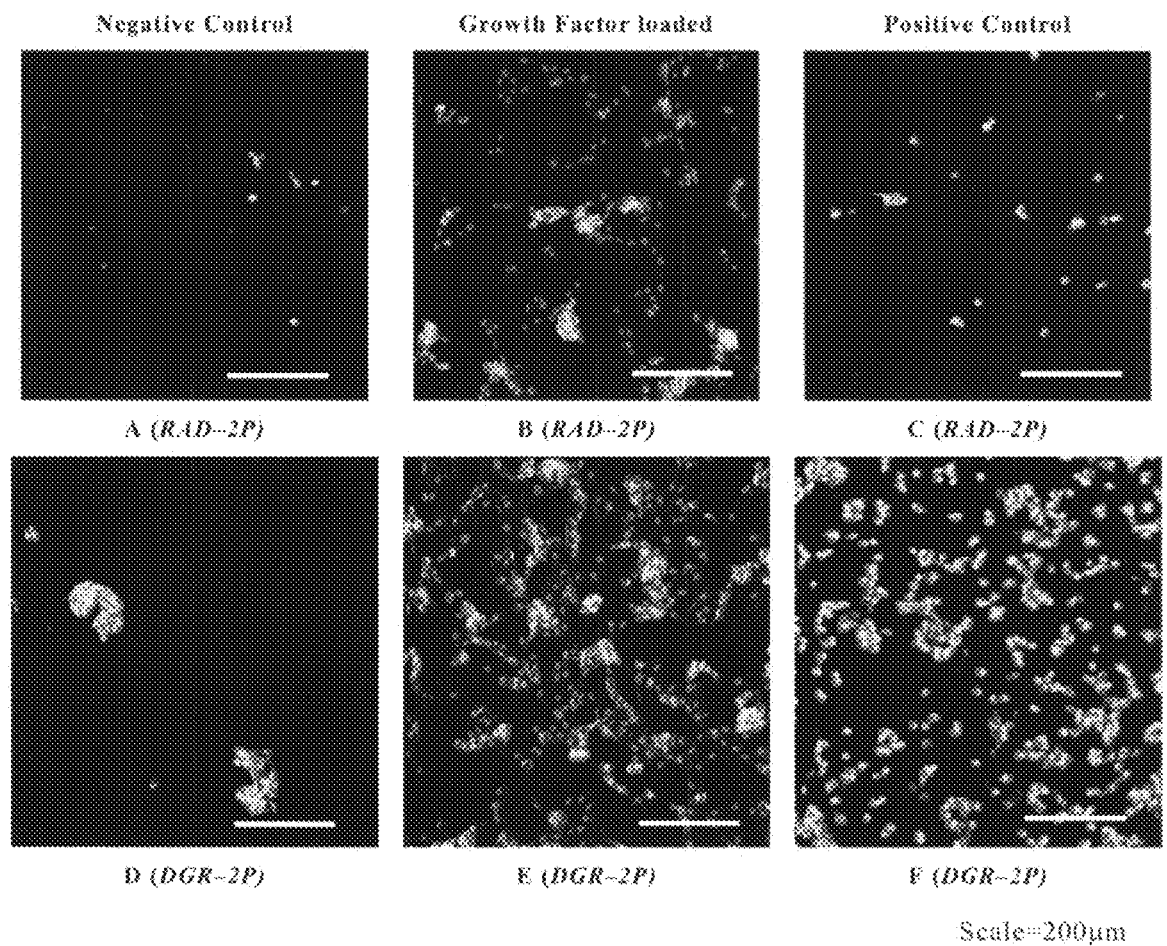
FIGS. 21A-21F. HUVEC images cultured on different peptide matrices. Top row: RAD-2P; Bottom row: DGR-2P.

FIG. 21 shows the fluorescence microscopy image of cell on the peptide matrix (RAD-2P and DGR-2P) at Day 3. The green stain shows nuclei, the red stain shows actin fiber. Until Day 2, the cell attachment was well maintained both in bFGF loaded and positive control (Growth factor addes medium) (not shown in image). However, the cell attachment and cell spread (shown by the spread of actin fiber area) was superior in growth factor loaded compared not only to negative control but also to positive control, and both in RAD-2P and DGR-2P. RAD-2P shows the dominant effect. This data indicates that the growth factor retention using charge controlled peptide matrix is useful for cell maintenance. This also indicates that the retention or immobilization of the growth factor in the peptide matrix may be more effective than that provided in soluble form.

Figure 22:
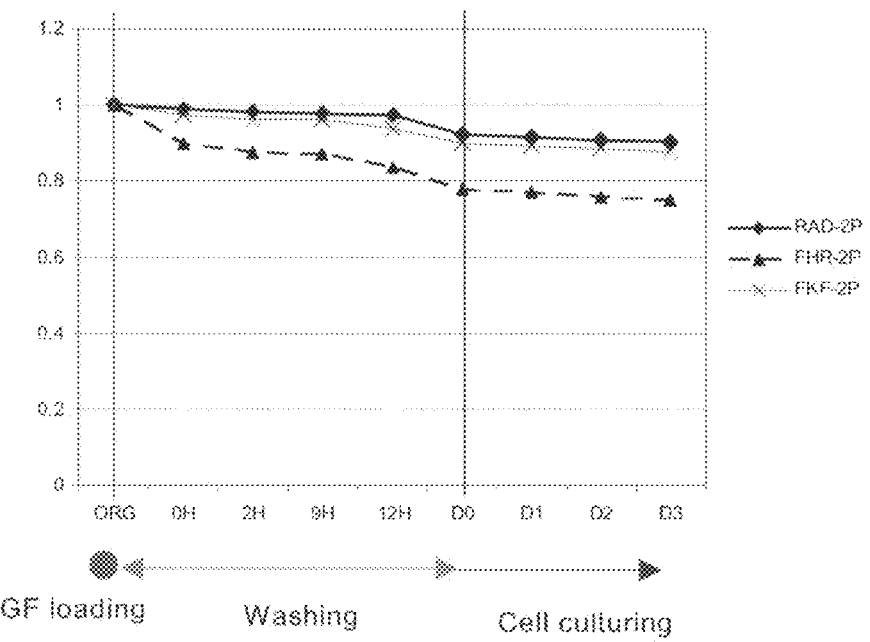
FIG. 22. Growth factor retention when growth factor is mixed before gelation.

The protein loading to the peptide matrix can be done employing other methods than that previously described. FIG. 22 shows the growth factor retention rate when bFGF was mixed to the peptide solution first and form gel. They kept much higher retention rate compared to when bFGF was loaded after gelation (i.e., as depicted in FIG. 19) while the bFGF release rate become smaller.

Example 5

In vivo Application of the Functionalized Peptides

The effects of the functionalized peptide were evaluated in vivo in rats. 6 weeks male rat sculls were used for this evaluation (two samples for each experiment).

Figures 23A, 23B, 23C:
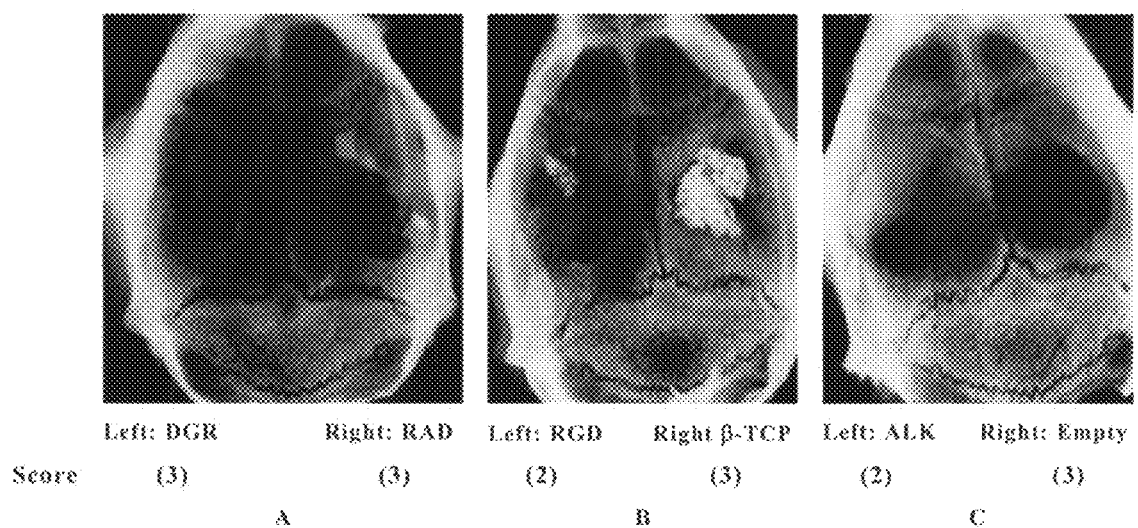
FIGS. 23A-23C. X-ray images of rat skulls after 2 weeks of implantation of materials.
Figures 24A, 24B, 24C, 24D, 24E, 24F, 24G, 24H, 24I, 24J, 24K, 24L, 24M:
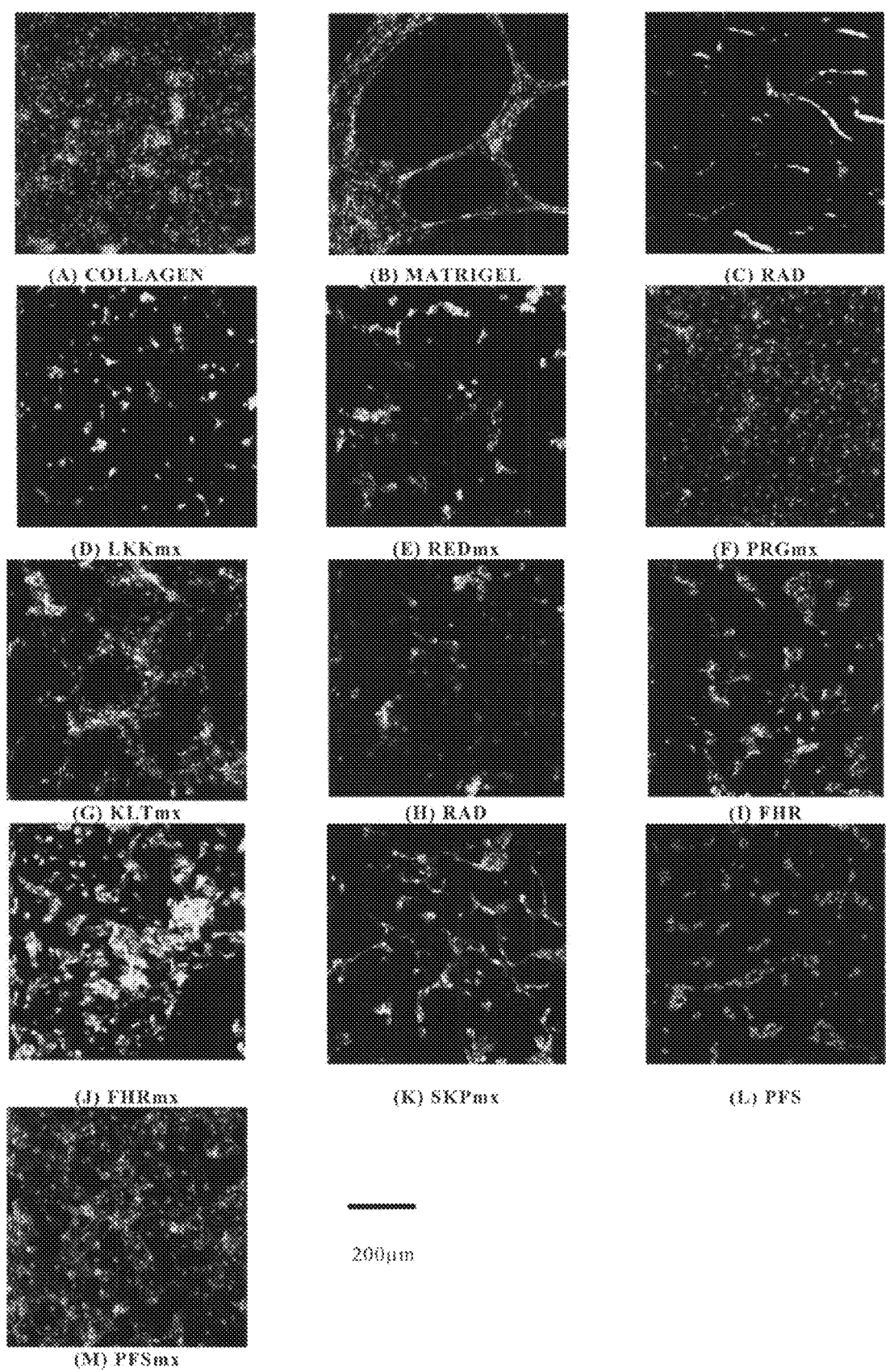
FIGS. 24A-24M. Fluorescence confocal microscopy images of HUVEC cultured on the hydrogels for two days. The green stain shows nuclei, the red stain shows actin fiber. Collagen, Matrigel, PRGmx, KLTmx, FHRmx, PFSmx gel had higher cell attachment compared to RAD. On Matrigel, HUVEC cells showed capillary structure which is considered to related to the vessel formation ability. On KLTmx, cells exhibited capillary structure resembles to Matrigel.

The rats in this study underwent creation of two bone defects of 4 mm diameter, bilaterally in each skull. The defects were filled with the hydrogels provided in Table 13. Some of the defects were left empty as controls. Beta-tricalcium phosphate (β-TCP) is a synthetic bone substitute and was used for comparison (as can be seen in FIG. 23B, β-TCP was placed into right side of the skull (white granules)).

TABLE 13

In vivo application of the functionalized peptides

| Code | Hydrogels |
|---|---|
| RAD | 1% RAD16-I peptide solution |
| ALKmx | 1% SEQ ID NO. 3 peptide solution and 1% RAD16-I peptide solution mix by 1:1 |
| PRGmx | 1% SEQ ID NO. 4 peptide solution and 1% RAD16-I peptide solution mix by 1:1 |
| DGRmx | 1% SEQ ID NO. 5 peptide solution and 1% RAD16-I peptide solution mix by 1:1 |
| TCP | β-TCP (beta-tricalcium phosphate: 70% porosity) |

The peptide solution was directly injected to the defects without cells. The peptide solution formed a hydrogel immediately after injection by the salt in the body fluid (e.g., blood, lymph fluid, and the like).

Bone Formation Evaluation: All animals from each group were euthanized 2 and 4 weeks later. The X-ray image of the skulls were taken. The skulls were collected, hemisected, and fixed in formalin. The defects were then trimmed, decalcified, embedded in paraffin, stained by HE staining method, and evaluated by a Veterinary pathologist, who characterized by histomorphometry the type of tissue contained within the defects. The degree of bone regeneration is graded as Complete recovery, 1 (more than 80%), 2 (more than 50%), or 3 (weak in X-ray).

The results of 2 weeks (Table 14 and FIGS. 23A-23C) suggests that ALKmx and PRGmx supports bone regeneration in the early stage of the repair (FIG. 23A-23C shows the X-ray images at the skull after 2 weeks). The results of 4 weeks (Table 15) suggests that the hydrogel composed by self-assembling peptide promotes bone regeneration. These results suggest that mixture of RAD16-I and SEQ3, SEQ4, SEQ5 can be used as bone filler which promotes bone regeneration.

TABLE 14

Two weeks

| | RAD | ALKmx | PRGmx | DGRmx | TCP | Empty Defects |
|---|---|---|---|---|---|---|
| Average score | 3.0 | 2.0 | 2.0 | 3.0 | 3.0 | 3.0 |

TABLE 15

Four weeks

| | RAD | ALKmx | PRGmx | DGRmx | TCP | Empty Defects |
|---|---|---|---|---|---|---|
| Average score | 1.0 | 1.5 | 1.5 | 1.0 | 2.0 | 2.0 |

The peptide hydrogel can be used in combination with synthetic bone substitutes such as beta-tricalcium phosphate or hydroxyapatite. Synthetic bone substitutes like beta-tricalcium phosphate or hydroxyapatite contains pores which are helpful for bone regeneration by providing mechanically stable space for osteoblast to function. They have porous structure which have more than 60% porosity and consists of pores diameter of 100-500 microns. The each pore is connected to the other pore so that the cell and blood vessel can be migrated into the material. The shape of the synthetic bone substitute is block of one of a few of centimeters, cylinder of a few centimeters length, plates of a few centimeter, and granules of a few millimeters so on. The shape is easily adjusted by the surgeon at the time of the implantation according to the defects size.

They also serve as calcium source for bone regeneration. The mixture of the peptide hydrogel and the synthetic bone substitute has possibility of enhancing the bone regeneration by providing both biological and mechanical support for osteoblast function.

However, peptide solutions consisting of no to little charged peptide in near neutral range cannot be mixed with basic salt like calcium phosphate, tricalcium phosphate or hydroxyapatite. This is because the no to little charged peptide molecule is soluble only when the pH of solution is highly acidic. In such acidic condition, basic salt like calcium phosphate, tricalcium phosphate and Hydroxyapatite are dissolved in the peptide solution and cannot maintain solid. Increasing the pH of the peptide solution turns the peptide solution into fragile hydrogel. This inhibits integration of the peptide hydrogel and the synthetic bone substitute.

As described in Example 3, the positively charged peptide solution like FHR (SEQ6) can be adjusted to the solution pH to near neutral without transforming into a hydrogel. This makes the mixture of the peptide solution and the basic salt porous matrix like calcium phosphate, tricalcium phosphate or hydroxyapatite possible. As the peptide solution is low-viscous liquid, the peptide migrates into the pore in the pore. When the peptides are self assembled by the effect of salty solution (such as a culture medium and/or bodily fluid, such as blood), the peptide hydrogel and the porous matrix become well integrated.

The same effect can be obtained by using other self-assembling peptide sequences, such as SEQ ID NO. 51 (Table 16). SEQ ID NO. 51 is positively charged in neutral pH range and FKF stays solution phase in neutral pH range (Caplan 2002a). The mixture of FKF and the basic salt porous matrix like calcium phosphate, tricalcium phosphate or hydroxyapatite in neutral pH range is possible. The hydrogel can be formed by adding salty solution (Table 17). FKF supports cell proliferation like pre-osteoblast when it becomes hydrogel. This kind of hydrogel consists of positively charged self-assembling peptide sequence is useful as protein retention as described in Example 3. Functionalized peptides, such as SEQ ID NO. 1-SEQ ID NO. 7, can be mixed with the charged peptide solution like FHR or FKF. Although the peptides have different charges, it can maintain charged peptide solution properties when the positively-charged peptide quantity is dominant. Thus, the mixture of the peptide and the synthetic bone substitute can be functionalized by functionalized peptides as well.

TABLE 16

| No. | Sequence | Description |
|---|---|---|
| SEQ ID NO 51 | Ac(FKFQ)3-CONH$_2$ | Charged self assembly sequence |

TABLE 17

| Code | Hydrogel contents |
|------|-------------------|
| FKF  | 1% SEQ ID NO 51 peptide solution |

Example 6

Functional Modified Peptide Matrix for Angiogenesis and Vascularization

Promoting angiogenesis and vascularization itself has a huge potential in therapeutic field, especially ischemic diseases like myocardial infarction, peripheral vascular disease and cerebral infarction. Angiogenesis and vascularization have also important roles in tissue regeneration, such as wound healing and bone regeneration. They also are very important in the construction of various types of three dimensional engineered tissue, such as skin, liver, pancreas, bone, muscle and the like. It is important to develop matrices which help and promote angiogenesis and vascularization by providing proper microenvironments to the cells which consists the vessel structure, such as endothelial cells, smooth muscle cells, pericytes, and fibroblasts which form connective tissue which supports vessels.

Several functional motif peptide sequences are known to promote angiogenesis. For example, the actin binding site on thymosin β4 (-LKKTETQ-) (SEQ ID NO. 66) can promote endothelial cell migration and adhesion, tubule formation, aortic ring sprouting, and angiogenesis (Huff et al., FASEB Journal (2003) 17:2103-2105). The III-CS domain of human plasma fibronectin (-REDV-) (SEQ ID NO. 65) supports the attachment of vascular endothelial cells and the spreading of endothelial cells (Shin et al., Biomaterials (2003) 24:4353-4364; Welsh et al., Biomaterials (2000) 1:23-30). The VEGF binding interface (-KLTWQELYQLKYKGI-) (SEQ ID NO. 59) reproducing a region of the VEGF helix region 17-25 induces endothelial cells proliferation, activated cell signaling dependent on VEGF, and promotes capillary formation and organization in in vitro assays (D'Andrea et al., PNAS (2005) 102: 14215-14220).

The effect of functional modified peptide matrix to HUVEC (human umbilical vein endothelial cells) was evaluated by culturing cells 2-dimensionally on the gel. The self-assembling peptides studied are provided in Table 18.

The peptide solutions shown in Table 19 were loaded in the culture inserts (10 mm diameter, Millicell-CM, Millipore) and gels were formed using cell culture medium (EGM-2-MV, Camblex). Collagen-1 and Matrigel were used as control matrices. HUVEC (human umbilical vein endothelial cells) were plated at $8 \times 10^4$ cells on the inserts and cultured up to 7 Days.

TABLE 19

| Hydrogel components | |
|---|---|
| Code | Hydrogel contents |
| RAD | 1% RAD16-1 peptide solution |
| LKKmx | 1% SEQ ID NO 9 peptide solution and 1% RAD16-I peptide solution mix by 1:1 |
| REDmx | 1% SEQ ID NO 10 peptide solution and 1% RAD16-I peptide solution mix by 1:1 |
| PRGmx | 1% SEQ ID NO 4 peptide solution and 1% RAD16-I peptide solution mix by 1:1 |
| KLTmx | 1% SEQ ID NO 11 peptide solution and 1% RAD16-I peptide solution mix by 1:1 |
| FHR | 1% SEQ ID NO 6 peptide solution |
| FHRmx | 1% SEQ ID NO 6 peptide solution and 1% RAD16-I peptide solution mix by 1:1 |
| PFS | 1% SEQ ID NO 1 peptide solution |
| PFSmx | 1% SEQ ID NO 1 peptide solution and 1% RAD16-I peptide solution mix by 1:1 |
| SKPmx | 1% SEQ ID NO 12 peptide solution and 1% RAD16-I peptide solution mix by 1:1 |
| COL | Collagen-1 gel (0.25%) |
| MTG | Matrigel |

FIGS. 24A-24M shows the fluorescence confocal microscopy images of HUVEC cultured on the hydrogels for two days. The green stain shows nuclei, the red stain shows actin fiber. Collagen, Matrigel, PRGmx, KLTmx, FHRmx, PFSmx gel had higher cell attachment compared to RAD. On Matrigel, HUVEC cells showed capillary structure which is considered to related to the vessel formation ability. On KLTmx, cells exhibited capillary structure resembling Matrigel.

Figure 25:
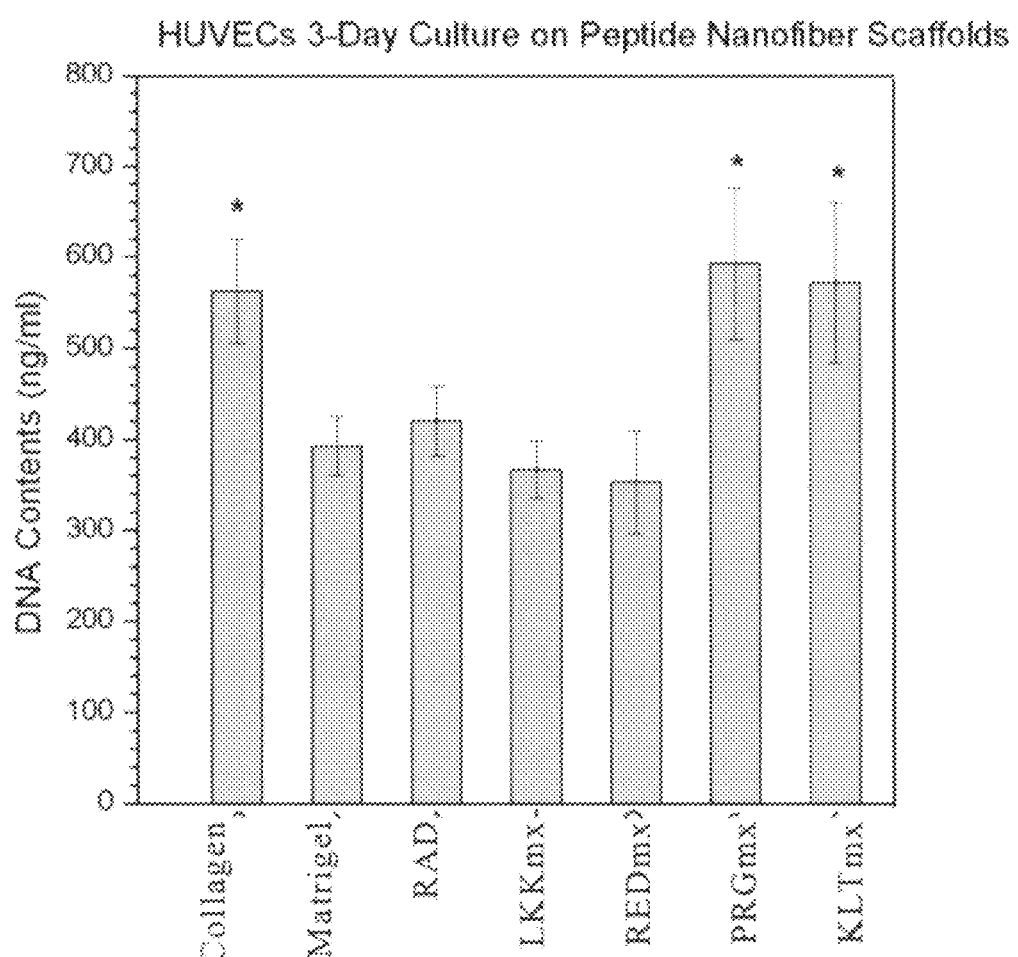
FIG. 25. HUVECs 3-Day Culture on Peptide Nanofiber Matrices.
Figure 26A:
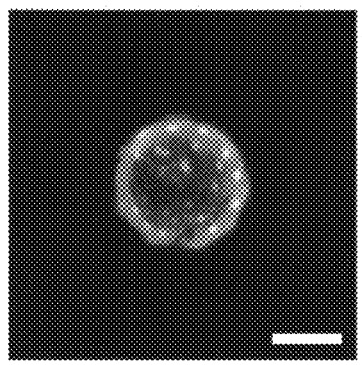
FIG. 26A-26F. Fluorescence microscopy image of beads on the peptide matrix at Day 1 and Day 2 after placing the beads. The green stain shows nuclei, the red stain shows actin fiber. The white bar represents 100 um. On the Day 1, most of the cells stayed on the beads. On the Day 2, the cells were well migrated from the beads to Collagen, PRGmx and KLTmx hydrogel compared to RAD. On Matrigel, only small amount of the cells were migrating to the gel.
Figure 26B:
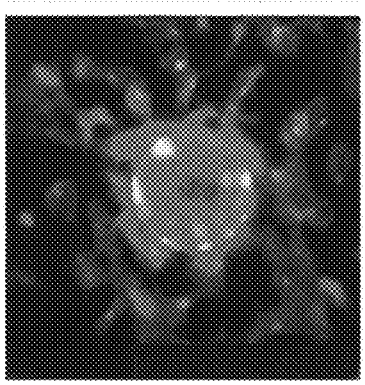
Figure 26C:
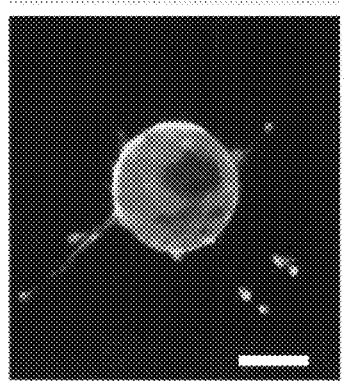
Figure 26D:
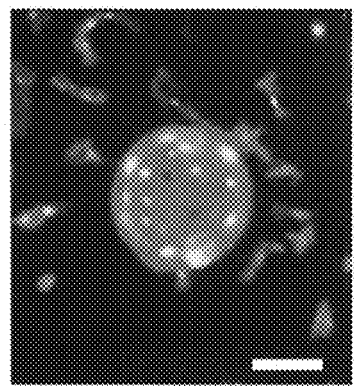
Figure 26E:
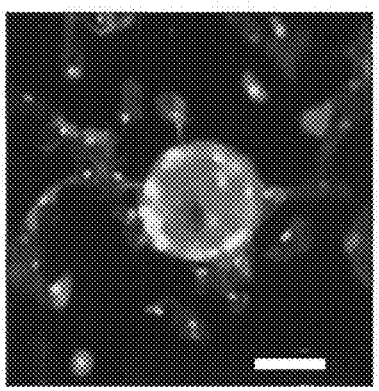
Figure 26F:
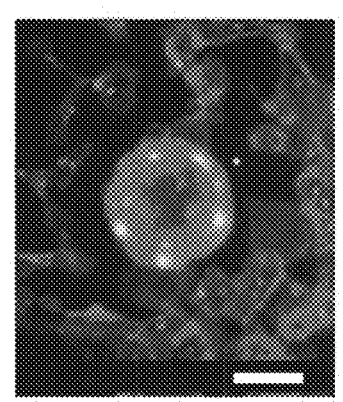

The results are summarized in Table 20 and FIG. 25. The amount of DNA in the well after three days culture was evaluated in selected hydrogels of Table 19. The DNA amount is proportional to the number of the cells. FIG. 25 indicates collagen, PRGmx and KLTmx gel had statically higher DNA amounts compared to RAD. These results showed that functionalized peptide matrixes have superior endothelial cell attachment compared to the non-functionalized peptide

TABLE 18

| No. | Sequence | Description |
|-----|----------|-------------|
| RAD16-I | Ac(RADA)$_4$-CONH$_2$ | |
| SEQ ID NO 9 | Ac(RADA)4GGGGLKKTETQ-CONH$_2$ | The actin binding site on thymosin β4 |
| SEQ ID NO 10 | Ac(RADA)$_4$GGGGREDV-CONH$_2$ | Fibronectin/Endothelial cells adhesion |
| SEQ ID NO 4 | Ac(RADA)$_4$GPRGDSGYRGDS CONH$_2$ | Repetitive RGD binding sequence |
| SEQ ID NO 11 | Ac(RADA)$_4$-GGGGKLTWQELYQLKYKGI-CONH$_2$ | VEGF mimicking peptide/Bind to VEGF receptors |
| SEQ ID NO 6 | Ac(RADA)$_4$GGFHRRIKA-CONH$_2$ | Heparin binding domain |
| SEQ ID NO 1 | Ac(RADA)$_4$GGPFSSTKT-CONH$_2$ | Bone marrow homing |
| SEQ ID NO 12 | Ac(RADA)$_4$GGSKPPGTSS-CONH$_2$ | Bone marrow homing | matrix and they have similar function in cell morphology comparable to nature derived matrix such as collagen or Matrigel, depending on the functional motif attached to the original self-assembling sequence.

TABLE 20

Cell attachment and morphology

| Code | Cell attachment | Capillary like morphology |
|------|-----------------|---------------------------|
| RAD | + | |
| LKKmx | + | |
| REDmx | + | |
| PRGmx | ++++ | |
| KLTmx | +++ | +++ |
| FHR | ++ | + |
| FHRmx | +++ | |
| PFS | ++ | + |
| PFSmx | ++++ | |
| SKPmx | ++ | ++ |
| COL | ++++ | |
| MTG | +++ | ++++ |

Key:
(a) Cell attachment [+: Weak(<20%); ++: 20-50%; +++: 50-70%; ++++: near confluence (>70%)];
(b) Capillary like morphology [+ shows the number of features observed: branch, elongation of the cell, circular cell alignment (weak: +; medium: ++; strong: +++; very strong: ++++)].

Endothelial cell migration effect on the hydrogels was evaluated. The endothelial cell migration is important when the vessel has in-growth into the matrix. HUVEC (human umbilical vein endothelial cells) were seeded on Collagen coated Dextran beads (Cytodex3, microcarrier beads, Sigma), then transferred to different hydrogels which selected from Table 19.

FIGS. 26A-26F show the fluorescence microscopy image of beads on the peptide matrix at Day 1 and Day 2 after placing the beads. The green stain shows nuclei, the red stain shows actin fiber. The white bar represents 100 um. On the Day 1, most of the cells stayed on the beads. On the Day 2, the cells were well migrated from the beads to Collagen, PRGmx and KLTmx gel compared to RAD. On Matrigel, only small amount of the cells were migrating to the hydrogel.

Figure 27:
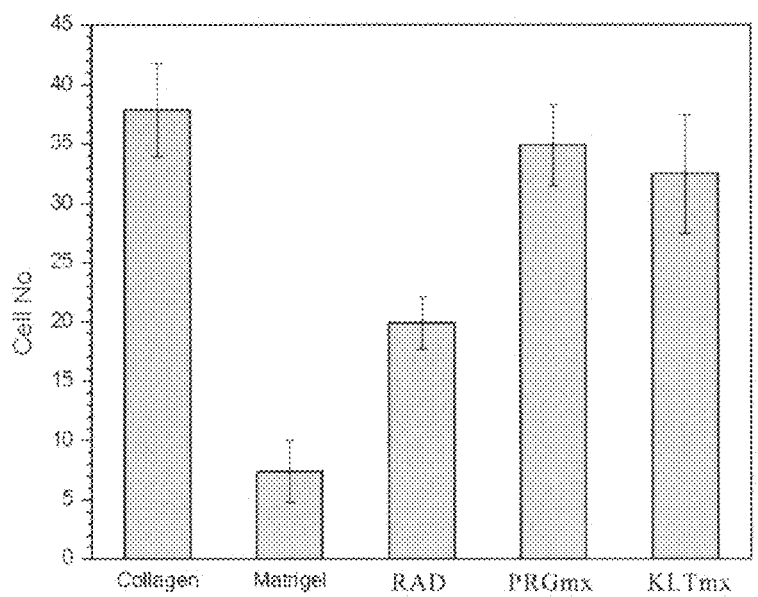
FIG. 27. Cell numbers from migration from beads on Day 2. The cells are counted from the fluorescence microscopy images provided in FIGS. 26A-26F.

FIG. 27 shows the number of the cells migrated from the beads on Day 2. The cells are counted in fluorescence microscopy image. The above observation were also confirmed in the graph.

Figures 28A, 28B, 28C:
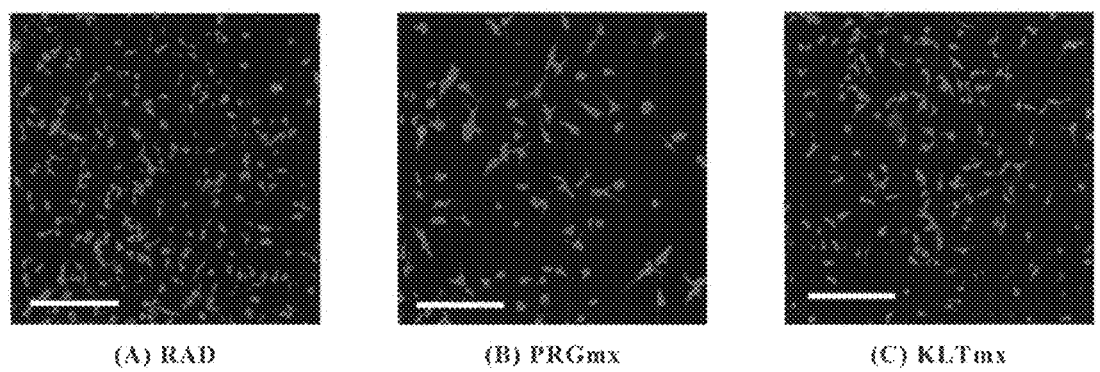
FIGS. 28A-28C. Reconstructed fluorescence confocal microscopy image of Day 2 from the seeding. The green shows live cell using calcein staining, red shows dead cells nuclei. These images shows high cell viability in the hydrogels.

3D endothelial cell culturing in the functionalized peptide matrixes was performed. HUVEC cells were suspended in 10% sucrose solution and mixed with peptide solution. The cell suspended peptide solutions were transferred to the culture inserts (10 mm diameter, Millicell-CM, Millipore) and gels were immediately formed using cell culture medium (EGM-2-MV, Camblex). Cell numbers seeded in the well were 1×10$^5$ cells/well. FIG. 28 shows the reconstructed fluorescence confocal microscopy image of Day 2 from the seeding. The green shows live cell using calcein staining, red shows dead cells nuclei. These images shows high cell viability in the hydrogels. PRGmx and KLTmx shows extended cell morphology which implies good cell attachment.

Figures 29A, 29B:
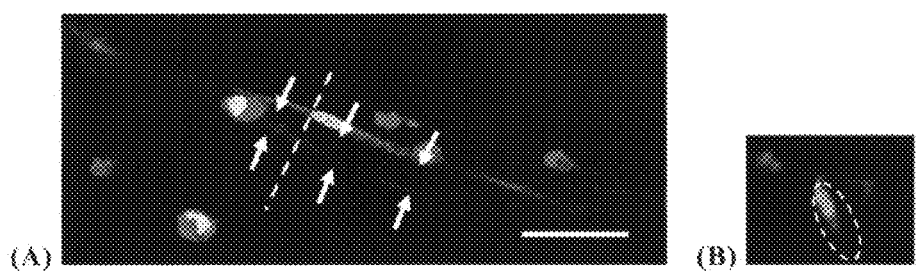
FIGS. 29A-29B. Capillary formation in 3D culture. The green stain shows nuclei, the red stain shows actin fiber.
Figure 30A:
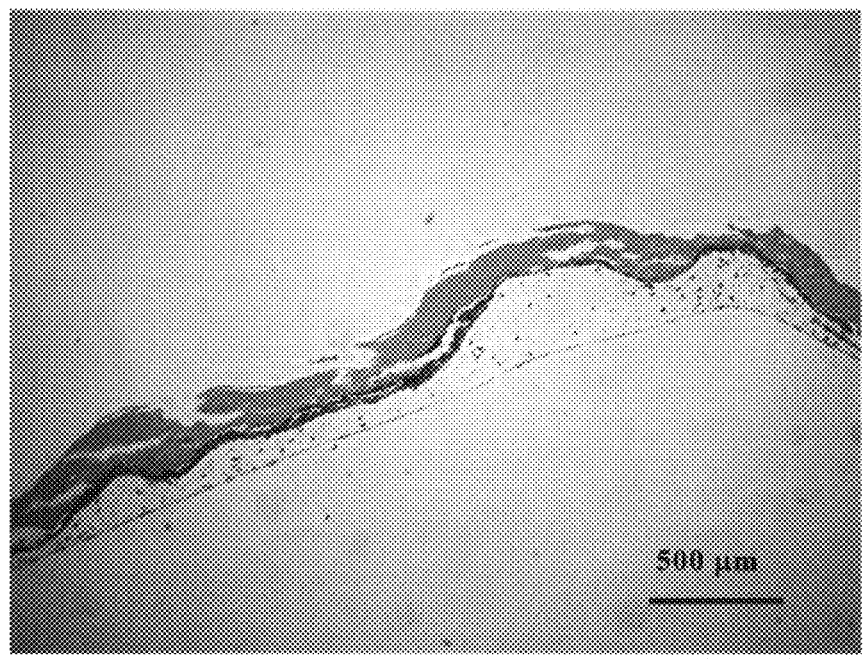
FIGS. 30A-30G. Histological images of Chorioallantoic Membrane (CAM) incubated with different hydrogels.
Figure 30B:
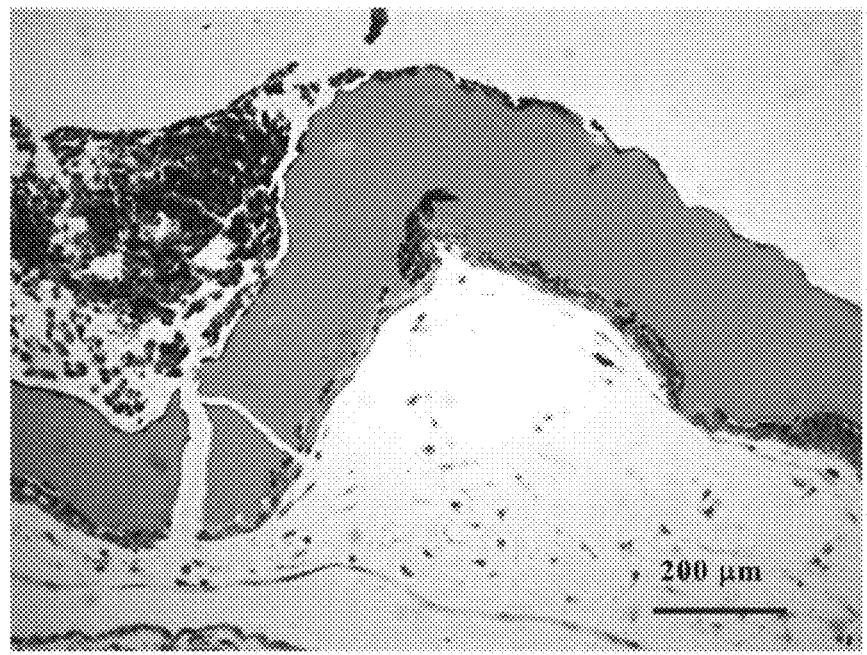
Figure 30C:
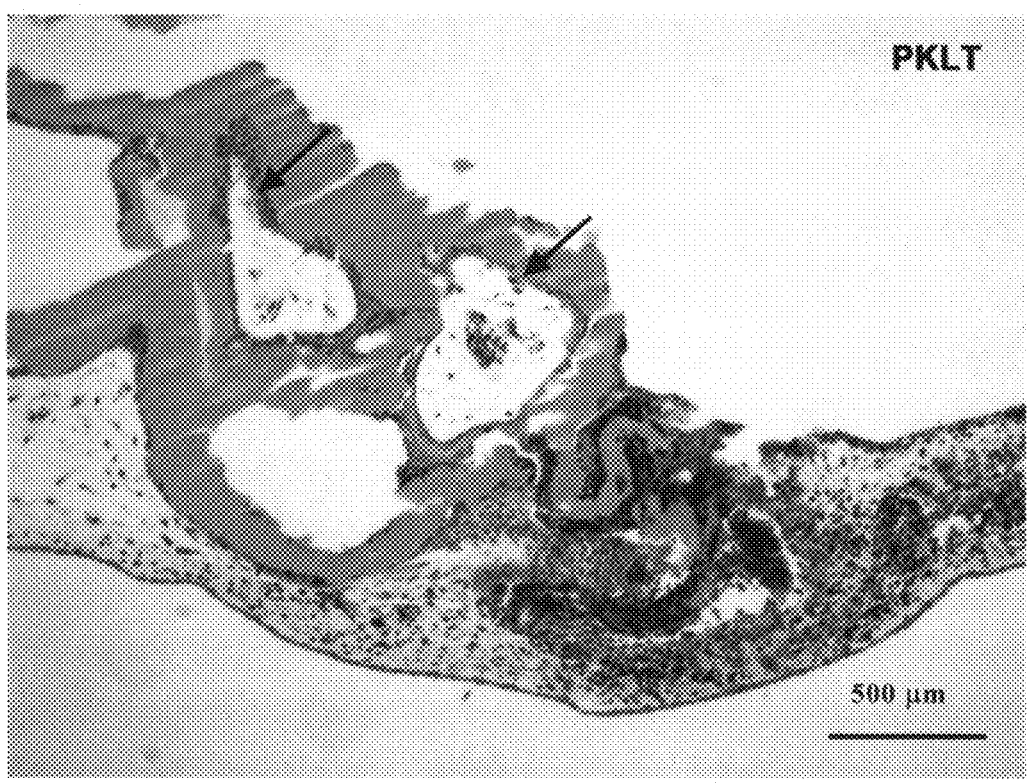
Figure 30D:
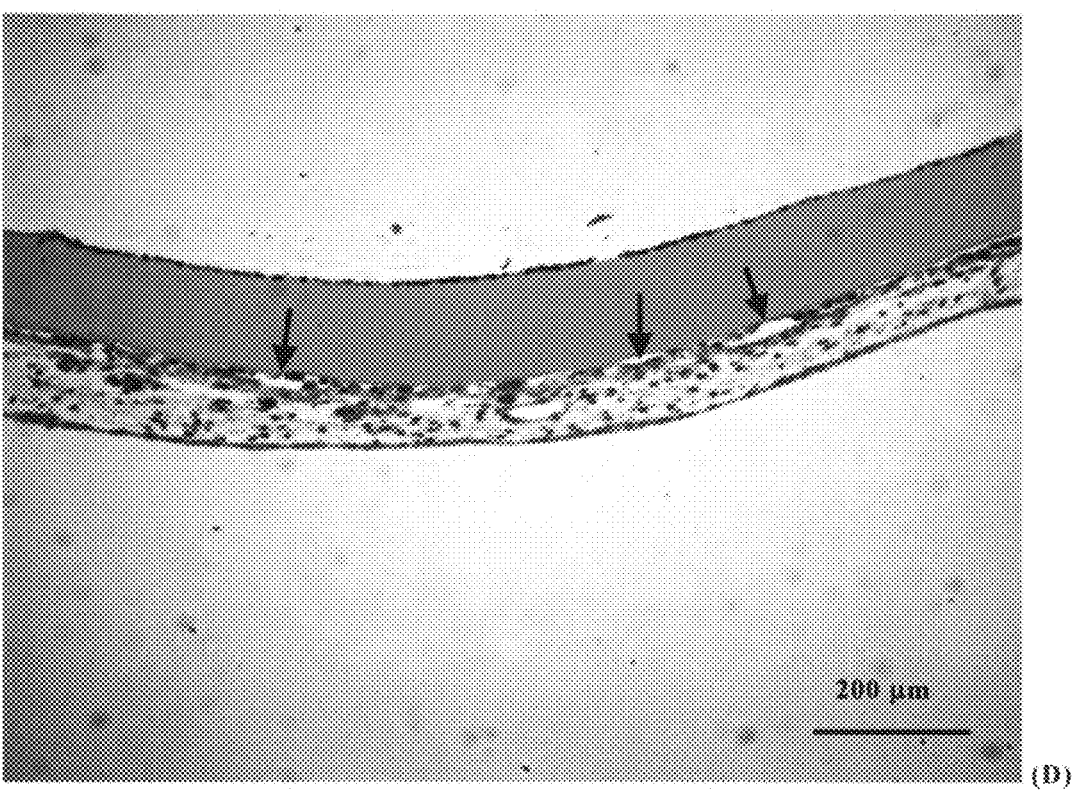
Figure 30E:
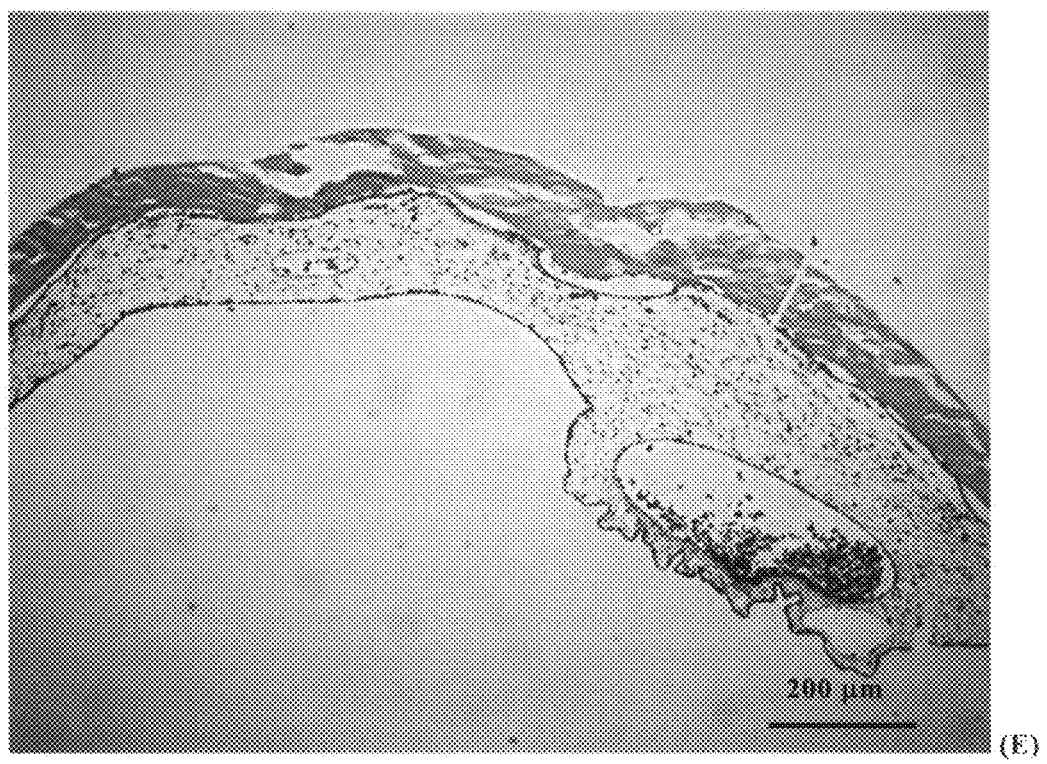
Figure 30F:
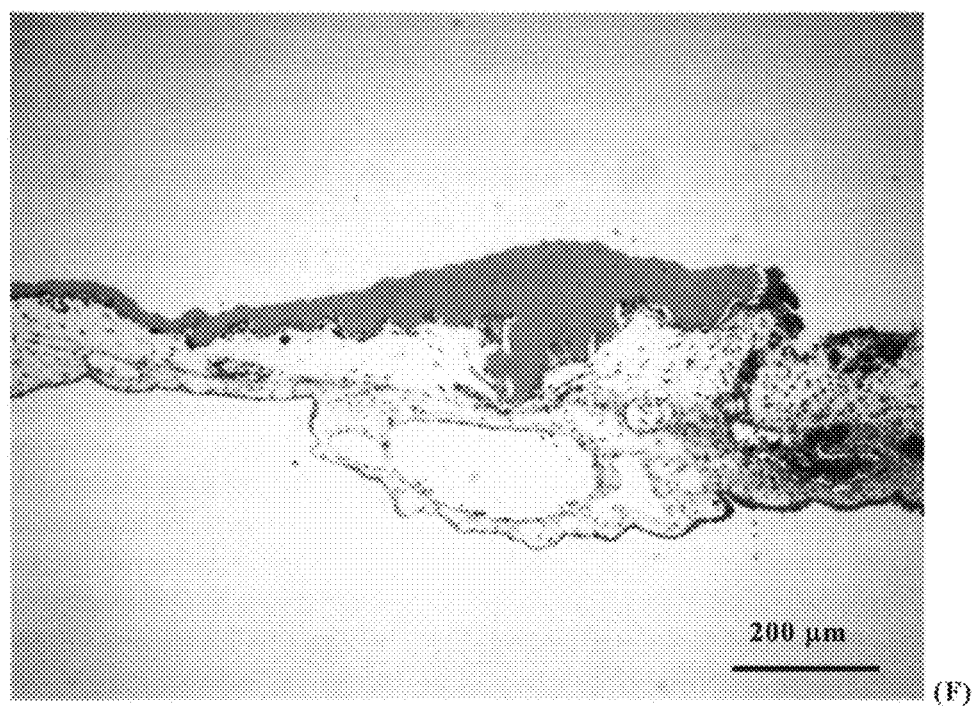
Figure 30G:
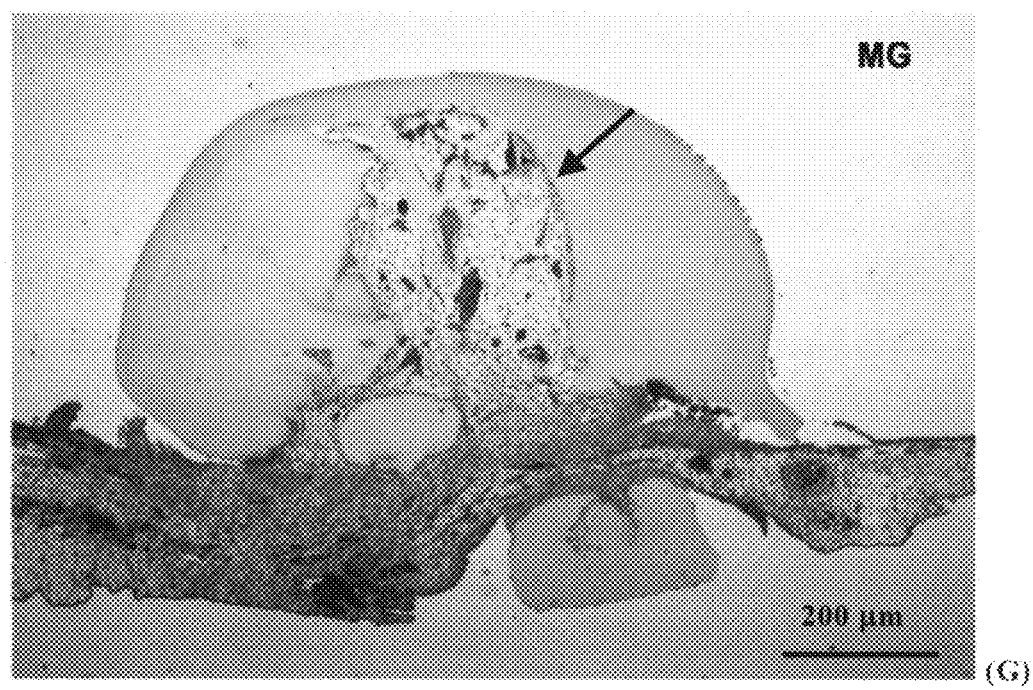
Figure 31A:
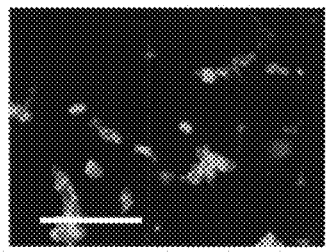
FIGS. 31A-31K. HUVEC Attachment with different hydrogels.
Figure 31B:
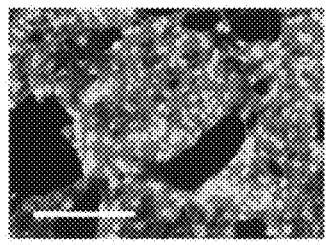
Figure 31C:
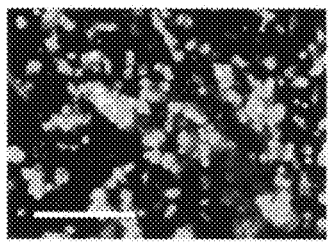
Figure 31D:
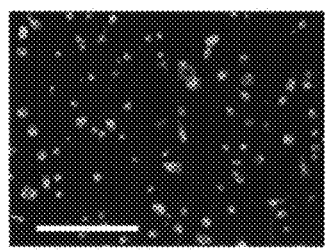
Figure 31E:
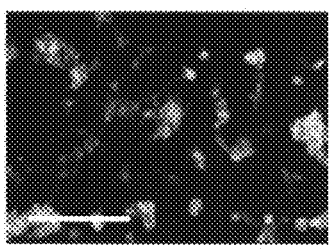
Figure 31F:
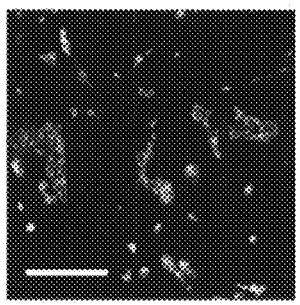
Figure 31G:
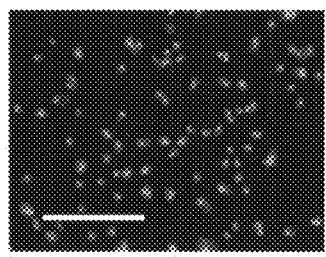
Figure 31H:
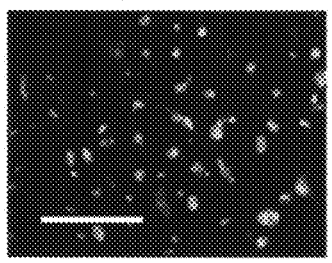
Figure 31I:
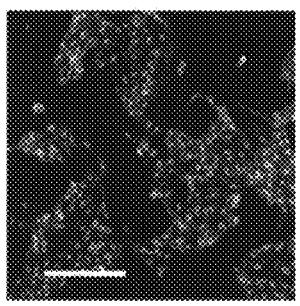
Figure 31J:
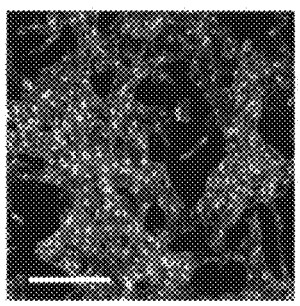
Figure 31K:
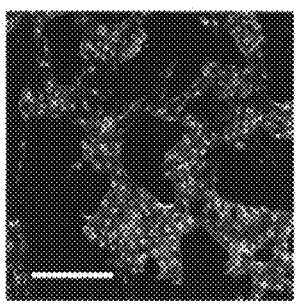
Figure 32A:
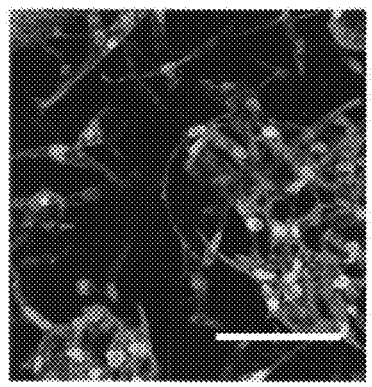
FIGS. 32A-32J. 3-dimensional culture of ADSC in functionalized peptides matrixes.
Figure 32B:
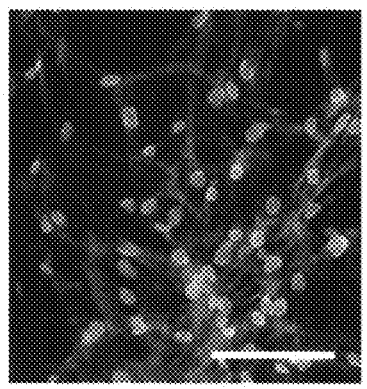
Figure 32C:
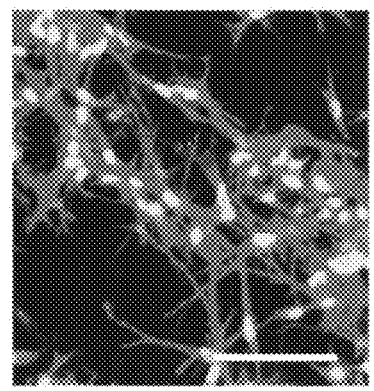
Figure 32D:
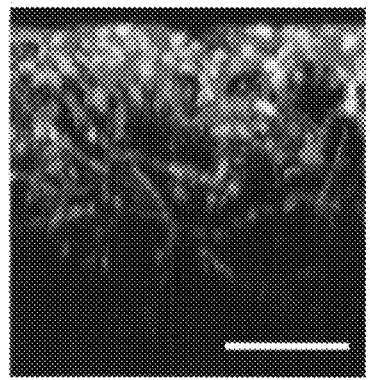
Figure 32E:
Figure 32F:
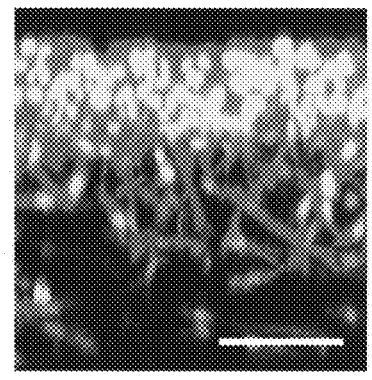
Figure 32G:
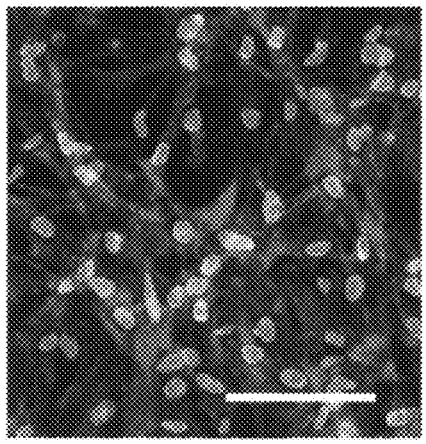
Figure 32H:
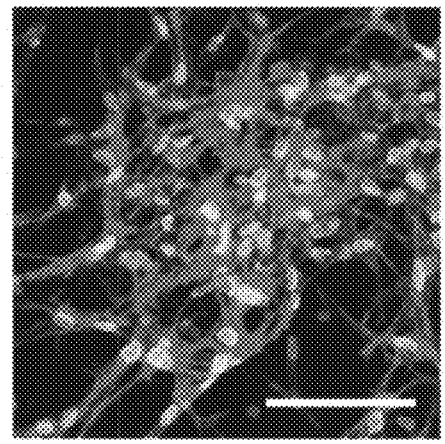
Figure 32I:
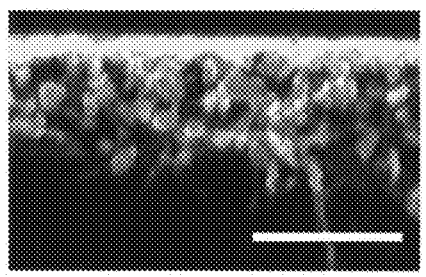
Figure 32J:
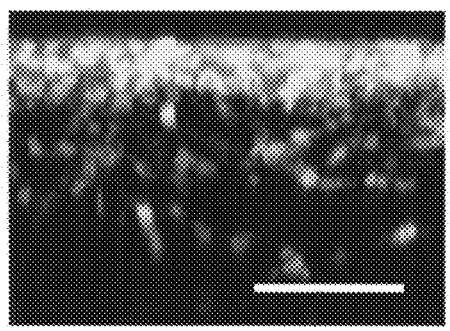

VEGF (20 ng/ml) was added to the cell culture medium and the cells were cultured for 7 days. The 3-dimensional capillary structure was observed in PRGmx using the fluorescence confocal microscopy. FIGS. 29A-29B show the reconstructed image. The green stain shows nuclei, the red stain shows actin fiber. FIG. 29A shows the capillary cavity (arrows). FIG. 29B shows the cross-section at the dotted line in FIG. 29A. The capillary cavity are also shown in the cross section image (dotted circle).

In vivo study of angiogenesis was performed using Chorioallantoic Membrane (CAM) assay. At Day 8 of fertilized chicken egg incubation, hydrogels of 10 mm diameter with 1 mm thickness were transferred to chick Chorioallantoic Membrane. The hydrogels were selected from Table 19 and gels were formed before the transfer. On Day 12, CAMs were collected for histology. The angiogenesis inside and below the hydrogel were evaluated by histological cross section.

FIG. 30A-30G shows histological images of Chorioallantoic Membrane (CAM) incubated with different hydrogels. RAD (FIGS. 30A-B), PRGmx (FIG. 30E) and Collagen (FIG. 30F) shows no angiogenesis both inside and below the hydrogel. On the other hand, KLTmx (FIGS. 30C-D) and Matrigel (FIG. 30G) shows angiogenesis with ingrowth of the connective tissue inside the gel (black arrows). KLTmx also shows angiogenesis on the border of gel and Chorioallantoic Membrane (black arrows).

Example 6

Functional Peptides Based on Various Self-assembling Sequence

In previous examples, RAD16-1 ((RADA)4) (SEQ ID NO. 21) was used as basic building block of self-assembling. By changing basic self-assembly sequence, the properties of hydrogel can be controlled. (IEIK)2 (SEQ ID NO. 52) is short sequence consists from 8 residues, but forms stiffer gels compared to (RADA)4 (SEQ ID NO. 21) as it uses Isoleucine (I) as hydrophilic amino acid components which are less flexible to Alanine (A). Stiffer gels can be obtained by making the self-assembling repetitive sequence longer, such as (IEIK)3 (SEQ ID NO. 80), (IEIK)4 (SEQ ID NO. 81), and the like.

(FKFQ)$_3$ (SEQ ID NO. 51) is positively charged in neutral pH range and FKF stays in solution at neutral pH range as described previously.

Functionalized peptides based on (IEIK)2 (SEQ ID NO. 52) and (FKFQ)$_3$ (SEQ ID NO. 51) were synthesized as shown in Table 21. The hydrogel composed from the peptides in Table 22 are shown in Table 22. Solutions are provided from functionalized peptide or from a mixture of functionalized peptide with basic repetitive sequence (SEQ ID NO. 54 or SEQ ID NO. 55).

TABLE 21

Functional peptides based on various self-assembling sequence

| No. | Sequence | Description |
|-----|----------|-------------|
| SEQ ID NO. 52 | Ac-IEIKIEIKI-CONH$_2$ | Neutral self assembly sequence |
| SEQ ID NO. 13 | Ac-IEIKIEIKIGGPRGSYRGDS-CONH$_2$ | Repetitive RGD binding sequence |
| SEQ ID NO. 14 | Ac-IEIKIEIKIGGPFSSTKT-CONH$_2$ | Bone marrow homing |
| SEQ ID NO. 15 | Ac-IEIKIEIKIGGSKPPGTS-CONH$_2$ | Bone marrow homing |
| SEQ ID NO. 51 | Ac(FKFQ)3-CONH$_2$ | Charged self assembly sequence |

TABLE 21-continued

Functional peptides based on various self-assembling sequence

| No. | Sequence | Description |
|---|---|---|
| SEQ ID NO. 16 | Ac-FKFQFKFQFKFQGPRGDSGYRGDS-CONH$_2$ | Repetitive RGD binding sequence |
| SEQ ID NO. 17 | Ac-FKFQFKFQFKFQGGFHRRIKA-CONH$_2$ | Heparin binding domain |

TABLE 22

Hydrogel components

| Code | Hydrogel contents |
|---|---|
| EIK | 1% SEQ ID NO. 55 peptide solution |
| EPRG | 1% SEQ ID NO. 13 peptide solution |
| EPRGmx | 1% SEQ ID NO. 13 peptide solution and EIK mix by 1:1 |
| EPFS | 2% SEQ ID NO. 14 peptide solution |
| EPFSmx | 1% SEQ ID NO. 14 peptide solution and EIK mix by 1:1 |
| ESKP | 2% SEQ ID NO. 15 peptide solution |
| ESKPmx | 1% SEQ ID NO. 15 peptide solution and EIK mix by 1:1 |
| FKF | 1% SEQ ID NO. 54 peptide solution |
| KPRG | 1% SEQ ID NO. 16 peptide solution |
| KPRGmx | 1% SEQ ID NO. 16 peptide solution and FKF mix by 1:1 |
| KFHRmx | 1% SEQ ID NO. 17 peptide solution and FKF mix by 1:1 |

All (FKFQ)$_3$ (SEQ ID NO. 51) based peptide solutions (FKF, KPRG, KPRGmx and KFHRmx) stay in solution at neutral pH range and up to pH 8. This property is useful when incorporating cells, basic material like tricalcium phosphate and/or acidic sensitive reagents (such as proteins and/or growth factors) into self-assembling peptide hydrogels.

Cell attachment and viability of the hydrogels were evaluated using HUVEC (human umbilical vein endothelial cells). The peptide solutions shown in Table 22 were loaded in the culture inserts (10 mm diameter, Millicell-CM, Millipore) and gels were formed using cell culture medium (EGM-2-MV, Camblex). HUVEC were plated at $8 \times 10^4$ cells on the inserts and cultured for three days.

FIGS. 31A-31K shows the fluorescence microscopy images of HUVEC. The green stain shows cell nuclei, the red stain shows actin fiber. Hydrogels which contain repetitive RGD binding sequences have higher cell attachment compared to basic self-assembling peptide hydrogel (EIK and FKF). The results are summarized in Table 23. These results resemble Table 20, Example 5. This implies that functionalization of the self-assembling peptide is useful regardless of the basic repetitive sequence, while the properties of hydrogel can be controlled by altering basic repetitive sequence in amino acid and length.

TABLE 23

Summary of cell attachment

| Code | Cell attachment |
|---|---|
| EIK | ++ |
| EPRG | ++++ |
| EPRGmx | +++ |
| EPFS | + |
| EPFSmx | ++ |
| ESKP | + |
| ESKPmx | + |
| FKF | ++ |
| KPRG | ++++ |
| KPRGmx | +++ |
| KFHRmx | +++ |

Key:
Cell attachment [+: Weak(<20%); ++: 20-50%; +++: 50-70%; ++++: near confluence (>70%)]

Example 7

Functionalized Peptides Matrix for Supporting Stem Cell

Recently, many stem cells, especially mesenchymal stem cell such as bone marrow derived mesenchymal stem cells (MSC), and adipose derived stem cells (ADSC) were clinically evaluated for therapeutic purpose. It is important in cell-based therapies to maintain cell viability until the implanted cells are supported by the surrounding microenvironment. Stem cells require not only keeping cell viability but also maintaining cellular status. For example, in orthopedic regeneration, such as bone or cartilage regeneration, it is important to maintain differentiation ability to form a specific cell type or to direct to a specific differentiation lineage. In contrast, for ischemic disease such as like myocardial infarction, peripheral vascular disease and cerebral infarction, it is important to maintain stemness to keep the ability for secreting cytokine growth factors useful for anti-apoptosis or angiogenesis in supporting damaged tissue cells.

In order to maintain stem cell viability, differentiation ability or stemness, it is important to provide a temporal microenvironment to support the stem cells. The functionalized self-assembling peptide matrixes are useful when injected to the damaged region in combination with stem cells. RGD cell adhesion motifs, heparin binding domain and bone marrow homing motifs have already shown the ability of maintaining cell viability in various cell types, including osteoblast and endothelial cells, and can be used for stem cell maintenance. Laminin is the main component in basement membrane and considered to be important for stem cell maintenance. IKVAV (included in SEQ62) and IKLLS (included in SEQ75) are known as the cell adhesion sequences in laminin. They are useful to preserve viability, reduce apoptosis and reduce secretion of insulin in encapsulated beta-cells (Laney et al., *Biomaterials* (2007) 28:3004-3011).

3-dimensional adipose derived stem cells (ADSC) were cultured in the functionalized peptide matrixes (Table 24) and cell maintenance ability of functionalized self-assembling peptide matrixes was evaluated. ADSCs were suspended in 10% sucrose solution and mixed with peptide solution selected from Table 25. The cell suspended peptide solutions were transferred to the culture inserts (10 mm diameter, Millicell-CM, Millipore) and gels were immediately formed using cell culture medium. Cell numbers seeded in the well were $4 \times 10^4$ cells/well.

TABLE 24

Functionalized peptides matrix for supporting stem cell

| No. | Sequence | Description |
| --- | --- | --- |
| RAD16-I | Ac(RADA)$_4$-CONH$_2$ | |
| SEQ ID NO. 4 | Ac(RADA)$_4$GPRGDSGYRGDS CONH$_2$ | Repetitive RGD binding sequence |
| SEQ ID NO. 6 | Ac(RADA)$_4$GGFHRRIKA CONH$_2$ | Heparin binding domain |
| SEQ ID NO. 1 | Ac(RADA)$_4$GGPFSSTKT CONH$_2$ | Bone marrow homing |
| SEQ ID NO. 12 | Ac(RADA)$_4$GGSKPPGTSS CONH$_2$ | Bone marrow homing |
| SEQ ID NO. 18 | Ac(RADA)$_4$GGSTFTKSP-CONH$_2$ | Bone marrow homing |
| SEQ ID NO. 19 | Ac(RADA)$_4$GGSTKVAVS-CONH$_2$ | Laminin (110 kDa laminin receptor protein) |
| SEQ ID NO. 20 | Ac(RADA)$_4$GGSEIKLLIS-CONH$_2$ | Laminin (a3b1 and cell surface heparin) |

TABLE 25

Hydrogel components

| Code | Hydrogel contents |
| --- | --- |
| RAD | 1% RAD16-1 peptide solution |
| PRGmx | 1% SEQ ID NO. 4 peptide solution and 1% RAD16-I peptide solution mix by 1:1 |
| FHR | 1% SEQ ID NO. 6 peptide solution |
| FHRmx | 1% SEQ ID NO. 6 peptide solution and 1% RAD16-I peptide solution mix by 1:1 |
| PFS | 1% SEQ ID NO. 1 peptide solution |
| PFSmx | 1% SEQ ID NO. 1 peptide solution and 1% RAD16-I peptide solution mix by 1:1 |
| SKPmx | 1% SEQ ID NO. 12 peptide solution and 1% RAD16-I peptide solution mix by 1:1 |
| STF | 1% SEQ ID NO. 18 peptide solution |
| STFmx | 1% SEQ ID NO. 18 peptide solution and 1% RAD16-I peptide solution mix by 1:1 |
| SIK | 1% SEQ ID NO. 19 peptide solution |
| SIKmx | 1% SEQ ID NO. 19 peptide solution and 1% RAD16-I peptide solution mix by 1:1 |
| SEI | 1% SEQ ID NO. 20 peptide solution |
| SEImx | 1% SEQ ID NO. 20 peptide solution and 1% RAD16-I peptide solution mix by 1:1 |

The peptide solutions shown in Table 25 were loaded in the culture inserts (10 mm diameter, Millicell-CM, Millipore) and gels were formed using cell culture medium (DMEM-F12+10% FBS, Gibco). ADSC were plated at $4 \times 10^4$ cells on the inserts and cultured up to 7 Days.

FIGS. 32A-32E shows the reconstructed extended focus view of fluorescence confocal microscopy image after 7 days of culturing. The upper shows vertical view, the lower shows corresponding horizontal view. The green shows cell nuclei, red shows actin fiber in the cell. Although the cells were seeded on the surface of the matrix, the cells were migrated well into the matrix.

Figure 33:
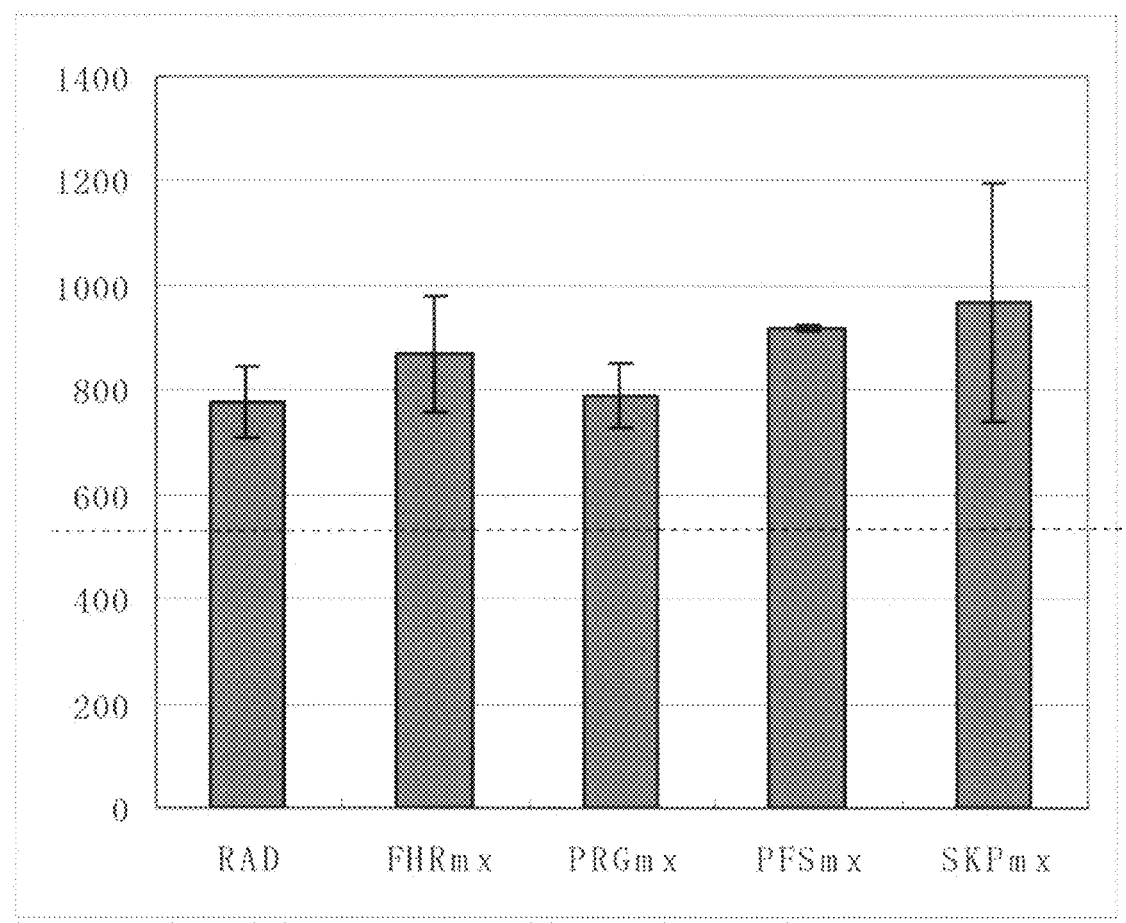
FIG. 33. Cell density in ADSC culture in functionalized peptides matrix.

FIG. 33 shows the density of the cells. The density of the cells were increased from the initial seeding density (shown in dotted line). This shows that ADSC were proliferated on and in the matrix.

Figure 34:
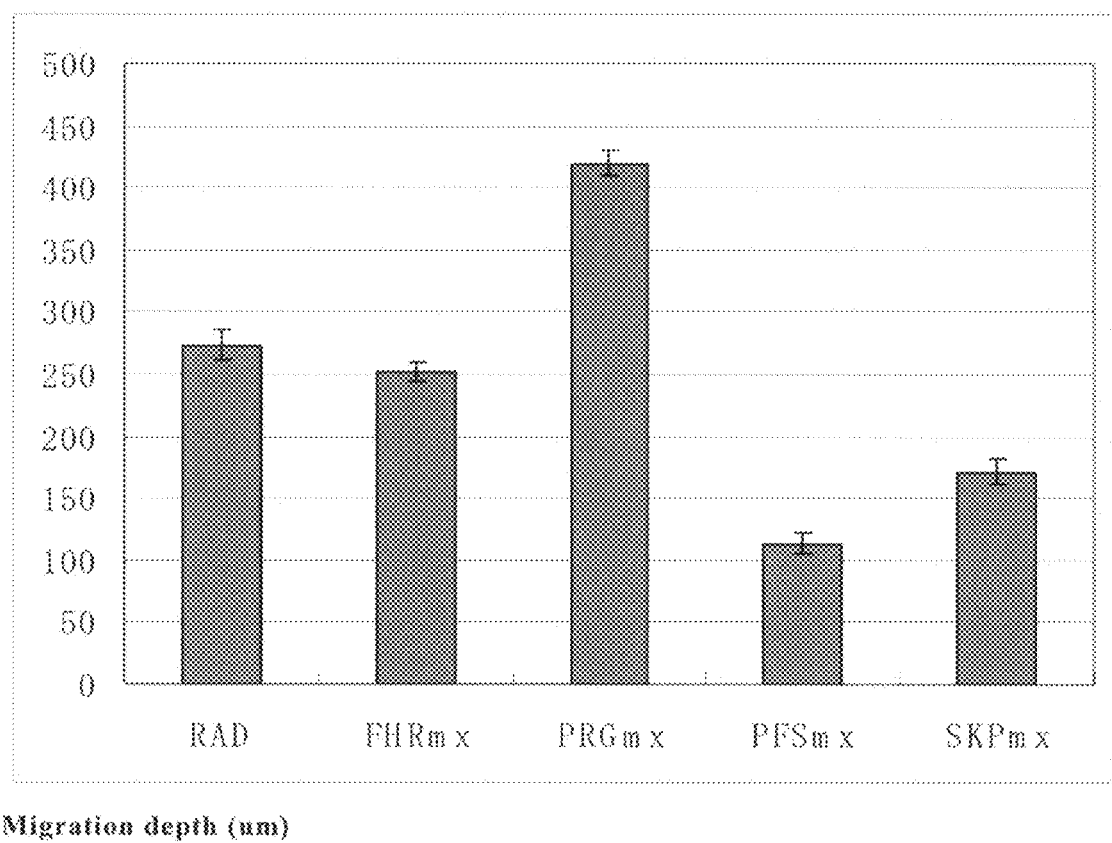
FIG. 34. Cell migration depth in ADSC culture in functionalized peptides matrix.

FIG. 34 shows the migration depth of cells. The cells were migrated deeply in PRGmx hydrogel. In RADmx and FHRmx, the cells were migrated less deeper than PRGmx, but the portion of the cell migrated into the hydrogels were larger. These results shows that the self-assembling peptide matrix and functionalized peptide matrix are potential to maintain stem cells viability, especially mesenchymal stem cell.

Figure 35A:
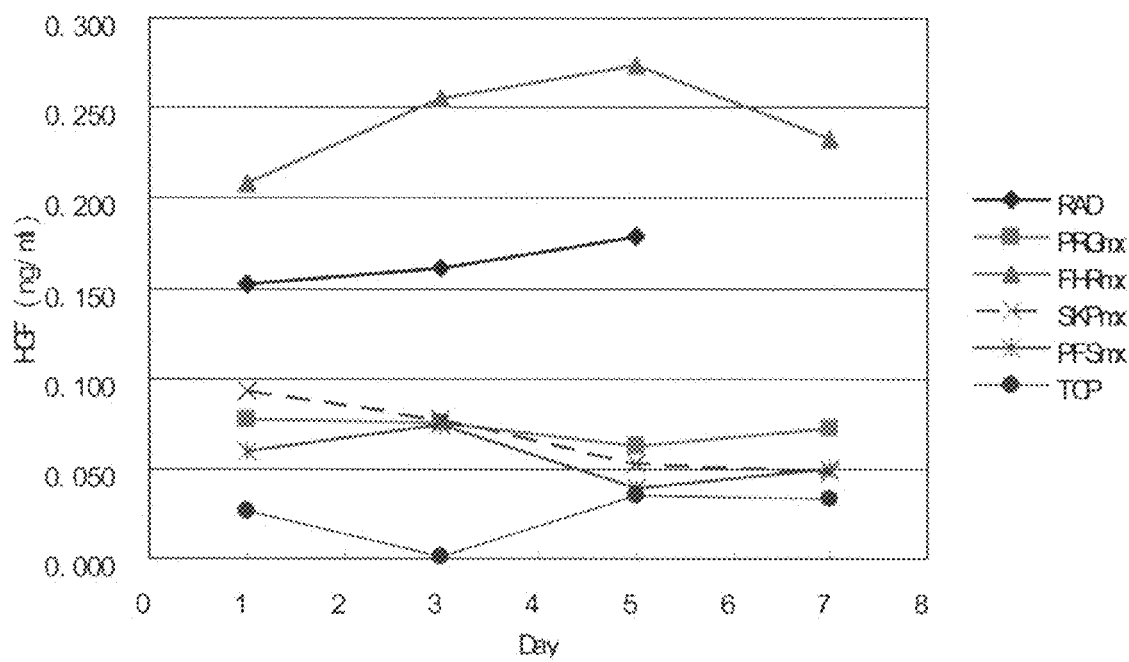
FIGS. 35A-35B. Secretion of growth factors into the medium.
Figure 35B:
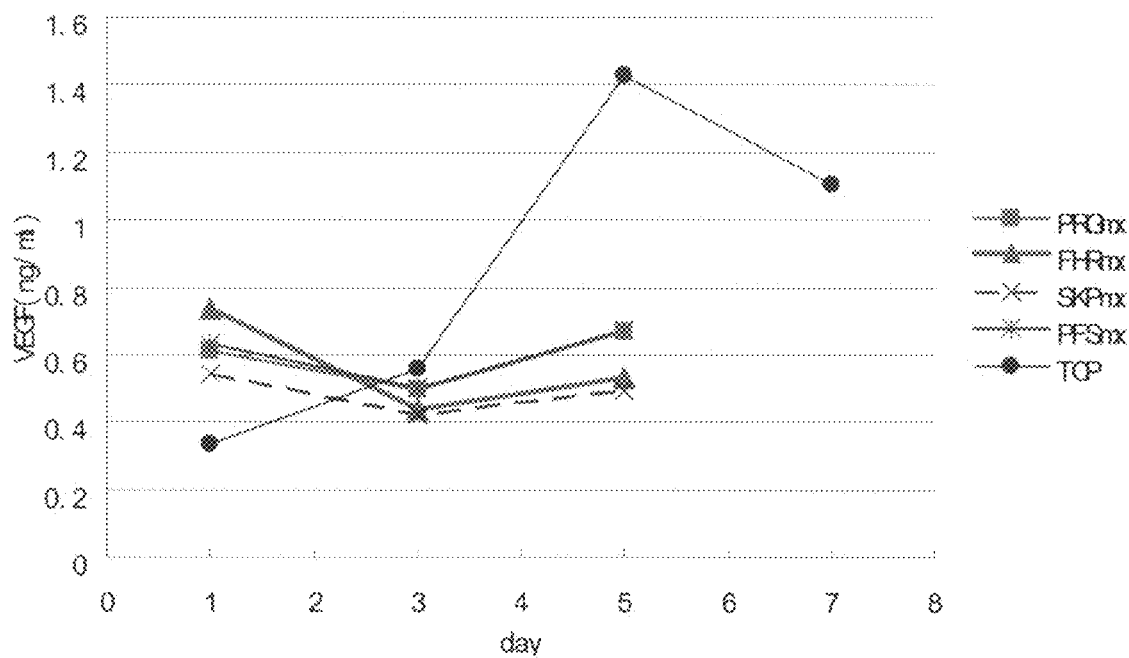

The growth factors secreted into the culture medium were also evaluated using ELISA method (FIGS. 35A-35B). The growth factors secreted from stem cell are considered to be main source of the cell therapy by reducing apotosis and increasing angiogenesis. Especially HGF and VEGF are considered to key components for reducing apotosis and increasing angiogenesis. The medium of ADSC cultured on tissue culture plate was used as control (shown as TCP). There was a significant increase of HGF when cultured in FHRmx and RAD from 1 day up to 7 days of culture. For VEGF, all peptide matrix had increase of VEGF secretion in 1 day culture medium.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

We claim:

1. A self-assembling peptide comprising:
   a) a first amino acid domain that mediates self-assembly of the peptide, which first amino acid domain is at least 8 amino acids in length and has an amino acid sequence made up of repeated units, each repeated unit being at least two amino acids in length and comprising alternating hydrophobic and hydrophilic amino acids,
   b) a second amino acid domain comprising a minimal biologically active sequence selected from the group consisting of:
   -PRGDSGYRGD-; -DGRGDSVAYG-; -ALKRQGRTLYGF-;
   -PFSSTKT-; -FLGFPT-; -KLTWQELYQLKYKGI-;
   -SKPPGTSS-; -STFTKSP-; -IKVAV-;
   -FHRRIKA-; -IKLLI-; -RGD-;
   -REDV-; and -LKKTETQ-;
   which second amino acid domain does not self-assemble when isolated from the first amino acid domain, and
   c) a linker group of 1-4 glycine residues, connecting the C-terminus of the first amino acid domain to the N-terminus of the second amino acid domain.

2. The peptide according to claim 1, wherein the second amino acid domain comprises at least two minimal biologically active sequences.

3. The peptide according to claim 1, wherein the at least one minimal biologically active sequence comprises -RGD-.

4. The peptide according to claim 1, wherein the second amino acid domain is biologically active in isolated form.

5. The peptide according to claim 1, wherein the distance between the last amino acid of the first amino acid domain and the first amino acid of the minimal biological active sequence in the second amino acid domain is at least 2-mer (6.9 Angstrom).

6. The peptide according to claim 1, wherein the distance between the last amino acid of the first amino acid domain and the first amino acid of the minimal biological active sequence in the second amino acid domain is 4-mer (13.8 Angstrom).

7. The peptide according to claim 1, wherein the first amino acid domain comprises at least two instances of any one of the following amino acid sequences:
   -RADA-; -IEIK-; or -FKFQ-.

8. The peptide according to claim 1, wherein the first amino acid domain comprises any one of the following amino acid sequences:

```
SEQ ID NO: 21    n-RADARADARADARADA-c;
SEQ ID NO: 22    n-RADARGDARADARGDA-c;
SEQ ID NO: 23    n-RADARADA-c;
SEQ ID NO: 24    n-RARADADARARADADA-c;
SEQ ID NO: 25    n-RARADADA-c;
SEQ ID NO: 26    n-AEAKAEAKAEAKAEAK-c;
SEQ ID NO: 27    n-AEAKAEAK-c;
SEQ ID NO: 28    n-RAEARAEARAEARAEA-c;
SEQ ID NO: 29    n-RAEARAEA-c;
SEQ ID NO: 30    n-KADAKADAKADAKADA-c;
SEQ ID NO: 31    n-KADAKADA-c;
SEQ ID NO: 32    n-AEAEAHAHAEAEAHAH-c;
SEQ ID NO: 33    n-AEAEAHAH-c;
SEQ ID NO: 34    n-FEFEFKFKFEFEFKFK-c;
SEQ ID NO: 35    n-FEFKFEFK-c;
SEQ ID NO: 36    n-LELELKLKLELELKLK-c;
SEQ ID NO: 37    n-LELELKLK-c;
SEQ ID NO: 38    n-AEAEAKAKAEAEAKAK-c;
SEQ ID NO: 39    n-AEAEAEAEAKAK-c;
SEQ ID NO: 40    n-AEAEAKAK-c;
SEQ ID NO: 41    n-KAKAKAKAEAEAEAEA-c;
SEQ ID NO: 42    n-AEAEAEAEAKAKAKAK-c;
SEQ ID NO: 43    n-RARARARADADADADA-c;
SEQ ID NO: 44    n-ADADADADARARARAR-c;
SEQ ID NO: 45    n-DADADADARARARARA-c;
SEQ ID NO: 46    n-(ADADADADARARARAR)-c;
SEQ ID NO: 47    n-HEHEHKHKHEHEHKHK-c;
SEQ ID NO: 48    n-HEHEHKHK-c;
SEQ ID NO: 49    n-VEVEVEVEVEVEVEVE-c;
SEQ ID NO: 50    n-RFRFRFRFRFRFRFRF-c;
SEQ ID NO: 51    n-FKFQFKFQFKFQ-c;
SEQ ID NO: 52    n-IEIKIEIK-c;
          or
SEQ ID NO: 53    n-KLDLKLDLKLDL-c.
```

9. The peptide according to claim 8, wherein the first amino acid domain comprises any one of the following amino acid sequences:

```
SEQ ID NO: 21    RADARADARADARADA;
SEQ ID NO: 51    FKFQFKFQFKFQ;
```

```
SEQ ID NO: 52    IFIKIFIK;
          or
SEQ ID NO: 53    KLDLKLDLKLDL.
```

10. The peptide according to claim 1, wherein the second amino acid domain is derived from a heparin binding domain of a cell attachment protein.

11. The peptide according to claim 10, wherein the cell attachment protein is selected from the group consisting of fibronectin, vitronectin, laminin, collagen, VEGF, FGFs, PDGF, HGF, TGF-β and BMP.

12. The peptide according to claim 10, wherein the heparin binding domain is of the formulae (I) or (II):

$$-XBBXBX- \quad (I)$$

or $$-XBBBXXBX- \quad (II)$$

wherein X represents a hydrophobic amino acid selected from the group consisting of F, I, L, P, M, W, Y, V, A, C and Q;
and B represents a positively charged amino acid selected from the group consisting of R, H and K.

13. The peptide according to claim 1, wherein the self-assembling peptide is selected from the group consisting of:

```
SEQ ID NO. 1   Ac(RADA)4GGPFSSTKT-CONH2;
SEQ ID NO. 2   Ac(RADA)4GGFLGFPT-CONH2;
SEQ ID NO. 3   Ac(RADA)4GGALKRQGRTLYGF-CONH2;
SEQ ID NO. 4   Ac(RADA)4GPRGDSGYRGDS-CONH2;
SEQ ID NO. 5   Ac(RADA)4GGDGRGDSVAYG-CONH2;
SEQ ID NO. 6   Ac(RADA)4GGFHRRIKA-CONH2;
SEQ ID NO. 7   Ac(RADA)4GPRGDSGYRGDSG-CONH2;
SEQ ID NO. 8   Ac(RADA)4GGRGDSCONH2;
SEQ ID NO. 9   Ac(RADA)4GGGGRGDSCONH2;
SEQ ID NO. 10  Ac(RADA)4GGGGREDV-CONH2;
SEQ ID NO. 11  Ac(RADA)4GGGGKLTWQELYQLKYKGI-CONH2;
SEQ ID NO. 12  Ac(RADA)4GGSKPPGTSS-CONH2;
SEQ ID NO. 13  AcIEIKIEIKIGGPRGSYRGDS-CONH2;
SEQ ID NO. 14  AcIEIKIEIKIGGPFSSTKT-CONH2;
SEQ ID NO. 15  AcIEIKIEIKIGGSKPPGTS-CONH2;
SEQ ID NO. 16  AcFKFQFKFQFKFQGPRGDSGYRGDS-CONH2;
SEQ ID NO. 17  AcFKFQFKFQFKFQGGFHRRIKA-CONH2;
SEQ ID NO. 18  Ac(RADA)4GGSTFTKSP-CONH2;
SEQ ID NO. 19  Ac(RADA)4GGSIKVAVS-CONH2;
and
SEQ ID NO. 20  Ac(RADA)4GGSEIKLLIS-CONH2.
```

14. The peptide according to claim 1, wherein the self-assembling peptide has a net positive or negative charge in an aqueous solution of pH of between about 5-9, inclusive.

15. The peptide according to claim 14, wherein the first amino acid domain is near-neutral, or has a positive or negative charge.

16. The peptide according to claim 14, wherein the second amino acid domain has a positive or negative charge.

17. The peptide according to claim 15, wherein the charge of the first amino acid domain is between −1 to 1 when the pH of the solution is between about 6-8, inclusive.

18. The peptide according to claim 16, wherein the charge of the second amino acid domain is less than or equal to −2 when the pH of the solution is between about 6-8, inclusive.

19. The peptide according to claim 14, wherein the first amino acid domain has a pH of between 5 to 9, inclusive.

20. The peptide according to claim 14, wherein the self-assembling peptide has a pH of greater than or equal to 8.

21. The peptide according to claim 14, wherein the net charge of the self-assembling peptide is greater than or equal to about 2 when the pH of the solution is between about 6-8, inclusive.

22. The self-assembling peptide of claim 1 wherein the second amino acid domain does not self-assemble when present in isolated form but permits assembly of the first amino acid domain such that the peptide assembles to form a macroscopic structure.

23. The self-assembling peptide according to claim 22, wherein the macroscopic structure comprises nanofibers and/or beta-sheets.

24. The self-assembling peptide of claim 1, wherein the peptide self-assembles when present as the sole peptide in an aqueous solution.

25. The self-assembling peptide of claim 1, wherein the peptide does not self-assemble when present as the only peptide in an aqueous solution but does self-assemble when present in an aqueous solution with an unmodified self-assembling peptide.

26. A solution comprising the self-assembling peptide of claim 1.

27. A pharmaceutical composition comprising the self-assembling peptide of claim 1 and a pharmaceutically acceptable excipient.

28. The pharmaceutical composition according to claim 27, wherein the pharmaceutical composition is substantially free of a gellation agent and self-assembles within the body to form a macroscopic structure.

29. The pharmaceutical composition according to claim 28, wherein the macroscopic structure comprises nanofibers and/or beta-sheets.

30. The pharmaceutical composition according to claim 27, wherein the composition further comprises an additional self-assembling peptide comprising alternating hydrophobic and hydrophilic amino acids that are complementary and structurally compatible and self-assemble into a beta-sheet, and wherein the additional self-assembling peptide does not contain an amino acid domain that reduces compatibility of the peptide with cell attachment or cell viability.

31. The pharmaceutical composition according to claim 30, wherein the self-assembling peptide of claim 1 and the additional self-assembling peptide are present in a ratio of approximately 1:1.

32. The pharmaceutical composition according to claim 30, wherein the self-assembling peptide of claim 1 and the additional self-assembling peptide are present in a ratio of approximately 5:1.

33. The pharmaceutical composition according to claim 30, wherein the self-assembling peptide of claim 1 and the additional self-assembling peptide are present in a ratio of approximately 9:1.

34. The pharmaceutical composition according to claim 30, wherein the self-assembling peptide of claim 1 and the additional self-assembling peptide are present in a ratio of approximately 99:1.

35. A matrix comprising the self assembling peptide of claim 1.

36. The matrix according to claim 35, wherein the matrix is a gel or a hydrogel.

37. The matrix according to claim 35, wherein the matrix further comprises an additional biological molecule.

38. The matrix according to claim 37, wherein the additional biological molecule has a net positive or negative charge.

39. The matrix according to claim 37, wherein the additional biological molecule is a protein or peptide.

40. The matrix according to claim 39, wherein the protein or peptide is a growth factor or a self-assembling peptide.

41. The matrix according to claim 40, wherein the self-assembling peptide is selected from the group consisting of:

| | |
|---|---|
| SEQ ID NO: 21 | n-RADARADARADARADA-c; |
| SEQ ID NO: 22 | n-RADARGDARADARGDA-c; |
| SEQ ID NO: 23 | n-RADARADA-c; |
| SEQ ID NO: 24 | n-RARADADARARADADA-c; |
| SEQ ID NO: 25 | n-RARADADA-c; |
| SEQ ID NO: 26 | n-AEAKAEAKAEAKAEAK-c; |
| SEQ ID NO: 27 | n-AEAKAEAK-c; |
| SEQ ID NO: 28 | n-RAEARAEARAEARAEA-c; |
| SEQ ID NO: 29 | n-RAEARAEA-c; |
| SEQ ID NO: 30 | n-KADAKADAKADAKADA-c; |
| SEQ ID NO: 31 | n-KADAKADA-c; |
| SEQ ID NO: 32 | n-AEAEAHAHAEAEAHAH-c; |
| SEQ ID NO: 33 | n-AEAEAHAH-c; |
| SEQ ID NO: 34 | n-FEFEFKFKFEFEFKFK-c; |
| SEQ ID NO: 35 | n-FEFKFEFK-c; |
| SEQ ID NO: 36 | n-LELELKLKLELELKLK-c; |
| SEQ ID NO: 37 | n-LELELKLK-c; |
| SEQ ID NO: 38 | n-AEAEAKAKAEAEAKAK-c; |
| SEQ ID NO: 39 | n-AEAEAEAEAKAK-c; |
| SEQ ID NO: 40 | n-AEAEAKAK-c; |
| SEQ ID NO: 41 | n-KAKAKAKAEAEAEAEA-c; |
| SEQ ID NO: 42 | n-AEAEAEAEAKAKAKAK-c; |
| SEQ ID NO: 43 | n-RARARARADADADADA-c; |
| SEQ ID NO: 44 | n-ADADADADARARARAR-c; |
| SEQ ID NO: 45 | n-DADADADARARARARA-c; |
| SEQ ID NO: 46 | n-(ADADADADARARARAR)-c; |
| SEQ ID NO: 47 | n-HEHEHKHKHEHEHKHK-c; |
| SEQ ID NO: 48 | n-HEHEHKHK-c; |

-continued

```
SEQ ID NO: 49    n-VEVEVEVEVEVEVEVEVE-c;
SEQ ID NO: 50    n-RFRFRFRFRFRFRFRFRF-c;
SEQ ID NO: 51    n-FKFQFKFQFKFQ-c;
SEQ ID NO: 52    n-IEIKIEIK-c;
   or
SEQ ID NO: 53    n-KLDLKLDLKLDL-c.
```

42. The matrix according to claim 40, wherein the growth factor is a heparin-binding growth factor.

43. The matrix according to claim 42, wherein the heparin-binding growth factor is selected from the group consisting of VEGF, FGFs, PDGF, HGF, TGF-β and BMP.

44. The matrix according to claim 37, wherein the additional biological molecule is a glycosaminoglycan.

45. The matrix according to claim 44, wherein the glycosaminoglycan is heparin or heparin sulfate.

46. The matrix according to claim 35, further comprising a plurality of cells attached to the surface of the matrix or encapsulated within the matrix.

47. The matrix according to claim 46, wherein the cells are substantially uniformly distributed within the matrix.

48. The matrix according to claim 46, wherein the cells are selected from the group consisting of osteoblasts, chondrocytes, bone marrow cells, osteocytes, periosteal cells, perichondrial cells, fibroblasts, mesenchymal cell, mesenchymal stem cell, adipose derived cells, adipose derived stem cells, neuronal cells, hippocampal cells, epidermal cells, endothelial cells, epithelial cells, keratinocytes, basal cells, spinous cells, granular cells, embryonic stem cells, ovarian cells, pancreatic cells, cervical cells, liver cells, foreskin cells, neutrophils, lymphocytes, macrophages, dendritic cells, or precursors of any of the foregoing.

49. The matrix of claim 35, wherein the matrix is three-dimensional.

50. The matrix according to claim 35, further comprising a solid material.

51. The matrix according to claim 50, wherein the solid material is an inorganic salt.

52. The matrix according to claim 51, wherein the inorganic salt comprises calcium and/or phosphate.

53. The matrix according to claim 52, wherein the inorganic salt is selected from the group consisting of calcium phosphate, tricalcium phosphate, hydroxyapatite and calcium carbonate.

54. The matrix according to claim 50, wherein the solid material has pore diameter of between about 100-500 microns, inclusive.

55. The matrix according to claim 50, wherein the solid material has a block-like, cylindrical, plate-like or granule-like shape.

56. A method of making a matrix according to claim 35 comprising the steps of (i) dissolving the self-assembling peptide in an aqueous solution and (ii) adjusting the pH.

57. The method according to claim 56, wherein the method further comprises (iii) adding a gellation agent.

58. A method of making a matrix of claim 35 comprising the steps of (i) dissolving the self-assembling peptide in an aqueous solution and (ii) adding a gellation agent.

59. The method according to claim 58, wherein the method further comprises (iii) adjusting the pH of the solution.

60. The method according to claim 57 or 58, wherein the gellation agent is an electrolyte.

61. The method according to claim 60, wherein the gellation agent is NaCl, saline, PBS, cell culture medium, or a biological fluid.

62. The method according to claim 61, wherein the biological fluid is blood or lymph.

63. The method according to claim 56 or 59, wherein the pH is adjusted to about 5-9, inclusive.

64. The method according to claim 63, wherein the pH is adjusted to about 6-8, inclusive.

65. The method according to claim 64, wherein the pH is adjusted to about 5-7, inclusive.

66. The method according to claim 65, wherein the pH is adjusted to about 5.7 to 5.8, inclusive.

67. A method of using the matrix of claim 35 as a defect filler of bone or tissue comprising administering the matrix to a subject in need thereof.

68. The method according to claim 67, wherein the tissue is brain, skin, liver, pancreas, stomach, kidney, gastrointestinal tract, esophageal tract, heart, muscle, connective tissue, cartilage, nerve, fat, or bone marrow.

69. The method according to claim 67, wherein the filler comprises the self-assembling peptide in an aqueous solution.

70. The method according to claim 67, wherein the filler comprises a hydrogel of the self-assembling peptide.

71. The method according to claim 70, wherein the hydrogel is formed from mixing an aqueous solution of the self-assembling peptide with a gellation agent.

72. The method according to claim 71, herein the gellation agent is biological fluid.

73. The method according to claim 72, wherein the biological fluid is lymph or blood.

74. The method according to claim 70, wherein the hydrogel is formed by adjusting the pH of an aqueous solution of the self-assembling peptide.

75. The method according to claim 67, further comprising a solid material.

76. The method according to claim 75, wherein the solid material is an inorganic salt.

77. The method according to claim 76, wherein the inorganic salt comprises calcium and/or phosphate.

78. The method according to claim 77, wherein the inorganic salt is selected from the group consisting of calcium phosphate, tricalcium phosphate, hydroxyapatite and calcium carbonate.

79. The method according to claim 75, wherein the solid material has pore diameter of between about 100-500 microns, inclusive.

80. The method according to claim 75, wherein the solid material has a block-like, cylindrical, plate-like, or granule-like shape.

81. The method according to claim 67, wherein the defect is damaged tissue; damaged orthopedic field; a bone defect; a bone adjent; an ectopic bone formation; an ischemic region; a myocardial infarction region; peripheral vascular region; cerebral infarction region; or a skin defect.

82. A culture kit comprising:
 (a) (i) the self-assembling peptide of claim 1;
  (ii) the pharmaceutical composition of claim 27; or
  (iii) the matrix of claim 35;
 (b) instructions for initiating self-assembly of the peptide into a macroscopic structure; and
 (c) at least one component selected from the group consisting of: a population of cells, cell or tissue culture medium, a predetermined amount of a growth factor, a predetermined amount of an ion or salt thereof, instructions for preparing the self assembling peptide for cell culture, instructions for culturing cells on or within a peptide hydrogel structure, instructions for introducing the self-assembling peptide into a subject, a vessel in which cell culture may be performed, a liquid in which the peptide can be dissolved, a syringe, an ion or salt thereof for initiating peptide self-assembly, and one or more growth or differentiation factors.

83. A method of culturing cells comprising contacting the cells with a self-assembling peptide of claim 1, a pharmaceutical composition of claim 27, or a matrix of claim 35, and maintaining the matrix for a period of time under conditions suitable for cell culture.

84. The method of claim 82, wherein the cells are cultured on the surface of the matrix and/or are cultured embedded within the matrix.

85. The peptide according to claim 1, wherein the overall length of the self-assembling peptide is less than 36 amino acids.

86. The peptide according to claim 1, wherein the overall length of the self-assembling peptide is less than 31 amino acids.

87. The peptide according to claim 1, wherein the overall length of the self-assembling peptide is at least 18 amino acids.

88. The peptide according to claim 1, wherein the overall length of the self-assembling peptide is between 18 and 36 amino acids.

89. The peptide according to claim 1, wherein the overall length of the self-assembling peptide is 28 amino acids.

90. The peptide according to claim 1, wherein the first amino acid domain is at least 16 amino acids in length.

91. The peptide according to claim 1, wherein the first amino acid domain comprises four repeated, identical sequences.

92. The peptide according to claim 91, wherein the first amino acid domain comprises four repeated, identical sequences.

93. The peptide according to claim 1, wherein the second amino acid domain comprises at least five amino acids.

94. The self-assembling peptide according to claim 1, which is capable of self-assembling into a gel.

95. A plurality of self-assembling peptides according to claim 1, assembled into a gel form.

* * * * *

SEQUENCE LISTING

```
<160> NUMBER OF SEQ ID NOS: 82

<210> SEQ ID NO 1
<211> LENGTH: 25
<212> TYPE: PRT
<213> ORGANISM: Artificial Sequence
<220> FEATURE:
<223> OTHER INFORMATION: Bone marrow homing
```

-continued

<400> SEQUENCE: 1

Arg Ala Asp Ala Arg Ala Asp Ala Arg Ala Asp Ala Arg Ala Asp Ala
1               5                   10                  15

Gly Gly Pro Phe Ser Ser Thr Lys Thr
            20                  25

<210> SEQ ID NO 2
<211> LENGTH: 24
<212> TYPE: PRT
<213> ORGANISM: Artificial Sequence
<220> FEATURE:
<223> OTHER INFORMATION: MP-1 (bone marrow purification)

<400> SEQUENCE: 2

Arg Ala Asp Ala Arg Ala Asp Ala Arg Ala Asp Ala Arg Ala Asp Ala
1               5                   10                  15

Gly Gly Phe Leu Gly Phe Pro Thr
            20

<210> SEQ ID NO 3
<211> LENGTH: 30
<212> TYPE: PRT
<213> ORGANISM: Artificial Sequence
<220> FEATURE:
<223> OTHER INFORMATION: Osteogenic growth peptide

<400> SEQUENCE: 3

Arg Ala Asp Ala Arg Ala Asp Ala Arg Ala Asp Ala Arg Ala Asp Ala
1               5                   10                  15

Gly Gly Ala Leu Lys Arg Gln Gly Arg Thr Leu Tyr Gly Phe
            20                  25                  30

<210> SEQ ID NO 4
<211> LENGTH: 28
<212> TYPE: PRT
<213> ORGANISM: Artificial Sequence
<220> FEATURE:
<223> OTHER INFORMATION: Repetitive RGD binding sequence

<400> SEQUENCE: 4

Arg Ala Asp Ala Arg Ala Asp Ala Arg Ala Asp Ala Arg Ala Asp Ala
1               5                   10                  15

Gly Pro Arg Gly Asp Ser Gly Tyr Arg Gly Asp Ser
            20                  25

<210> SEQ ID NO 5
<211> LENGTH: 28
<212> TYPE: PRT
<213> ORGANISM: Artificial Sequence
<220> FEATURE:
<223> OTHER INFORMATION: Cell adhes dom. (Osteopontin)

<400> SEQUENCE: 5

Arg Ala Asp Ala Arg Ala Asp Ala Arg Ala Asp Ala Arg Ala Asp Ala
1               5                   10                  15

Gly Gly Asp Gly Arg Gly Asp Ser Val Ala Tyr Gly
            20                  25

<210> SEQ ID NO 6
<211> LENGTH: 25
<212> TYPE: PRT
<213> ORGANISM: Artificial Sequence
<220> FEATURE:
<223> OTHER INFORMATION: Heparin binding domain -continued

```
<400> SEQUENCE: 6

Arg Ala Asp Ala Arg Ala Asp Ala Arg Ala Asp Ala Arg Ala Asp Ala
1               5                   10                  15

Gly Gly Phe His Arg Arg Ile Lys Ala
            20                  25

<210> SEQ ID NO 7
<211> LENGTH: 29
<212> TYPE: PRT
<213> ORGANISM: Artificial Sequence
<220> FEATURE:
<223> OTHER INFORMATION: Repetitive RGD binding sequence

<400> SEQUENCE: 7

Arg Ala Asp Ala Arg Ala Asp Ala Arg Ala Asp Ala Arg Ala Asp Ala
1               5                   10                  15

Gly Pro Arg Gly Asp Ser Gly Tyr Arg Gly Asp Ser Gly
            20                  25

<210> SEQ ID NO 8
<211> LENGTH: 25
<212> TYPE: PRT
<213> ORGANISM: Artificial Sequence
<220> FEATURE:
<223> OTHER INFORMATION: RGD binding sequence with 4 linker Glycine

<400> SEQUENCE: 8

Arg Ala Asp Ala Arg Ala Asp Ala Arg Ala Asp Ala Arg Ala Asp Ala
1               5                   10                  15

Gly Gly Arg Gly Asp Ser Cys Asn His
            20                  25

<210> SEQ ID NO 9
<211> LENGTH: 27
<212> TYPE: PRT
<213> ORGANISM: Artificial Sequence
<220> FEATURE:
<223> OTHER INFORMATION: RGD binding sequence with 4 linker Glycine

<400> SEQUENCE: 9

Arg Ala Asp Ala Arg Ala Asp Ala Arg Ala Asp Ala Arg Ala Asp Ala
1               5                   10                  15

Gly Gly Gly Gly Arg Gly Asp Ser Cys Asn His
            20                  25

<210> SEQ ID NO 10
<211> LENGTH: 24
<212> TYPE: PRT
<213> ORGANISM: Artificial Sequence
<220> FEATURE:
<223> OTHER INFORMATION: Fibronectin/Endothelial cells adhesion

<400> SEQUENCE: 10

Arg Ala Asp Ala Arg Ala Asp Ala Arg Ala Asp Ala Arg Ala Asp Ala
1               5                   10                  15

Gly Gly Gly Gly Arg Glu Asp Val
            20

<210> SEQ ID NO 11
<211> LENGTH: 35
<212> TYPE: PRT
<213> ORGANISM: Artificial Sequence
<220> FEATURE:
<223> OTHER INFORMATION: VEGF mimicking peptide/Bind to VEGF receptors
```

<400> SEQUENCE: 11

Arg Ala Asp Ala Arg Ala Asp Ala Arg Ala Asp Ala Arg Ala Asp Ala
1               5                   10                  15

Gly Gly Gly Gly Lys Leu Thr Trp Gln Glu Leu Tyr Gln Leu Lys Tyr
                20                  25                  30

Lys Gly Ile
        35

<210> SEQ ID NO 12
<211> LENGTH: 26
<212> TYPE: PRT
<213> ORGANISM: Artificial Sequence
<220> FEATURE:
<223> OTHER INFORMATION: Bone marrow homing

<400> SEQUENCE: 12

Arg Ala Asp Ala Arg Ala Asp Ala Arg Ala Asp Ala Arg Ala Asp Ala
1               5                   10                  15

Gly Gly Ser Lys Pro Pro Gly Thr Ser Ser
                20                  25

<210> SEQ ID NO 13
<211> LENGTH: 22
<212> TYPE: PRT
<213> ORGANISM: Artificial Sequence
<220> FEATURE:
<223> OTHER INFORMATION: Repetitive RGD binding sequence

<400> SEQUENCE: 13

Ala Cys Ile Glu Ile Lys Ile Glu Ile Lys Ile Gly Gly Pro Arg Gly
1               5                   10                  15

Ser Tyr Arg Gly Asp Ser
            20

<210> SEQ ID NO 14
<211> LENGTH: 20
<212> TYPE: PRT
<213> ORGANISM: Artificial Sequence
<220> FEATURE:
<223> OTHER INFORMATION: Bone marrow homing

<400> SEQUENCE: 14

Ala Cys Ile Glu Ile Lys Ile Glu Ile Lys Ile Gly Gly Pro Phe Ser
1               5                   10                  15

Ser Thr Lys Thr
        20

<210> SEQ ID NO 15
<211> LENGTH: 20
<212> TYPE: PRT
<213> ORGANISM: Artificial Sequence
<220> FEATURE:
<223> OTHER INFORMATION: Bone marrow homing

<400> SEQUENCE: 15

Ala Cys Ile Glu Ile Lys Ile Glu Ile Lys Ile Gly Gly Ser Lys Pro
1               5                   10                  15

Pro Gly Thr Ser
        20

<210> SEQ ID NO 16
<211> LENGTH: 26
<212> TYPE: PRT

```
<213> ORGANISM: Artificial Sequence
<220> FEATURE:
<223> OTHER INFORMATION: Repetitive RGD binding sequence

<400> SEQUENCE: 16

Ala Cys Phe Lys Phe Gln Phe Lys Phe Gln Phe Lys Phe Gln Gly Pro
1               5                   10                  15

Arg Gly Asp Ser Gly Tyr Arg Gly Asp Ser
            20                  25

<210> SEQ ID NO 17
<211> LENGTH: 23
<212> TYPE: PRT
<213> ORGANISM: Artificial Sequence
<220> FEATURE:
<223> OTHER INFORMATION: Heparin binding domain

<400> SEQUENCE: 17

Ala Cys Phe Lys Phe Gln Phe Lys Phe Gln Phe Lys Phe Gln Gly Gly
1               5                   10                  15

Phe His Arg Arg Ile Lys Ala
            20

<210> SEQ ID NO 18
<211> LENGTH: 25
<212> TYPE: PRT
<213> ORGANISM: Artificial Sequence
<220> FEATURE:
<223> OTHER INFORMATION: Bone marrow homing

<400> SEQUENCE: 18

Arg Ala Asp Ala Arg Ala Asp Ala Arg Ala Asp Ala Arg Ala Asp Ala
1               5                   10                  15

Gly Gly Ser Thr Phe Thr Lys Ser Pro
            20                  25

<210> SEQ ID NO 19
<211> LENGTH: 25
<212> TYPE: PRT
<213> ORGANISM: Artificial Sequence
<220> FEATURE:
<223> OTHER INFORMATION: Laminin (110 kDa laminin receptor protein)

<400> SEQUENCE: 19

Arg Ala Asp Ala Arg Ala Asp Ala Arg Ala Asp Ala Arg Ala Asp Ala
1               5                   10                  15

Gly Gly Ser Ile Lys Val Ala Val Ser
            20                  25

<210> SEQ ID NO 20
<211> LENGTH: 26
<212> TYPE: PRT
<213> ORGANISM: Artificial Sequence
<220> FEATURE:
<223> OTHER INFORMATION: Laminin (a3b1 and cell surface heparin)

<400> SEQUENCE: 20

Arg Ala Asp Ala Arg Ala Asp Ala Arg Ala Asp Ala Arg Ala Asp Ala
1               5                   10                  15

Gly Gly Ser Glu Ile Lys Leu Leu Ile Ser
            20                  25

<210> SEQ ID NO 21
<211> LENGTH: 16
<212> TYPE: PRT
```

```
<213> ORGANISM: Artificial Sequence
<220> FEATURE:
<223> OTHER INFORMATION: from Self-Assembling peptide - invented
      sequence

<400> SEQUENCE: 21

Arg Ala Asp Ala Arg Ala Asp Ala Arg Ala Asp Ala Arg Ala Asp Ala
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 22

Arg Ala Asp Ala Arg Gly Asp Ala Arg Ala Asp Ala Arg Gly Asp Ala
1               5                   10                  15

<210> SEQ ID NO 23
<211> LENGTH: 8
<212> TYPE: PRT
<213> ORGANISM: Artificial Sequence
<220> FEATURE:
<223> OTHER INFORMATION: from Self-Assembling peptide - invented
      sequence

<400> SEQUENCE: 23

Arg Ala Asp Ala Arg Ala Asp Ala
1               5

<210> SEQ ID NO 24
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 24

Arg Ala Arg Ala Asp Ala Asp Ala Arg Ala Arg Ala Asp Ala Asp Ala
1               5                   10                  15

<210> SEQ ID NO 25
<211> LENGTH: 8
<212> TYPE: PRT
<213> ORGANISM: Artificial Sequence
<220> FEATURE:
<223> OTHER INFORMATION: from Self-Assembling peptide - invented
      sequence

<400> SEQUENCE: 25

Arg Ala Arg Ala Asp Ala Asp Ala
1               5

<210> SEQ ID NO 26
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 26

Ala Glu Ala Lys Ala Glu Ala Lys Ala Glu Ala Lys Ala Glu Ala Lys
1               5                   10                  15
```

```
<210> SEQ ID NO 27
<211> LENGTH: 8
<212> TYPE: PRT
<213> ORGANISM: Artificial Sequence
<220> FEATURE:
<223> OTHER INFORMATION: from Self-Assembling peptide - invented
      sequence

<400> SEQUENCE: 27

Ala Glu Ala Lys Ala Glu Ala Lys
1               5

<210> SEQ ID NO 28
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 28

Arg Ala Glu Ala Arg Ala Glu Ala Arg Ala Glu Ala Arg Ala Glu Ala
1               5                   10                  15

<210> SEQ ID NO 29
<211> LENGTH: 8
<212> TYPE: PRT
<213> ORGANISM: Artificial Sequence
<220> FEATURE:
<223> OTHER INFORMATION: from Self-Assembling peptide - invented
      sequence

<400> SEQUENCE: 29

Arg Ala Glu Ala Arg Ala Glu Ala
1               5

<210> SEQ ID NO 30
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 30

Lys Ala Asp Ala Lys Ala Asp Ala Lys Ala Asp Ala Lys Ala Asp Ala
1               5                   10                  15

<210> SEQ ID NO 31
<211> LENGTH: 8
<212> TYPE: PRT
<213> ORGANISM: Artificial Sequence
<220> FEATURE:
<223> OTHER INFORMATION: from Self-Assembling peptide - invented
      sequence

<400> SEQUENCE: 31

Lys Ala Asp Ala Lys Ala Asp Ala
1               5

<210> SEQ ID NO 32
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 32
```

Ala Glu Ala Glu Ala His Ala His Ala Glu Ala Glu Ala His Ala His
1               5                   10                  15

<210> SEQ ID NO 33
<211> LENGTH: 8
<212> TYPE: PRT
<213> ORGANISM: Artificial Sequence
<220> FEATURE:
<223> OTHER INFORMATION: from Self-Assembling peptide - invented
      sequence

<400> SEQUENCE: 33

Ala Glu Ala Glu Ala His Ala His
1               5

<210> SEQ ID NO 34
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 34

Phe Glu Phe Glu Phe Lys Phe Lys Phe Glu Phe Glu Phe Lys Phe Lys
1               5                   10                  15

<210> SEQ ID NO 35
<211> LENGTH: 8
<212> TYPE: PRT
<213> ORGANISM: Artificial Sequence
<220> FEATURE:
<223> OTHER INFORMATION: from Self-Assembling peptide - invented
      sequence

<400> SEQUENCE: 35

Phe Glu Phe Lys Phe Glu Phe Lys
1               5

<210> SEQ ID NO 36
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 36

Leu Glu Leu Glu Leu Lys Leu Lys Leu Glu Leu Glu Leu Lys Leu Lys
1               5                   10                  15

<210> SEQ ID NO 37
<211> LENGTH: 8
<212> TYPE: PRT
<213> ORGANISM: Artificial Sequence
<220> FEATURE:
<223> OTHER INFORMATION: from Self-Assembling peptide - invented
      sequence

<400> SEQUENCE: 37

Leu Glu Leu Glu Leu Lys Leu Lys
1               5

<210> SEQ ID NO 38
<211> LENGTH: 16
<212> TYPE: PRT
<213> ORGANISM: Artificial Sequence
<220> FEATURE:

```
<223> OTHER INFORMATION: from Self-Assembling peptide - invented
      sequence

<400> SEQUENCE: 38

Ala Glu Ala Glu Ala Lys Ala Lys Ala Glu Ala Glu Ala Lys Ala Lys
1               5                   10                  15

<210> SEQ ID NO 39
<211> LENGTH: 12
<212> TYPE: PRT
<213> ORGANISM: Artificial Sequence
<220> FEATURE:
<223> OTHER INFORMATION: from Self-Assembling peptide - invented
      sequence

<400> SEQUENCE: 39

Ala Glu Ala Glu Ala Glu Ala Glu Ala Lys Ala Lys
1               5                   10

<210> SEQ ID NO 40
<211> LENGTH: 8
<212> TYPE: PRT
<213> ORGANISM: Artificial Sequence
<220> FEATURE:
<223> OTHER INFORMATION: from Self-Assembling peptide - invented
      sequence

<400> SEQUENCE: 40

Ala Glu Ala Glu Ala Lys Ala Lys
1               5

<210> SEQ ID NO 41
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 41

Lys Ala Lys Ala Lys Ala Lys Ala Glu Ala Glu Ala Glu Ala Glu Ala
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 42

Ala Glu Ala Glu Ala Glu Ala Glu Ala Lys Ala Lys Ala Lys Ala Lys
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 43

Arg Ala Arg Ala Arg Ala Arg Ala Asp Ala Asp Ala Asp Ala Asp Ala
1               5                   10                  15

<210> SEQ ID NO 44
```

```
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 44

Ala Asp Ala Asp Ala Asp Ala Asp Ala Arg Ala Arg Ala Arg Ala Arg
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 45

Asp Ala Asp Ala Asp Ala Asp Ala Arg Ala Arg Ala Arg Ala Arg Ala
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 46

Ala Asp Ala Asp Ala Asp Ala Asp Ala Arg Ala Arg Ala Arg Ala Arg
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: from Self-Assembling peptide - invented
      sequence

<400> SEQUENCE: 47

His Glu His Glu His Lys His Lys His Glu His Glu His Lys His Lys
1               5                   10                  15

<210> SEQ ID NO 48
<211> LENGTH: 8
<212> TYPE: PRT
<213> ORGANISM: Artificial Sequence
<220> FEATURE:
<223> OTHER INFORMATION: from Self-Assembling peptide - invented
      sequence

<400> SEQUENCE: 48

His Glu His Glu His Lys His Lys
1               5

<210> SEQ ID NO 49
<211> LENGTH: 20
<212> TYPE: PRT
<213> ORGANISM: Artificial Sequence
<220> FEATURE:
<223> OTHER INFORMATION: from Self-Assembling peptide - invented
      sequence

<400> SEQUENCE: 49

Val Glu Val Glu Val Glu Val Glu Val Glu Val Glu Val Glu Val Glu
```

-continued

```
1               5                   10                  15

Val Glu Val Glu
            20

<210> SEQ ID NO 50
<211> LENGTH: 20
<212> TYPE: PRT
<213> ORGANISM: Artificial Sequence
<220> FEATURE:
<223> OTHER INFORMATION: from Self-Assembling peptide - invented
      sequence

<400> SEQUENCE: 50

Phe Arg Phe Arg Phe Arg Phe Arg Phe Arg Phe Arg Phe Arg Phe Arg
1               5                   10                  15

Phe Arg Phe Arg
            20

<210> SEQ ID NO 51
<211> LENGTH: 12
<212> TYPE: PRT
<213> ORGANISM: Artificial Sequence
<220> FEATURE:
<223> OTHER INFORMATION: from Self-Assembling peptide - invented
      sequence

<400> SEQUENCE: 51

Phe Lys Phe Gln Phe Lys Phe Gln Phe Lys Phe Gln
1               5                   10

<210> SEQ ID NO 52
<211> LENGTH: 8
<212> TYPE: PRT
<213> ORGANISM: Artificial Sequence
<220> FEATURE:
<223> OTHER INFORMATION: from Self-Assembling peptide - invented
      sequence

<400> SEQUENCE: 52

Ile Glu Ile Lys Ile Glu Ile Lys
1               5

<210> SEQ ID NO 53
<211> LENGTH: 12
<212> TYPE: PRT
<213> ORGANISM: Artificial Sequence
<220> FEATURE:
<223> OTHER INFORMATION: from Self-Assembling peptide - invented
      sequence

<400> SEQUENCE: 53

Lys Leu Asp Leu Lys Leu Asp Leu Lys Leu Asp Leu
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Repetitive RGD binding sequence

<400> SEQUENCE: 54

Pro Arg Gly Asp Ser Gly Tyr Arg Gly Asp
1               5                   10

<210> SEQ ID NO 55
<211> LENGTH: 10
```

```
<212> TYPE: PRT
<213> ORGANISM: Artificial Sequence
<220> FEATURE:
<223> OTHER INFORMATION: Cell adhesion domain (Osteopontin)

<400> SEQUENCE: 55

Asp Gly Arg Gly Asp Ser Val Ala Tyr Gly
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Osteogenic growth peptide

<400> SEQUENCE: 56

Ala Leu Lys Arg Gln Gly Arg Thr Leu Tyr Gly Phe
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Bone marrow homing

<400> SEQUENCE: 57

Pro Phe Ser Ser Thr Lys Thr
1               5

<210> SEQ ID NO 58
<211> LENGTH: 6
<212> TYPE: PRT
<213> ORGANISM: Artificial Sequence
<220> FEATURE:
<223> OTHER INFORMATION: MP-1 (bone marrow purification)

<400> SEQUENCE: 58

Phe Leu Gly Phe Pro Thr
1               5

<210> SEQ ID NO 59
<211> LENGTH: 15
<212> TYPE: PRT
<213> ORGANISM: Artificial Sequence
<220> FEATURE:
<223> OTHER INFORMATION: VEGF mimicking peptide/Bind to VEGF

<400> SEQUENCE: 59

Lys Leu Thr Trp Gln Glu Leu Tyr Gln Leu Lys Tyr Lys Gly Ile
1               5                   10                  15

<210> SEQ ID NO 60
<211> LENGTH: 8
<212> TYPE: PRT
<213> ORGANISM: Artificial Sequence
<220> FEATURE:
<223> OTHER INFORMATION: Bone marrow homing

<400> SEQUENCE: 60

Ser Lys Pro Pro Gly Thr Ser Ser
1               5

<210> SEQ ID NO 61
<211> LENGTH: 7
<212> TYPE: PRT
<213> ORGANISM: Artificial Sequence
```

```
<220> FEATURE:
<223> OTHER INFORMATION: Bone marrow homing

<400> SEQUENCE: 61

Ser Thr Phe Thr Lys Ser Pro
1               5

<210> SEQ ID NO 62
<211> LENGTH: 5
<212> TYPE: PRT
<213> ORGANISM: Artificial Sequence
<220> FEATURE:
<223> OTHER INFORMATION: Laminin (110 kDa Laminin receptor protein)

<400> SEQUENCE: 62

Ile Lys Val Ala Val
1               5

<210> SEQ ID NO 63
<211> LENGTH: 7
<212> TYPE: PRT
<213> ORGANISM: Artificial Sequence
<220> FEATURE:
<223> OTHER INFORMATION: Heparin binding domain

<400> SEQUENCE: 63

Phe His Arg Arg Ile Lys Ala
1               5

<210> SEQ ID NO 64
<211> LENGTH: 5
<212> TYPE: PRT
<213> ORGANISM: Artificial Sequence
<220> FEATURE:
<223> OTHER INFORMATION: Laminin (a3b1 and cell surface heparin)

<400> SEQUENCE: 64

Ile Lys Leu Leu Ile
1               5

<210> SEQ ID NO 65
<211> LENGTH: 4
<212> TYPE: PRT
<213> ORGANISM: Artificial Sequence
<220> FEATURE:
<223> OTHER INFORMATION: Fibronectin/Endothelial cells adhesion

<400> SEQUENCE: 65

Arg Glu Asp Val
1

<210> SEQ ID NO 66
<211> LENGTH: 7
<212> TYPE: PRT
<213> ORGANISM: Artificial Sequence
<220> FEATURE:
<223> OTHER INFORMATION: actin binding site on thymosin beta-4

<400> SEQUENCE: 66

Leu Lys Lys Thr Glu Thr Gln
1               5

<210> SEQ ID NO 67
<211> LENGTH: 4
<212> TYPE: PRT
<213> ORGANISM: Artificial Sequence
<220> FEATURE:
<223> OTHER INFORMATION: from Self-Assembling peptide - invented
```

```
               sequence

<400> SEQUENCE: 67

Arg Ala Asp Ala
1

<210> SEQ ID NO 68
<211> LENGTH: 4
<212> TYPE: PRT
<213> ORGANISM: Artificial Sequence
<220> FEATURE:
<223> OTHER INFORMATION: Bone marrow homing

<400> SEQUENCE: 68

Ile Glu Ile Lys
1

<210> SEQ ID NO 69
<211> LENGTH: 4
<212> TYPE: PRT
<213> ORGANISM: Artificial Sequence
<220> FEATURE:
<223> OTHER INFORMATION: from Self-Assembling peptide - invented
      sequence

<400> SEQUENCE: 69

Phe Lys Phe Gln
1

<210> SEQ ID NO 70
<211> LENGTH: 8
<212> TYPE: PRT
<213> ORGANISM: Artificial Sequence
<220> FEATURE:
<223> OTHER INFORMATION: Laminin (a3b1 and cell surface heparin)

<400> SEQUENCE: 70

Ser Glu Ile Lys Leu Leu Ile Ser
1               5

<210> SEQ ID NO 71
<211> LENGTH: 11
<212> TYPE: PRT
<213> ORGANISM: Artificial Sequence
<220> FEATURE:
<223> OTHER INFORMATION: Repetitive RGD binding sequence

<400> SEQUENCE: 71

Pro Arg Gly Asp Ser Gly Tyr Arg Gly Asp Ser
1               5                   10

<210> SEQ ID NO 72
<211> LENGTH: 5
<212> TYPE: PRT
<213> ORGANISM: Artificial Sequence
<220> FEATURE:
<223> OTHER INFORMATION: Repetitive RGD binding sequence

<400> SEQUENCE: 72

Pro Arg Gly Asp Ser
1               5

<210> SEQ ID NO 73
<211> LENGTH: 5
<212> TYPE: PRT
<213> ORGANISM: Artificial Sequence
<220> FEATURE:
<223> OTHER INFORMATION: Repetitive RGD binding sequence
```

```
<400> SEQUENCE: 73

Tyr Arg Gly Asp Ser
1               5

<210> SEQ ID NO 74
<211> LENGTH: 14
<212> TYPE: PRT
<213> ORGANISM: Artificial Sequence
<220> FEATURE:
<223> OTHER INFORMATION: Repetitive RGD binding sequence

<400> SEQUENCE: 74

Ala Leu Lys Arg Gln Gly Arg Thr Leu Tyr Gly Phe Gly Gly
1               5                   10

<210> SEQ ID NO 75
<211> LENGTH: 5
<212> TYPE: PRT
<213> ORGANISM: Artificial Sequence
<220> FEATURE:
<223> OTHER INFORMATION: Repetitive RGD binding sequence

<400> SEQUENCE: 75

Ile Lys Leu Leu Ser
1               5

<210> SEQ ID NO 76
<211> LENGTH: 4
<212> TYPE: PRT
<213> ORGANISM: Artificial Sequence
<220> FEATURE:
<223> OTHER INFORMATION: from Self-Assembling peptide - invented
      sequence

<400> SEQUENCE: 76

Lys Leu Asp Leu
1

<210> SEQ ID NO 77
<211> LENGTH: 27
<212> TYPE: PRT
<213> ORGANISM: Artificial Sequence
<220> FEATURE:
<223> OTHER INFORMATION: Repetitive RGD binding sequence

<400> SEQUENCE: 77

Ala Asp Ala Arg Ala Asp Ala Arg Ala Asp Ala Arg Ala Asp Ala Gly
1               5                   10                  15

Pro Arg Gly Asp Ser Gly Tyr Arg Gly Asp Ser
            20                  25

<210> SEQ ID NO 78
<211> LENGTH: 23
<212> TYPE: PRT
<213> ORGANISM: Artificial Sequence
<220> FEATURE:
<223> OTHER INFORMATION: Repetitive RGD binding sequence

<400> SEQUENCE: 78

Ala Asp Ala Arg Ala Asp Ala Arg Ala Asp Ala Gly Pro Arg Gly Asp
1               5                   10                  15

Ser Gly Tyr Arg Gly Asp Ser
            20

<210> SEQ ID NO 79
```

```
<211> LENGTH: 20
<212> TYPE: PRT
<213> ORGANISM: Artificial Sequence
<220> FEATURE:
<223> OTHER INFORMATION: Repetitive RGD binding sequence

<400> SEQUENCE: 79

Arg Ala Asp Ala Arg Ala Asp Ala Gly Pro Arg Gly Asp Ser Gly Tyr
1               5                   10                  15

Arg Gly Asp Ser
            20

<210> SEQ ID NO 80
<211> LENGTH: 12
<212> TYPE: PRT
<213> ORGANISM: Artificial Sequence
<220> FEATURE:
<223> OTHER INFORMATION: Bone marrow homing

<400> SEQUENCE: 80

Ile Glu Ile Lys Ile Glu Ile Lys Ile Glu Ile Lys
1               5                   10

<210> SEQ ID NO 81
<211> LENGTH: 16
<212> TYPE: PRT
<213> ORGANISM: Artificial Sequence
<220> FEATURE:
<223> OTHER INFORMATION: Bone marrow homing

<400> SEQUENCE: 81

Ile Glu Ile Lys Ile Glu Ile Lys Ile Glu Ile Lys Ile Glu Ile Lys
1               5                   10                  15

<210> SEQ ID NO 82
<211> LENGTH: 12
<212> TYPE: PRT
<213> ORGANISM: Artificial Sequence
<220> FEATURE:
<223> OTHER INFORMATION: Repetitive RGD binding sequence

<400> SEQUENCE: 82

Pro Arg Gly Asp Ser Gly Tyr Arg Gly Asp Ser Gly
1               5                   10
```